United States Patent
Wang et al.

(10) Patent No.: US 12,016,701 B2
(45) Date of Patent: Jun. 25, 2024

(54) QUANTITATIVE DIFFERENTIATION OF TUMOR HETEROGENEITY USING DIFFUSION MR IMAGING DATA

(71) Applicants: Yong Wang, St. Louis, MO (US); Gloria Guzman, St. Louis, MO (US); Qing Wang, St. Louis, MO (US); Tammie Benzinger, St. Louis, MO (US)

(72) Inventors: Yong Wang, St. Louis, MO (US); Gloria Guzman, St. Louis, MO (US); Qing Wang, St. Louis, MO (US); Tammie Benzinger, St. Louis, MO (US)

(73) Assignee: Washington University, St. Louis, MO (US)

( * ) Notice: Subject to any disclaimer, the term of this patent is extended or adjusted under 35 U.S.C. 154(b) by 486 days.

(21) Appl. No.: 16/329,608

(22) PCT Filed: Aug. 30, 2017

(86) PCT No.: PCT/US2017/049440
§ 371 (c)(1),
(2) Date: Feb. 28, 2019

(87) PCT Pub. No.: WO2018/045072
PCT Pub. Date: Mar. 8, 2018

(65) Prior Publication Data
US 2019/0223789 A1  Jul. 25, 2019
US 2021/0177348 A9  Jun. 17, 2021

Related U.S. Application Data

(60) Provisional application No. 62/381,223, filed on Aug. 30, 2016.

(51) Int. Cl.
*A61B 5/00* (2006.01)
*A61B 5/055* (2006.01)
(Continued)

(52) U.S. Cl.
CPC ............ *A61B 5/4887* (2013.01); *A61B 5/004* (2013.01); *A61B 5/055* (2013.01); *A61B 5/7264* (2013.01);
(Continued)

(58) Field of Classification Search
CPC ....... A61B 5/4887; A61B 5/004; A61B 5/743; A61B 5/055; G01R 33/5602; G01R 33/56341
See application file for complete search history.

(56) References Cited

U.S. PATENT DOCUMENTS

2003/0208116 A1* 11/2003 Liang .................... A61B 5/055
600/407
2008/0267468 A1* 10/2008 Geiger ................ G01S 7/52036
382/128
(Continued)

FOREIGN PATENT DOCUMENTS

WO  2013025487 A1  2/2013
WO  2015057745 A1  4/2015

OTHER PUBLICATIONS

Murakami, R., Author Affiliations1From the Departments of Radiation Oncology (R.M., Caulo, M., Chu, H. H., Kang, Y. (Jun. 1, 2009). Grading Astrocytic Tumors by Using Apparent Diffusion Coefficient Parameters: Superiority of a One- versus Two-Parameter Pilot Method. Radiology. (Year: 2009).*
(Continued)

*Primary Examiner* — Patrick Fernandes
*Assistant Examiner* — Nicholas A Robinson
(74) *Attorney, Agent, or Firm* — Armstrong Teasdale LLP

(57) ABSTRACT

Provided herein are methods for imaging and diagnosing at least one disorder in a patient utilizing diffusion basis
(Continued)

spectrum imaging MRI with extended isotropic spectrum (DBSI-EIS). The methods may be used as a tool to image and diagnose heterogeneities within tumors. As a result, different tumor types can be detected, distinguished from one another, and individually quantified without the need to inject exogenous contrast agents.

19 Claims, 94 Drawing Sheets
(26 of 94 Drawing Sheet(s) Filed in Color)

(51) Int. Cl.
  *G01R 33/56* (2006.01)
  *G01R 33/563* (2006.01)
(52) U.S. Cl.
  CPC ............ *A61B 5/7271* (2013.01); *A61B 5/743* (2013.01); *G01R 33/5602* (2013.01); *G01R 33/56341* (2013.01)

(56) References Cited

U.S. PATENT DOCUMENTS

| | | | |
|---|---|---|---|
| 2010/0309223 A1* | 12/2010 | Roth | G06T 5/50 |
| | | | 711/E12.001 |
| 2011/0282183 A1* | 11/2011 | Song | G01R 33/56341 |
| | | | 600/410 |
| 2012/0049845 A1 | 3/2012 | Bito et al. | |
| 2012/0280686 A1 | 11/2012 | White et al. | |
| 2015/0253410 A1 | 9/2015 | Warfield et al. | |
| 2016/0157746 A1* | 6/2016 | Ellingson | G01R 33/56341 |
| | | | 600/420 |

OTHER PUBLICATIONS

Huisman, T A G M. "Diffusion-weighted and diffusion tensor imaging of the brain, made easy." Cancer imaging : the official publication of the International Cancer Imaging Society vol. 10 Spec No. A, 1A S163-71. Oct. 4, 2010, doi: 10.1102/1470-7330. 2010.9023 (Year: 2010).*
Osamu Togao, Akio Hiwatashi, Koji Yamashita, Kazufumi Kikuchi, Masahiro Mizoguchi, Koji Yoshimoto, Satoshi O. Suzuki, Toru Iwaki, Makoto Obara, Marc Van Cauteren, Hiroshi Honda, Differentiation of high-grade and low-grade diffuse gliomas by intravoxel incoherent motion MR imaging, Neuro-Oncology (Year: 2015).*
Huisman TA. Diffusion-weighted and diffusion tensor imaging of the brain, made easy. Cancer Imaging. Oct. 4, 2010;10 Spec No. A(1A):S163-71. doi: 10.1102/1470-7330.2010.9023. PMID: 20880787; PMCID: PMC2967146. (Year: 2010).*
Wang Y, Sun P, Wang Q, Trinkaus K, Schmidt RE, Naismith RT, Cross AH, Song SK. Differentiation and quantification of inflammation, demyelination and axon injury or loss in multiple sclerosis. Brain. May 2015;138(Pt 5):1223-38. doi: 10.1093/brain/awv046. Epub Feb. 26, 2015. (Year: 2015).*
Castillo M, Smith JK, Kwock L, Wilber K. Apparent diffusion coefficients in the evaluation of high-grade cerebral gliomas. AJNR Am J Neuroradiol. Jan. 2001;22(1):60-4. PMID: 11158889; PMCID: PMC7975568. (Year: 2001).*
Murakami R, Hirai T, Sugahara T, Fukuoka H, Toya R, Nishimura S, Kitajima M, Okuda T, Nakamura H, Oya N, Kuratsu J, Yamashita Y. Grading astrocytic tumors by using apparent diffusion coefficient parameters: superiority of a one- versus two-parameter pilot method. Radiology. Jun. 2009; (Year: 2009).*
Cheng YS, Lin C, Cheng YP, Yu YL, Tang CT, Hueng DY. Epithelial cell transformation sequence 2 is a potential biomarker of unfavorable survival in human gliomas. Neurol India. Jul.-Aug. 2014;62(4):406-9. doi: 10.4103/0028-3886.141278. PMID: 25237947. (Year: 2014).*
Togao O, Hiwatashi A, Yamashita K, Kikuchi K, Mizoguchi M, Yoshimoto K, Suzuki SO, Iwaki T, Obara M, Van Cauteren M, Honda H. Differentiation of high-grade and low-grade diffuse gliomas by intravoxel incoherent motion MR imaging. Neuro Oncol. Jan. 2016; 18 (Year: 2016).*
Chiang CW, Wang Y, Sun P, Lin TH, Trinkaus K, Cross AH, Song SK. Quantifying white matter tract diffusion parameters in the presence of increased extra-fiber cellularity and vasogenic edema. Neuroimage. Nov. 1, 2014;101:310-9. doi: 10.1016/j.neuroimage. 2014.06.064. Epub Jul. 11, 2014. (Year: 2014).*
Cheng YW, Chung HW, Chen CY, Chou MC. Diffusion tensor imaging with cerebrospinal fluid suppression and signal-to-noise preservation using acquisition combining fluid-attenuated inversion recovery and conventional imaging: comparison of fiber tracking . Eur J Radiol. Jul. 2011;79(1): (Year: 2011).*
Pradhan S, Bonekamp S, Gillen JS, Rowland LM, Wijtenburg SA, Edden RA, Barker PB. Comparison of single voxel brain MRS AT 3T and 7T using 32-channel head coils. Magn Reson Imaging. Oct. 2015;33(8):1013-8. doi: 10.1016/j.mri.2015.06.003. Epub Jun. 25, 2015. PMID: 26117693; PMCID: PMC4549223. (Year: 2015).*
Murphy et al., "Magnetic Resonance Imaging Biomarker of Axon Loss Reflects Cervical Spondylotic Myelopathy Severity," Spine 41(9): 751-756 (May 2016). Retrieved from the Internet: <URL: https://www.ncbi.nlm.nih.gov/pubmed/26650876>.
International Search Report and Written Opinion for PCT Application No. PCT/US2017/049440 dated Nov. 7, 2017 (7 pages).
Bihan, Denis Le., The 'wet mind': water and functional neuroimaging, Physics In Medicine and Biology, 2007, pp. R57-R90, vol. 52, IOP Publishing.

\* cited by examiner

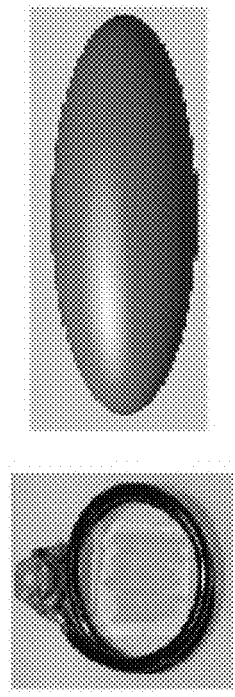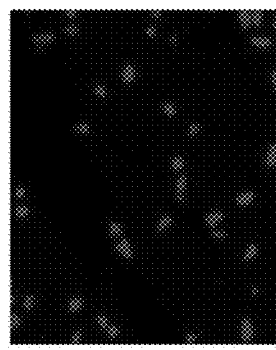
FIG. 18

MBP

SMI-31

DAPI

WATER

FIG. 36
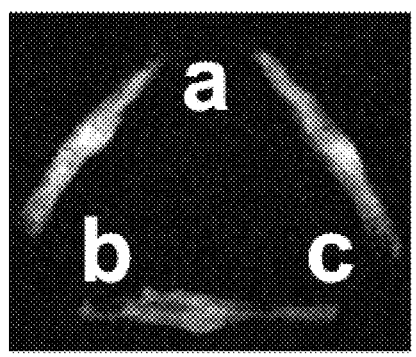 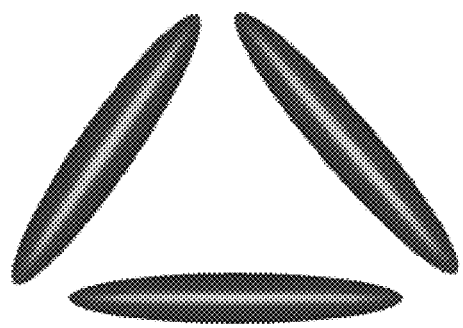

Slice = 45    Slice = 35

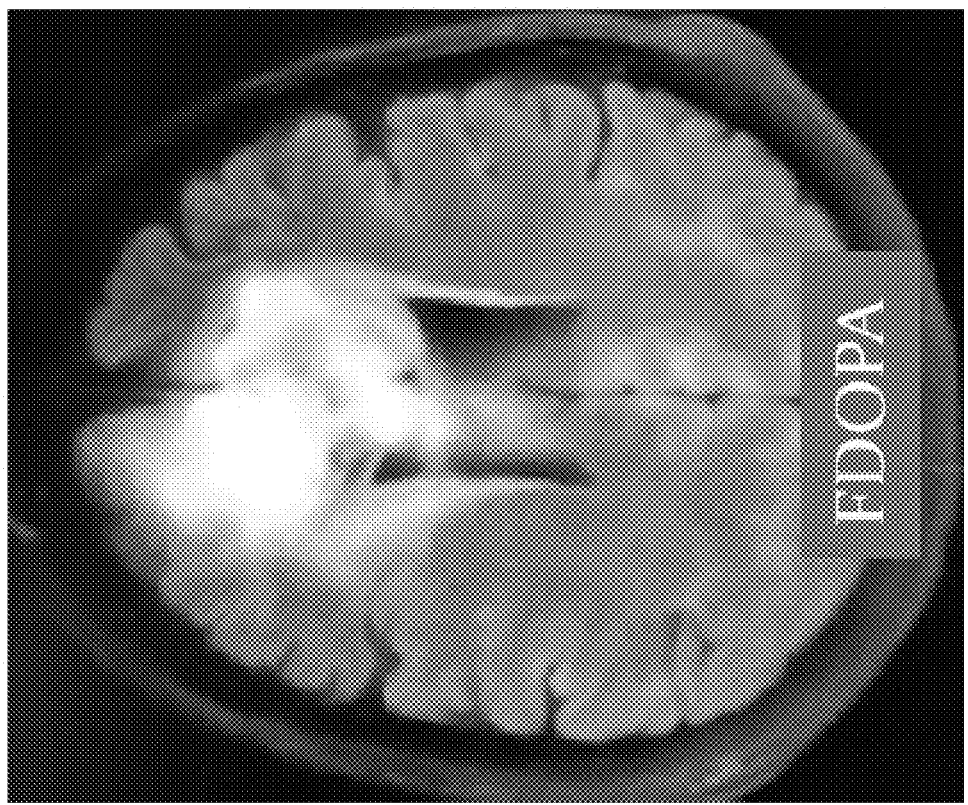
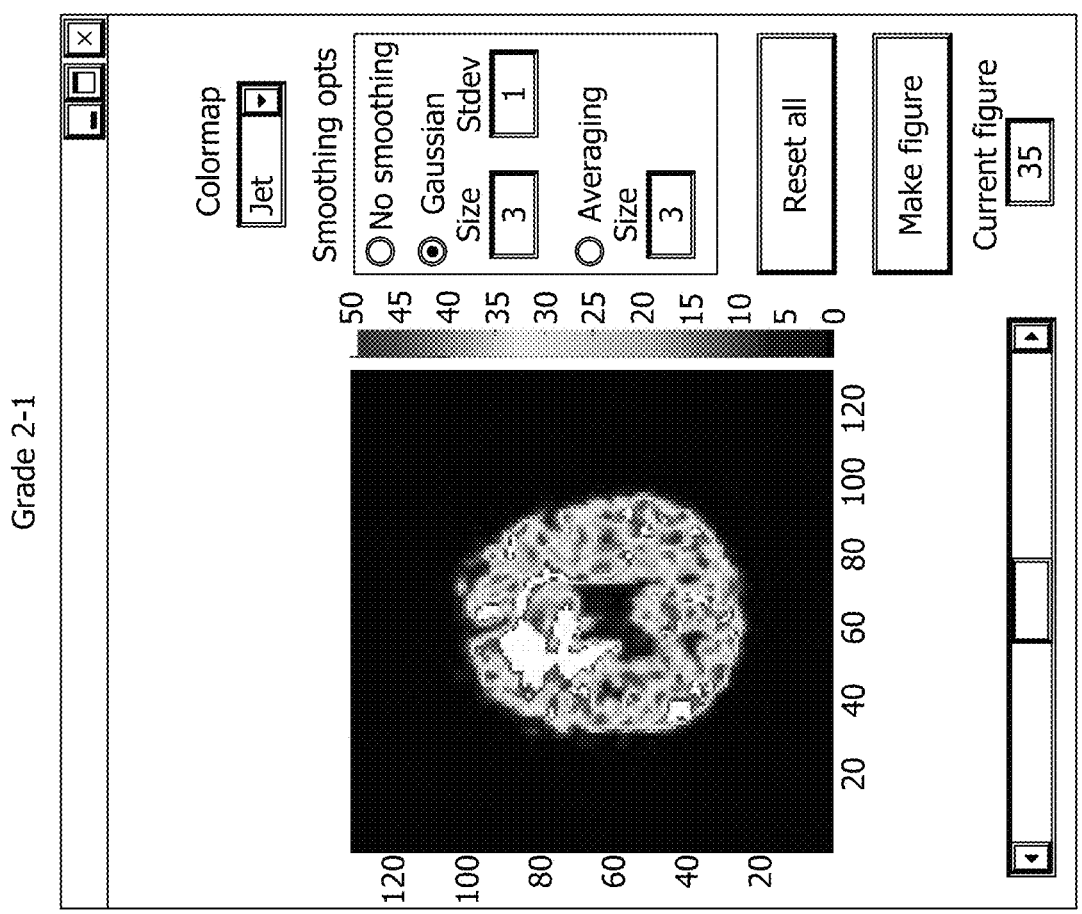
FIG. 59(b)

Slice 49

DBSI

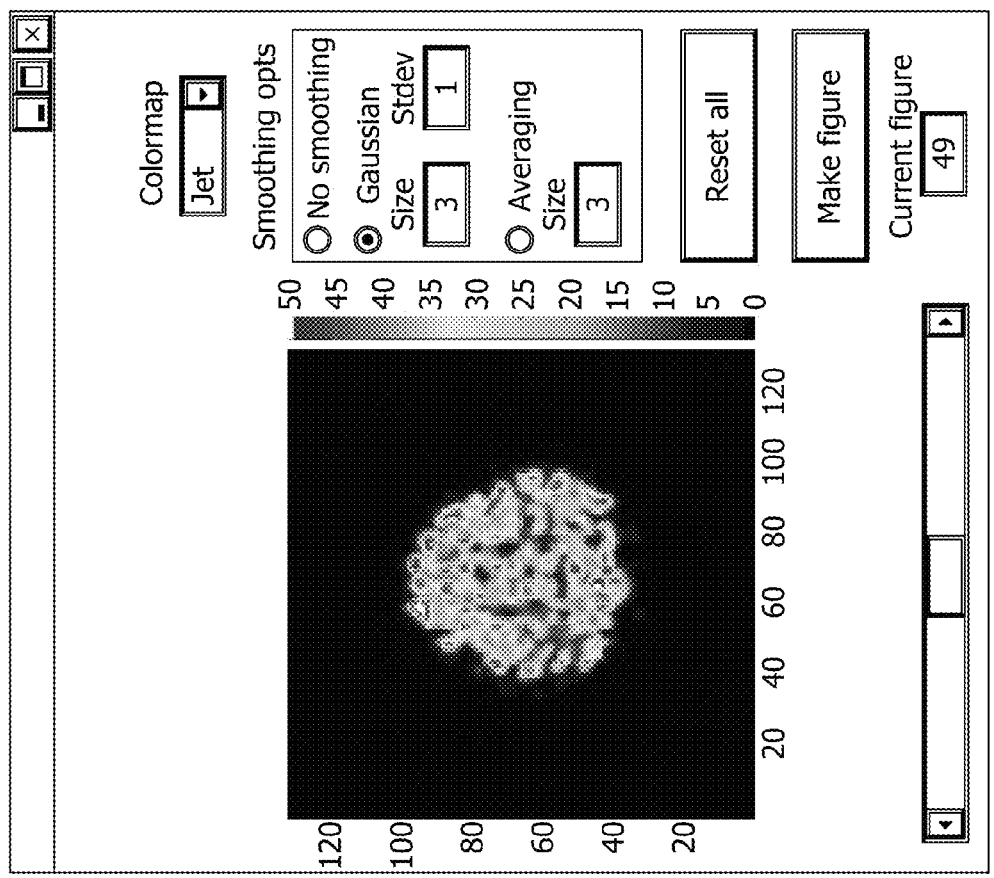
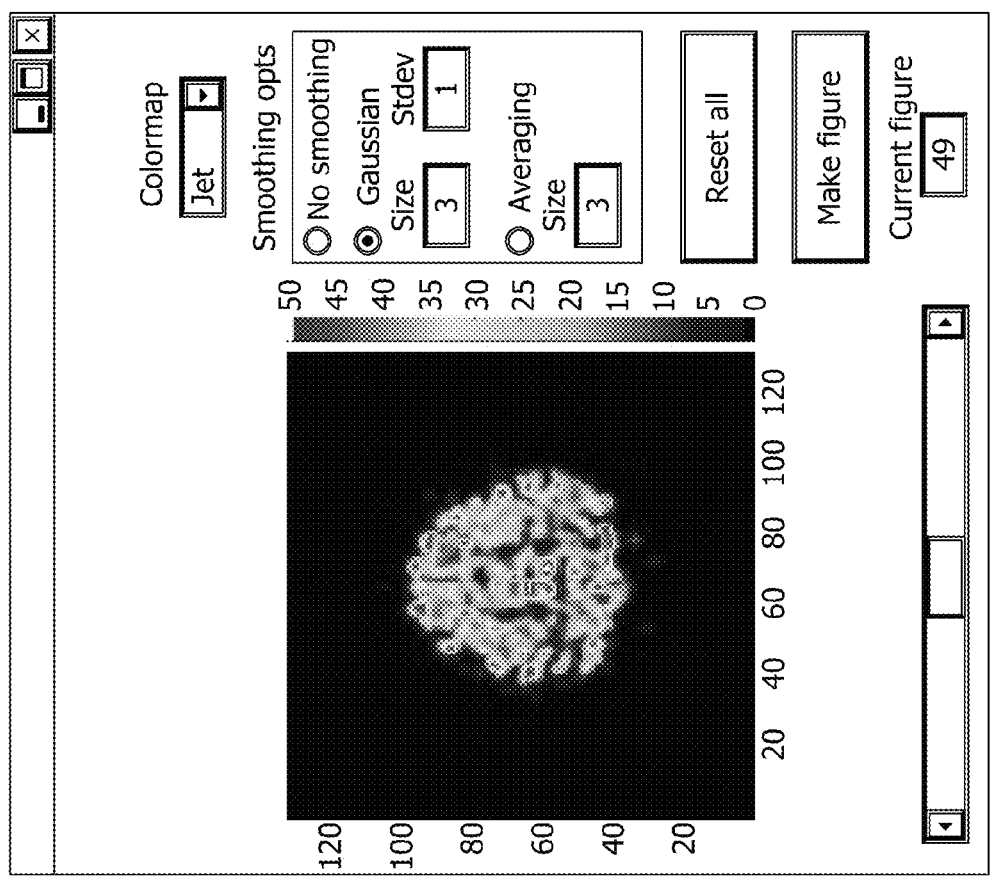
FIG. 63(a)

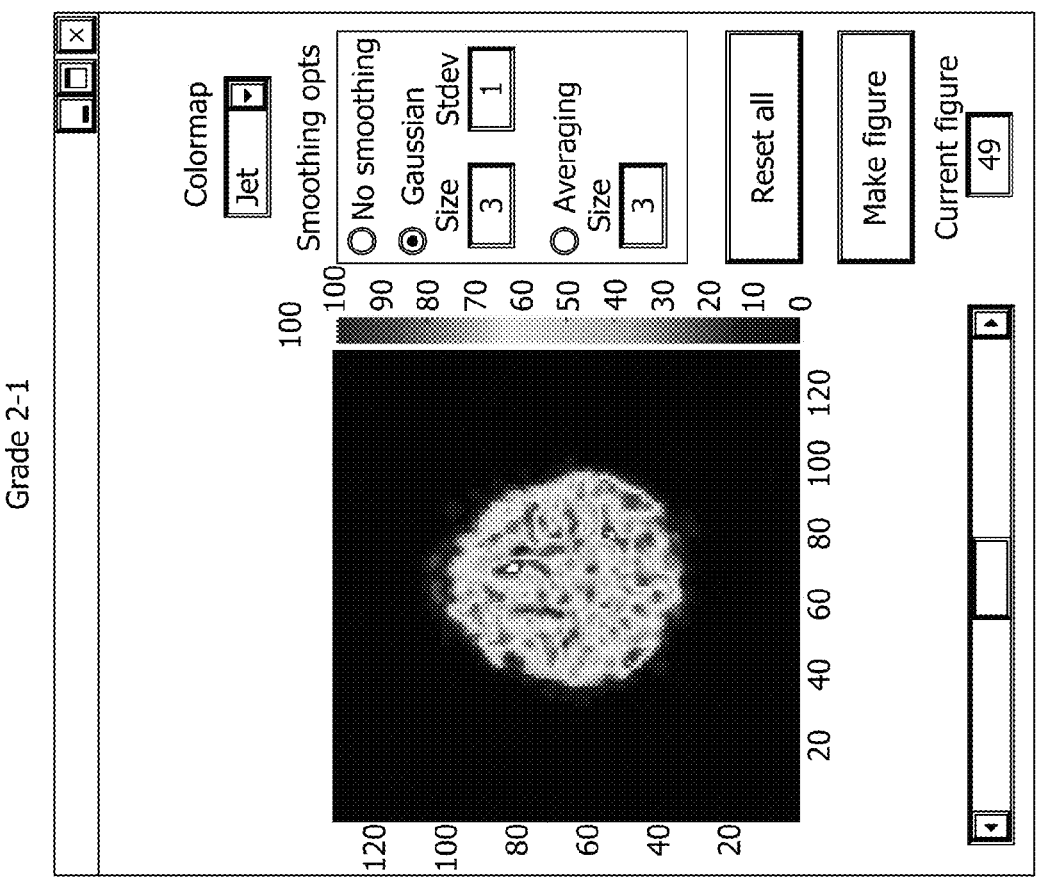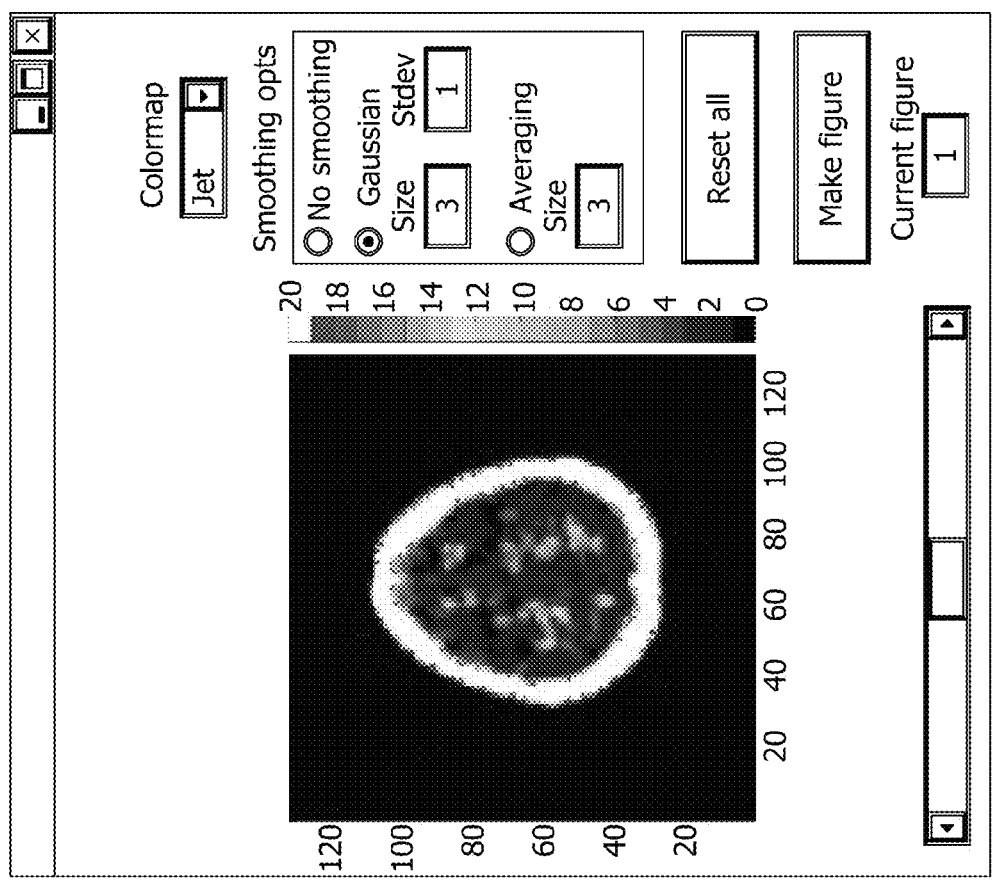
FIG. 63(b)

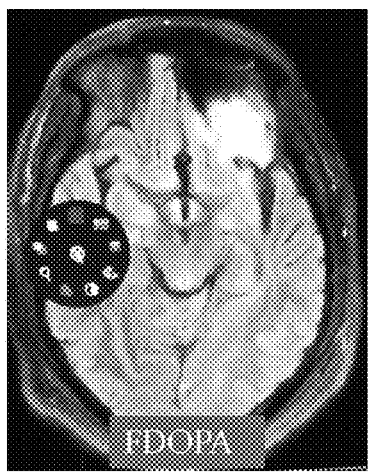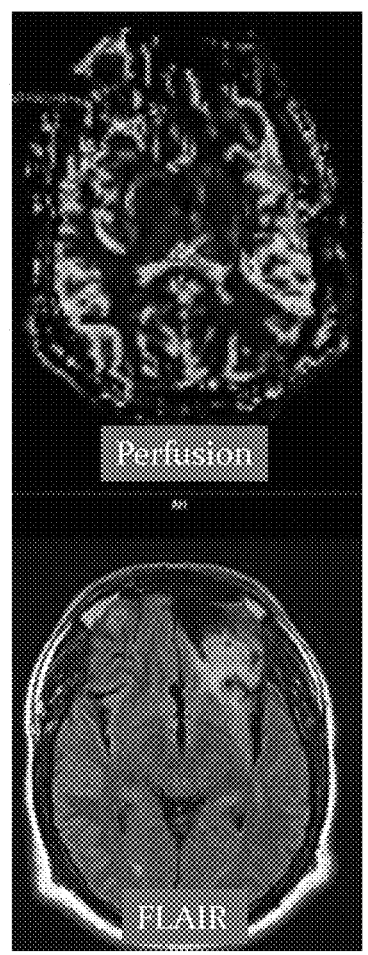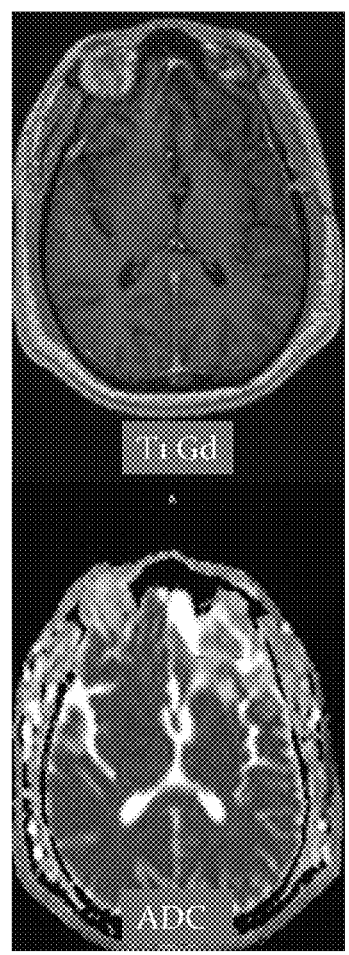
FIG. 64

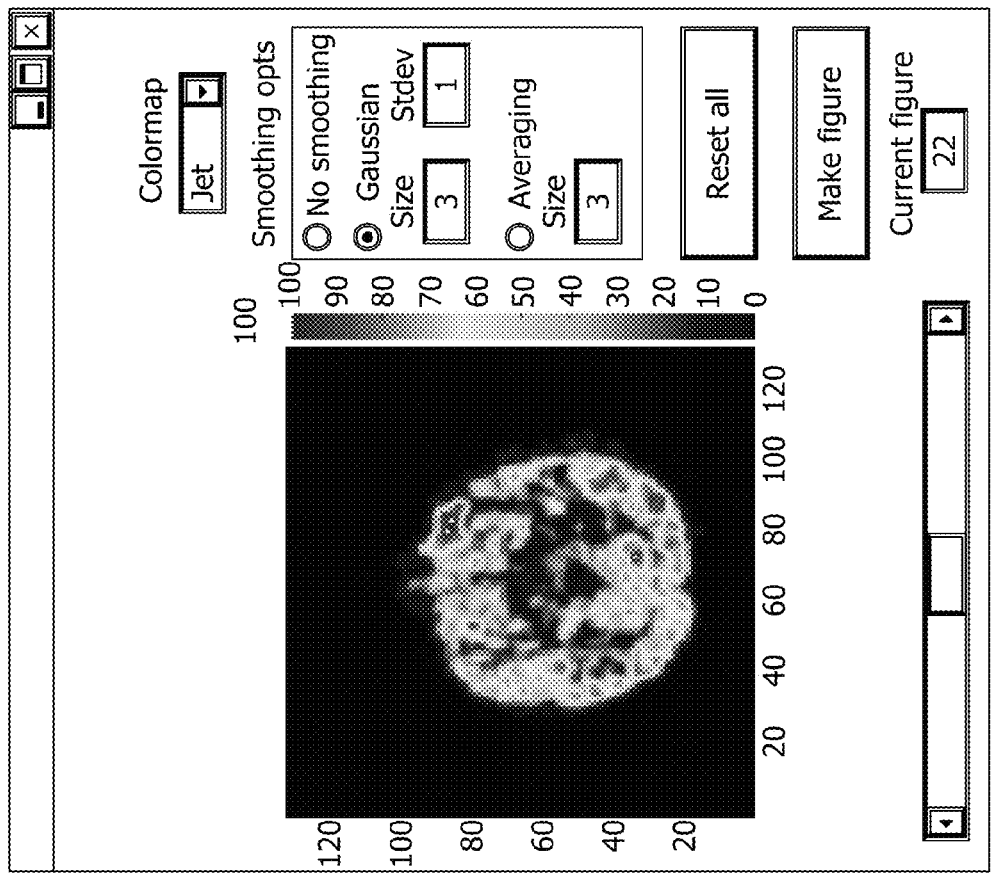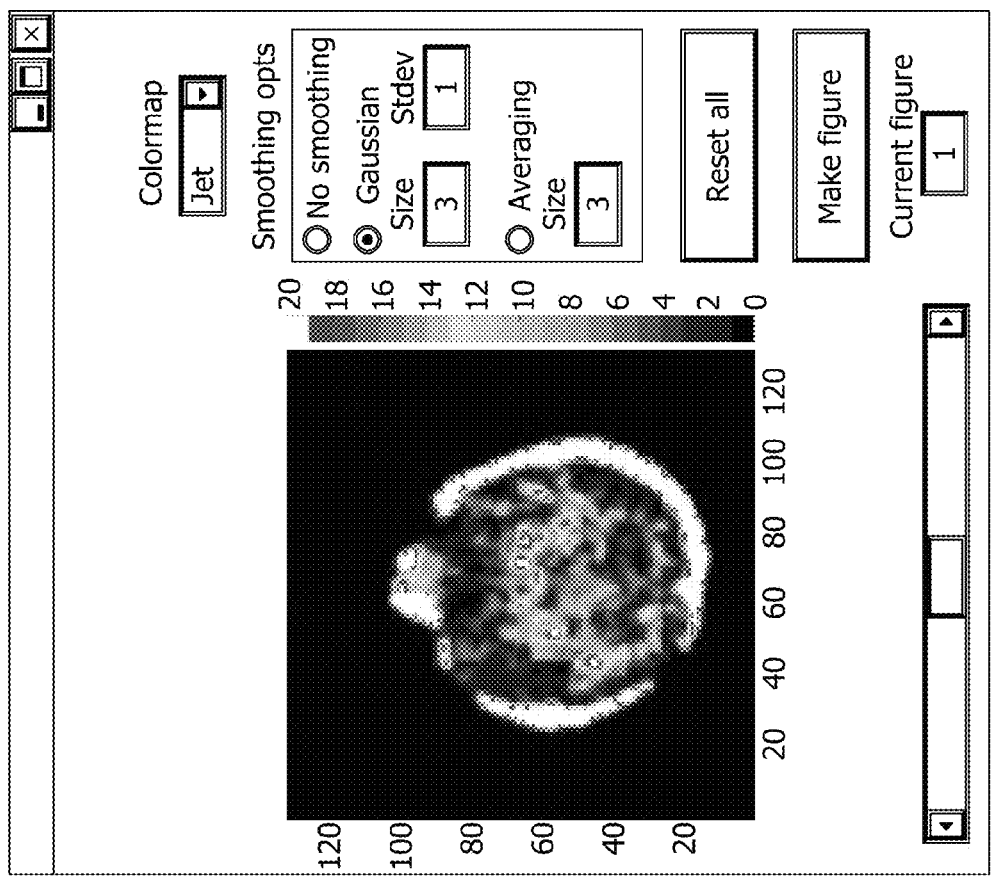
FIG. 66(b)

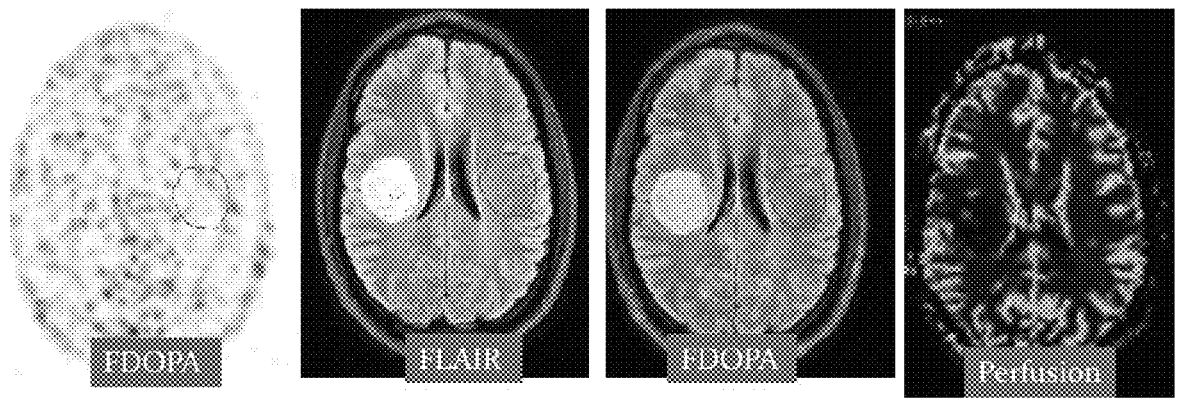
Slice 36
FIG. 68
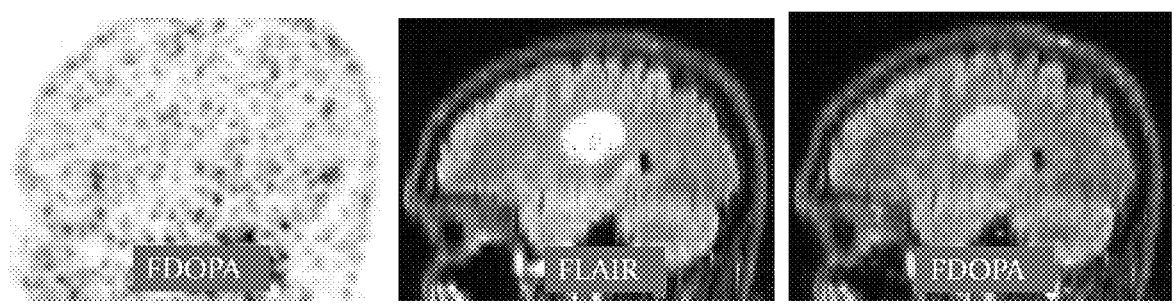
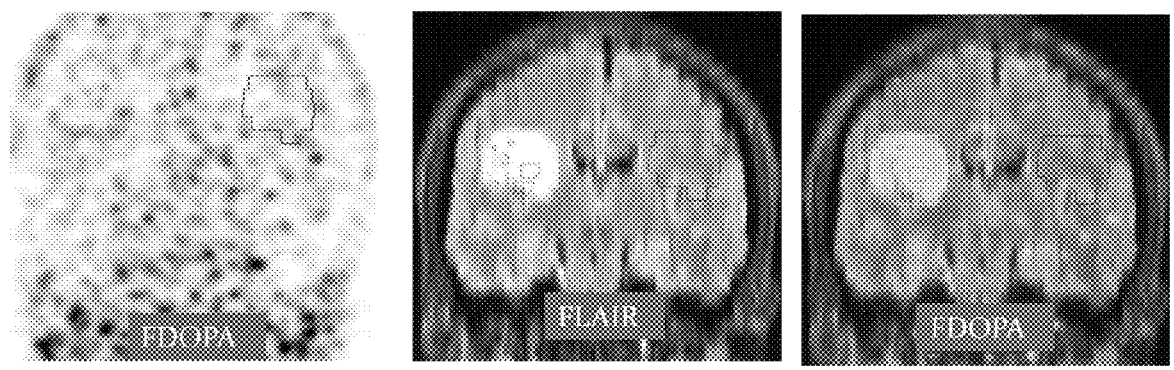
FIG. 69

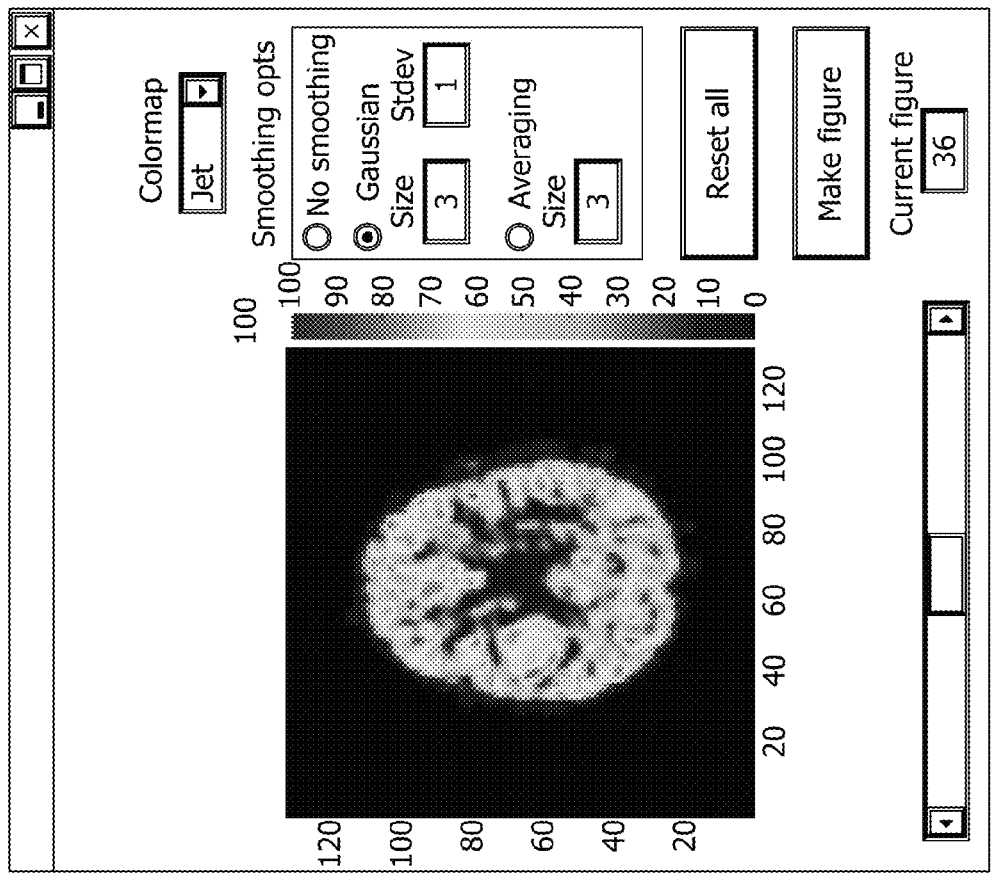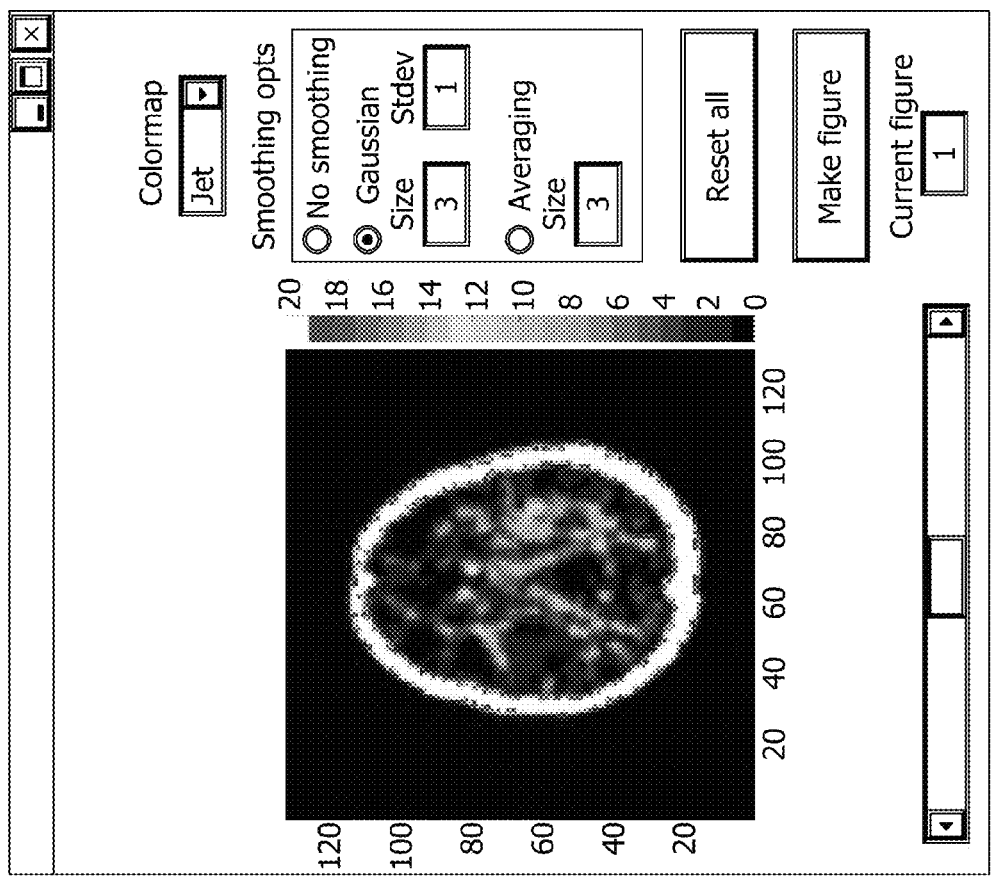
FIG. 70(b)

Slice 42

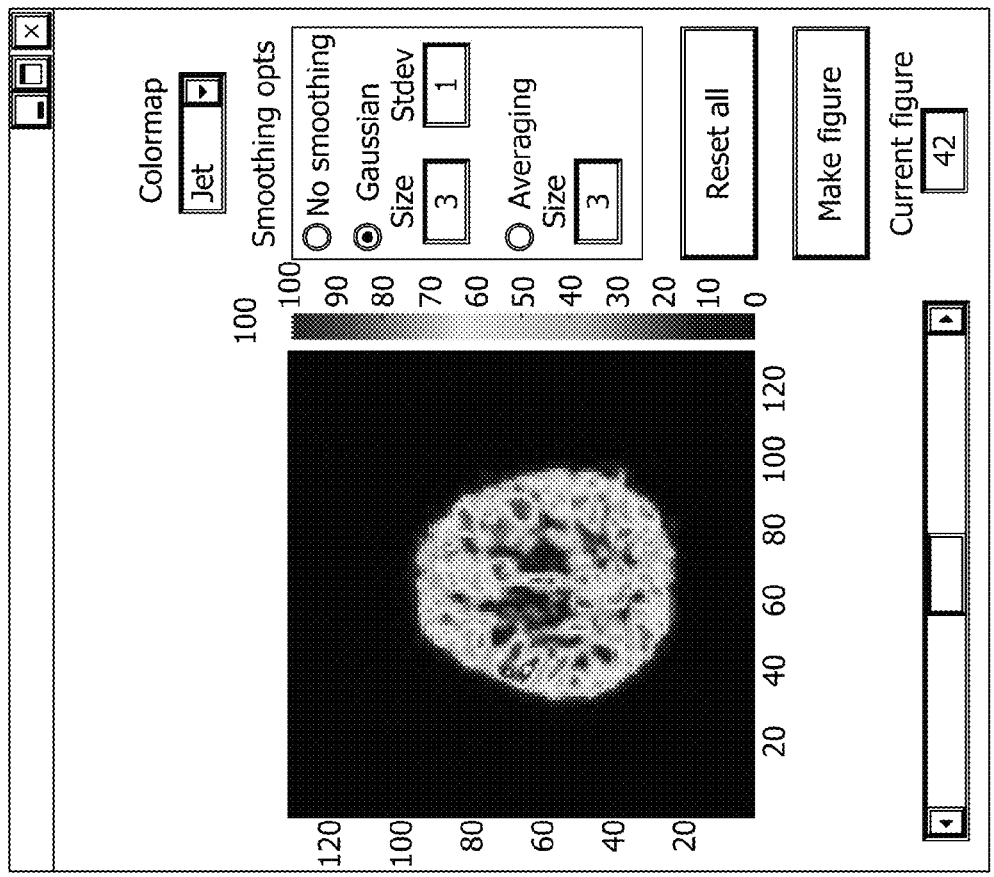
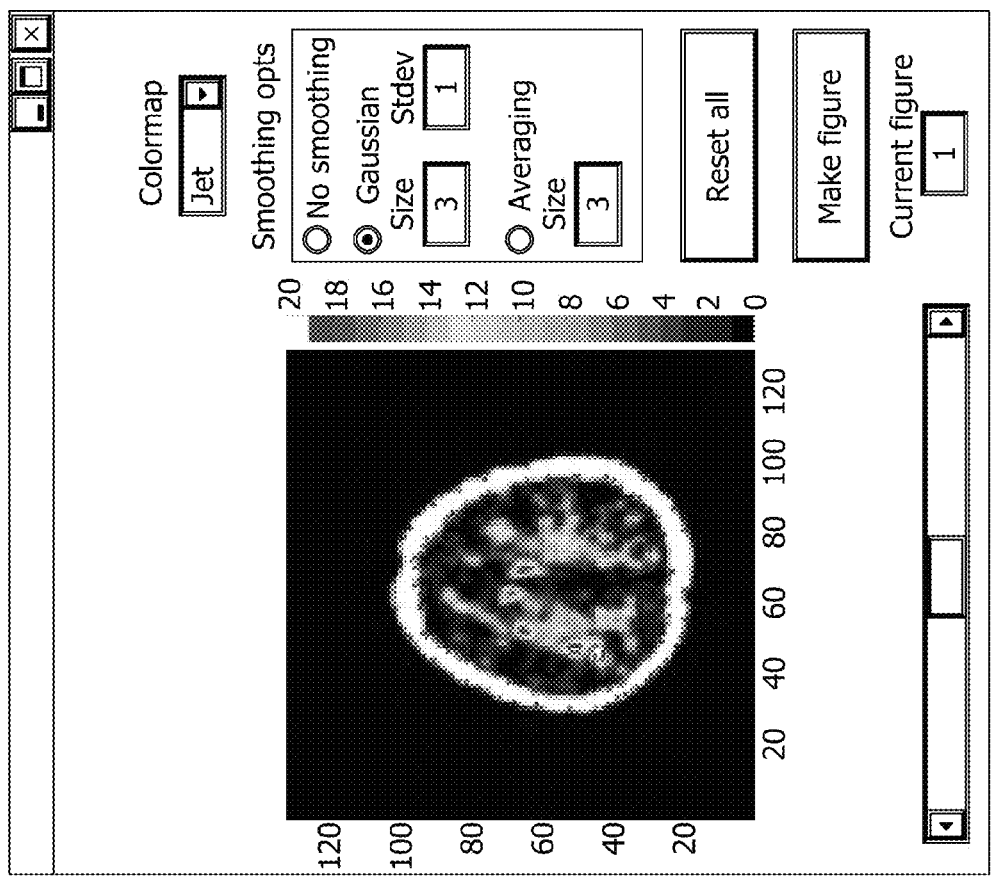
FIG. 73(b)

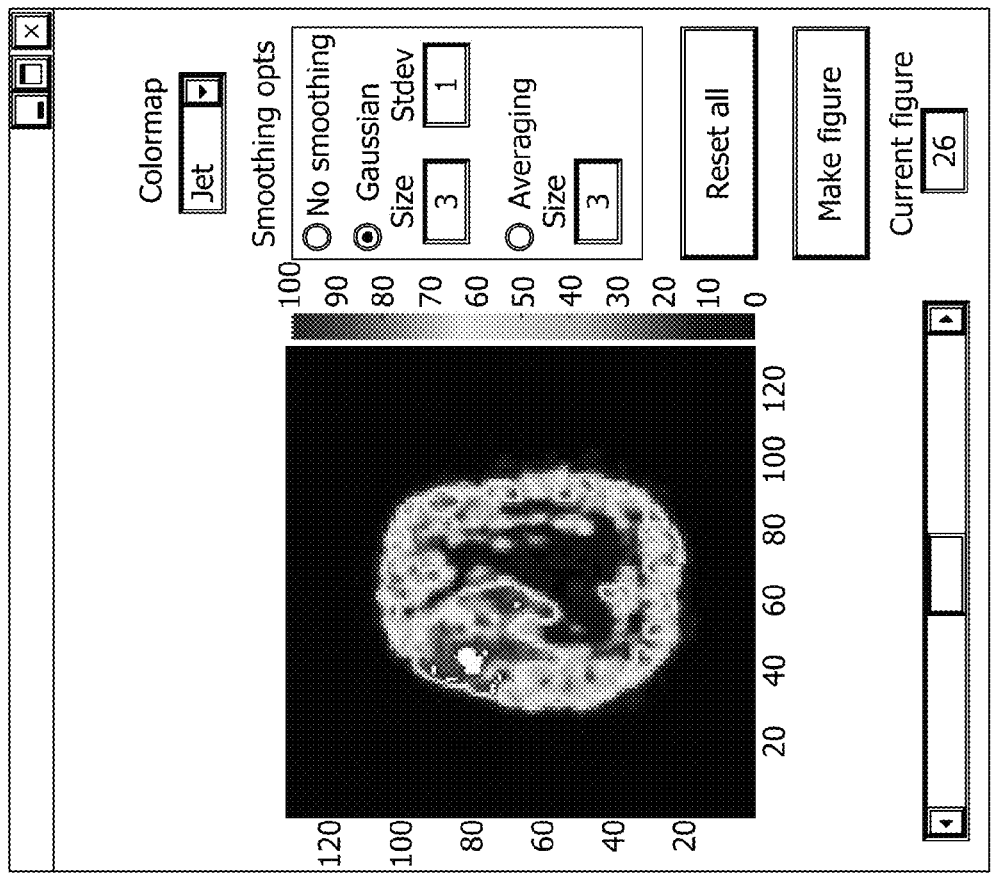
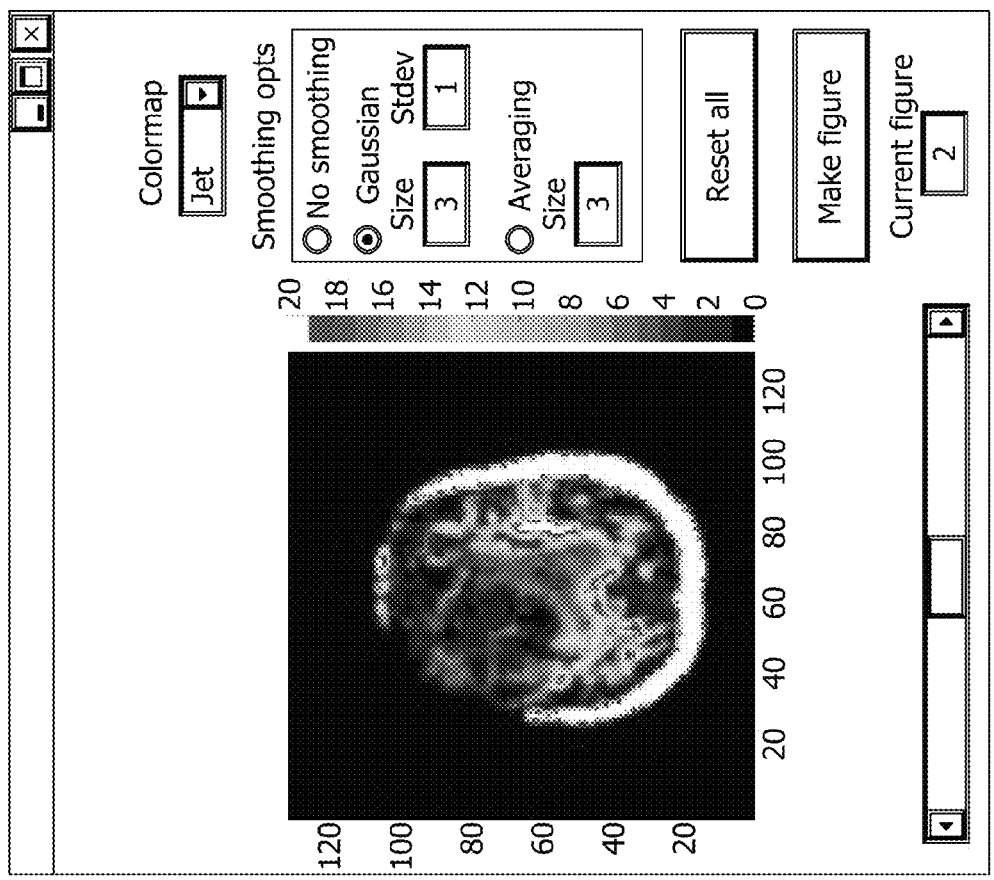
FIG. 76(b)

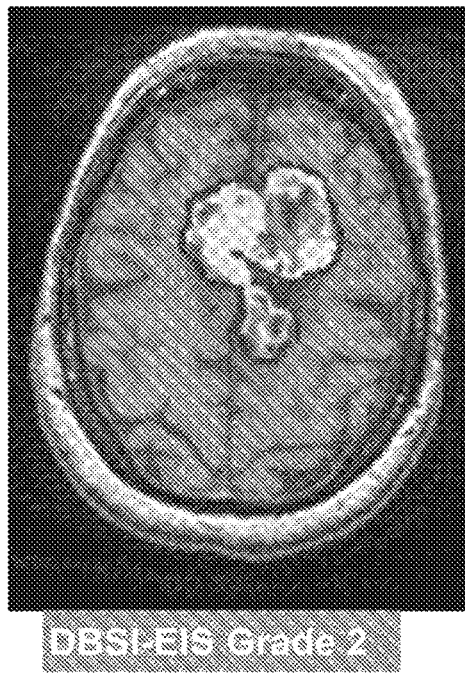 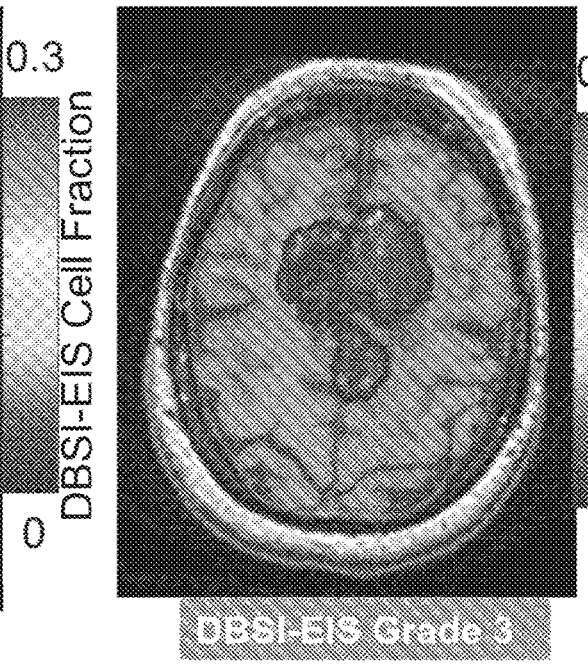
FIG. 83A  FIG. 83B
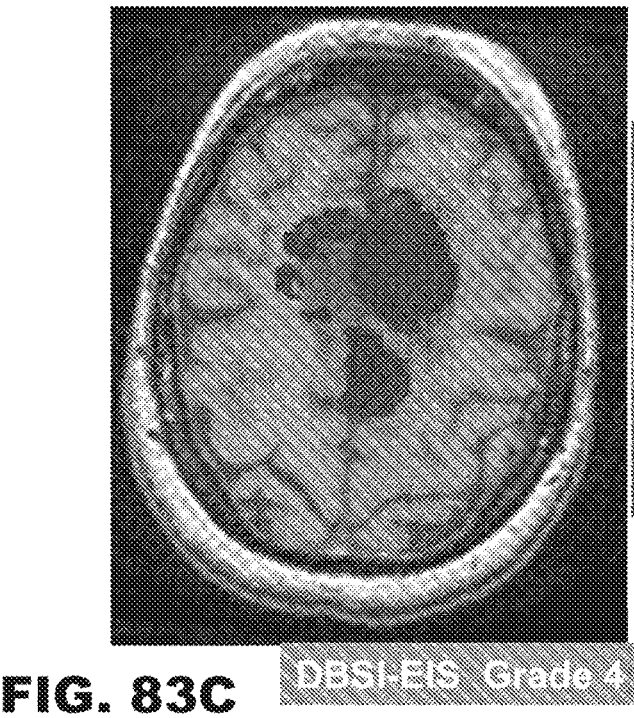
FIG. 83C

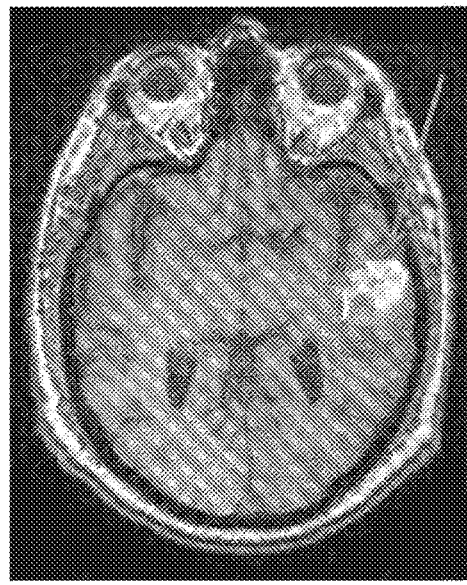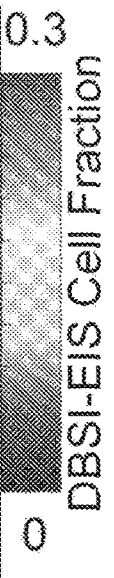  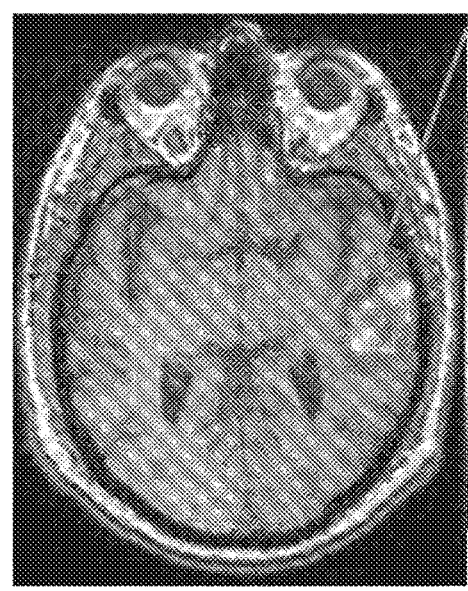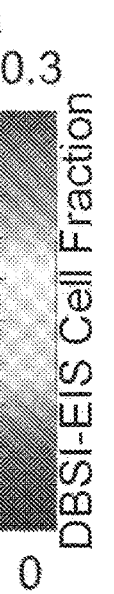
FIG. 86A  FIG. 86B
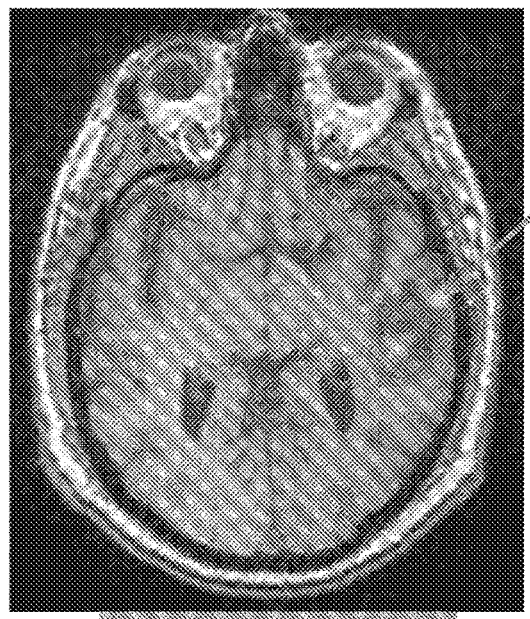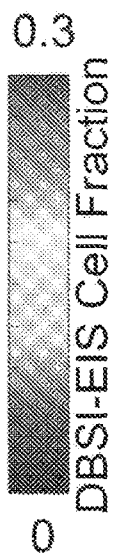
FIG. 86C

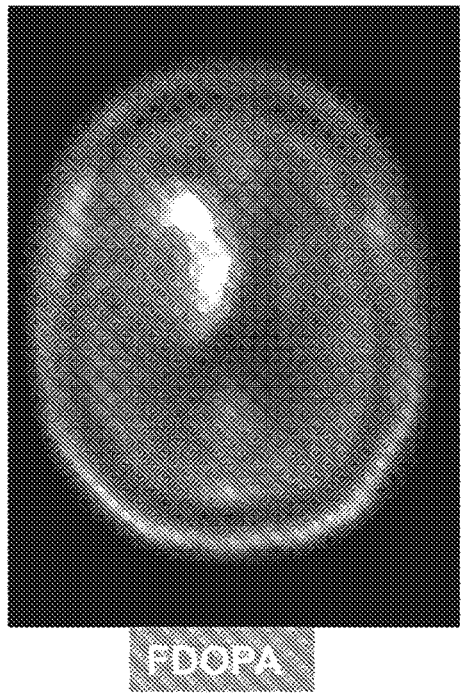 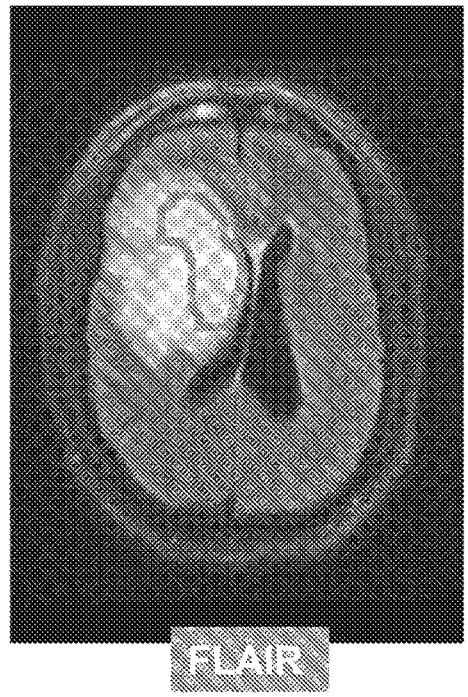
FIG. 89A  FIG. 89B
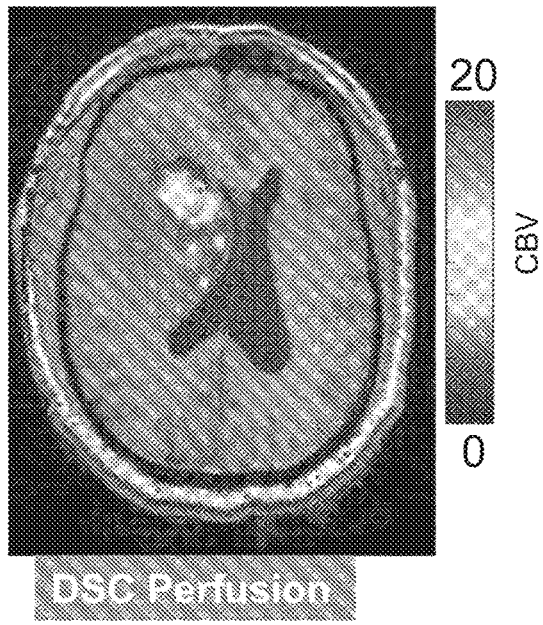 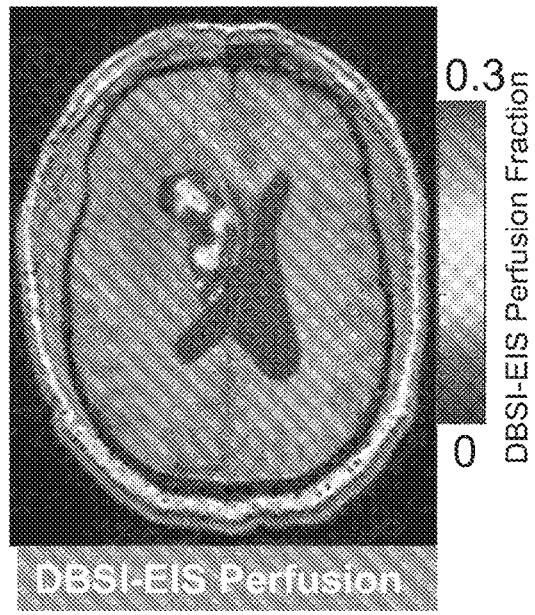
FIG. 89C  FIG. 89D

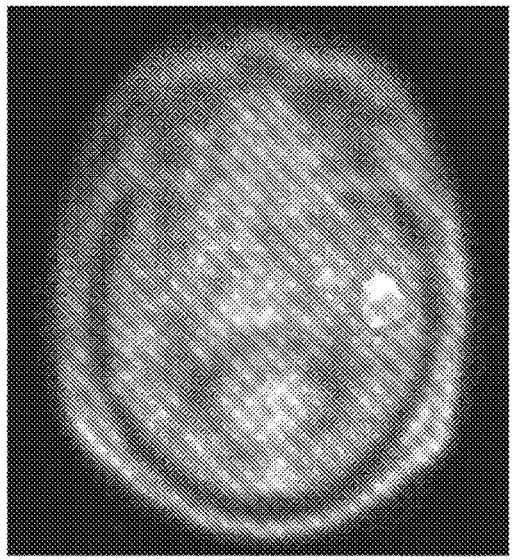 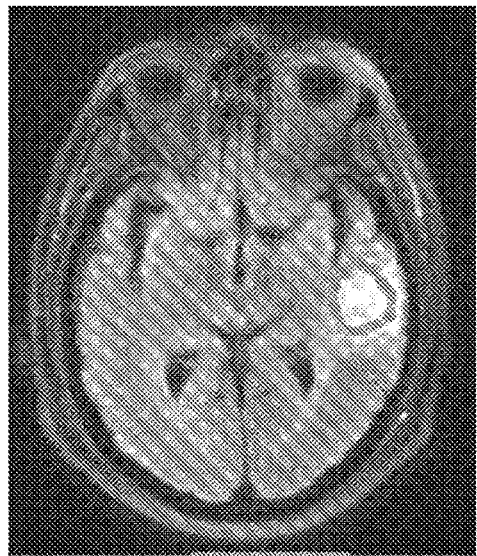
FIG. 90A  FIG. 90B
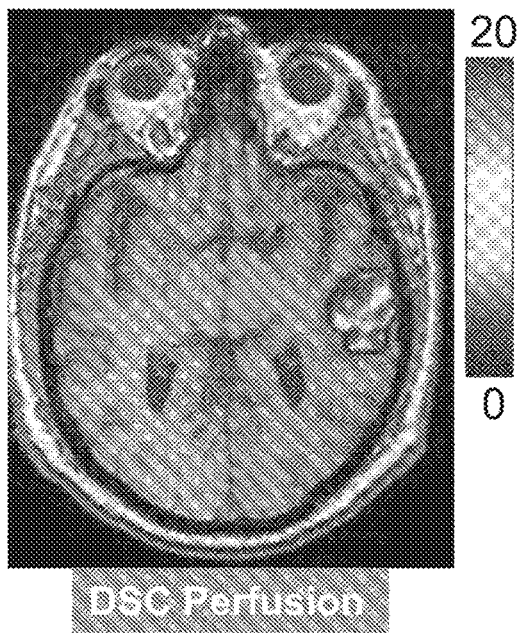 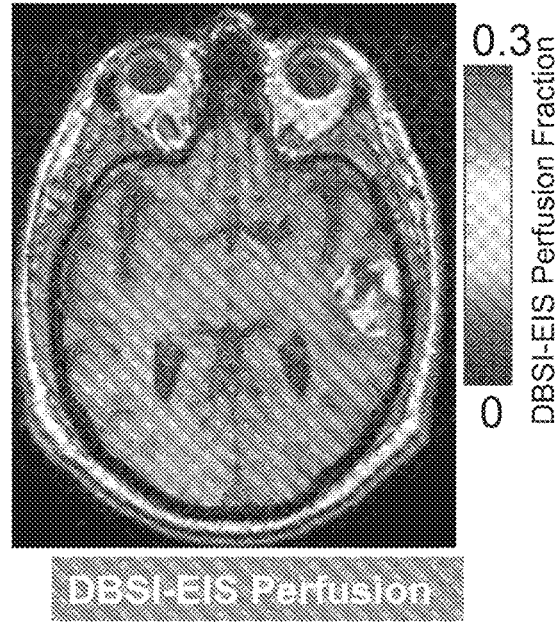
FIG. 90C  FIG. 90D

QUANTITATIVE DIFFERENTIATION OF TUMOR HETEROGENEITY USING DIFFUSION MR IMAGING DATA

CROSS-REFERENCE TO RELATED APPLICATIONS

This application is a U.S. National Phase Patent Application of International Application Serial Number PCT/US2017/049440, filed Aug. 30, 2017, the contents of which are entirely incorporated by reference herein. International Application Serial Number PCT/US2017/049440 claims the benefit of priority to U.S. Provisional Application No. 62/381,223, filed Aug. 30, 2016, the contents of which are entirely incorporated by reference herein.

STATEMENT REGARDING FEDERALLY SPONSORED RESEARCH & DEVELOPMENT

This invention was made with government support under AG026276 awarded by the National Institutes of Health. The government has certain rights in the invention.

FIELD

The present disclosure generally relates to methods for imaging and diagnosing tumors using diffusion basis spectrum imaging MRI with extended isotropic spectrum (DBSI-EIS). More particularly, the disclosure related to quantitatively differentiating tumor heterogeneity using DBSI-EIS.

BACKGROUND

Tumors are typically heterogeneous in structure, and may contain different grades of tumor cells, different types of tumor cells, abnormal edema and/or abnormal vascular structures. A noninvasive, non-radiative technique to provide multiple parametric and quantitative images for better profiling the heterogeneity of tumors is disclosed. With the disclosed method, tumor cell microstructures (cells with different types and grades), edema, and vascular structure that perfuse the tumor can be measured in a single clinical imaging scan. The feasibility and effectiveness have been tested using clinical data, which make it a new and unique technique to clinically evaluate tumors for comprehensive diagnosis and accurate treatment evaluation.

Existing standards of care for diagnosing many tumors such as brain tumors includes MRI imaging to identify general characterizing features of the lesion or tumor, including the location, size, and extent of the tumor. In some cases, the MRI visualization is followed by a biopsy to better characterize the cells and other structures associated with the tumor including grade(s) of tumor cells, vascularization of the tumor, and the heterogeneity of the tumor cells. The biopsy may provide information used to inform an appropriate course of treatment.

In some cases, the tumor may be positioned within close proximity to delicate structures and as a result may not be amenable to biopsy. For example, the tumor may be positioned deep within the brain beneath brain tissues associated with important cognitive function. Because the insertion of a biopsy needle into a tumor so located would potentially result in significant brain damage to the patient, other diagnostic tools may be used instead of biopsy. To date, the gold standard of non-invasive imaging of tumors is PET imaging, such as fluoradopa (FDOPA) PET imaging using to image brain tumors. However, the PET tracers intrinsically intrude radiation into the patient, may be challenging to introduce across the blood brain barrier into the brain of a patient. In addition, PET tracers are designed to bind specifically to particular cell types, and may provide an incomplete visualization due to the heterogeneity of tumor cell types within some tumors.

There exists an unmet clinical need to better quantify the heterogeneity of the tumors for the purpose of more accurate and complete biopsy strategy, treatment planning and post-treatment evaluation. A non-invasive imaging method for tumors that includes non-radiative and multiple contrast features will provide a tool to enhance the standard of care for tumor patients.

SUMMARY

Methods and systems disclosed herein utilize modifications of diffusion basis spectrum imaging (DBSI) as a tool to image and diagnose heterogeneities within tumors. As a result, different tumor types can be detected, distinguished from one another, and individually quantified without the need to inject exogenous contrast agents.

BRIEF DESCRIPTION OF THE DRAWINGS

The application file contains at least one drawing executed in color. Copies of this patent application publication with color drawing(s) will be provided by the Office upon request and payment of the necessary fee.

The drawings below illustrate various aspects of the disclosure.

FIG. 18 is an exemplary phantom of mouse trigeminal nerves embedded in gel with known in vivo DTI character.

FIG. 36 is an illustration of a three-fiber crossing phantom forming a triangle.

FIG. 63 contains a series of DBSI-EIS images of a patient with contrast corresponding to grade of brain tumor cell.

FIG. 64 contains images of a patient using perfusion imaging, FLAIR imaging, FDOPA PET imaging, and ADC contrast imaging.

FIG. 68 contains images of a patient using perfusion imaging, FLAIR imaging, and FDOPA PET imaging.

FIG. 69 contains additional images of a patient of FIG. 68 using FLAIR imaging and FDOPA PET imaging.

FIG. 83A is a DBSI-EIS grade 2 image of the patient of FIG. 82A. FIG. 83B is a DBSI-EIS grade 3 image of the patient of FIG. 82A. FIG. 83C is a DBSI-EIS grade 4 image of the patient of FIG. 82A.

FIG. 86A is a DBSI-EIS grade 2 image of a patient with a glioblastoma WHO grade IV. FIG. 86B is a DBSI-EIS grade 3 image of the patient of FIG. 86A. FIG. 86C is a DBSI-EIS grade 4 image of the patient of FIG. 86A.

FIG. 89A is an FDOPA image of the patient of FIG. 85A with an oligodendroglioma WHO grade III. FIG. 89B is a FLAIR image of the patient of FIG. 85A. FIG. 89C is a DSC perfusion image of the patient of FIG. 85A. FIG. 89D is a DBSI-EIS perfusion image of the patient of FIG. 85A.

FIG. 90A is an FDOPA image of the patient of FIG. 86A with an oligodendroglioma WHO grade IV. FIG. 90B is a FLAIR image of the patient of FIG. 86A. FIG. 90C is a DSC perfusion image of the patient of FIG. 86A. FIG. 90D is a DBSI-EIS perfusion image of the patient of FIG. 86A.

DETAILED DESCRIPTION

Figure 1:
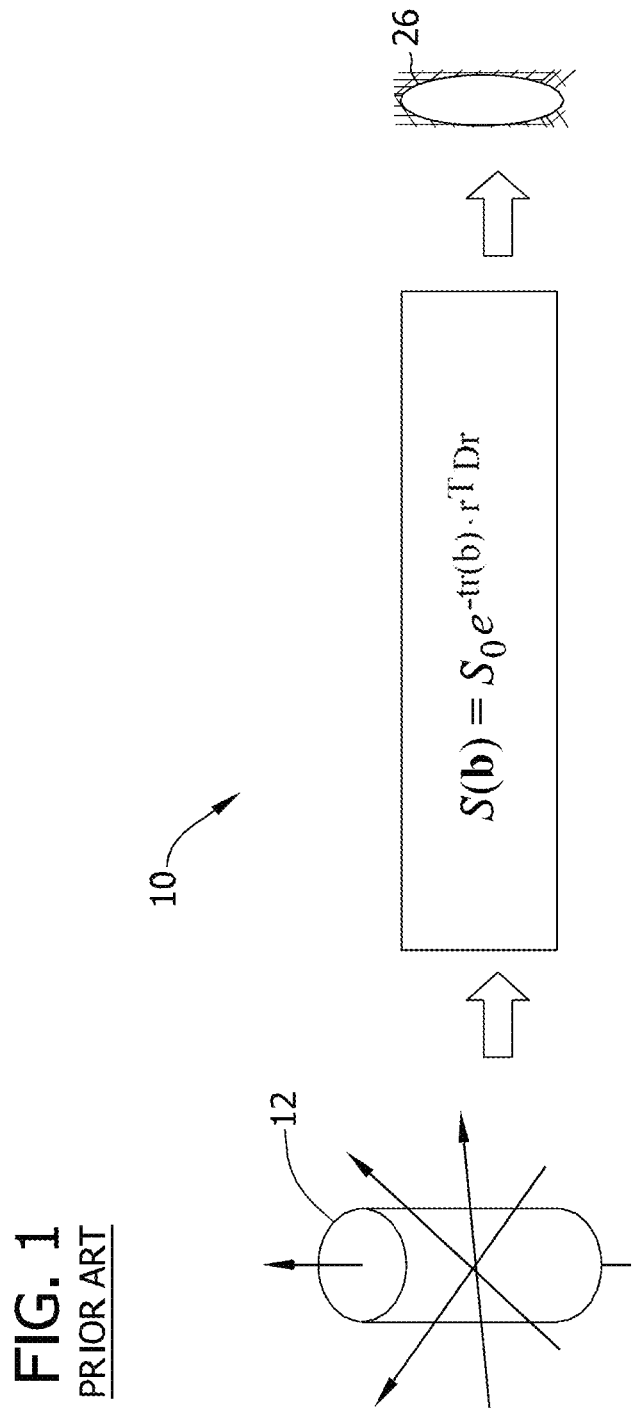
FIG. 1 is an illustration of diffusion magnetic resonance (MR) signal response when diffusion tensor imaging (DTI) is applied to a single white matter tract of coherent axonal fibers.

For the context of the present disclosure, an in-depth discussion of diffusion MRI is first provided, followed by a detailed description of quantitative differentiation of inflammation and solid tumor.

Abbreviations: MRI, magnetic resonance imaging; DBSI, diffusion basis spectrum imaging; dMRI, diffusion MRI; DTI, diffusion tensor imaging; ADC, apparent diffusion coefficient; mDBSI, modified DBSI; H&E staining, haemotoxylin and eosin staining; DWI, diffusion-weighted imaging; DCE, Dynamic Contrast Enhanced Imaging; T1W, T1-weighted imaging; T2W, T2-weighted imaging.

Diffusion MRI

The following discussion relates generally to magnetic resonance imaging (MRI) and, more particularly, to diffusion magnetic resonance data provided by an MRI scanner.

The following discussion relates generally to magnetic resonance imaging (MRI) and, more particularly, to diffusion magnetic resonance data provided by an MRI scanner.

White matter injury is common in central nervous system (CNS) disorders and plays an important role in neurological dysfunctions in patients. Understanding the pathology of complex and heterogeneous central nervous system diseases such as multiple sclerosis (MS) has been greatly hampered by the dearth of histological specimens obtained serially during the disease. Clinicians are reluctant to perform invasive CNS biopsies on patients with white matter disorders, due to the potential injury to the patients.

The insight of CNS white matter neuropathology has been derived typically from occasional biopsies consisting of small tissue samples of unusual cases. These autopsies usually derive from patients with end-stage disease and often have long postmortem delay artifacts due tissue degradation. It is therefore advantageous to have a noninvasive imaging tool to accurately quantify and better understand the chronic and non-fatal injury in CNS disease during the whole course of the individual patient.

Diffusion tensor imaging (DTI) is a commonly used MRI modality in CNS disease/injury diagnosis. However, the current use of DTI technique is not capable of resolving the complex underlying pathologies correctly, despite being considered better than other techniques.

A diffusion MRI technique is discussed herein to noninvasively study and quantify complicated CNS diseases in a noninvasive fashion without the limitation of invasive histological examinations.

Such embodiments facilitate improved results compared to diffusion tensor imaging (DTI). The directional diffusivities derived from DTI measurements describe water movement parallel to ($\lambda_{11}$, axial diffusivity) and perpendicular to ($\lambda_L$, radial diffusivity) axonal tracts. It was previously proposed and validated that decreased $\lambda_{11}$ is associated with axonal injury and dysfunction, and increased $\lambda_L$ is associated with myelin injury in mouse models of white matter injury.

The presence of inflammation, edema, or gliosis during CNS white matter injury may impact the DTI measurement. One significant effect of inflammation is the resulting isotropic component of diffusion, due to the increased extracellular water and the infiltrating immune cells. This component complicates the DTI measurements and distorts the estimated directional diffusivity and anisotropy preventing its accurate interpretation of underlying pathologies. In addition to inflammation, similar isotropic diffusion tensor component may result from the loss of CNS tissues in the chronic MS lesions, spinal cord injury (SCI), or traumatic brain injury (TBI). The currently used DTI protocol is not able to resolve this isotropic component or differentiate inflammation from tissue loss. Only an averaged diffusion tensor reflecting the overall effect can be obtained from existing DTI methods.

DTI fails to (1) correctly describe axonal fiber directions in crossing white matter tracts, or (2) accurately reflect the complex white matter pathologies such as vasogenic edema, inflammation, and tissue loss commonly coexisting with axonal and myelin damages. Even recently developed existing systems are not capable of resolving white matter pathologies in complex tissue scenarios.

A noninvasive process based on diffusion MRI technique is described herein to facilitate accurately quantifying the complex human CNS white matter pathology where the current DTI and its relevant improvements have failed. As an exemplary embodiment, diffusion basis spectrum imaging (DBSI) is implemented and provided herein to demonstrate the feasibility and detailed operation of the process. The quantity and primary direction of diffusion tensor components within a tissue volume resulting from white matter pathology is determined using diffusion MRI before constructing the multi-tensor model. After the identification of each diffusion tensor component corresponding to individual pathology, the diffusivity and volume ratio of each component can be derived accordingly.

In some embodiments, the quantity of candidate fibers and their associated primary directions are calculated first by DBSI based on a combination of diffusion basis set best describing the measured diffusion magnetic resonance data. An isotropic diffusion component is also considered to improve the computation accuracy. Based on all candidate fibers' primary directions, DBSI is used to compute the axial diffusivity, indicating water diffusion parallel to the fiber, and radial diffusivity, indicating water diffusion perpendicular to the fiber. A diffusivity spectrum of isotropic diffusion components, such as those resulting from inflammation or tissue loss, as well as associated volume ratios of all candidate fibers and isotropic components may be calculated.

An exemplary embodiment employs diffusion basis spectrum imaging (DBSI) to facilitate an accurate diagnosis of CNS white matter pathology. Each diffusion tensor's directional diffusivity as well as its primary orientation is derived using the less stringent diffusion tensor acquisition schemes retaining DTI's applicability in clinical settings. Preliminary data in mouse corpus callosum, spinal cord injury, and phantoms demonstrates that DBSI is capable of identifying different underlying pathologies accurately estimating the extent of cell infiltration, axonal fiber density in corpus callosum of cuprizone treatment, as well as estimating tissue loss in chronic mouse spinal cord injury. Diffusion phantoms have also been designed and fabricated for a quantitative evaluation of DBSI and existing DTI methods.

The exemplary embodiment of diffusion MRI described herein resolves the multi-tensor complication resulting from diverse pathologies in CNS white matter to quantitatively derive diffusion parameters of crossing fibers as well as reflecting the actual pathologies. This unique capability of the proposed process and the exemplary DBSI method has the potential to differentiate acute inflammation from chronic tissue loss in patients. Such capability can estimate the extent of acute inflammation guiding the use of anti-inflammatory treatment and chronic tissue damage guiding the effort in axonal/neuronal preservation. There are many potential clinical applications of the proposed process. For example, it can document the efficacy of stem cell treatment in axonal regeneration by clearly estimating the isotropic component of the implanted cells while reflecting the axonal regeneration by quantifying the anisotropic component changes after cell transplantation. It could also be used to estimate the degree of CNS tumor growth by accurately estimating the isotropic tensor component representing the tumor cells. Methods described further facilitate evaluating the effectiveness of a drug in treating one or more medical conditions. For example, DBSI could be applied in clinical drug trial treating CNS diseases, tumors, and injury by accurately reflecting the progression of clinical and preclinical pathologies.

One important characteristic of DTI is its ability to measure diffusion anisotropy of CNS tissues for a detailed description of the underlying tissue injury based on the changed diffusion character. However, such measurement is not always obtainable in diseased tissues due to the complicated cellular responses to the pathology or the presence of crossing fibers.

The fundamental operation of DTI 10 can be explained by examining an MRI signal 12 under the influence of diffusion weighting gradients 14. When applying DTI to measure the single white matter tract of coherent axonal fibers, the MRI signal response can be expressed as shown in FIG. 1.

DTI assumes that there is only a pure coherent axonal fiber tract in the measured tissue and the signal response to diffusion weighting gradients is well described by the diffusion weighted (DW) profile. The insufficiency of DTI can be demonstrated by examining the diffusion ellipsoid responding to the different tissue components that typically seen in CNS tissues with and without pathology, as shown in FIG. 2.

Figure 2:
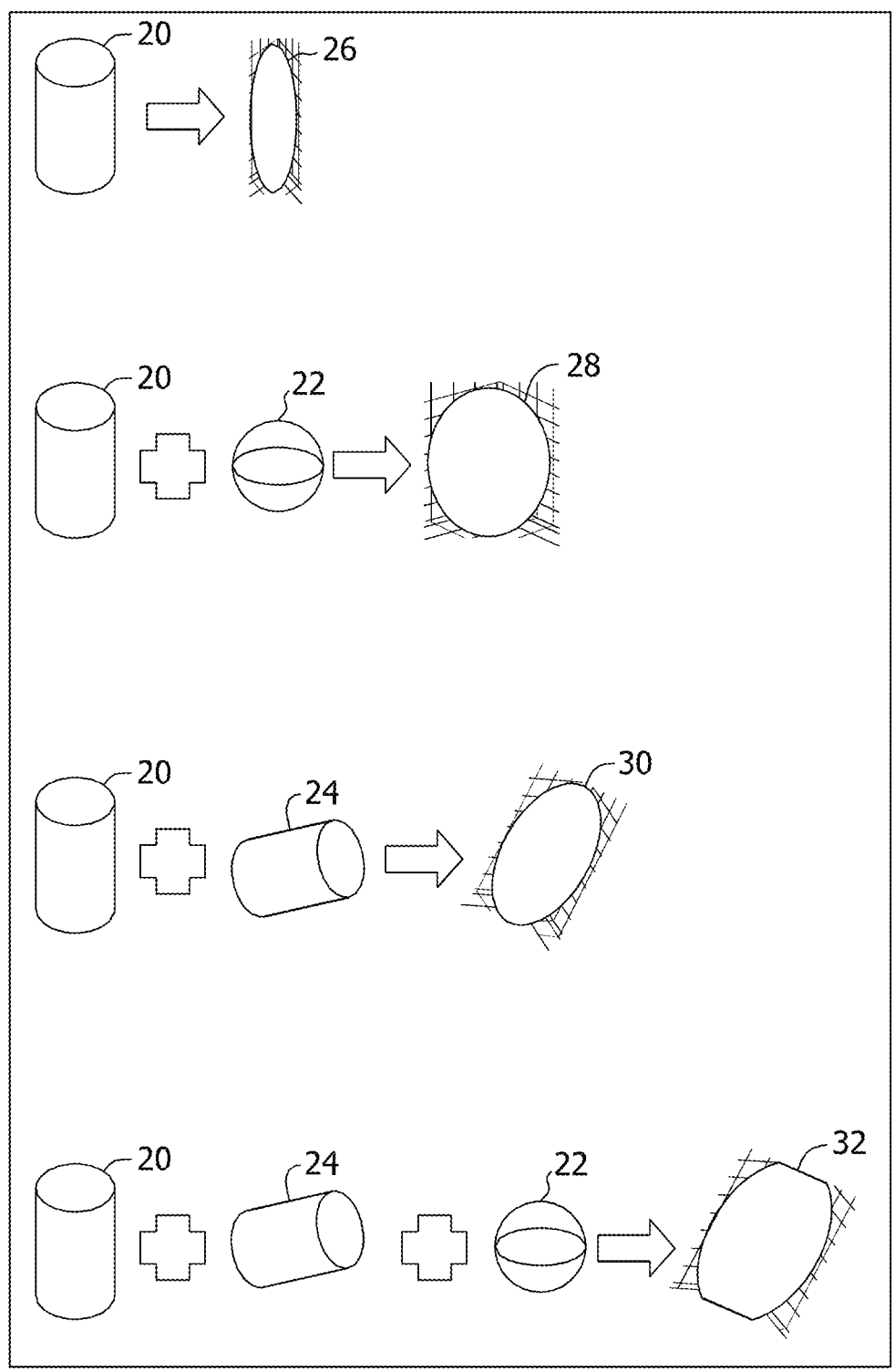
FIG. 2 is an illustration of exemplary DTI results corresponding to scenarios in which different tissue components are included within a scanned volume.

FIG. 2 illustrates exemplary DTI results corresponding to scenarios with the different tissue components (objects), including (A) ideal coherent single fiber 20 (spinal cord white matter or optic nerves), (B) fiber 20 plus an isotropic component 22 (tissue loss, inflammation, or edema), (C) two crossing fibers 24, and (D) two crossing fibers 24 with an isotropic component 22. If fiber 20 of (A) is of interest and the target for a DTI measurement as demonstrated, the correct DTI result for the ideal fiber result 26. Nevertheless, the various mixed conditions result in misrepresentations 28, 30, and 32 of the targeted fiber, which is the major shortcoming of DTI.

To definitively resolve the issue regarding the utility of directional diffusivity in detecting white matter injury in MS and/or other CNS white matter disorders, a careful evaluation was performed on the mouse model of cuprizone intoxication that is widely employed to examine the mechanisms of CNS white matter de- and re-myelination. It has been demonstrated that axonal injury, inflammation, and demyelination co-exist at 4 weeks of continuous cuprizone feeding. Previous DTI studies showed that decreased $\lambda_\parallel$ correlated with histology-confirmed axonal injury, while no significant increase of $\lambda_\perp$ was seen, thus failing to reflect the concurrent demyelination. A Monte Carlo simulation modeling the three underlying pathologies was performed. Preliminary results suggested that the presence of infiltrating inflammatory cells exerted significant effect on the derived directional diffusivity reducing both $\lambda_\parallel$ and $\lambda_\perp$, exaggerating the effect of axonal injury while diminishing the sensitivity to demyelination. This finding suggests that the current DTI analysis is suboptimal to accurately depict the underlying pathology in diseases with inflammation, such as MS.

Figure 3A:
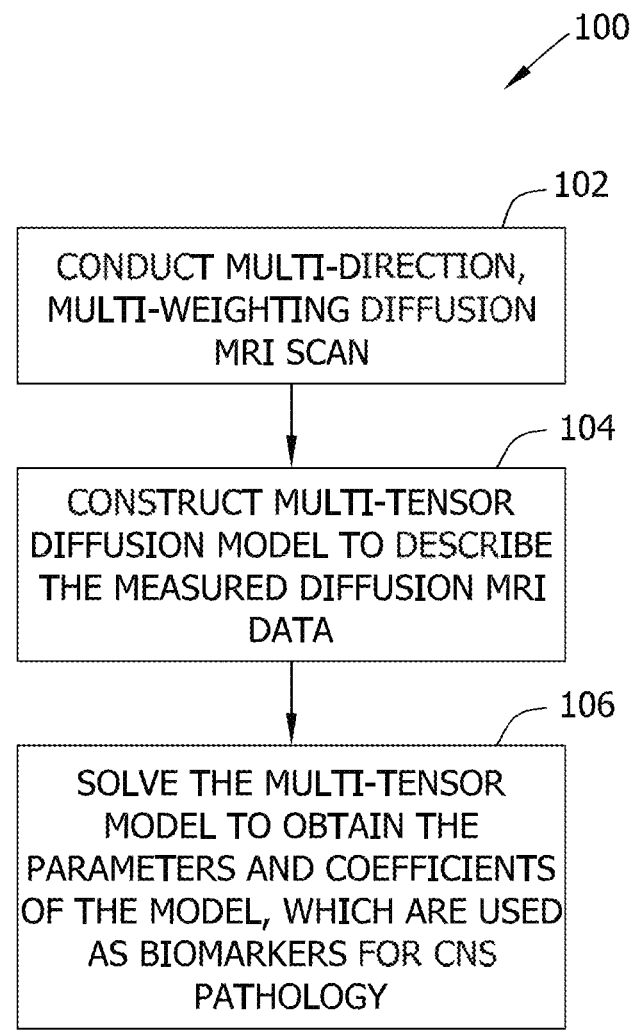
FIG. 3A is a flowchart of an exemplary noninvasive process to quantify complex CNS white matter pathology.

To address this shortcoming of DTI, a process allowing an accurate description of the underlying tissue pathology is described herein. FIG. 3A is a flow chart 100 illustrating the basic steps contemplated to detect and differentiate the underlying CNS white matter pathologies. First, a multi-direction, multi-weighting diffusion MRI scan is conducted 102 utilizing a signal acquisition and processing component. A multi-tensor diffusion model is constructed 104, and the multi-tensor model is solved 106 to obtain the parameters and coefficients of the model.

Figure 3B:
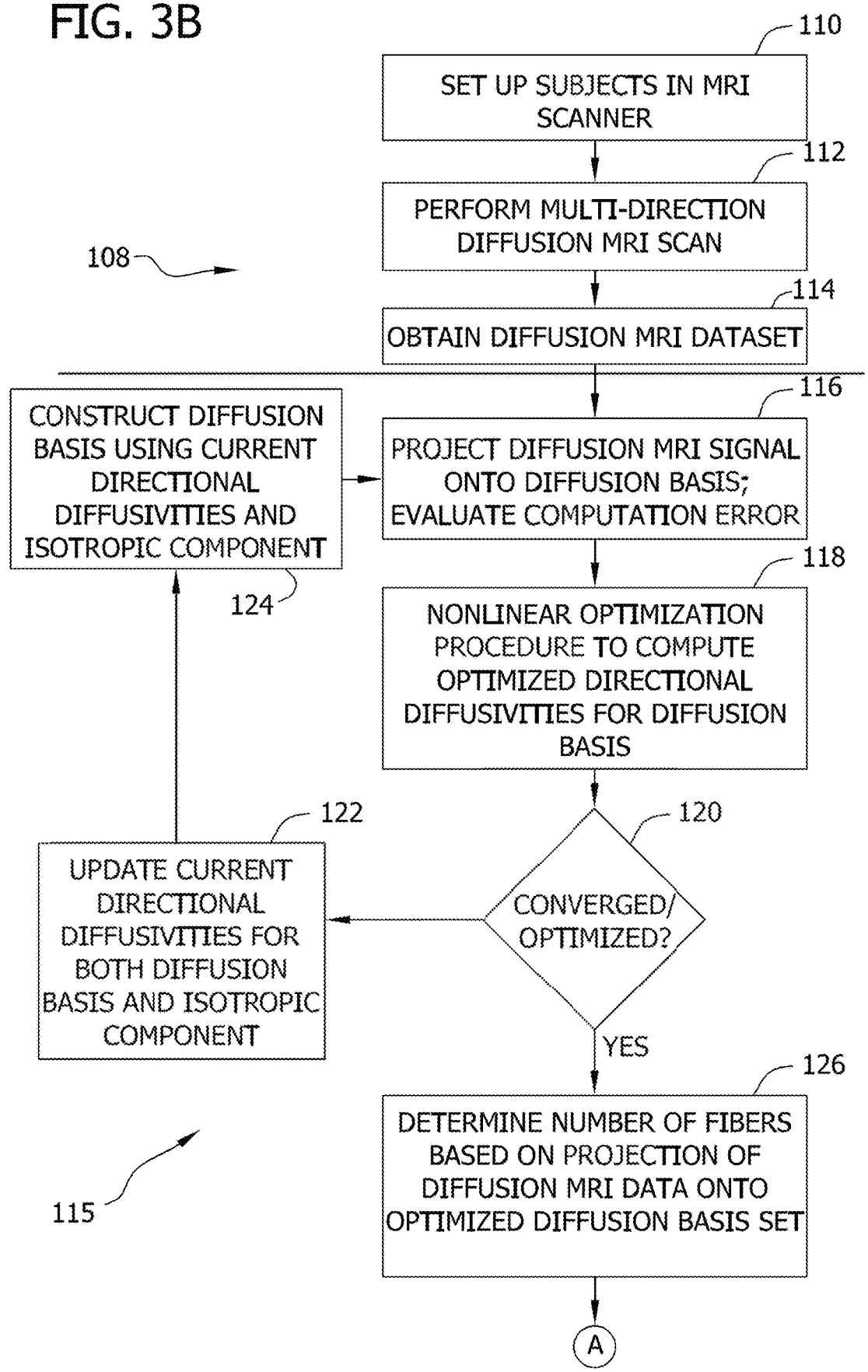
FIGS. 3B and 3C are a flowchart of an exemplary method for determining diffusivities of fibers and isotropic components within a tissue.
Figure 3C:
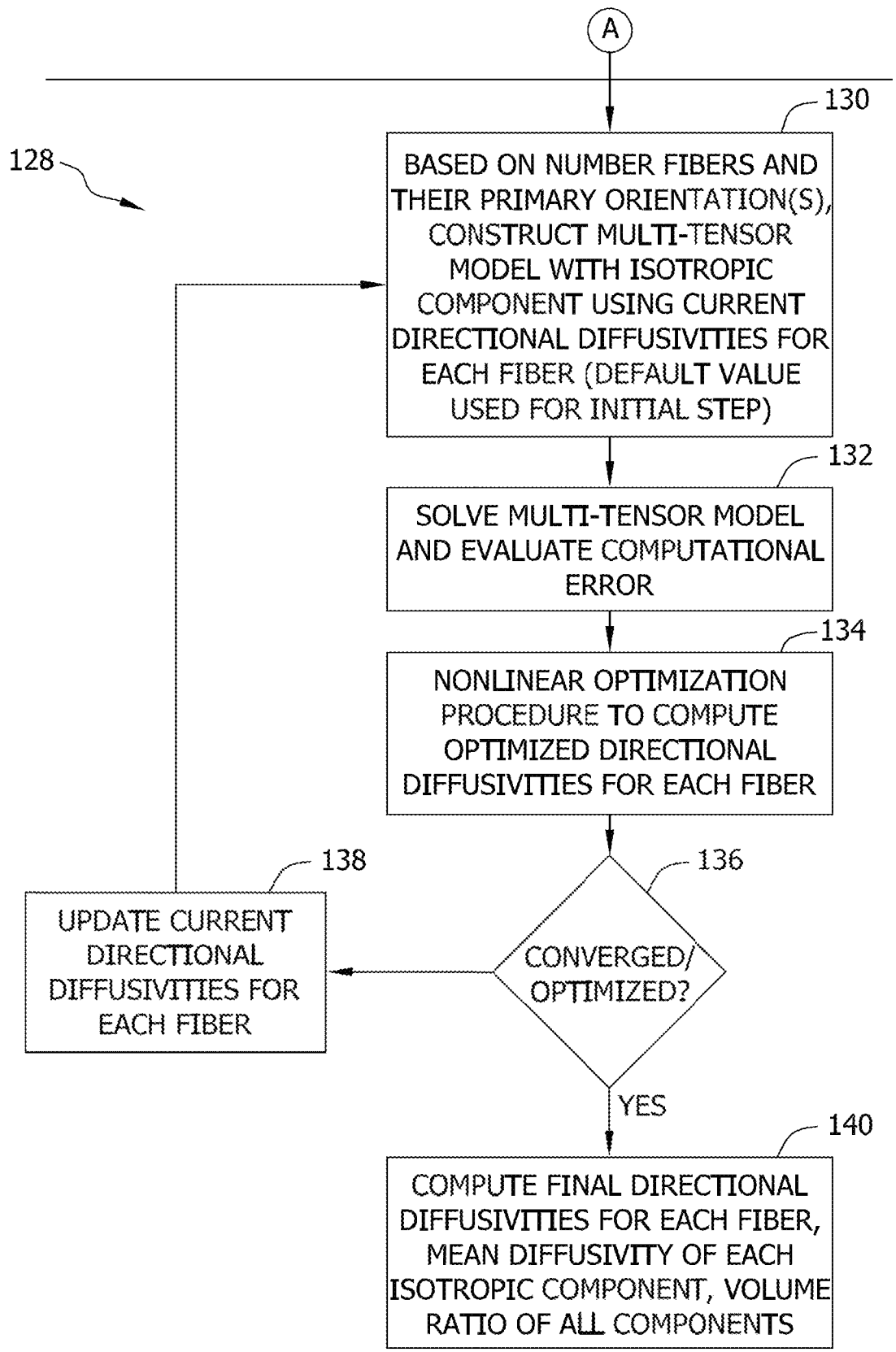

In the exemplary embodiment, a multiple-tensor based DBSI, or diffusivity component, is provided (FIGS. 3B and 3C). The method illustrated may be used to determine diffusivity of each diffusion tensor component within a tissue. In the multiple-tensor based DBSI, an MRI scan is performed 108. In performing the MRI scan, subjects are set up 110 in MRI scanner and a multi-direction diffusion MRI scan is performed 112. From the performed 112 MRI scan, a diffusion MRI dataset is obtained 114.

After an MRI scan is performed 108, number of fibers and their primary orientation is determined 115. In determining 115 the number of fibers and their primary orientation a diffusion MRI signal is projected 116 onto diffusion a basis and a computation error is evaluated. Next, a nonlinear optimization procedure is performed 118 to compute optimized directional diffusivities for diffusion basis. It is determined 120 whether the fibers are converged and optimized. If the fibers are determined 120 not to have been converged and optimized, the current directional diffusivities for both diffusion basis and isotropic components are updated 122. After update 122, a diffusion basis using current directional diffusivities and isotropic component is constructed 124 and projected 116 is performed again. If the fibers are determined 120 to have been converged and optimized, the number of fibers based on projection of diffusion MRI data onto optimized diffusion basis set is determined 126.

After the number of fibers and their primary orientation is determined 115, diffusivities of each fiber and isotropic components are determined 128. In determining 128 the diffusivities of each fiber and isotropic components, a multi-tensor model with isotropic component using current directional diffusivities for each fiber is constructed 130. A multi-tensor model is solved 132 and evaluated for computational error. Next, a nonlinear optimization procedure is performed 134 to compute optimized directional diffusivities for each fiber. It is determined 136 whether the fibers are converged and optimized. If the fibers are determined 136 not to have been converged and optimized, the current directional diffusivities for each fiber are updated 138 and the multi-tensor model is constructed 130 again. If the fibers are determined 136 to have been converged and optimized, a final directional diffusivity for each fiber is computed 140. Additionally, a mean diffusivity of each isotropic component, and a volume ratio of all components is computed 140.

Figure 4A:
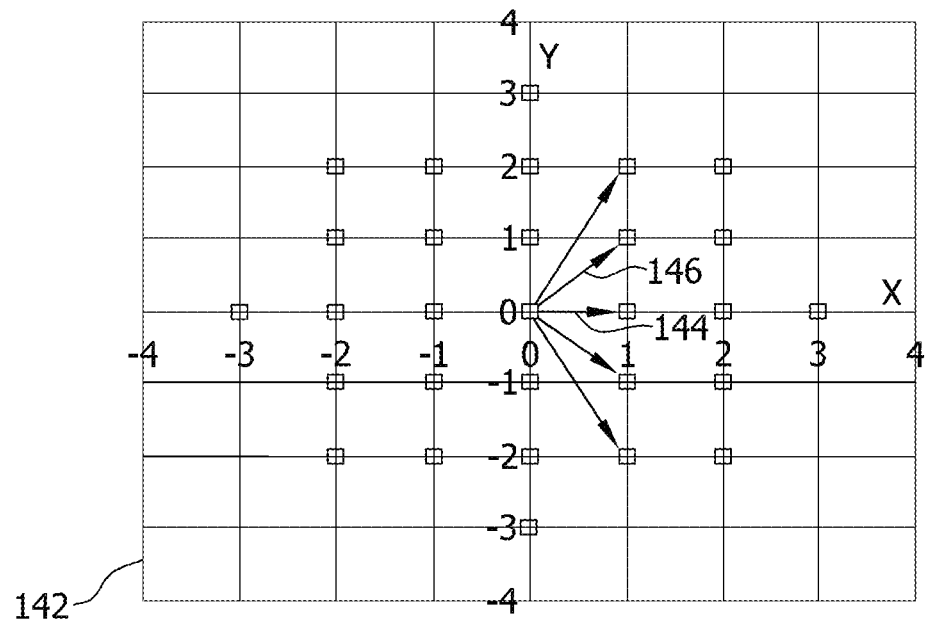
FIG. 4A is a 2D illustration of the design of an exemplary 99-direction diffusion-weighting scheme, where each diffusion-weighting direction is selected based on the grid point location.
Figure 4B:
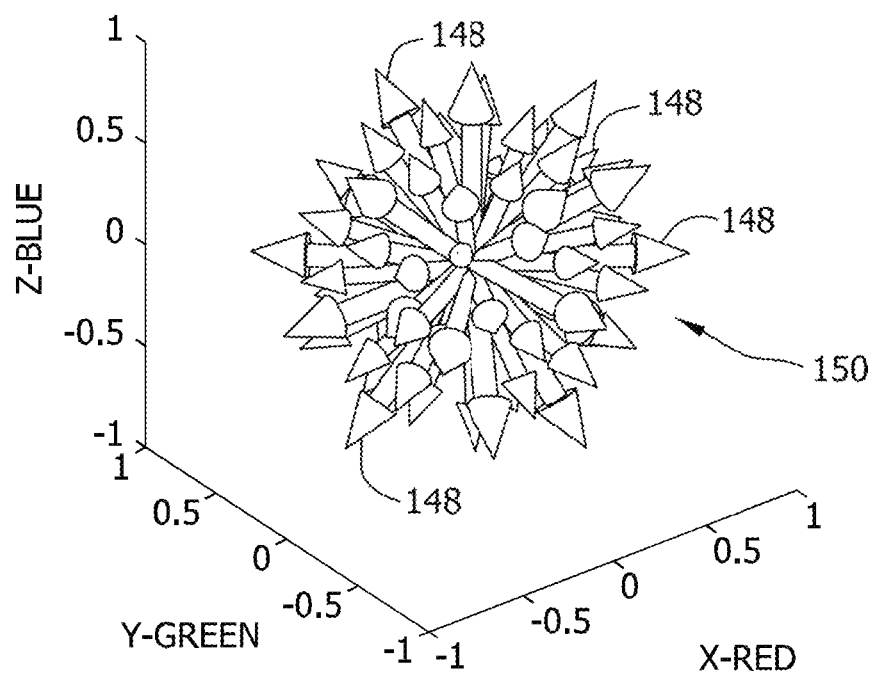
FIG. 4B is a 3D model of the design of an exemplary 99-direction diffusion-weighting scheme, where each diffusion-weighting direction is selected based on the 3D grid locations.

FIGS. 4A and 4B are an illustration of the design of an exemplary 99-direction diffusion-weighting scheme. As shown in FIG. 4A, which is the 2D schematic 142, each diffusion-weighting direction is selected based on the grid point location. For example, the first diffusion weighting direction 144 is from origin (0, 0) to grid point (1, 0), the second diffusion weighting direction 146 is from (0, 0) to (1, 1), and so on. In the exemplary embodiment, 99 diffusion directions are selected based on the 3D grid locations 148 shown by 3D model 150 in FIG. 4B.

An advantage of designing the 99-direction diffusion weighting gradients 148 based on regular grid locations is that the directions are uniformly sampled in the 3D space. No matter which direction the real axonal fiber orients, the scheme has no bias to it. Another advantage is that the weighting of diffusion gradients is naturally set as different values in this grid-based design, which is favorable in terms of determining multiple isotropic diffusion components.

However, embodiments described herein are not limited to this particular design. Any diffusion-weighting scheme that samples the whole 3D space uniformly and provides multiple weighting factors may work well resolving multiple-tensor reflecting the CNS white matter pathology.

Similar to diffusion basis function decomposition (DBFD), DBSI employs the following multi-tensor model as the first-step analysis:

$$S_k = \sum_{i=1}^{N} S_i \exp(-\vec{b}_k \cdot \lambda_\perp) \exp(-\vec{b}_k \cdot (\lambda_\square - \lambda_\perp) * \cos^2(\theta_i)), \quad \text{(Equation 1)}$$

$$k = 1, 2, \ldots, 99$$

In Equation 1, $\vec{b}_k$ is $k^{th}$ diffusion gradient (k=1, 2, ..., 99); $\lambda_\parallel$ is the axial diffusivity and $\lambda_\perp$ is the radial diffusivity; $S_k$ is the measured diffusion weighted signal at direction $\vec{b}_k$; $\theta_i$ is the angle between the diffusion gradient $\vec{b}_k$ and the primary direction of ith diffusion basis; N is the number of diffusion basis components uniformly distributed in 3D space.

Figure 5:
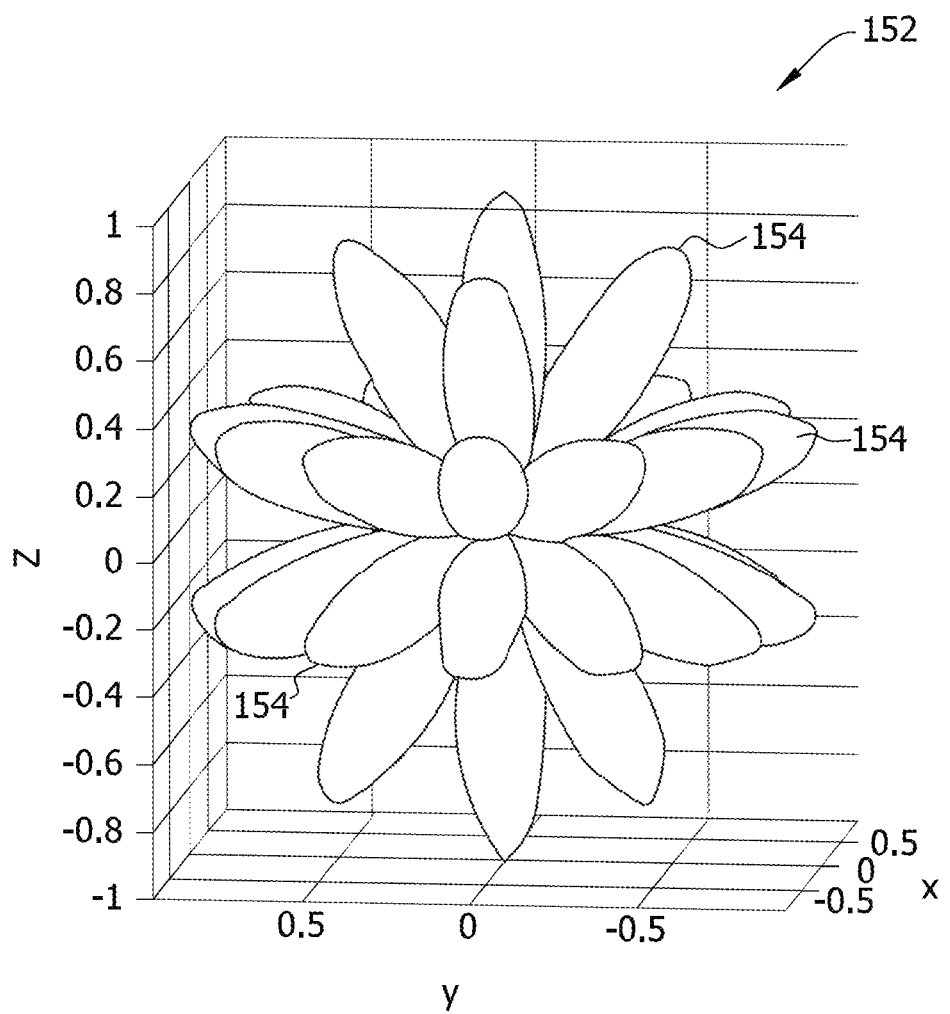
FIG. 5 is an illustration of an exemplary diffusion basis set for DBSI.

FIG. 5 illustrates a diffusion basis set 152 with 40 diffusion bases 154. As shown in FIG. 5, each diffusion basis 154 represents a candidate fiber orientation, and the diffusion basis 154 set is uniformly distributed in the 3D space. As described by Equation 1, the real fiber is treated as the linear combination of the entire diffusion basis set.

Instead of presetting $\lambda_\parallel$ and $\lambda_\perp$ at fixed values for the entire diffusion basis in DBFD, DBSI performs a nonlinear searching to estimate the optimal values of $\lambda_\parallel$ and $\lambda_\perp$ best fitting the acquired diffusion weighted data. Isotropic tensor component is uniquely incorporated in DBSI to improve the accuracy, as shown in Equation 2.

$$f(\lambda_\square, \lambda_\perp, d) = \qquad \text{(Equation 2)}$$

$$\min \left\| \sum_{k=1}^{99} \left\{ S_k - \sum_{i=1}^{N} S_i \, \exp(-\vec{b}_k \cdot \lambda_\perp) \exp(-\vec{b}_k \cdot (\lambda_\square - \lambda_\perp)\cos^2(\theta_i)) - S_{N+1} \cdot \exp(\vec{b}_k \cdot d) \right\}^2 \right\|$$

In Equation 2, $S_i$ (i=1, 2, . . . , N+1)≥0, $\lambda_\parallel$ and $\lambda_\perp$ are directional diffusivities, and d is the diffusivity of isotropic diffusion component with d, $\lambda_\parallel$, and $\lambda_\perp$ selected as the optimization variables. Unknown coefficients $S_i$ (i=1, 2, . . . , N+1) are not optimization variables because $S_i$ are not independent to $\lambda_\parallel$ or $\lambda_\perp$. Each $S_i$ is computed using the least square estimation under the nonnegative constraint ($S_i$≥0) and the basic principle of sparsity as employed in DBFD during the nonlinear optimization procedure. After the optimization, the number of fibers and their primary axis directions are estimated similar to DBFD.

Figure 6:
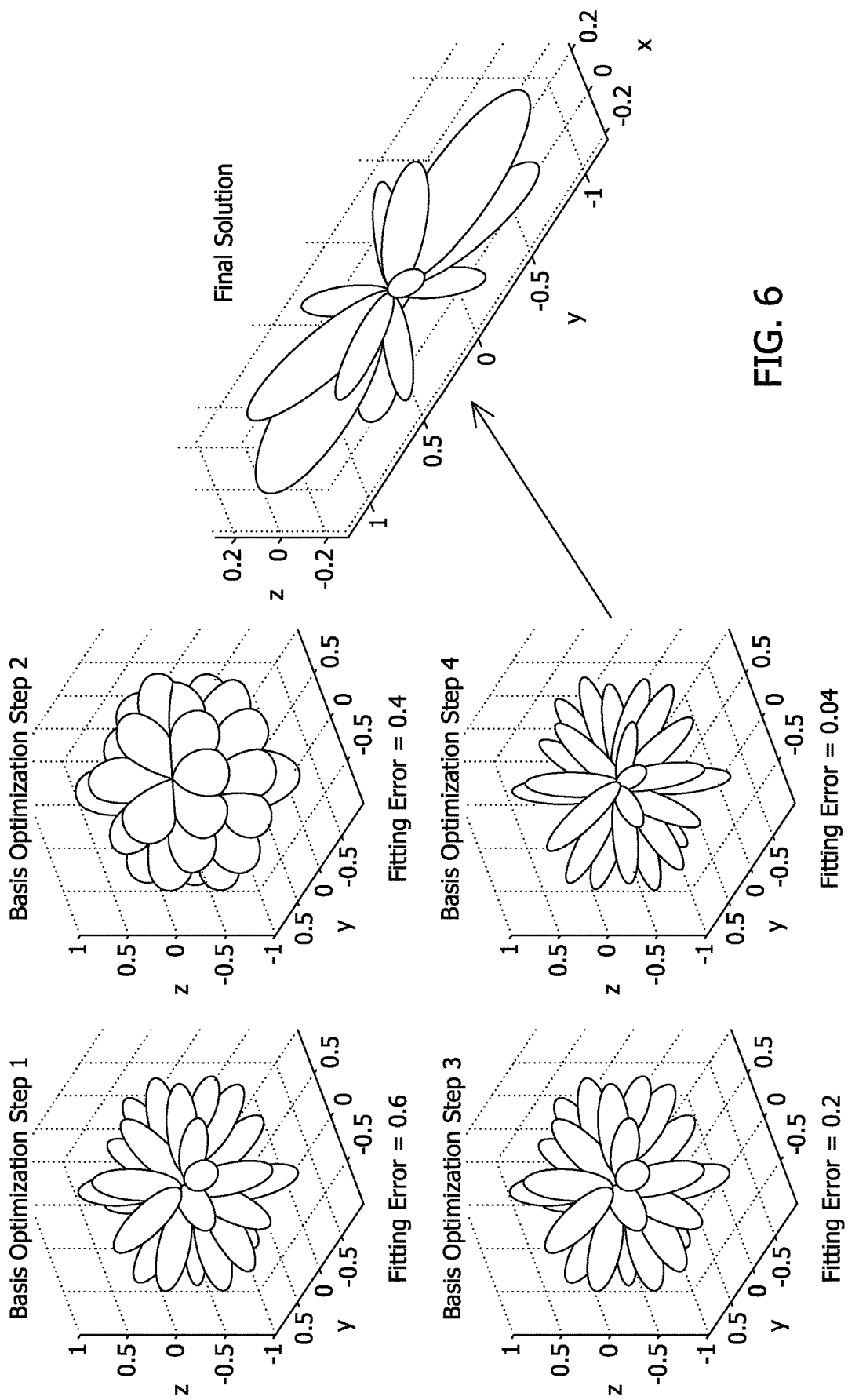
FIG. 6 is an illustration of an exemplary optimization process of DBSI basis set.

A unique feature of this disclosure is that the shape of each diffusion basis is not prefixed as in DBFD method. Instead, the basis shape is optimized during the optimization process to estimate both $\lambda_\parallel$ and $\lambda_\perp$. This optimization process is demonstrated in FIG. 6 using a single axonal fiber 156 as the example. In the exemplary embodiment, experimental data is fitted by the linear combination of a diffusion basis set 154 with fitting error improved through iterations 158, 160, 162, and 164 until the optimal coefficients of linear combination of diffusion basis are estimated 166. In the exemplar embodiment, iteration 158 has a fitting error of 0.6, iteration 160 has a fitting error of 0.4, iteration 162 has a fitting error of 0.2, and iteration 164 has a fitting error of 0.04. The isotropic component is also considered according to Equation 2 in this process (not shown) to improve the optimization accuracy.

Figure 7A:
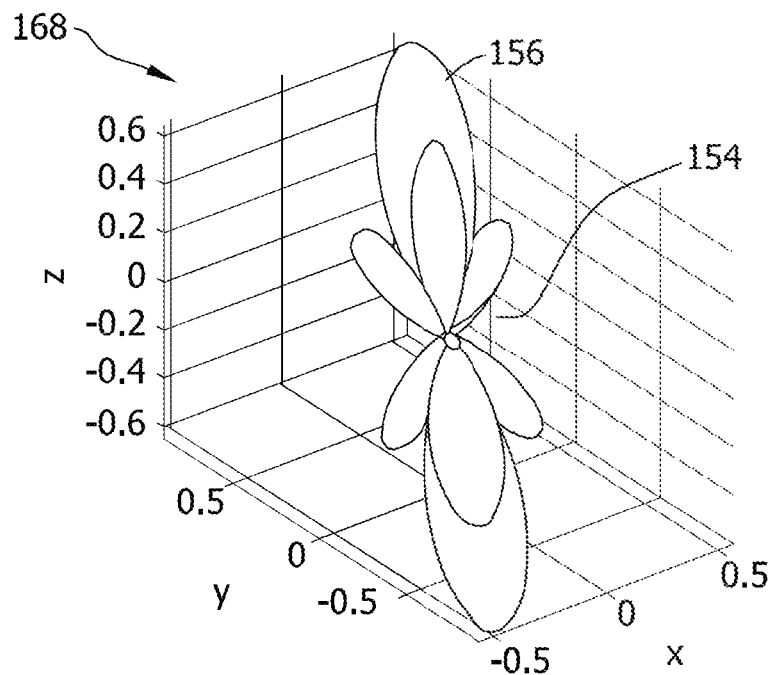
FIG. 7A is an illustration of determining the number of fibers and primary directions of candidate fibers using DBSI for a single fiber tract.
Figure 7B:
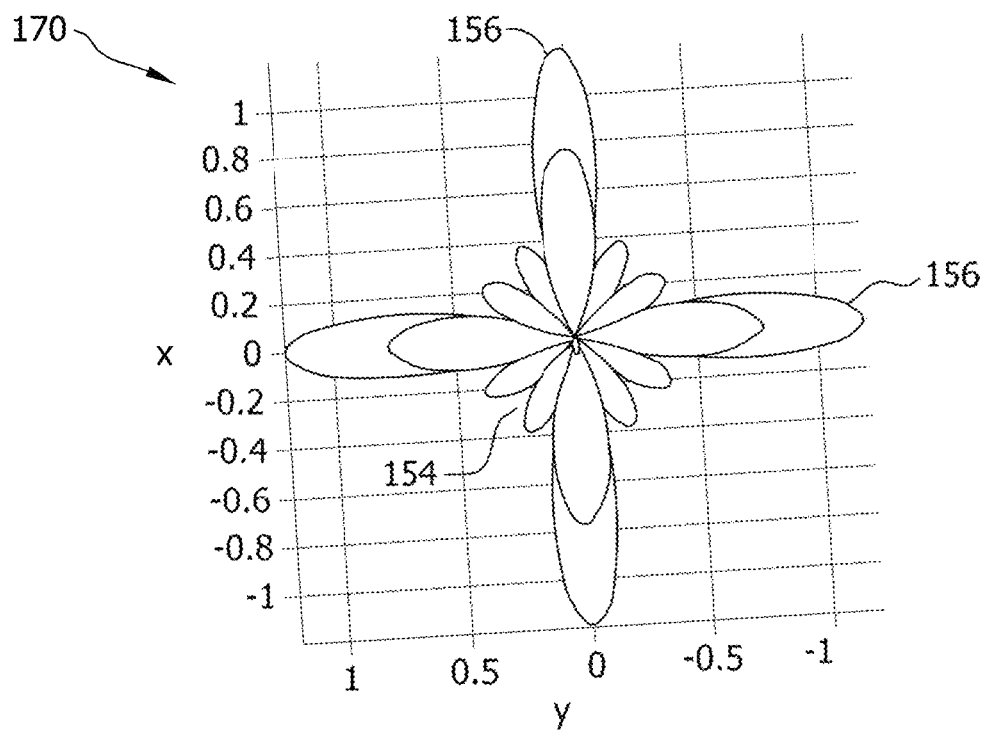
FIG. 7B is an illustration of determining the number of fibers and primary directions of candidate fibers using DBSI for a two-fiber 170 tract.

As shown in FIGS. 7A and 7B, the diffusion basis 154 with direction close to that of the axonal fiber 156 contributes more significantly to the linear combination with higher magnitude of the coefficients $S_i$. The diffusion basis 154 with direction away from that of the axonal fiber 156 has limited contribution to the coefficient of linear combination of the basis set fitting the experimental data. FIG. 7A demonstrates a single fiber 168 tract and FIG. 7B demonstrates a two-fiber 170 tract.

DBSI determines the number and primary direction of fibers according to the description of Equation 1. Each coefficient is associated with one diffusion tensor basis at a particular direction. These preliminary coefficients are grouped based on the magnitude and the closeness in orientations of the associated basis diffusion tensor. Coefficients smaller than a threshold determined by raw signal SNR are ignored. Significant coefficients with closely oriented (within 15 degrees) diffusion basis tensors are grouped as one fiber. The threshold of 15 degrees is set based on the desired angular resolution. Once the grouping process is complete, the averaged direction of the grouped diffusion basis is defined as the primary direction of the fiber.

Based on the number of fiber (anisotropic tensor) components and associated primary directions, DBSI constructs another multi-tensor model with the assumption of axial symmetry. A set of isotropic tensor components are included in the model:

$$h(\lambda_{\square\_i}, \lambda_{\perp\_i}, i = 1 \ldots L) = \qquad \text{(Equation 3)}$$

$$\min \left\| \sum_{k=1}^{99} \left\{ S_k - \sum_{i=1}^{L} S_i \, \exp(-\vec{b}_k \cdot \lambda_{\perp\_i}) \exp(-\vec{b}_k \cdot (\lambda_{\square\_i} - \lambda_{\perp\_i})\cos^2(\theta_i)) - \sum_{j=1}^{M} S_{L+j} \cdot \exp(\vec{b}_k \cdot d_j) \right\}^2 \right\|$$

In Equation 3, $S_k$ is the measured diffusion weighted signal at diffusion gradient direction $\vec{b}_k$. L is the number of estimated fibers in the imaging voxel. $\lambda_{\parallel\_i}$ and $\lambda_{\perp\_i}$ (i=1, 2, . . . , L) are the axial and radial diffusivity of the ith fiber. $\phi_i$ is the angle between the diffusion gradient $\vec{b}_k$ and the primary direction of ith estimated fiber. $d_j$ (j=1, M) are the diffusivities of M isotropic diffusion components. $S_i$ (i=1, 2, . . . , L) are fiber volume ratios and Si(i=L+1, L+2, . . . , L+M) are the volume ratio of isotropic components.

Based on this multi-tensor model, a nonlinear optimization search is constructed as following:

$$h(\lambda_{\square\_i}, \lambda_{\perp\_i}, i = 1 \ldots L) = \qquad \text{(Equation 4)}$$

$$\min \left\| \sum_{k=1}^{99} \left\{ S_k - \sum_{i=1}^{L} S_i \, \exp(-\vec{b}_k \cdot \lambda_{\perp\_i}) \exp(-\vec{b}_k \cdot (\lambda_{\square\_i} - \lambda_{\perp\_i})\cos^2(\theta_i)) - \sum_{j=1}^{M} S_{L+j} \cdot \exp(\vec{b}_k \cdot d_j) \right\}^2 \right\|$$

Equation 4 is subject to $S_i$ (i=1, 2, . . . , L+M)≥0. In this optimization procedure, isotropic diffusivity $d_j$ (j=1, . . . , M) are not selected as optimization variables to reduce the total number of the free variables. Instead, isotropic diffusivities are uniformly preset within the physiological range. Directional diffusivities, $\lambda_{\parallel\_i}$ and $\lambda_{\perp\_u}$ (i=1, . . . , L) of each anisotropic component are the only free variables to be optimized based on the experimental data and Equation 4 with the nonnegative constraint ($S_i$≥0). All diffusion tensor's volume ratios $S_i$ (i=1, 2, . . . , L+M) based on T2-weighted (i.e., non-diffusion weighted) image intensity are computed with least square fitting during the nonlinear optimization procedure.

Figure 8:
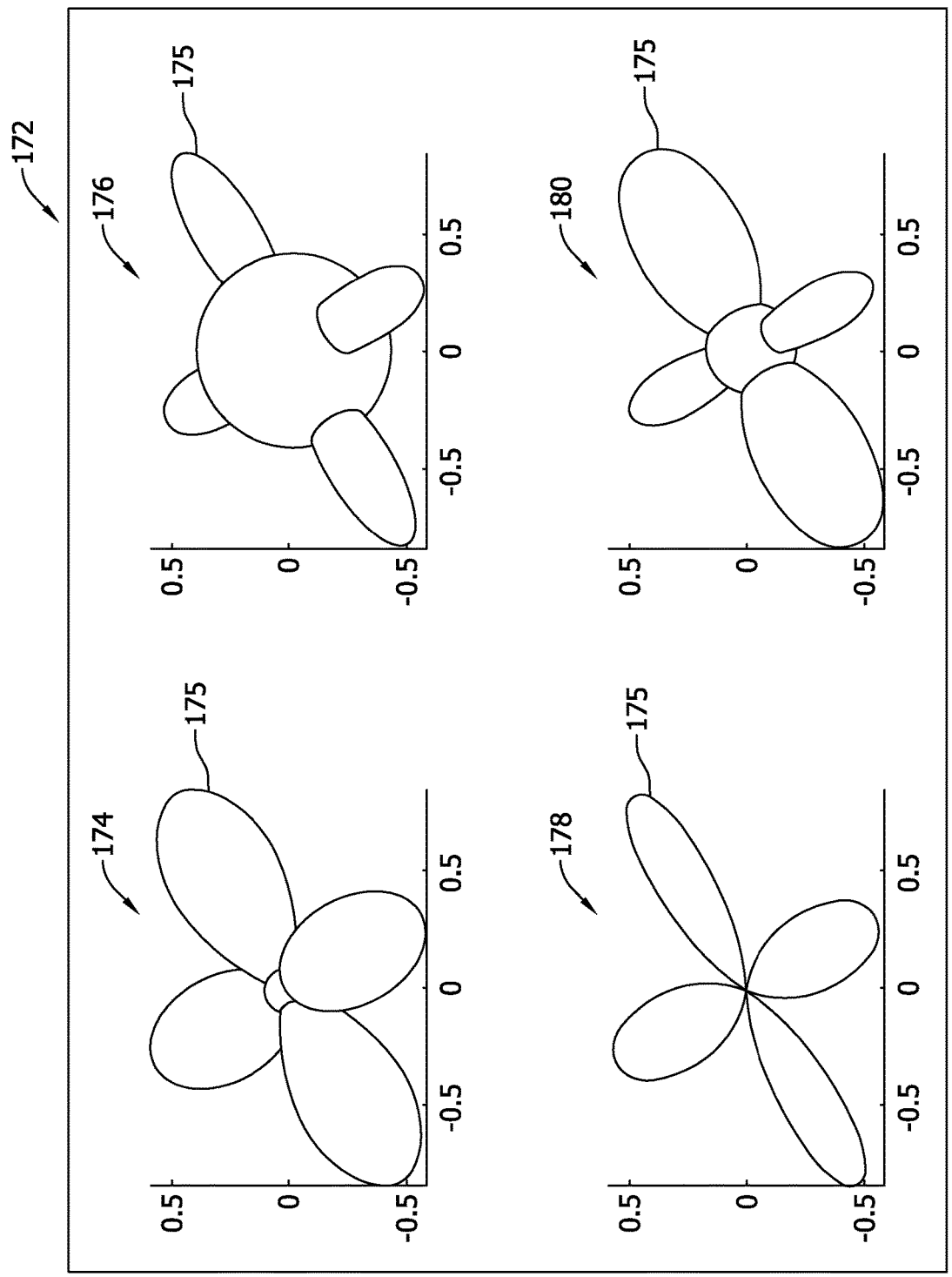
FIG. 8 is an illustration of an exemplar optimization process for determining the directional diffusivity of each candidate fiber, isotropic components and corresponding volume ratios using DBSI.

In one embodiment, an optimization process 170, as shown in FIG. 8, is used to search the best directional diffusivities for each candidate fiber and compute all the volume ratios of each diffusion component. Process 170 demonstrates two crossing fibers (L=2). In such an embodiment, a first optimization 174 includes candidate fibers 175 with a fitting error of 0.4. Likewise, a second optimization 176 includes candidate fibers 175 with a fitting error of 0.2, a third optimization 178 includes candidate fibers 175 with a fitting error of 0.1, and a fourth optimization 180 includes candidate fibers 175 with a fitting error of 0.02

After the fourth optimization 180, the fitting error is smaller than 2%, which falls within the acceptable range. Therefore, the directional diffusivity of each candidate fiber 175, and corresponding volume ratios computed after the optimization 180 are determined as the final DBSI results. In the DBSI algorithm, the nonlinear optimization procedure is executed based on criteria including maximal iteration numbers, tolerance of mesh size, tolerance of variable, tolerance of function, accepted accuracy, and many other criteria set according to the need. Once some or all of these criteria are met according to the preset level, the optimization procedure is considered satisfactorily fit the data and the optimization stops.

Figure 10:
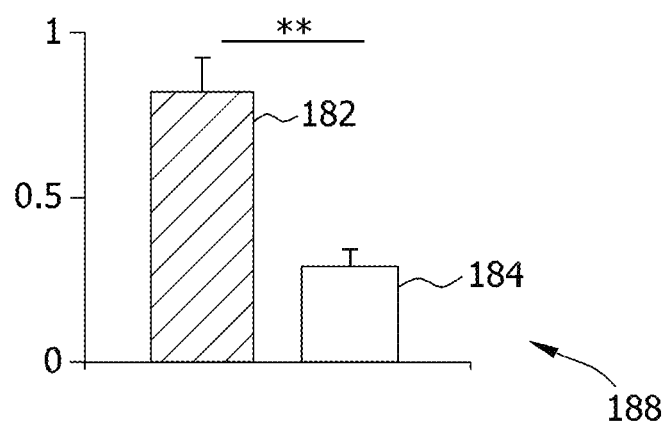
FIG. 10 is a graph of myelin basic protein in a MBP-positive area derived from DBSI of FIG. 9.
Figure 11:
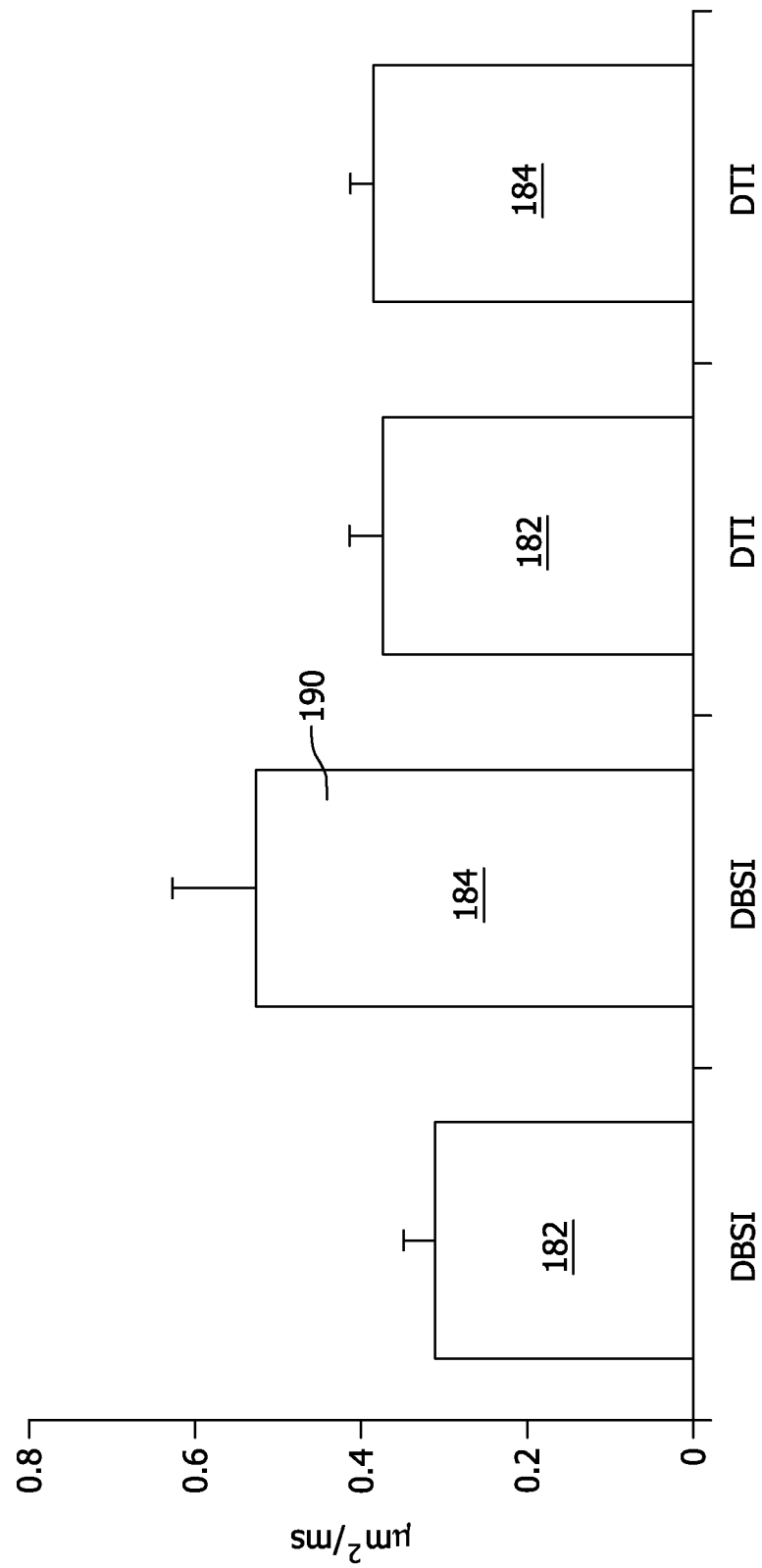
FIG. 11 is a graph of the radial diffusivity derived using DBSI of FIG. 9.

To determine the capability of the newly developed DBSI approach in detecting and differentiating the underlying co-existing pathology, the cuprizone model was again employed to compare conventional DTI with the new DBSI analysis. Striking contrast between DTI and DBSI was observed at the corpus callosum from C57BL/6 mice treated with cuprizone for 4 weeks. DTI failed to detect demyelination and overestimated axonal injury even with 99-direction diffusion weighting, while offering no information on inflammation. However, DBSI correctly reflected the presence of demyelination (FIG. 9), axonal injury (FIG. 10), and inflammation (FIG. 11).

Figure 9:
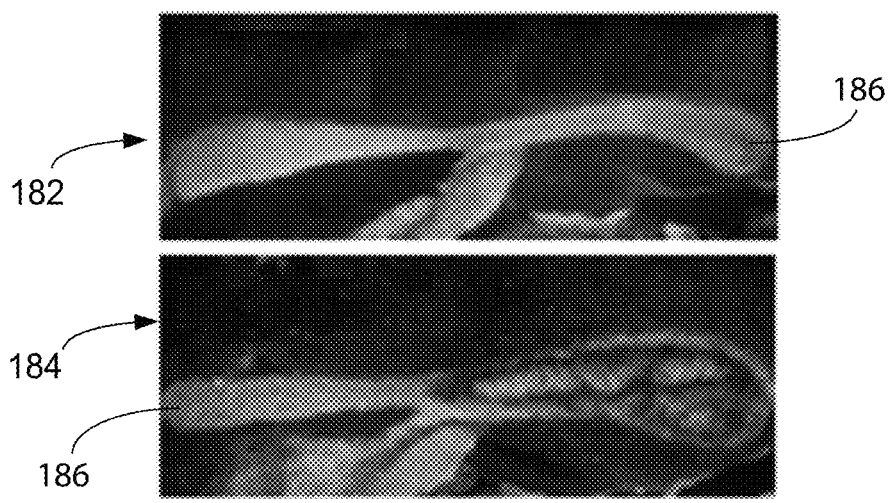
FIG. 9 is an image of diffusion basis spectrum imaging (DBSI) results reflecting demyelination as increased radial diffusivity in the presence of axonal injury, and inflammation in contrast to the failure of DTI to detect the pathology.

FIG. 9 is an illustration of a sagittal view of corpus callosum from a control 182 and a 4-week cuprizone fed male C57BL/6 mice (n=5) 184 examined using DBSI and DTI. As shown by myelin basic protein 186 immunostaining, significant demyelination in the caudal corpus callosum is seen by reduced MBP-positive area 188 (FIG. 10) and increased radial diffusivity 190 (FIG. 11) derived using DBSI. Consistent with previous reports, lack of increase in DTI derived radial diffusivity failed to reflect the histological finding of demyelination (FIG. 12).

Figure 12:
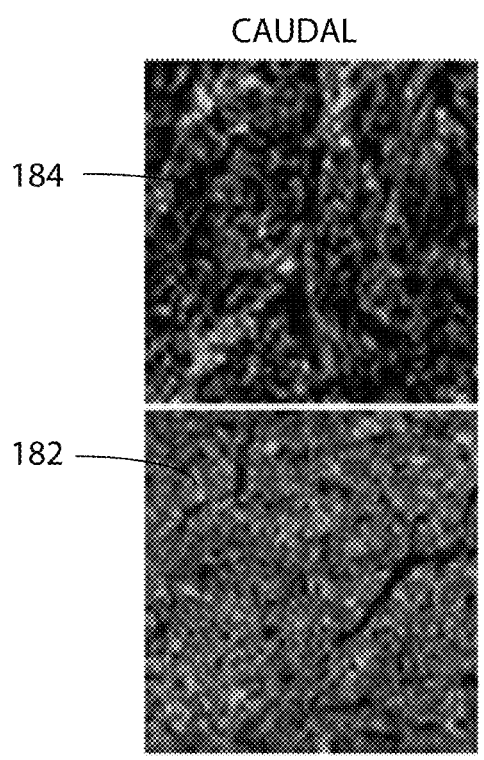
FIG. 12 is an image of DBSI results detecting axonal injury in the presence of demyelination and inflammation.
Figure 13:
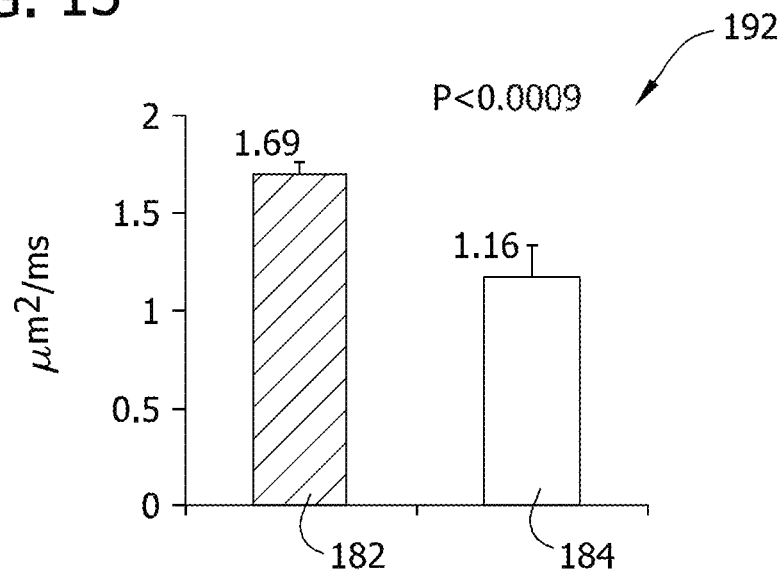
FIG. 13 is a graph of the axial diffusivity of the DBSI of FIG. 12.
Figure 14:
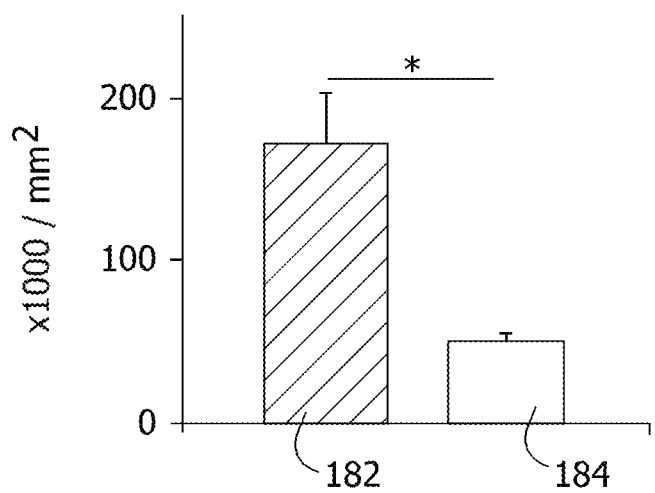
FIG. 14 is a graph of the SMI-31 stain of the DBSI of FIG. 12.
Figure 15:
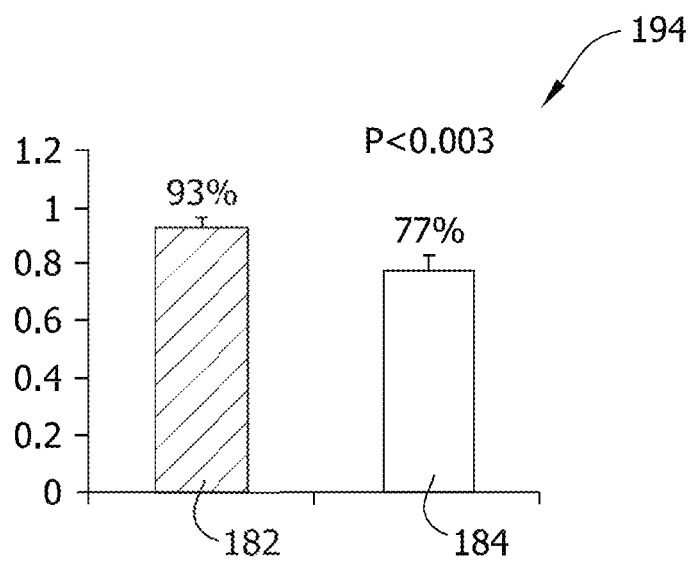
FIG. 15 is a graph of axonal fiber tract density was also derived using DBSI expressing as volume ratio of the DBSI of FIG. 12.

FIG. 12 illustrates that similar to previous findings that decreased DTI derived axial diffusivity was seen in corpus callosum from 4-week treated mice 184 (n=5, −43%) from control 182, DBSI derived axial diffusivity 192 (FIG. 13) decreased (−31% from the control 182) to reflect the histology proved axonal injury (FIG. 14). The axonal fiber tract density 194 (FIG. 15) was also derived using DBSI expressing as volume ratio. Due to the infiltrating inflammatory cells, the density of axonal fiber tracts was reduced from 93% to 77%, a finding not available for conventional DTI.

Figure 16:
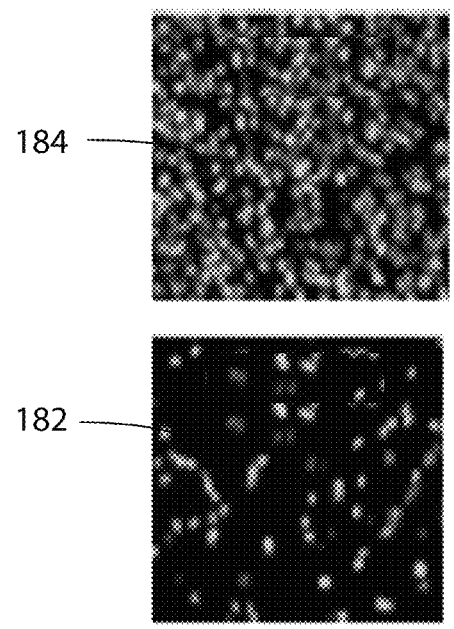
FIG. 16 is an image of DBSI results quantifying inflammation in the presence of axonal injury and demyelination.
Figure 17:
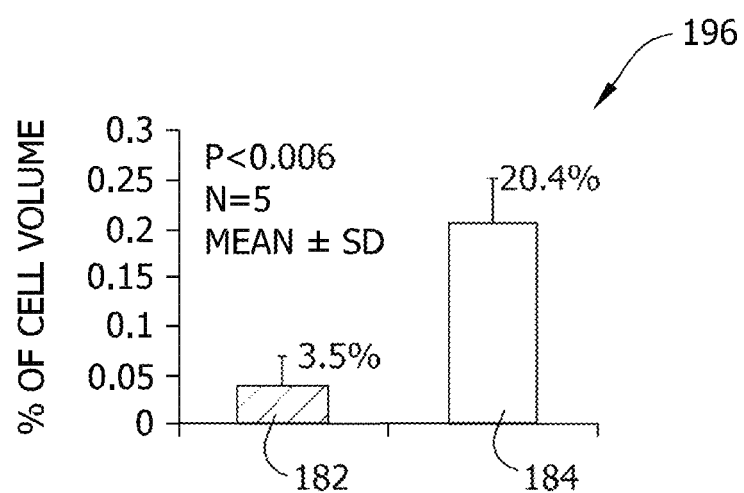
FIG. 17 is a graph of the percentage of inflammatory cell infiltration thought to be in the cells of the illustration of FIG. 16.

FIG. 16 illustrates inflammatory cell infiltration 196 derived using DBSI. In such an embodiment, the inflammatory cell infiltration 196 is to be 16.9% (20.4−3.5) of total volume in 4-week cuprizone treated corpus callosum 184, above the baseline 3.5% cellular content. This is consistent with the significantly increased DAPI positive stains in the same region; information has not been available using DTI.

In another embodiment, 99-direction diffusion weighted images are analyzed following one or more operations described above to determine the number of intravoxel fibers and isotropic components on a laboratory fabricated phantom containing mouse trigeminal nerves with known in vivo DTI character and isotropic gel as shown in FIG. 18.

Diffusion weighted MRI was performed on the phantom using 99 distinct diffusion weighting gradients for both DTI 200 and DBSI 202 analysis. For the pure gel, DTI 200 and DBSI 202 estimated the isotropic apparent diffusion coefficient to be identical at 1.91 $\mu m^2$/ms suggesting both methods are accurate for simple medium. When examining the mixture of fiber/gel in this phantom using DTI 202, the isotropic gel component was not identified. In addition, the true fiber diffusion anisotropy (FA=0.82±0.005) determined previously using an in vivo high resolution DTI was not obtained. In contrast, using the newly proposed DBSI identified a fiber ratio 204 of 21%, a gel ratio 206 of 74%, and a cell ratio of 5% with correct fiber diffusion anisotropy of FA=0.83. The anisotropy was compared because it was previously observed that diffusion anisotropy is preserved in vivo and ex vivo in mouse nerve fibers.

Another fiber phantom 210 was built to contain two mouse trigeminal nerves crossing each other at 90° with isotropic gel. As expected that DTI failed to identify the two crossing fibers or the gel. In contrast, DBSI was able to identify the presence of two fibers crossing at 90° estimating fiber orientations of (1, 0, 0) and (0, 0, 1). The diffusion anisotropy of the two fibers was estimated to be 0.81 and 0.83 respectively. Correct volume ratio was also estimated by DBSI to report 19% of (1, 0, 0) fiber, 19% of (0, 0, 1) fiber, 52% of gel, and 10% of cell component.

In the chronic CNS injury, tissue loss is common. Current DTI techniques have not been able to correctly reflect the status of chronic tissue injury. In a mouse spinal cord injury model, the non-injured and moderately injured cord tissues were examined. In the non-injured white matter of the mouse spinal cord, the DTI derived diffusion parameters were ADC=0.29 $\mu m^2$/ms, axial diffusivity=0.69 $\mu m^2$/ms, radial diffusivity=0.12 $\mu m^2$/ms, and FA=0.85. These are comparable with those obtained using DBSI where ADC=0.29 $\mu m^2$/ms, axial diffusivity=0.69 $\mu m^2$/ms, radial diffusivity=0.10 $\mu m^2$/ms, and FA=0.85. Both DTI and DBSI were successful in describing the non-injured white matter characteristics. However, when the moderately injured spinal cord tissues were examined, the DTI failed to capture the underlying pathology, i.e., the extent of tissue loss, resulting in overestimating axial diffusivities thus underestimating the severity of the injury. In contrast, DBSI was able to estimate that there is a 10% tissue loss in the injured white matter.

Methods described herein facilitate determination of an axial diffusivity, a radial diffusivity, and/or a volume ratio of a scanned volume of tissue with increased accuracy relative to known methods, which are distinguishable at least as follows.

Figure 19:
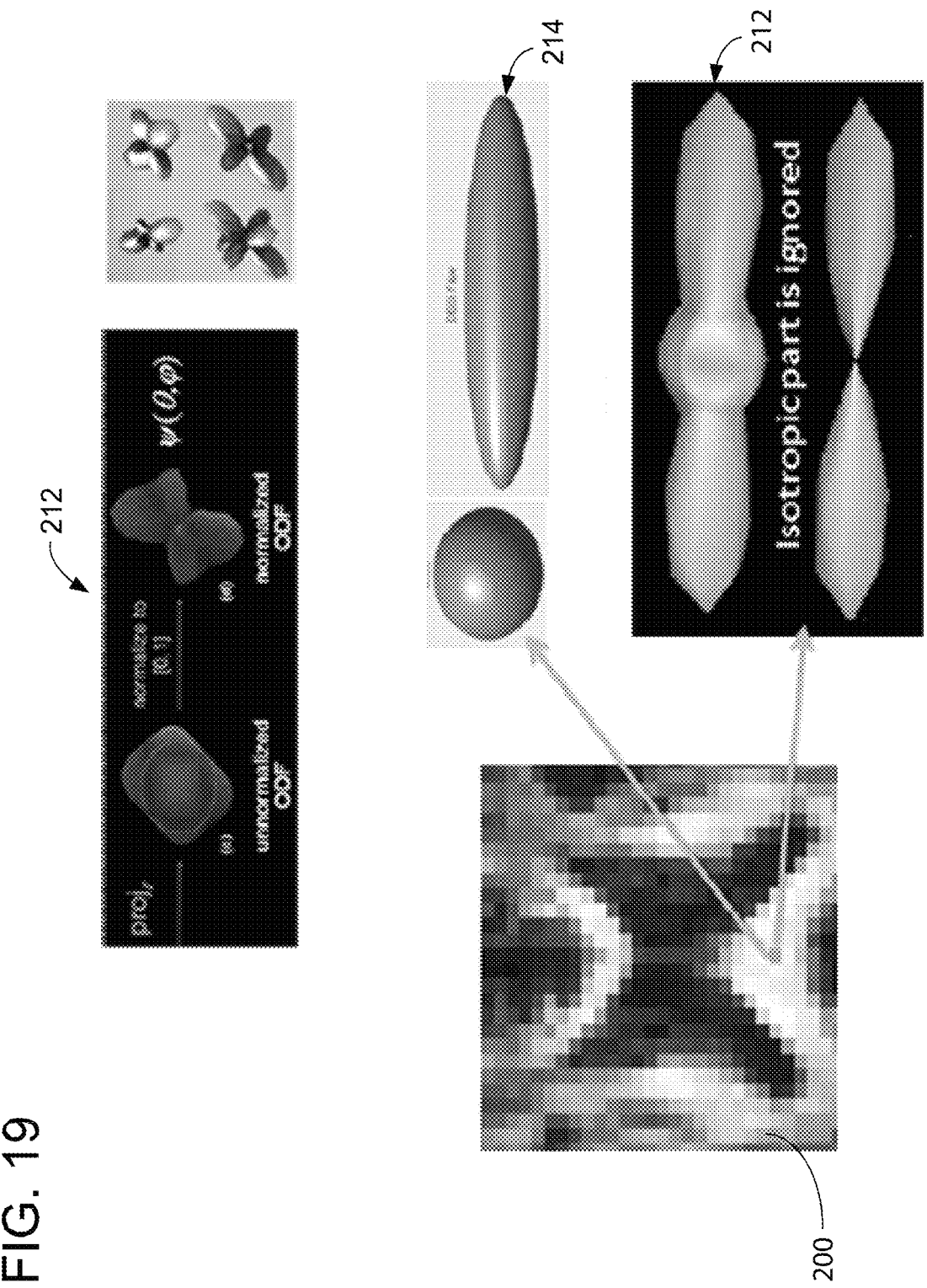
FIG. 19 is a comparison of diffusion spectrum imaging (DSI) and DBSI from a human subject.

FIG. 19 is a comparison of diffusion spectrum imaging (DSI) 212 and DBSI 214 from human subjects 216. DSI 212 is a method that attempts to directly measure the probability distribution function of the displacement of water molecules without an assumption of tissue structure or the shape of probability distribution function. It was proposed to identify multiple fibers within an image voxel. The use of orientation distribution function (ODF) by DSI effectively estimates angles of crossing fibers. However, its ODF based analysis does not offer other crucial quantitative information of water diffusion relevant to tissue physiology and pathology such as the apparent diffusion coefficients, diffusion anisotropy, or the volume ratio of different components. Therefore, DSI's applications are limited to fiber tracking.

The presence of an isotropic component within the image voxel is an important biomarker for cell infiltration, edema, and tissue loss. As shown in FIG. 19, the isotropic diffusion component is ignored in DSI 212 operation for the better estimation of the fiber orientation. In contrast, DBSI 214 quantitatively separates the isotropic from fiber component with accurate isotropic diffusivity assessment.

Operationally, DSI requires high diffusion weighting gradients of various magnitudes and directions to accurately estimate the ODF, a typically impractical challenge on regular clinical MR scanners. In contrast, DBSI facilitates operation with the clinically used diffusion weighting gradient strength and smaller number of directions. Thus, DBSI may be performed on clinical MR scanners with typical hardware resources.

Figure 20:
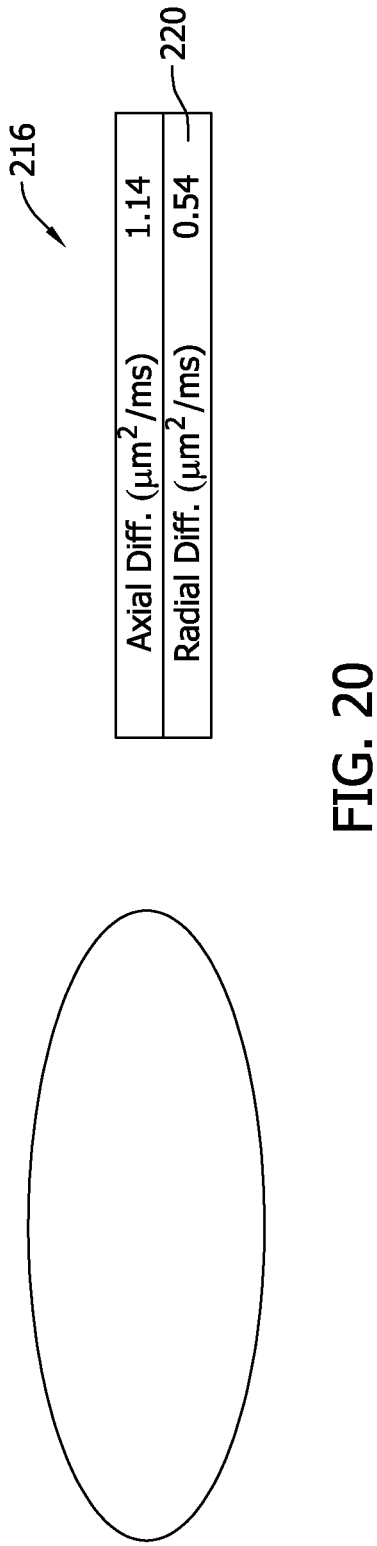
FIG. 20 is a diffusion tensor imaging (DTI) for mouse trigeminal nerve embedded in gel.
Figure 21:
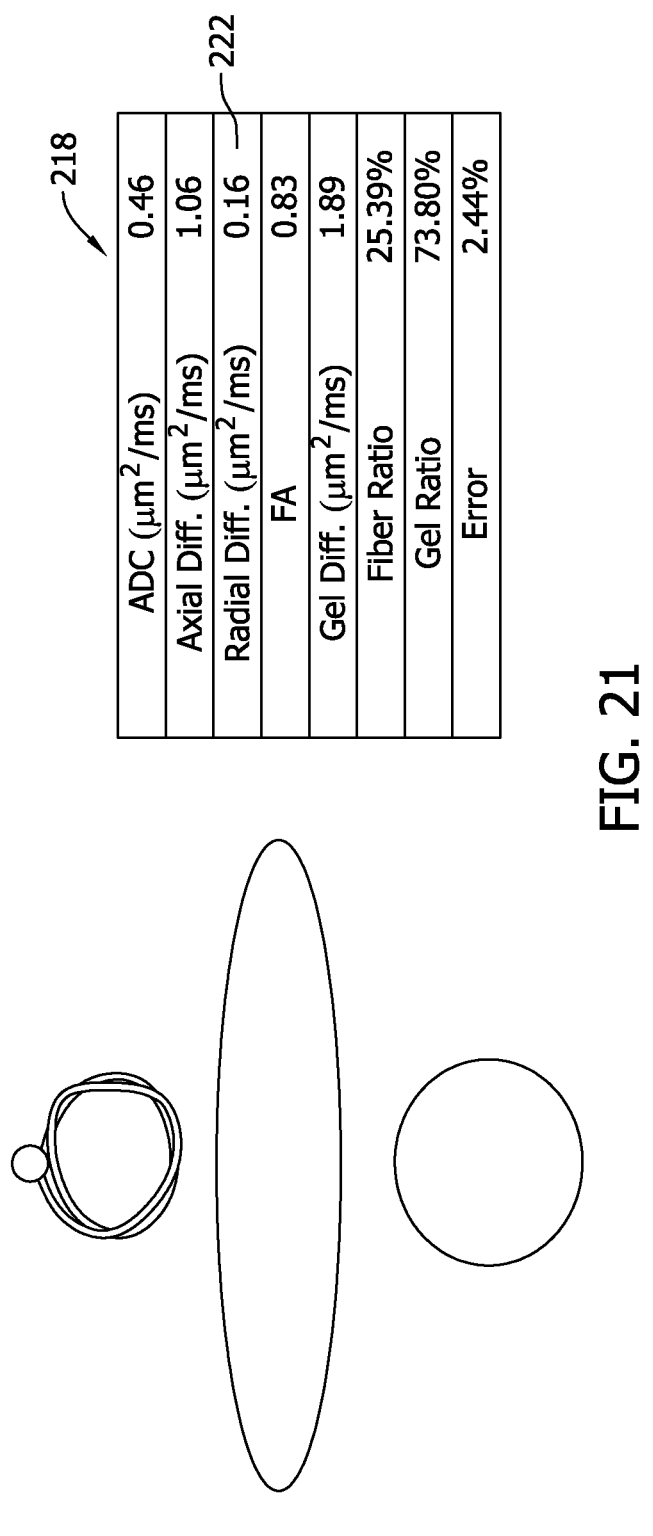
FIG. 21 is a DBSI for mouse trigeminal nerve embedded in gel.

FIG. 20 is a diffusion tensor imaging (DTI) 216 for mouse trigeminal nerve embedded in gel, and FIG. 21 is a DBSI 218 for mouse trigeminal nerve embedded in gel. DTI 216 derived radial diffusivity is very dependent on the tissue environment, and inaccurate assessment is common due to both the intra- and inter-voxel partial volume effect as demonstrated in FIG. 20. Using a simple yet realistic phantom constructed from fixed mouse trigeminal nerves and gel, as described above and as shown in FIG. 21, DTI 216 significantly over estimated the radial diffusivity 220, while DBSI 218 correctly quantified diffusivities 222, anisotropy, and volume ratios of all components.

This phantom study demonstrates the superior results enabled by DBSI in quantifying the overwhelming isotropic component within the image voxel and reporting correct diffusion properties of both the fiber and its environment. Embodiments described herein facilitate correctly estimating the extent of axonal loss noninvasively (e.g., in a clinical setting).

In one embodiment, eight trigeminal nerves from 4 normal male C57BL/6 mice were isolated after fixation. Diffusion MR spectroscopy was performed at 19° C. using a custom-built surface coil with the following parameters (common to all nerve fiber measurements): max b=3200 (s/mm$^2$), repetition time (TR) 2 s, echo time (TE) 49 ms, time between application of gradient pulses (Δ) 20 ms, duration of diffusion gradient on time (δ) 8 ms, number of averages 4, 99-direction diffusion weighting gradients 44. Three diffusion tensor components were observed: anisotropic diffusion (75.9±2.6%: axon fibers), restricted isotropic diffusion (12.1±0.99%: cells), and non-restricted isotropic diffusion (12.1±2.5%: extra-axonal and extracellular water). The assignment of cell and water components was based on the DBSI-derived spectrum of isotropic diffusion.

Figure 22:
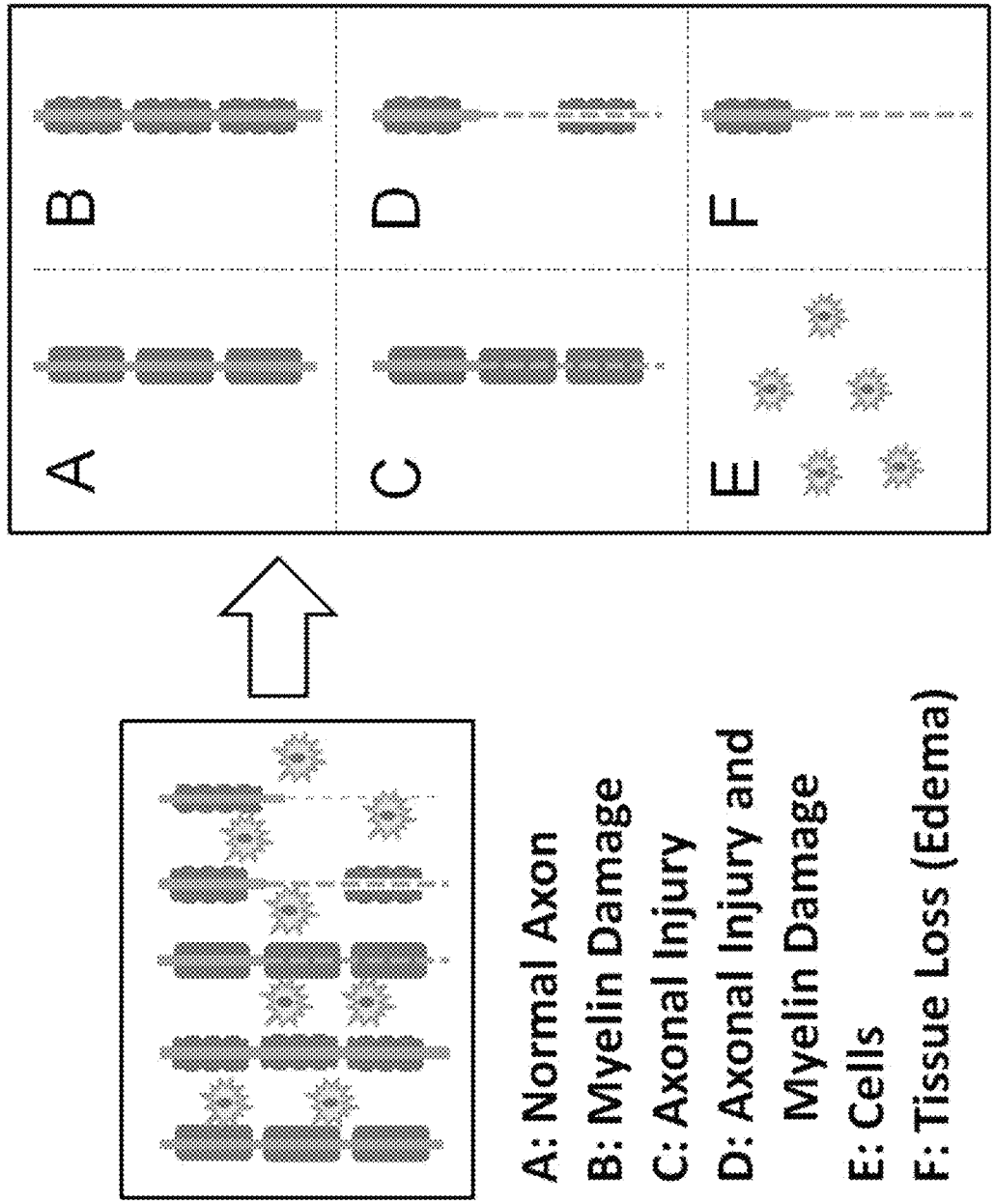
FIG. 22 is an illustration of heterogeneous pathology within one image voxel of interested white matter lesion.
Figure 23:
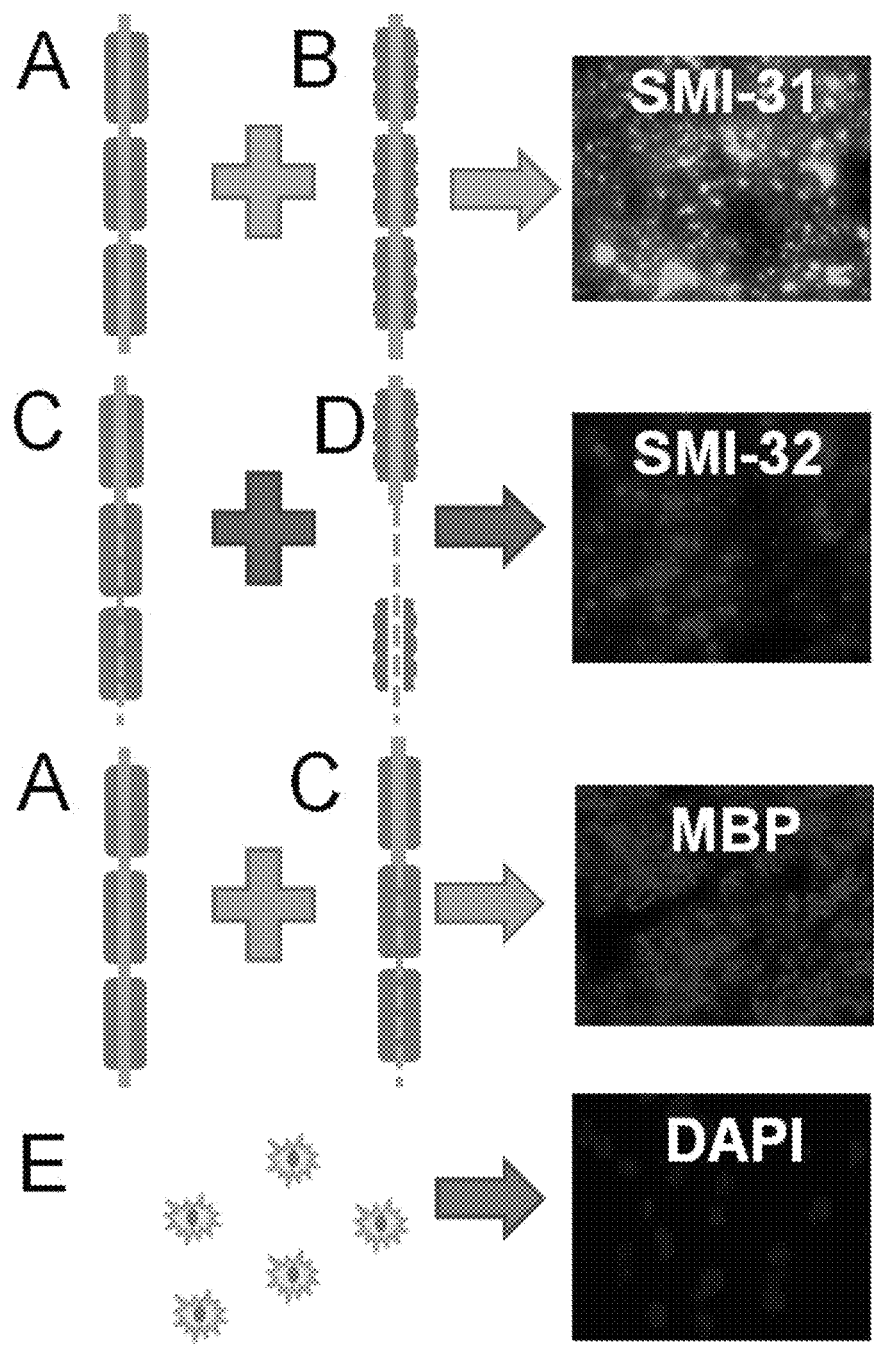
FIG. 23 is an illustration of conventional invasive histology.
Figure 24A:
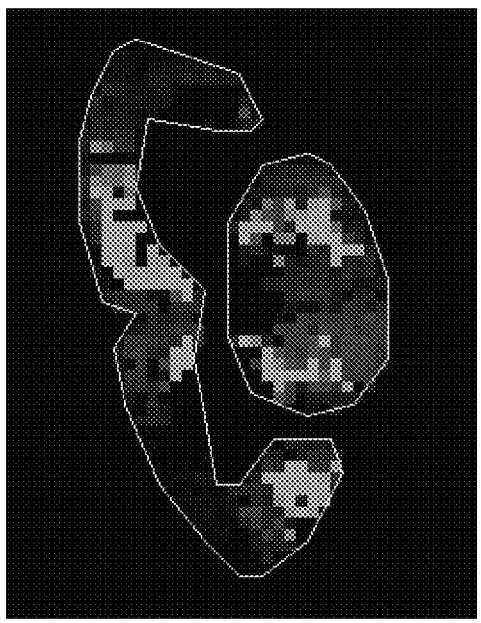
FIG. 24A is a detailed view of the DBSI-derived MBP fraction of the scan of FIG. 22.
Figure 24B:
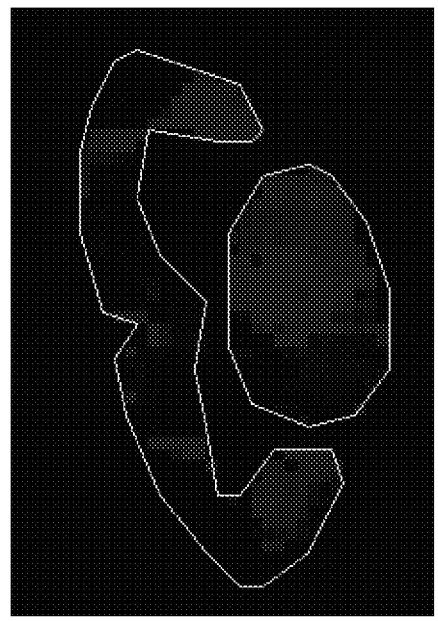
FIG. 24B is a detailed view of the DBSI-derived SMI-31 fraction of the scan of FIG. 22.
Figure 24C:
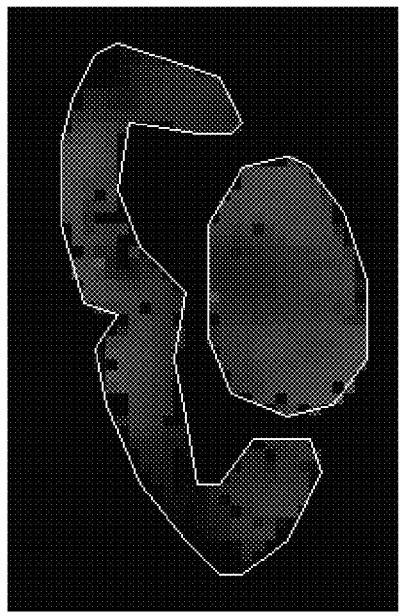
FIG. 24C is a detailed view of the DBSI-derived DAPI fraction of the scan of FIG. 22.
Figure 24D:
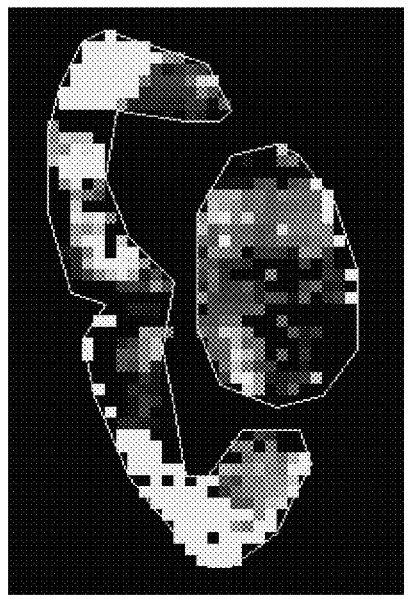
FIG. 24D is a detailed view of the DBSI-derived water fraction of the scan of FIG. 22.
Figure 25:
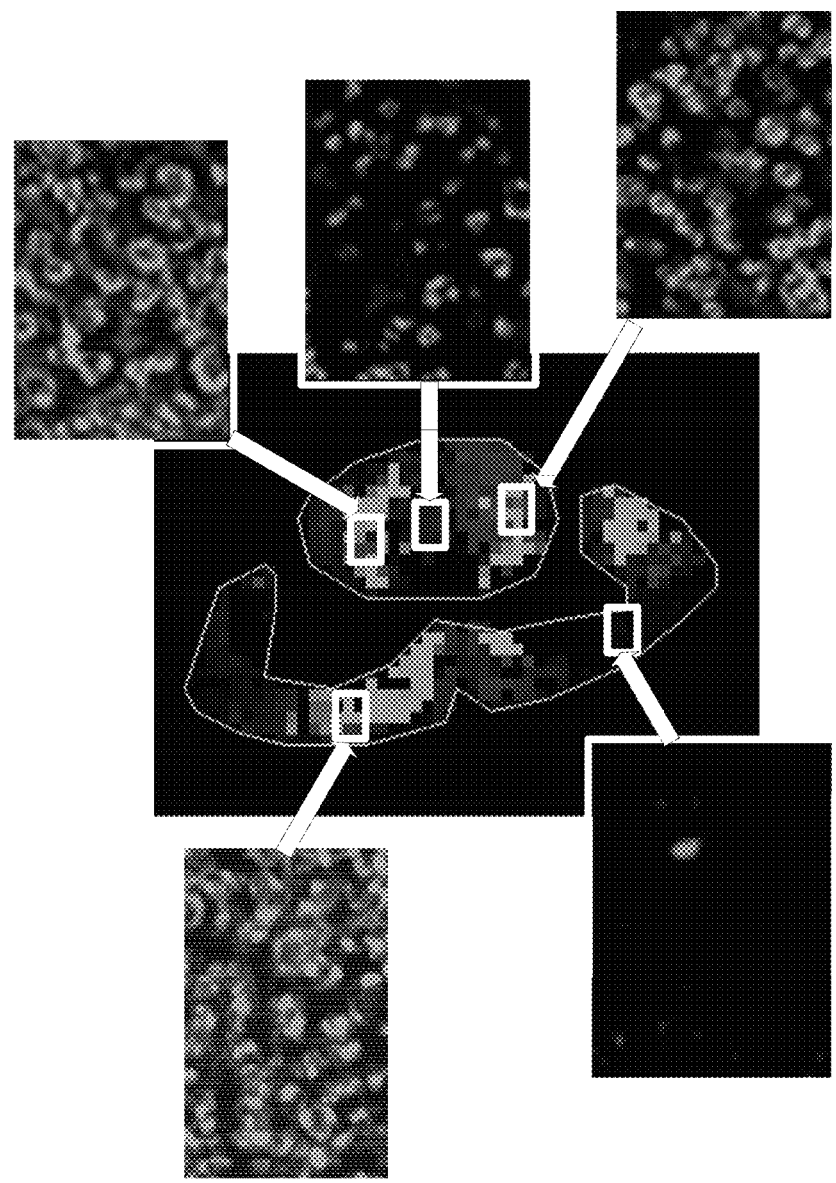
FIG. 25 is a detailed view of the DBSI-derived MBP fraction of the scan of FIG. 22 in the center surrounded by conventional invasive histology images from five selected regions.
Figure 26:
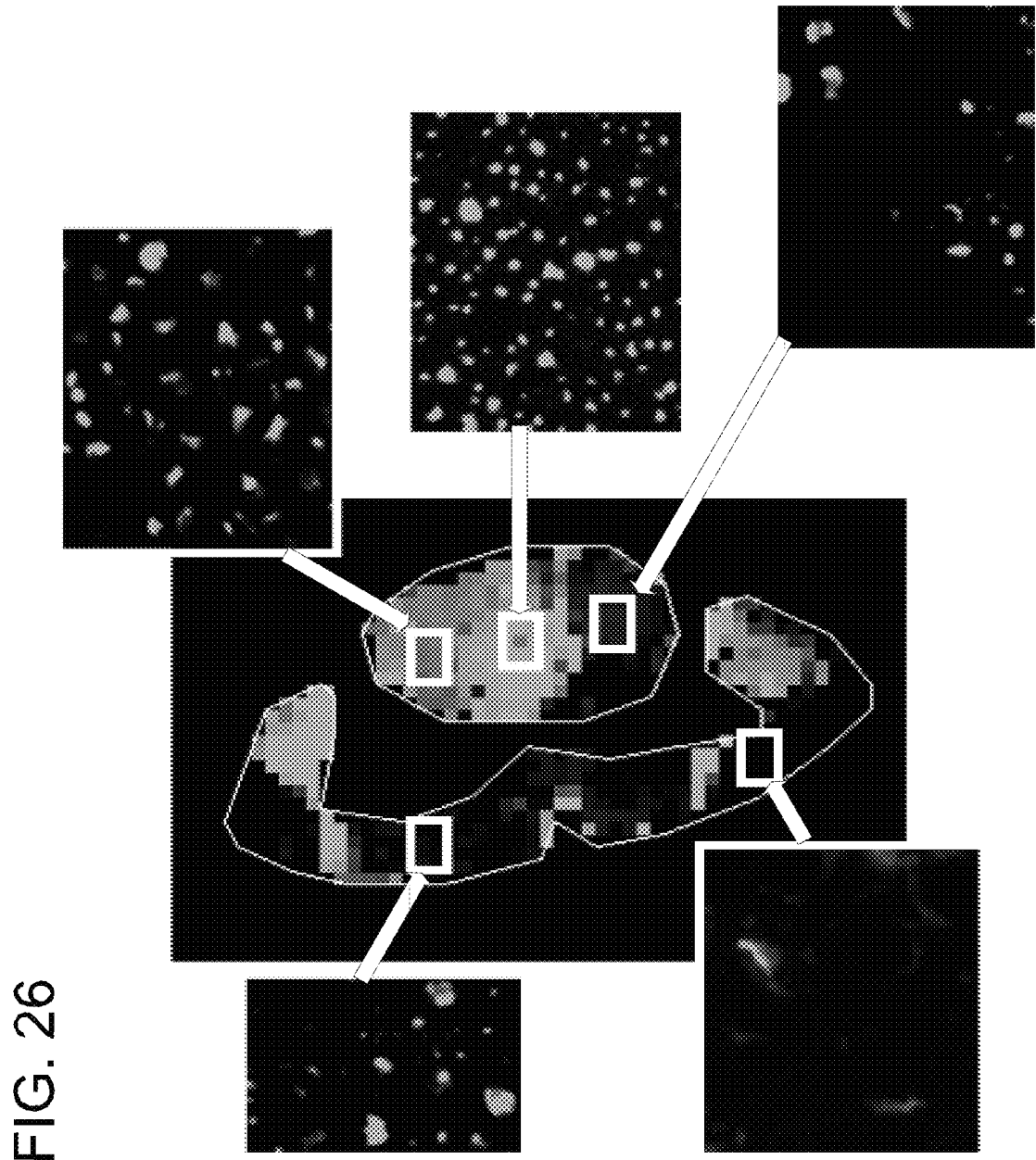
FIG. 26 is a detailed view of the DBSI-derived SMI-31 intensity of the scan of FIG. 22 in the center surrounded by conventional invasive histology images from five selected regions.
Figure 27:
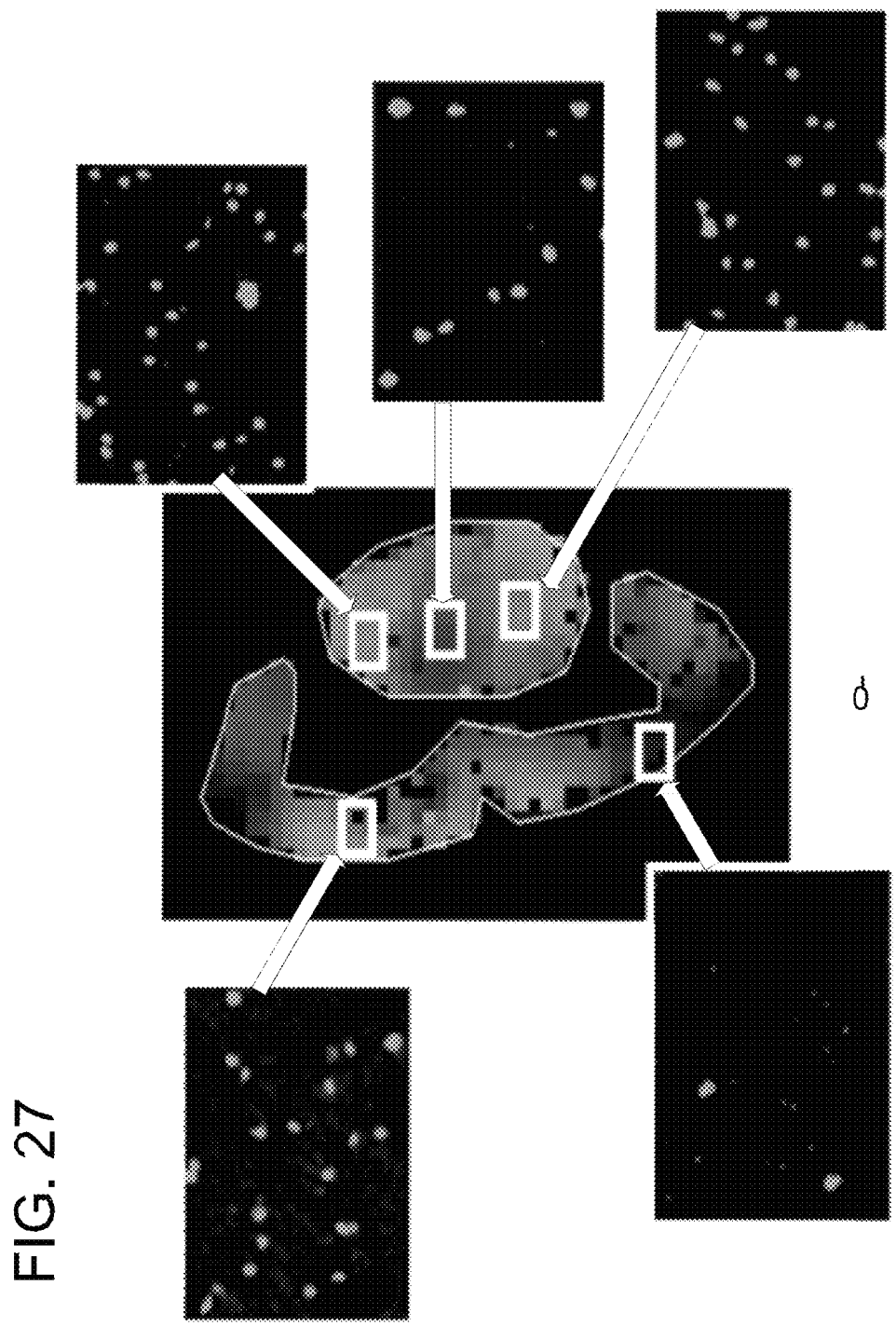
FIG. 27 is a detailed view of the DBSI-derived DAPI intensity of the scan of FIG. 22 in the center surrounded by conventional invasive histology images from five selected regions.
Figure 28A:
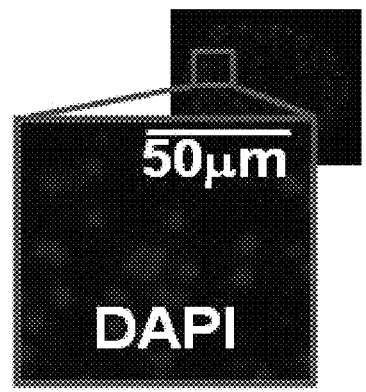
FIG. 28A is a view of a DAPI staining of a fixed mouse trigeminal nerve and a comparison of isotropic diffusion spectra with gel.
Figure 28B:
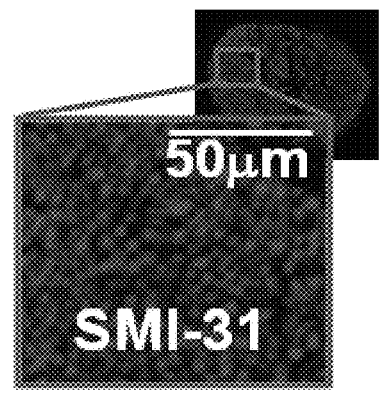
FIG. 28B is a view of a SMI-31 staining of a fixed mouse trigeminal nerve and a comparison of isotropic diffusion spectra with gel.

FIGS. 24A-24D are detailed views of the intensities of the scan of FIG. 22. In these figures, FIG. 24A represents intact myelin, FIG. 24B represents intact axons, FIG. 24C represents cell nucleus and FIG. 24D represents tissue loss.

Figure 40:
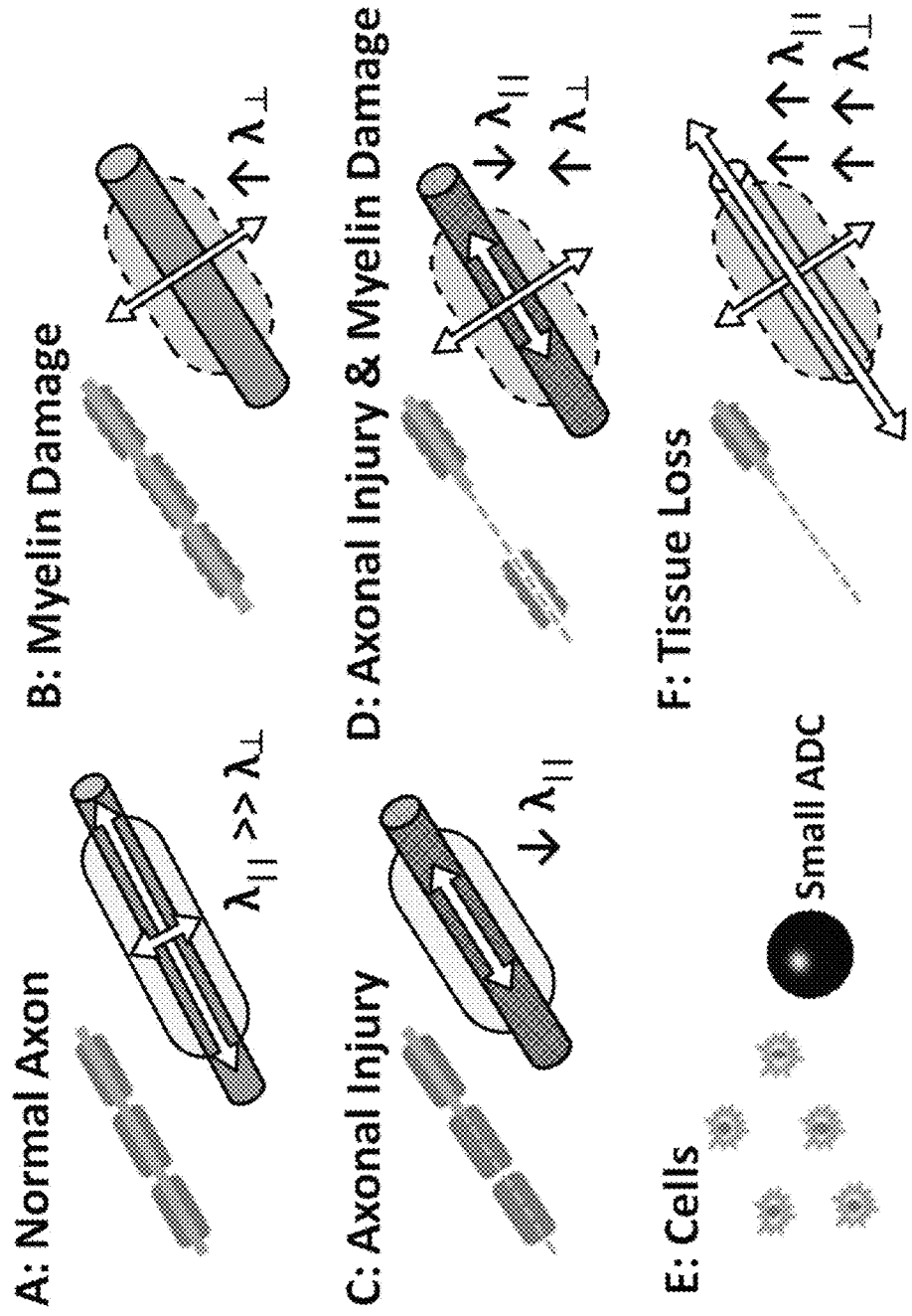
FIG. 40A is an illustration of the DTI signature of a normal axon.
FIG. 40B is an illustration of the DTI signature of myelin damage.
FIG. 40C is an illustration of the DTI signature of axonal injury.
FIG. 40D is an illustration of the DTI signature of axonal injury and myelin damage.
FIG. 40E is an illustration of the DTI signature of cells.
FIG. 40F is an illustration of the DTI signature of tissue loss.
Figure 41:
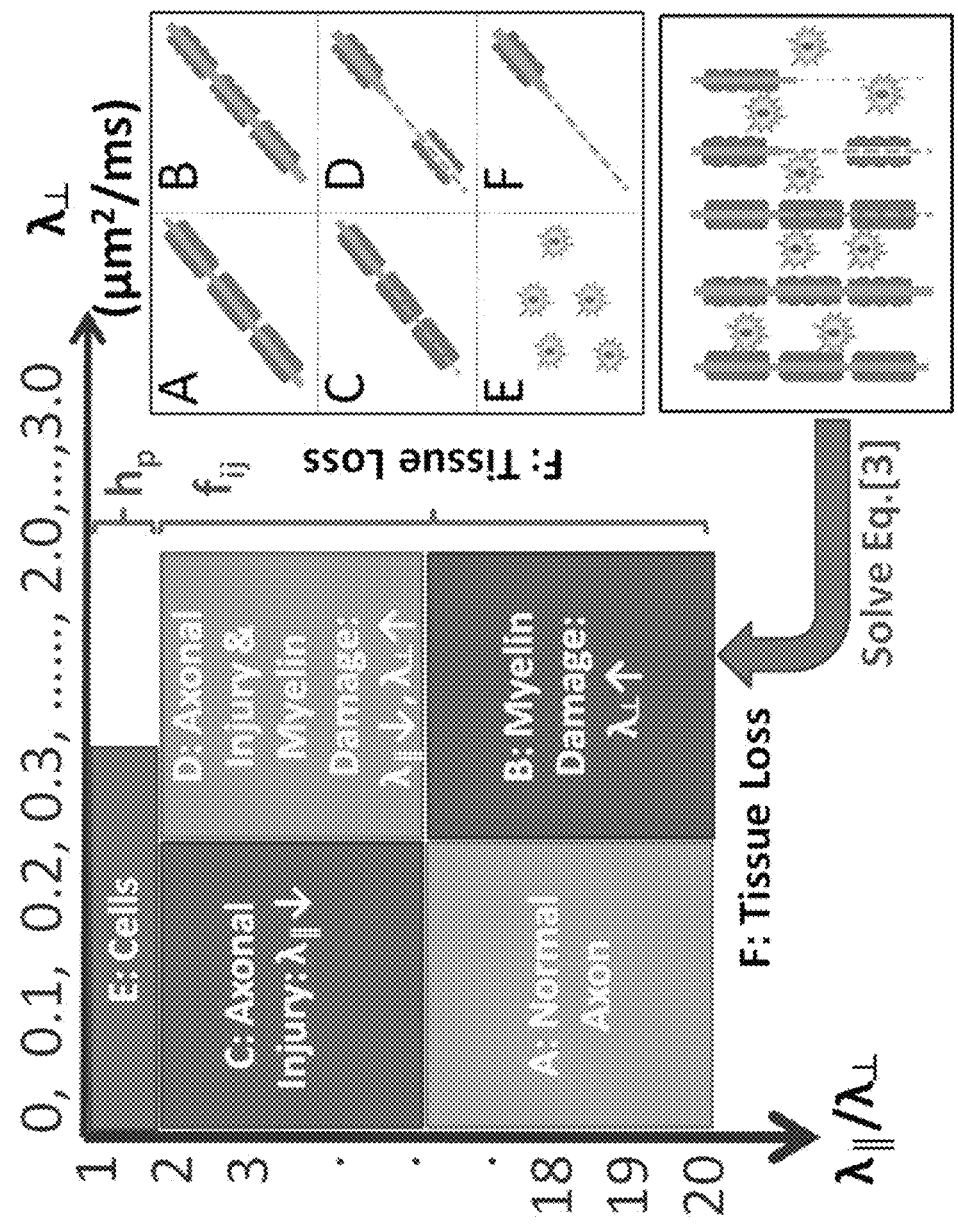
FIG. 41 is an illustration of the procedure to calculate individual pathology maps.

Based on DBSI-derived number fibers and the associated fiber principle orientations (Eq. [2]), the detailed composition of each nerve bundle can be further estimated and classified according to the structure and/or pathology (FIG. 40). Homogenous pathological change in a coherent white matter tract bundle exhibits a unique signature of DTI-derived directional diffusivities (FIG. 41A). To demonstrate the effect of complex pathologies, spinal cord white matter, a simple nerve bundle without fiber crossing, was examined. To properly model spinal cord white matter lesions containing heterogeneous and co-existing pathologies (FIG. 40), diffusion weighted MR signal was modeled as a linear combination of a series of anisotropic diffusion tensors (representing heterogeneous axon fibers with different pathology) plus a spectrum of isotropic diffusion components (representing inflammation associated cell infiltration and edema, or tissue loss), Eq. [5]:

$$S_k = \sum_{i=1}^{M}\sum_{j=1}^{N} f_{ij} e^{-|\vec{b}_k|\lambda_{\perp\_i}} e^{-|\vec{b}_k|(\lambda_{\parallel,j}-\lambda_{\perp\_i})\cos\theta_k} + \sum_{p=1}^{H} h_p e^{-|\vec{b}_k|\lambda_p} \quad \text{(Equation 5)}$$

$f_{ij}$ is the non-diffusion weighted signal intensity fraction of the anisotropic tensor delineated by $(\lambda_{\perp\_i}, \lambda_{\parallel\_i})$. As demonstrated by the schematic plot in FIG. 41B, $\lambda_{\perp\_i}$ are the $i^{th}$ (i=1, 2, . . . , M) radial diffusivity uniformly distributed within the limits of [0, 2] (μm$^t$/ms); $\lambda_{\parallel\_i}$ are the $j^{th}$ (i=1, 2, . . . , N) axial diffusivity uniformly discretized within the limits of [1.1, 20]×$\lambda_{\perp\_i}$. M×N is the total number of possible anisotropic tensor types distributed within physiological and pathological ranges, which can be classified into five groups: (A) normal axon; (B) demyelinated axon (increased $\lambda_{\perp\_i}$, and unchanged $\lambda_{\parallel\_i}$) (C) injured axon (unchanged $\lambda_{\perp\_i}$, and decreased $\lambda_{\parallel\_i}$), (D) injured axon with demyelination (increased $\lambda_{\perp\_i}$, and decreased $\lambda_{\parallel\_i}$), and (F) tissue loss (significantly increased $\lambda_{\parallel\_i}$ or $\lambda_{\perp\_i}$). Mean−2× STD of DBSI-derived $\lambda_\parallel$ on normal spinal cord white matter is used as threshold to define the decreased $\lambda_{ID}$>Mean−6× STD indicates significant $\lambda_{\parallel\_i}$ increase. Similarly, Mean+2× STD of DBSI-derived $\lambda_\perp$ is used as threshold to define the increased $\lambda_{\perp\_i}$. $h_p$ is the non-diffusion weighted signal intensity fraction of the $p^{th}$ (p=1, 2, . . . , H) isotropic tensor with mean diffusivity $\lambda_p$ uniformly distributed within the range of [0,3] (μm$^t$/ms). In the present pilot study, a diffusion-weighting scheme with K=100 distinct b-values and directions uniformly distributed on 3D Cartesian grid was employed. The detailed composition of the spinal cord white matter described by $f_{ij}$ together with the isotropic diffusion spectrum described by $h_p$ is determined by solving equation [5] through a regularized nonnegative least-squares (NNLS) analysis (FIG. 41B). The a priori information of nonnegative signal intensity and smooth signal intensity distribution is incorporated as penalty terms to effectively prevent the NNLS from over-fitting the measured noisy data while retaining the numerical accuracy of the solution. Based on the results of the second step, the non-diffusion weighted signal intensity fraction ($f_{ij}$) of the anisotropic tensors belonging to each group were summed up to compute individual pathology component map (FIG. 41B): (Map A) the normal axon density; (Map B) demyelinated axon density; (Map C) injured axon density; (Map D) injured and demyelinated axon density; and (Map F) density map of tissue loss. Isotropic diffusion component (Map E) was computed as the summation of fractions from all the isotropic components ($h_p$). The classic immunohistochemical SMI-31+ staining for the intact axons was approximated by the summation of maps A and B; SMI-32+ map (staining for injured axons) by the summation of maps C and D; MBP+ map (staining for axons with intact myelin) by the summation of maps A and C; DAPI+ map (staining for cell nucleus) by map F. Examples are shown in FIGS. 24-27.

Figure 29:
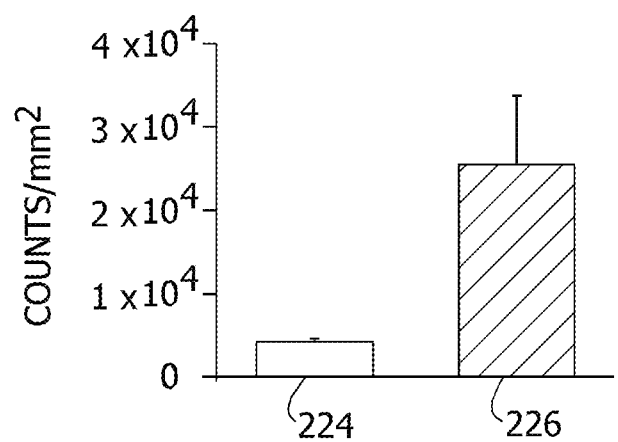
FIG. 29 is a graph of the nucleus and axon counts by IHC of FIG. 28B.
Figure 30:
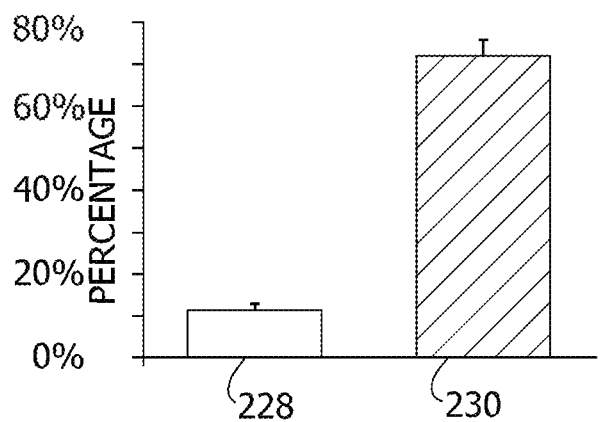
FIG. 30 is a graph of the DBSI derived cell percentage and fiber percentage of FIG. 28B.

FIG. 29 illustrates a DAPI 224 and SMI-31 226 staining of a fixed mouse trigeminal nerve and a comparison of isotropic diffusion spectra with gel. In such an embodiment, nucleus and axon staining was performed using 4',6'-diamidino-2-phenylindole (DAPI) and phosphorylated neurofilament (SMI-31) to count cells (4109±629/mm$^2$) and axons (25434±8505/mm$^2$). The powder-average effect of the 25% (FIG. 30) isotropic diffusion component in the fixed trigeminal nerve is apparent when comparing $\lambda_\parallel$ and $\lambda_\perp$ derived using DBSI ($\lambda_\parallel$=1.07±0.05 μm$^2$/ms, $\lambda_\perp$=0.12±0.01 μm$^2$/ms) vs. DTI ($\lambda_\parallel$=0.77±0.03 μm$^2$/ms, $\lambda_\perp$=0.17±0.02 μm$^2$/ms). Compared to DBSI, DTI underestimated $\lambda_\parallel$ by 28%, while overestimating $\lambda_\perp$ by 42%. Five fiber-gel samples were examined at 19° C. using DBSI to quantify anisotropic and isotropic diffusion, and T2W MRI to quantify total gel signal intensity.

Figure 31:
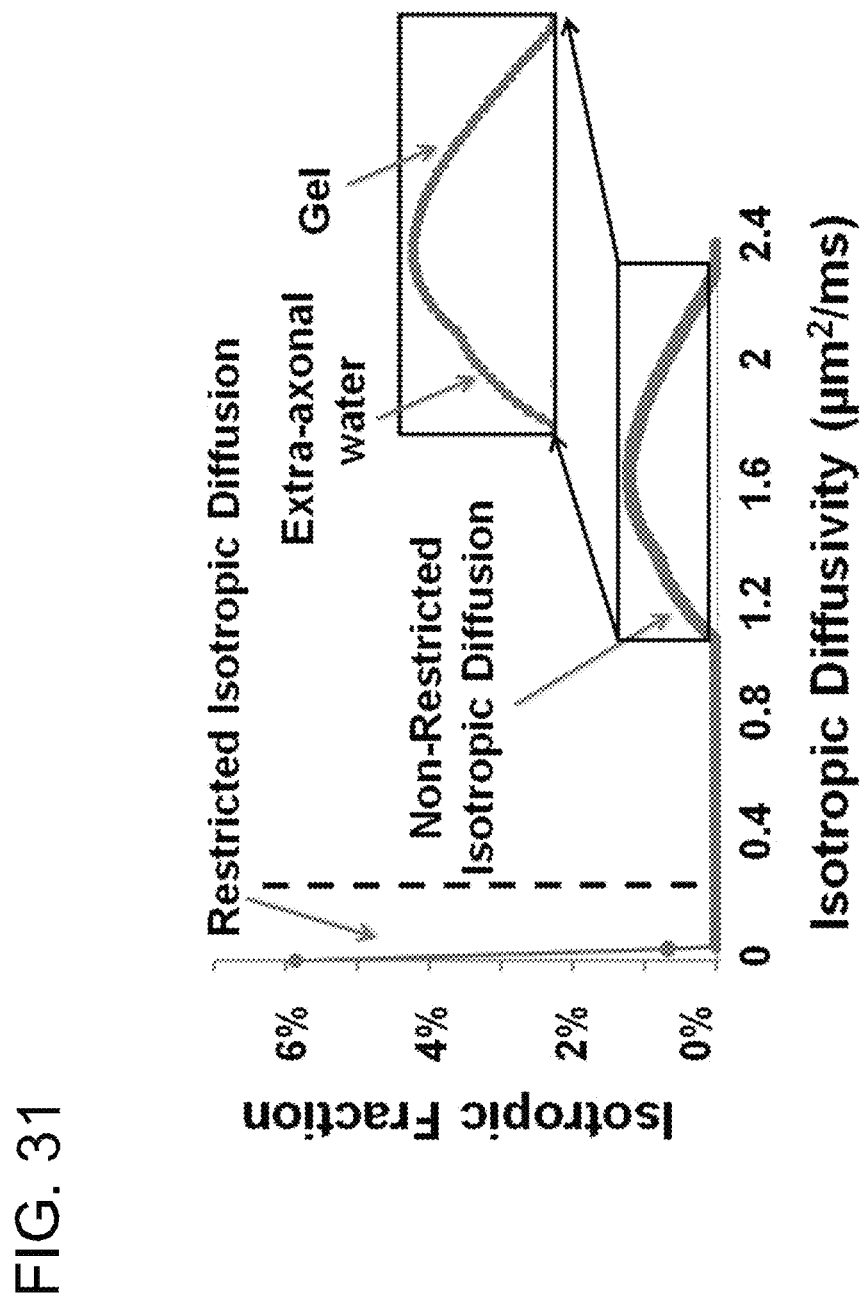
FIG. 31 is an illustration of a typical DBSI-derived spectrum of isotropic diffusivity from a fixed mouse trigeminal nerve juxtaposed with gel.
Figure 32:
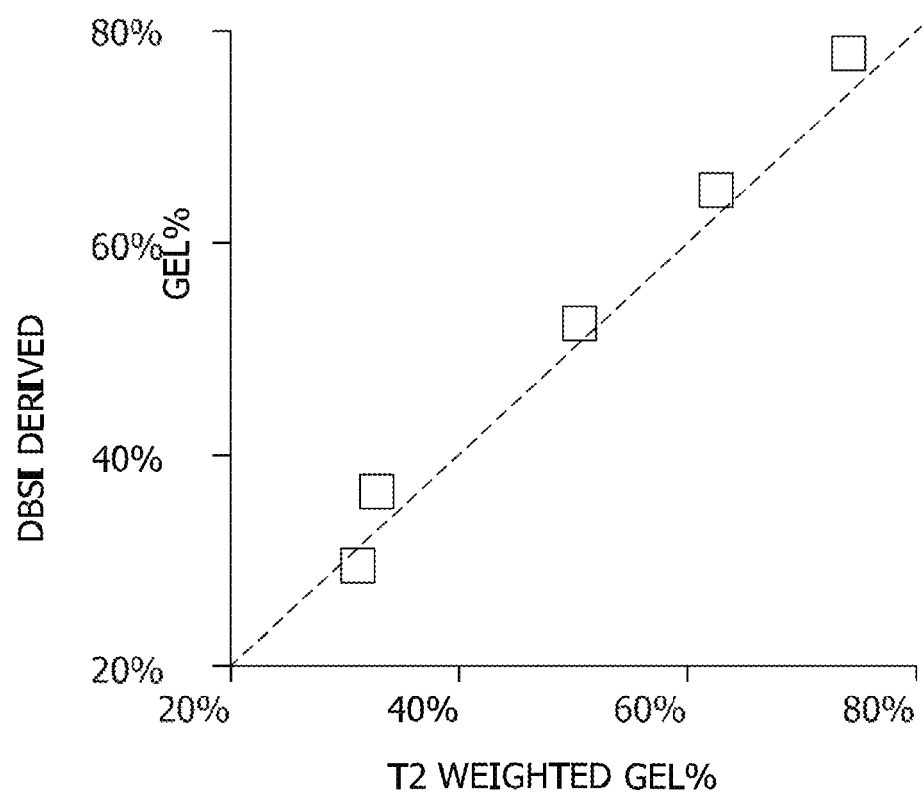
FIG. 32 is a comparison of DBSI-derived gel fractions to those measured by T2W MRI signal intensity.
Figure 33:
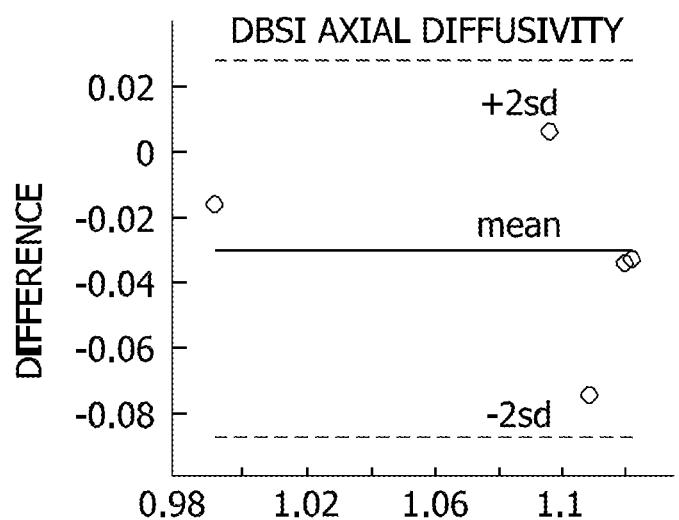
FIG. 33 is a graph of $\lambda_\parallel$ derived from trigeminal nerves with and without gel.
Figure 34:
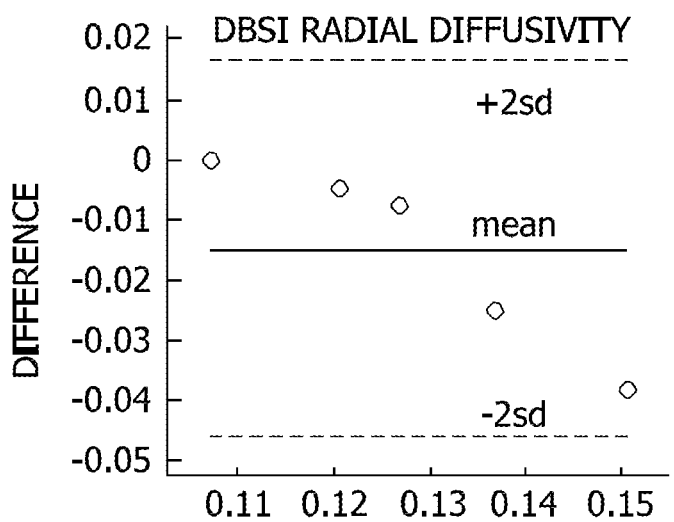
FIG. 34 is a graph of $\lambda_\perp$ derived from trigeminal nerves with and without gel.

The DBSI-determined gel water fraction closely matches that determined using T2W MRI as shown in FIG. 31-32, suggesting the potential of DBSI to estimate edematous water from more freely diffusing water in regions of tissue loss. The derived fiber directional diffusivities with and without gel are comparable as shown in FIGS. 33 and 34, indicating that DBSI can correctly assess fiber diffusion properties in the presence of edema or tissue loss.

Figure 35:
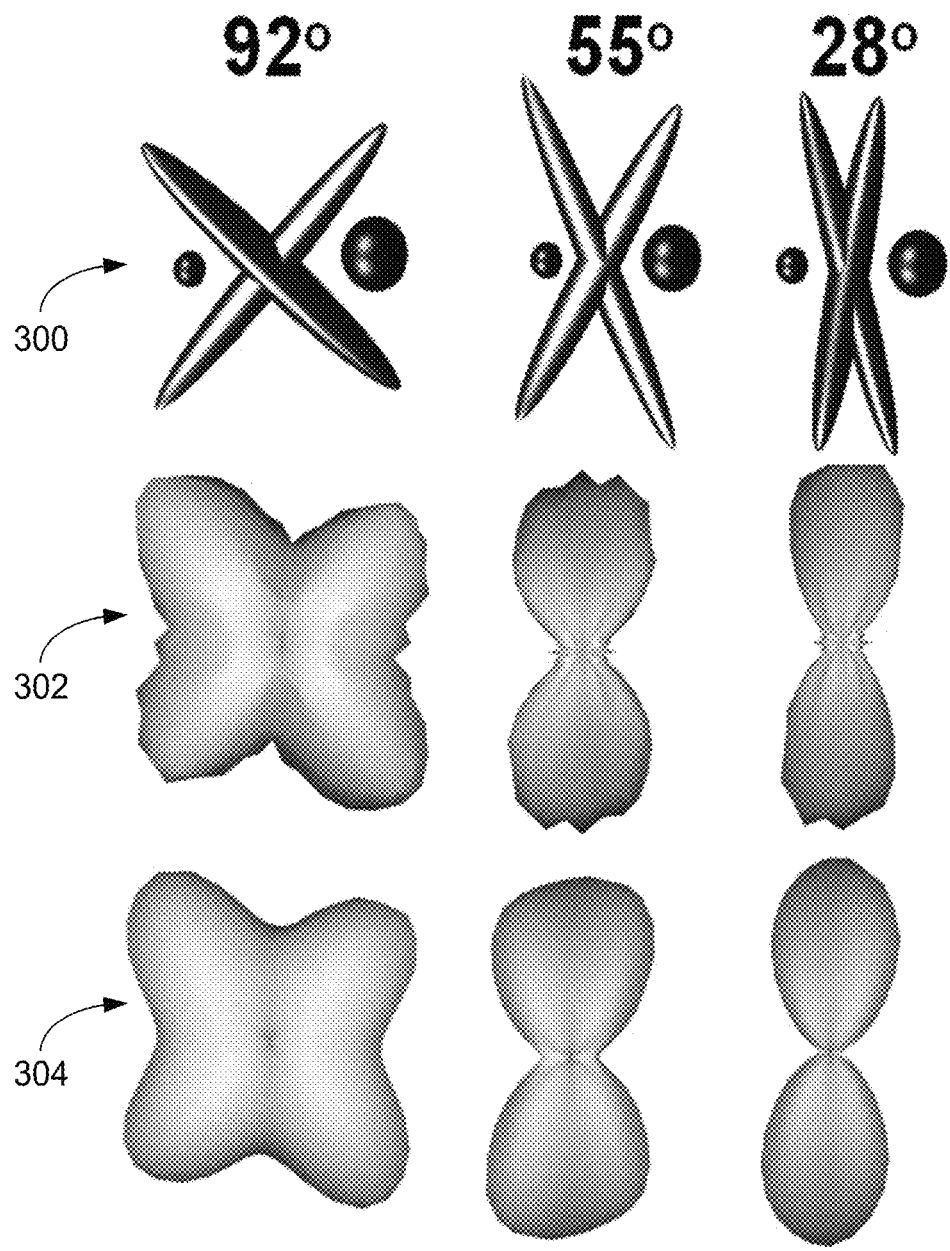
FIG. 35 is an illustration of six fixed trigeminal nerves grouped into three pairs of crossing fibers at 32°, 58°, and 91° juxtaposed with 2% agarose gel.
Figure 37A:
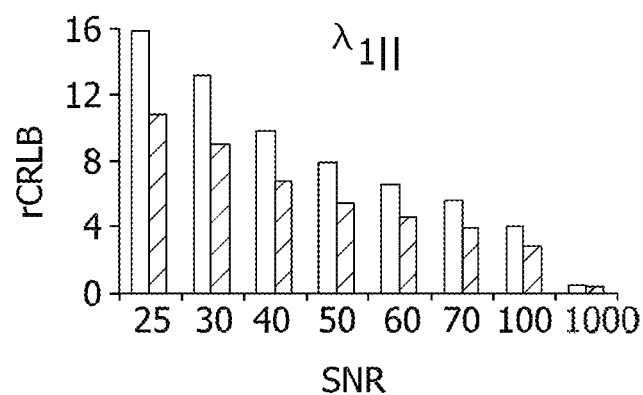
FIG. 37A is a graph of an axial diffusivity $\lambda_{1\parallel}$ of a first fiber.
Figure 37B:
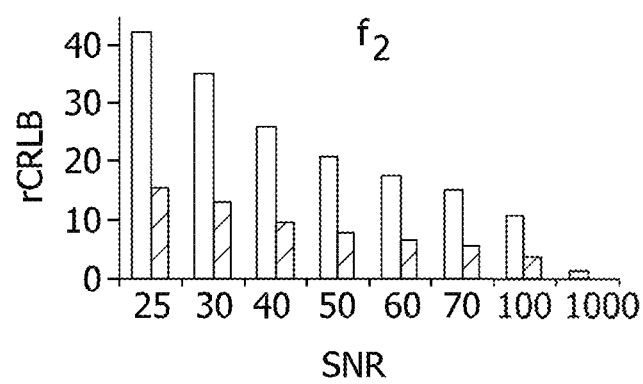
FIG. 37B is a graph of a volume ratio $f_2$ of a second fiber.
Figure 37C:
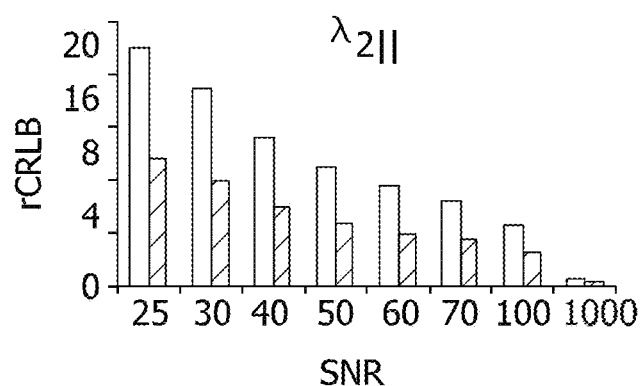
FIG. 37C is a graph of axial diffusivity $\lambda_{2\parallel}$ of the second fiber.
Figure 37D:
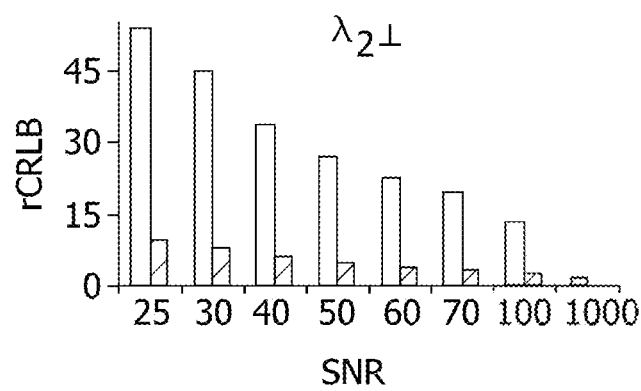
FIG. 37D is a graph of radial diffusivity $\lambda_{2\perp}$ of the second fiber.

FIG. 35 is an illustration of six fixed trigeminal nerves grouped into three pairs of crossing fibers at 32°, 58°, and 91° juxtaposed with 2% agarose gel. DBSI-estimated crossing fiber angles 300 compare favorably with those derived using an orientation distribution function (ODF) by DSI 302 and general q-sampling imaging (GQI) 304. DBSI-quantified mean fiber 300 $\lambda_\parallel$=1.14±0.06 μm$^2$/ms, $\lambda_\perp$=0.12±0.02 μm$^2$/ms agreed well with measured values for a single fiber without gel $\lambda_\parallel$=1.07±0.05 μm$^2$/ms, $\lambda_\perp$=0.14±0.02 μm$^2$/ms. For 91°, 58°, 32° phantoms, DBSI-derived gel percentages were 15%, 14%, and 50%, in close agreement with T2W MRI determined 18%, 13%, and 45%. DSI 302 and GQI 304 failed to resolve crossing FIGS. 33 and 34 comparable $\lambda_\parallel$ (A), $\lambda_\perp$ (B) derived from trigeminal nerves with and without gel was confirmed by Bland-Altman plots.

To further demonstrate the capability of DBSI to resolve multiple crossing fibers, a 3-fiber crossing phantom was built using fixed mouse trigeminal nerves arranged in an approximate equilateral triangle with inner angles of (a/b/c)= (75°/55°/50°, as is shown in FIG. 36.

A SNR dependent Monte Carlo simulation and a Cramér-Rao Lower Bound (CRLB) analysis on a model (two crossing fibers with one non-restricted isotropic component) and diffusion scheme (three-fold tessellated icosahedric gradient directions, 184 total directions, on two shells: $b_1/b_2$=1000, 3500 s/mm$^2$) was performed. FIGS. 37A-37D illustrate the relative CRLB (rCRLB for axial diffusivities ($\lambda_{1\parallel}$, $\lambda_{2\parallel}$) of both fibers, and the volume ratio ($f_2$) and radial diffusivity ($\lambda_{2\perp}$) of the second fiber as a function of SNR.

Figure 38A:
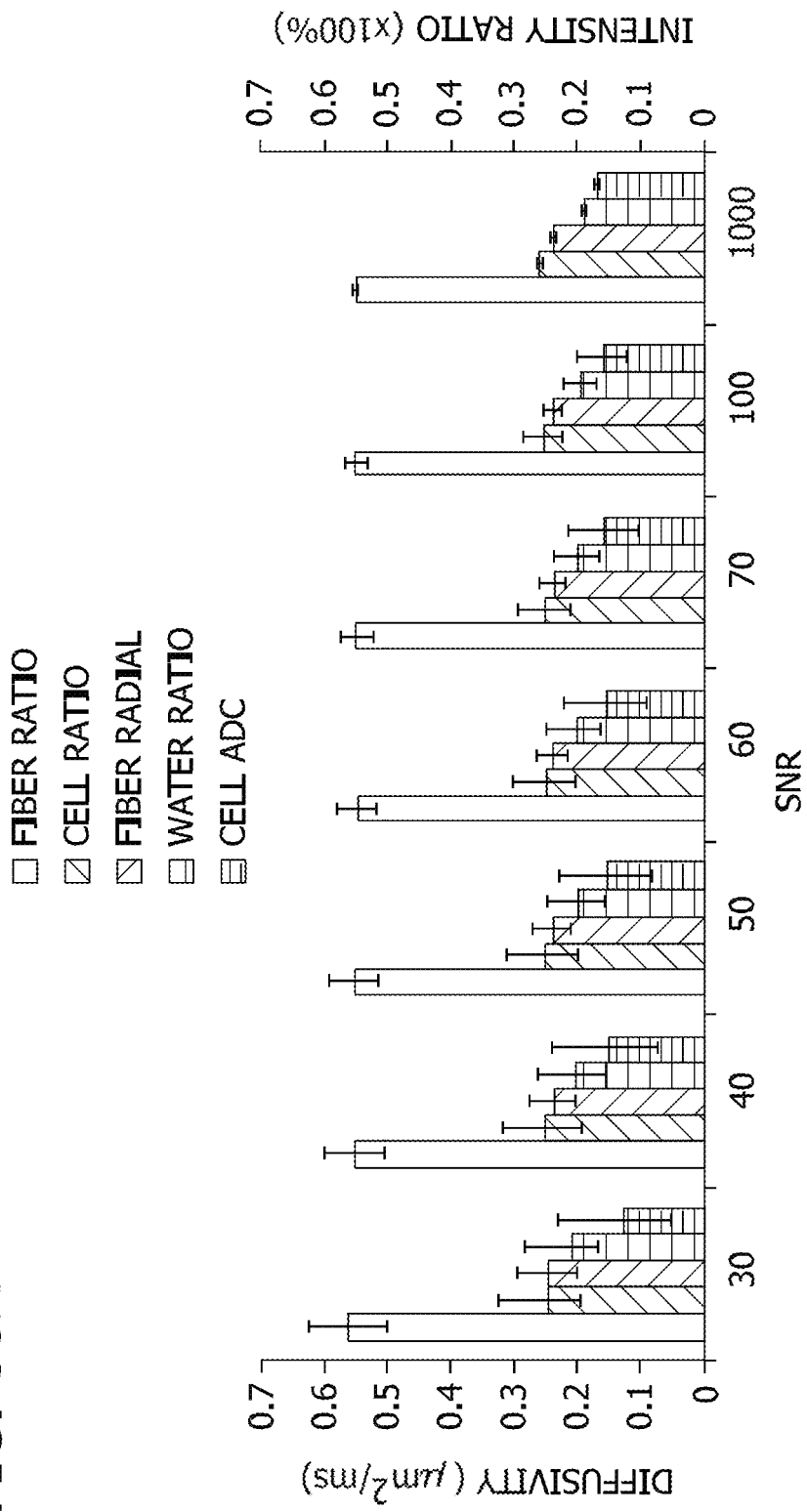
FIG. 38A is an MC-simulation-derived graph displaying fiber ratio, water ratio, cell ratio, cell ADC, and fiber radial diffusivity of diffusion MRI data generated in silico.
Figure 38B:
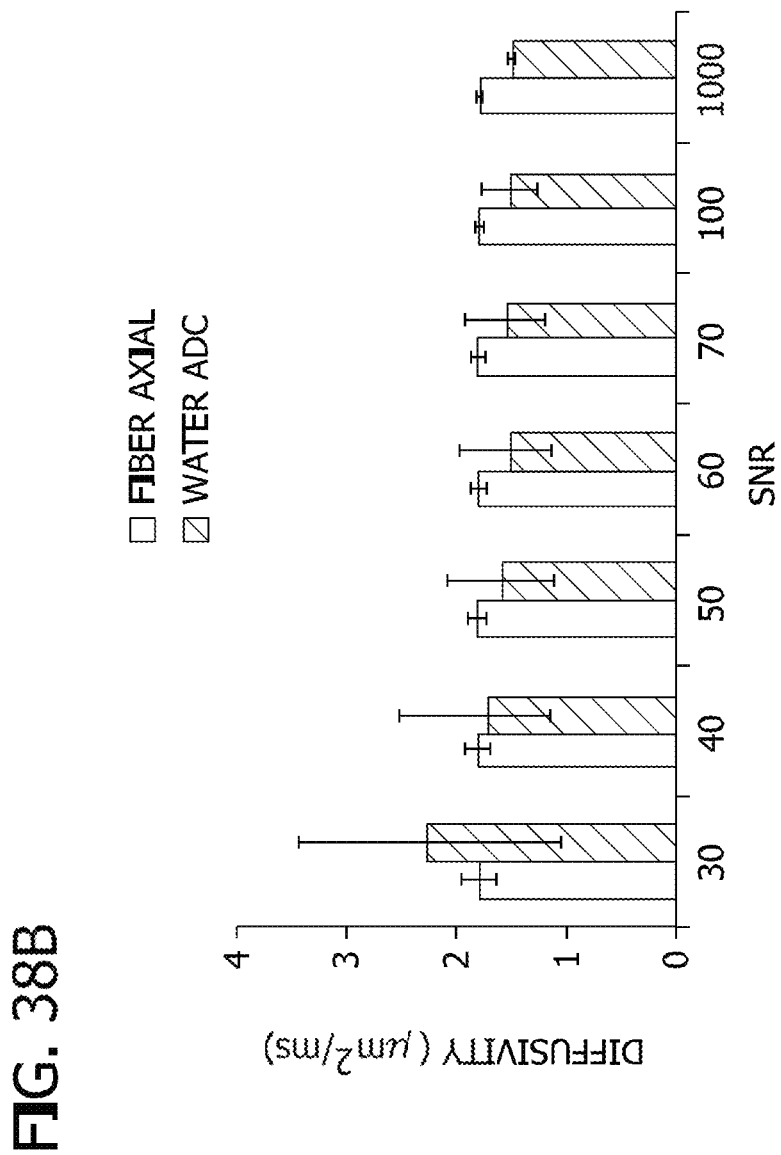
FIG. 38B is an MC-simulation-derived graph displaying fiber axial diffusivity, water ADC of diffusion MRI data generated in silico.
Figure 39:
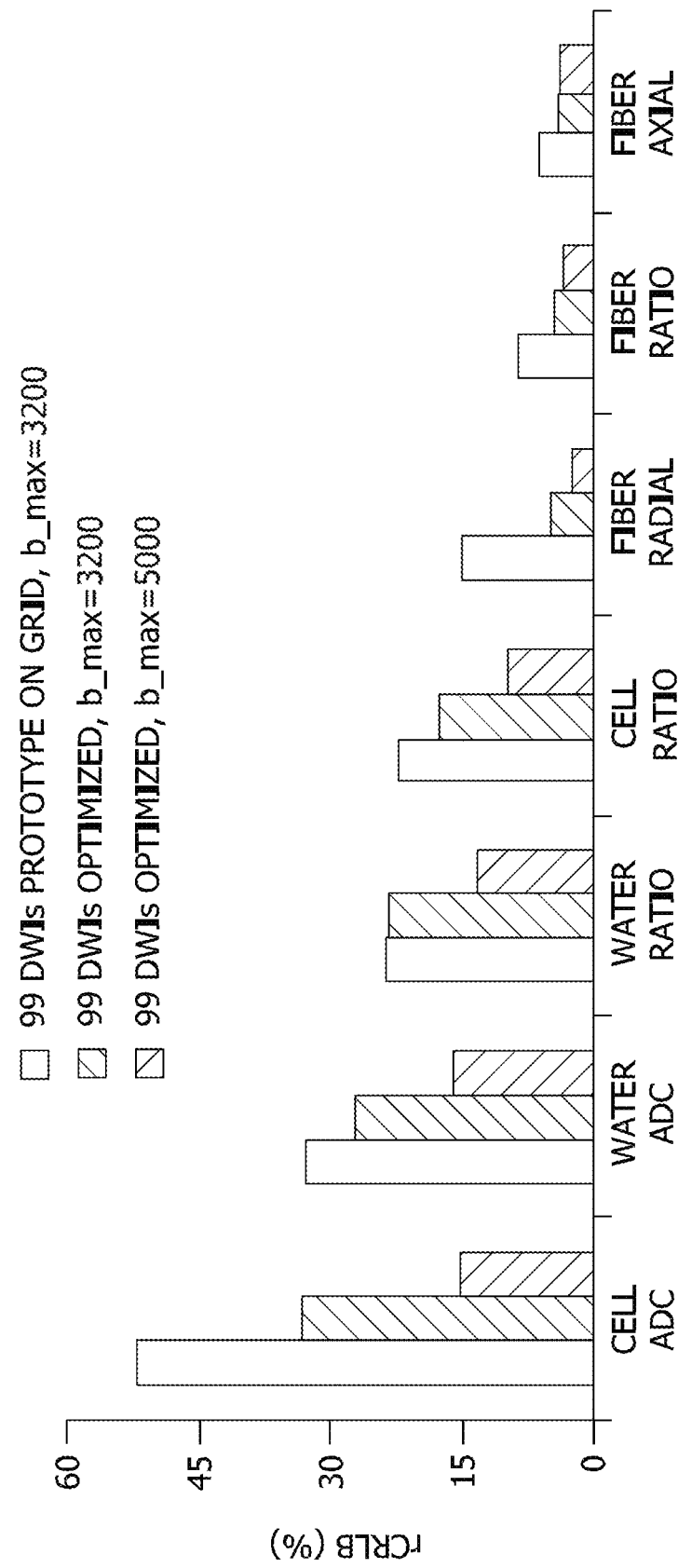
FIG. 39 is a CRLB based optimization of a one-fiber and a two-isotropic compartments diffusion model.

FIGS. 38A and 38B are graphs pertaining to diffusion MRI data representative of a single-fiber with restricted isotropic diffusion and nonrestricted isotropic diffusion were generated in silico via Monte Carlo simulations. The in silico generated data mimicked in vivo mouse spinal cord white-matter diffusion properties at the peak of EAE: single fiber (white-matter tract, $\lambda_\parallel$=1.8 μm$^2$/ms, $\lambda_\perp$=0.24 μm$^2$/ms, along z direction, fiber fraction 55%), restricted isotropic component (infiltrating cells, ADC=0.17 μm$^2$/ms, cell fraction 26%), and nonrestricted isotropic component (edema, ADC=1.8 μm$^2$/ms, 19%). All model parameters were estimated accurately at SNR=40, typical of the in vivo mouse spinal-cord measurements, with bias <15% (FIG. 10). MC simulation and CRLB derived variances agreed with each other, and improved with SNR. These results confirm that DBSI-derived diffusion parameters have sufficient precision to permit meaningful estimates of fiber ratio, water ratio, cell ratio, cell ADC, and fiber diffusivities in mice in vivo. Results suggest that with CRLB optimization at the same max b-value the precision can be improved by optimizing diffusion directions (~40% improvement vs. the prototype DBSI). The optimized directions with increased max b-value (=5000) yielded ~140% improvement over the prototype DBSI (b-value in s/mm$^2$.), as is shown in FIG. 39.

Figure 42:
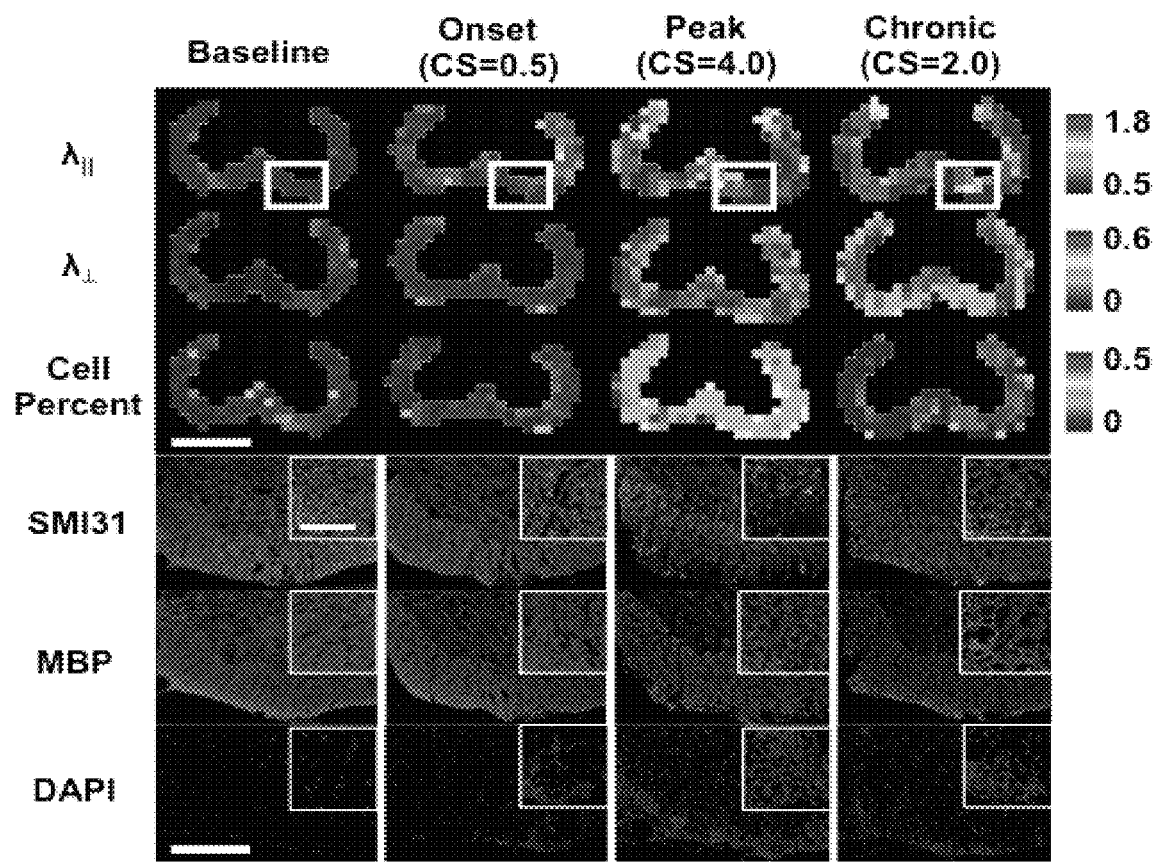
FIG. 42 is an image of in vivo DBSI derived $\lambda_\parallel$, $\lambda_\perp$, and cell fraction maps of mice from each time point with the corresponding axon (SMI-31), myelin (MBP), and nucleus (DAPI) staining.
Figure 43:
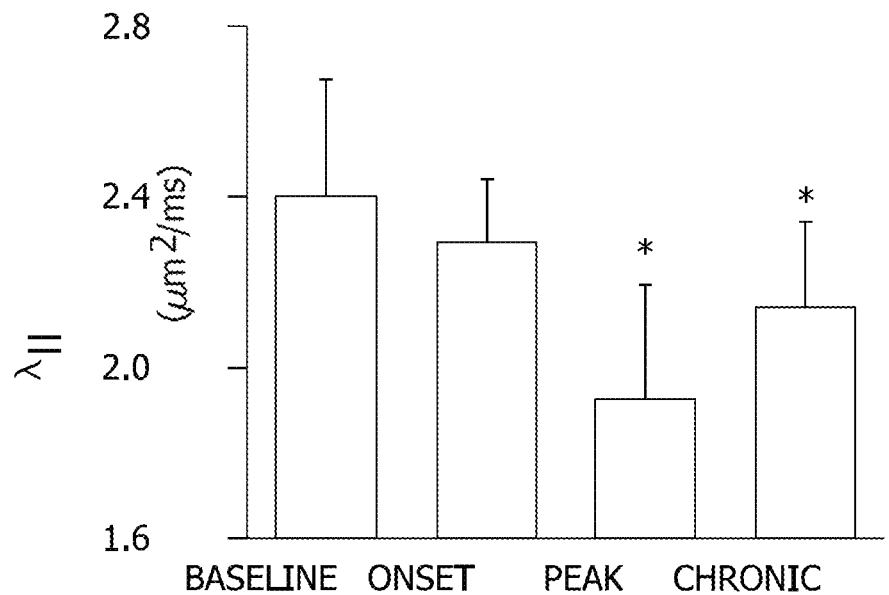
FIG. 43 is a cross-sectional time course of in vivo DBSI derived $\lambda_\parallel$ from B6-EAE mice at baseline (control), onset, peak, and chronic disease states.
Figure 44:
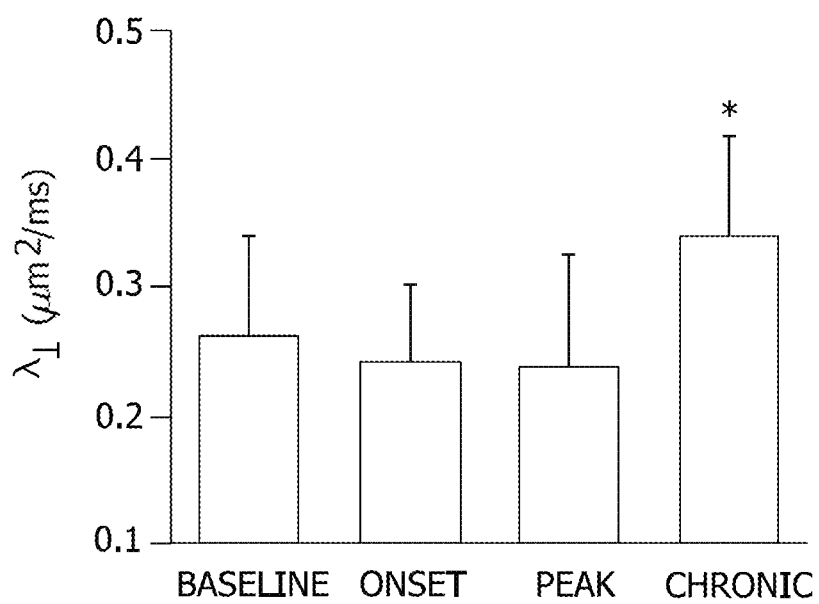
FIG. 44 is a cross-sectional time course of in vivo DBSI derived $\lambda_\perp$ from B6-EAE mice at baseline (control), onset, peak, and chronic disease states.

A cross-sectional study was performed on 12 B6-EAE mice spinal cords at baseline (control), onset, peak, and chronic states, followed by IHC (N=5 for each time point). In the representative mouse, $\lambda_\parallel$ decreased at the peak and recovered slightly at the chronic EAE stage, consistent with decreased SMI-31 staining followed by the recovery of the staining as is shown by FIGS. 42 and 43. Increased $\lambda_\perp$ was seen at EAE peak and continued to increase to the chronic EAE stage, consistent with the MBP staining gradually losing its intensity FIGS. 42, and 44.

Figure 45:
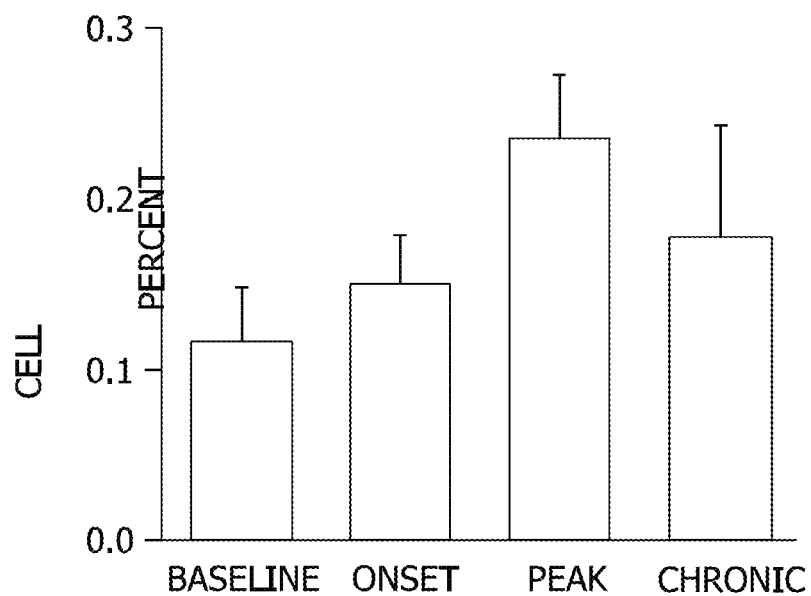
FIG. 45 is a cross-sectional time course of in vivo DBSI derived cell intensity percentage from B6-EAE mice at baseline (control), onset, peak, and chronic disease states.
Figure 46:
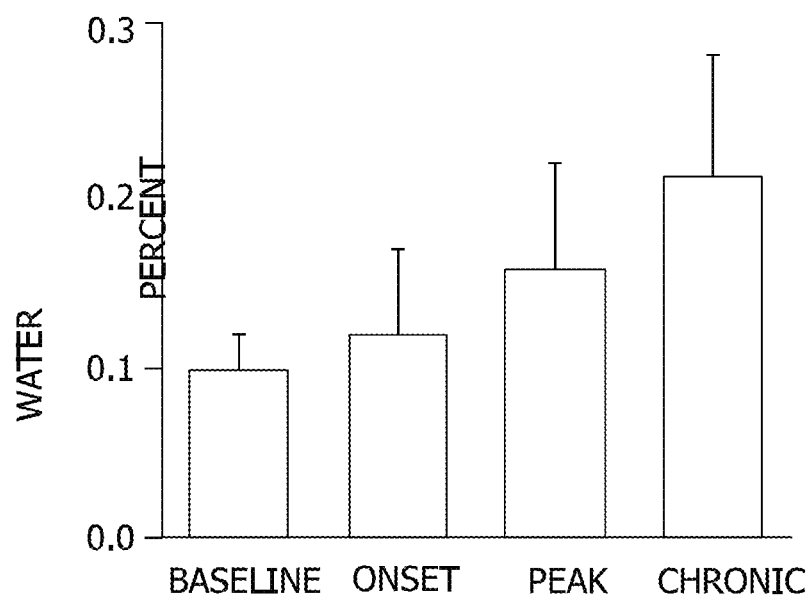
FIG. 46 is a cross-sectional time course of in vivo DBSI derived water intensity percentage from B6-EAE mice at baseline (control), onset, peak, and chronic disease states.

DBSI revealed cell infiltration at peak EAE, consistent with DAPI staining and clearly indicating the presence of inflammation (FIGS. 42 and 45). Quantitative analysis of the ventrolateral white matter DBSI parameters closely reflects the same pathology profile suggested by IHC shown in FIGS. 43-46. DBSI reflects axon and myelin injury more accurately than that previously determined by DTI, and correctly depicts inflammatory pathological features of the spinal cord white matter from EAE mice in terms of both cell infiltration and vasogenic edema as shown in FIGS. 45 and 46.

A segment of autopsy cervical spinal cord, fixed in 10% formalin, from 54 years old Caucasian female with 22-year disease duration was examined on a 4.7-T preclinical MR scanner: Varian DirectDrive™ console, 15-cm inner diameter, actively shielded Magnex gradient coil (60 G/cm, 270 μs rise time). Tissue contained in a 3-ml syringe with 10% formalin was placed in a custom-made solenoid coil for data acquisition using the following parameters: TR 2s, TE 39 ms, Δ 20 ms, δ 8 ms, slice thickness 0.5 mm, number of slices 5, field-of-view 2.4×2.4 cm$^2$, number of averages 1, data matrix 192×192.

Figure 47:
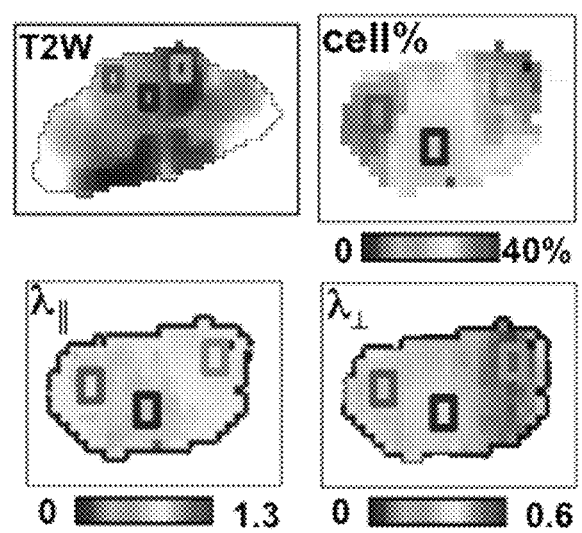
FIG. 47 is an ex vivo DBSI of a human MS autopsy spinal cord specimen.
Figure 48:
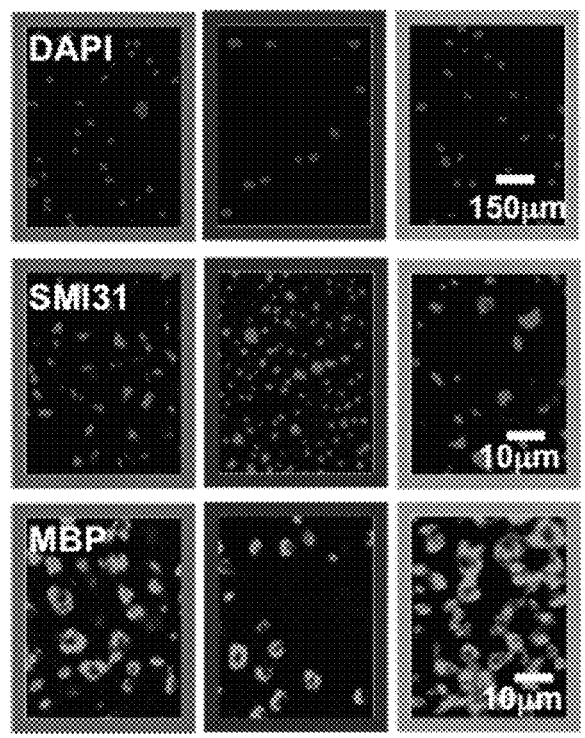
FIG. 48 is ex vivo histology images of a human MS autopsy spinal cord specimen.
Figure 49:
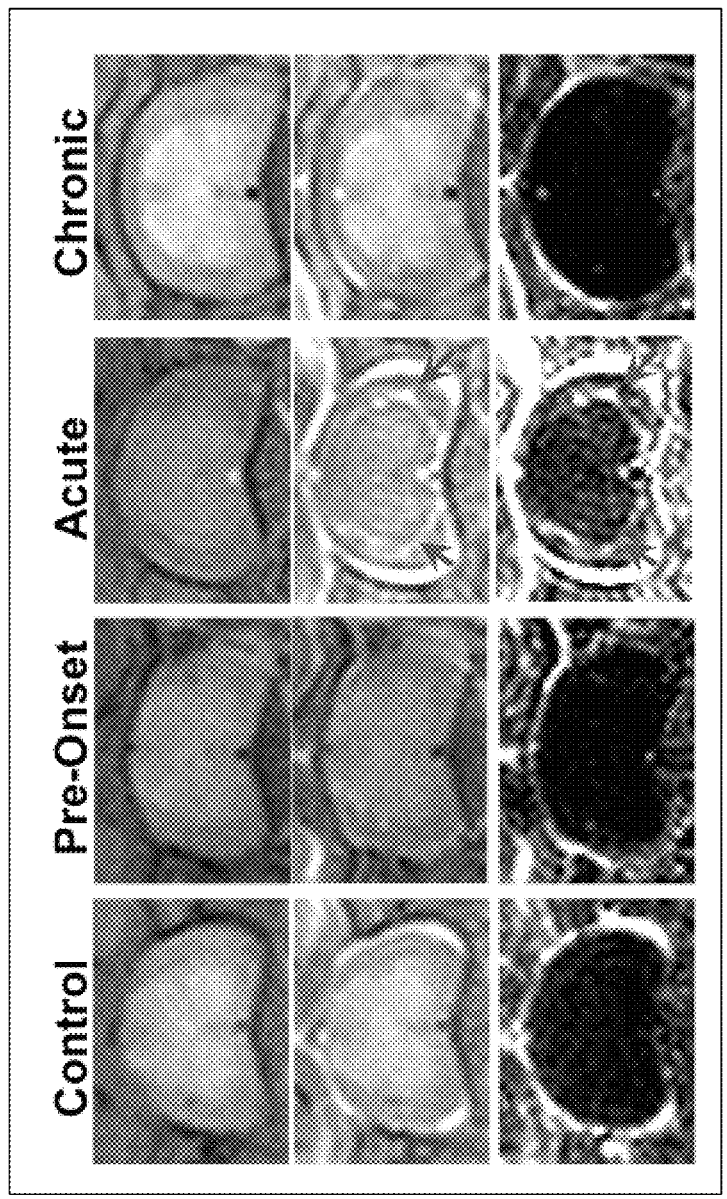
FIG. 49 is T1W MRI images of mouse spinal cords.
Figure 50:
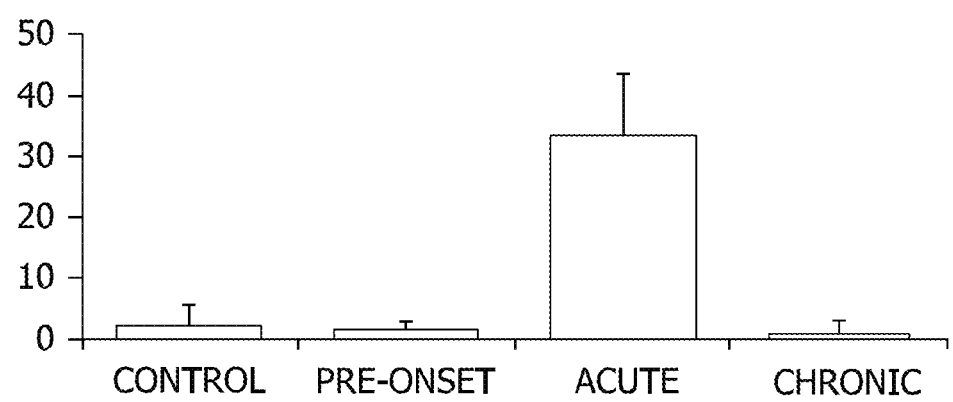
FIG. 50 is a quantitative analysis of a percentage enhancement map of FIG. 49.

Diffusion sensitizing gradients were applied in 99 directions with max b-value=3200 s/mm$^2$. In plane resolution was 125×125 μm$^t$. DBSI/DTI maps were coregistered with IHC images and an ROI analysis was employed after co-registration of MRI and IHC images as shown in FIGS. 47 and 48. Diffuse white-matter injury was present in the dorsal column, consistent with the recorded upper extremity numbness of this patient. Significantly increased cell infiltration was seen in all three ROIs, consistent with DAPI staining. The effect of infiltrating cells on diffusion is evident by examining DTI-derived $\lambda_\parallel$ at (0.36±0.02 μm$^2$/ms) and (0.31±0.01 μm$^2$/ms, total 16 image voxels, p=0.07) from the left and right ROI of the dorsal column, where more cell infiltration was noted. In contrast, DBSI-derived $\lambda_\parallel$ at the left (0.81±0.03 μm$^2$/ms) and right (0.74±0.03 μm$^2$/ms, total 16 voxels, p=0.0005) ROI was significantly different, revealing more axonal injury at the right ROI, consistent with the SMI-31 staining. Similarly, DBSI-derived $\lambda_\perp$ reveals that the severity of demyelination is again consistent with the MBP staining. This coregistered ROI analysis confirms that DBSI is consistent with IHC findings (FIGS. 47 and 48).

Spherical Harmonic Decomposition (SHD) has been proposed as a method for classifying imaging voxels into isotropic, single-, and multi-fiber components based on SHD coefficients. However, SHD cannot accurately estimate the intra-voxel fiber numbers, fiber volume fractions, fiber anisotropy, or fiber orientations. Even in the simple case of two fibers, it is not possible to use SHD to uniquely determine the intra-voxel fiber numbers and orientation since both the volume fraction and relative fiber orientations interfere with the higher order SHD components in a similar fashion. Similar to DSI, SHD also requires high diffusion weighting gradients. In contrast, DBSI facilitates separating and quantifying the isotropic and individual anisotropic (fiber) components while maintaining the use of low diffusion weighting gradient magnitudes.

Q-ball imaging of the human brain is a method closely related to DSI. In DSI, the ODF is reconstructed by sampling the diffusion signal on a Cartesian grid, Fourier transformation, followed by the radial projection. Q-ball imaging acquires the diffusion signal spherically and reconstructs the ODF directly on the sphere. The spherical inversion is accomplished with the reciprocal space funk radon transform (FRT), a transformation of spherical functions that maps one function of the sphere to another. Q-ball and DSI are theoretically equivalent and generate similar ODF. However, q-ball methods are not capable of estimating fiber angles as well as quantifying multiple tensor parameters.

Independent Component Analysis (ICA) has been proposed for application in DTI tractography to recover multiple fibers within a voxel. Although the angle of crossing fibers within voxels can be estimated to within 20 degrees of accuracy, eigenvalues cannot be recovered to obtain the complete tensor information such as the Fractional Anisotropy (FA).

Moreover, it has been proposed to use a high angular resolution diffusion imaging (HARDI) data set as a method that is capable of determining the orientation of intra-voxel multiple fibers. For example, up to 2 fiber components and one isotropic component may be considered. Similar to DBSI, HARDI methods have employed a mixed Gaussian model incorporating the isotropic diffusion component. However, HARDI is very different in nature compared with DBSI. For example, (i) HARDI fails in voxels with more than 2 fibers; (ii) HARDI does not work in voxels with more than 1 isotropic component, which is commonly seen in pathological conditions with both cell infiltration and edema; (iii) HARDI fails to compute isotropic diffusivity, improving fiber orientation estimation at the expense of removing the isotropic diffusion component; (iv) HARDI cannot compute the absolute axial and radial diffusivities for each component fiber; (v) HARDI cannot compute the true volume fractions of each fiber or isotropic component. In contrast, DBSI facilitates achieving all the goals enumerated above because it may be used to solve for issues that HARDI ignores or simplifies. HARDI-based methods have aimed to enhance the tools available for fiber tracking but do not compute the directional diffusivities of fibers, the isotropic diffusivity, or true volume fractions.

In summary, diffusion MRI methods in the field currently focus on determining the primary orientation of crossing fibers within one voxel. To achieve this goal, most have to relax the condition needed for accurate estimation of diffusivity or the volume ratio of individual component. DBSI facilitates not only resolving the primary direction of each fiber component, but also identifying and quantifying one or more other physical properties available from the diffusion measurements.

With the quantified fraction, axial diffusivity, and radial diffusivity of each fiber as well as the fraction and mean diffusivity of each isotropic diffusion tensor, CNS white matter pathology maps corresponding to the classic immunohistochemistry staining of excised tissues may be generated. For example, based on the axial diffusivity distribution intact (or injured) axonal fiber tract fraction may be estimated and the fraction distribution map may be generated to reflect the classic phosphorylated neurofilament (SMI-31, for intact axons), or dephosphorylated neurofilament (SMI-32, for injured axons), staining. The restricted isotropic diffusion component estimated using DBSI constitutes a map of cell distribution corresponding to nucleus counting using DAPI staining on the fixed tissue allowing a direct estimate the extent of inflammation in patient CNS white matter.

In the preceding discussion, a method approach has been developed incorporating the diffusion profile of each component within the image voxel to perform the tissue classification based on the raw diffusion MRI data. The typical classification is performed using the generated parameters, not the source data. This approach generates realistic "non-invasive histology" maps of various CNS white matter pathologies directly related to the actual immunohistochemistry staining that is only available after tissue excision and fixation. Although an accurate assessment of the underlying white matter pathologies may or may not correctly reflect clinical symptoms during the early phase of the disease, it would likely predict the long-term patient disability. Such a quantitative assessment of CNS white matter that tracks integrity would enable a clinically-based intervention for the patient. For example, current MS treatments follow a standard dosing regimen, with limited opportunity to adjust management for individual patient responses. By quantitatively distinguishing and tracking inflammation, and axon and myelin injury, DBSI provides the opportunity for efficient assessment of disease-modifying interventions and allows treatment planning to reflect individual patient response.

Quantitative Differentiation of Heterogeneous Tumor Structures

In various aspects, the DBSI method, or DBSI with extended isotropic spectrum (DBSI-EIS), disclosed herein above may be modified to enable a DBSI-based diagnostic method configured to quantitatively differentiate different types or grades of tumor cells as well as to identify regions of hyperperfusion or hypoperfusion associated with the tumor. In various aspects, a noninvasive, non-radiative technique to provide multiple parametric images to profile the heterogeneity of tumors is disclosed. Using the disclosed method, tumor cell microstructures (cells with different grades), edema, and vascular structures that perfuse the tumor may be measured in a single clinical imaging scan.

Provided herein is a method for analyzing a diffusion basis spectrum imaging MRI, the method including obtaining a plurality of diffusion magnetic resonance (MR) signals for a plurality of voxels representing at least a portion of a patient tissue; computing, by a processor, an anisotropic diffusion portion and an isotropic diffusion portion of the diffusion MR signals; calculating, by the processor, an isotropic diffusion spectrum from the isotropic diffusion portion of the diffusion MR signals, the isotropic diffusion spectrum comprising a plurality of apparent diffusion coefficient (ADC) values; and calculating, by the processor, an associated percent contribution of each ADC value to a total isotropic diffusion spectrum magnitude.

The isotropic diffusion spectrum may include an extended isotropic diffusion spectrum. The method may further include calculating at least one isotropic spectrum signal comprising a portion of the isotropic diffusion spectrum between a first ADC threshold value and a second ADC threshold value, wherein one or more isotropic spectrum signals are associated with a structure within the patient.

Further provided herein is a method for generating an image utilizing diffusion basis spectrum imaging (DBSI) MRI. The method may include obtaining a plurality of diffusion MR signals for a plurality of voxels representing at least a portion of a patient tissue; computing, by a processor, an anisotropic diffusion portion and an isotropic diffusion portion of the diffusion MR signals; calculating, by the processor, an isotropic diffusion spectrum from the isotropic diffusion portion of the diffusion MR signals, the isotropic diffusion spectrum comprising a plurality of apparent diffusion coefficient (ADC) values; calculating, by the processor, an associated percent contribution of each ADC value to a total isotropic spectrum magnitude; calculating, by the processor, at least one isotropic spectrum signal comprising a portion of the isotropic diffusion spectrum between a first ADC threshold value and a second ADC threshold value, each isotropic spectrum signal associated with a structure within the patient; and generating at least one DBSI image comprising a map of at least one isotropic spectrum signal, the map comprising a projection of a percent contribution of one isotropic spectrum signal to the total isotropic spectrum onto an image reconstructed using the plurality of voxels.

27. The method of claim 26, wherein the isotropic diffusion spectrum comprises an extended isotropic diffusion spectrum.

It was surprisingly discovered that DBSI-EIS parameter values and pathology findings exhibited an excellent correlation. In particular, it was discovered that various grades of tumor cells produced isotropic diffusion signals that were selectively partitioned into subranges of apparent diffusion coefficients (ADCs) within the isotropic diffusion spectrum produced by DBSI-EIS methods. Further, it was discovered that perfusion associated with tumors produced isotropic diffusion signals that occupy a range of the isotropic spectrum characterized by ADC values above the ADC range previously analyzed using the previous DBSI method described herein above.

In various aspects, the DBSI-EIS method may visualize and quantify the heterogeneity of tumor grade, indicating those areas where the tumor is more aggressive, and therefore may require different treatment strategies. The ability to identify tumor heterogeneity in various aspects of the disclosed method has significant clinical implications during the diagnosis and treatment period, since the most malignant portion of a tumor may be targeted and under-diagnosis due to incorrect biopsy sampling can be avoided. Further, areas of recurrent tumor may be more easily identified in the treatment follow-up period against a background of abnormal signals that typically includes a mix of both tumor-related and post-treatment changes.

The DBSI-EIS method disclosed herein overcomes at least several of the limitations of existing methods. The disclosed DBSI-EIS method may reduce the time to diagnose a tumor in a patient. Anatomical imaging alone requires ominous time-dependent morphological changes such as invasion, gross tumor growth or new lymphadenopathy required to diagnose failure of treatment. PET/CT physiological imaging requires a time delay before accurate diagnosis, as it can only be performed 6-8 weeks after end of treatment of most tumors to avoid false positive results. This time lag in imaging diagnosis may result in delayed treatment or treatment modification, which potentially negatively impacts the patients' morbidity and mortality. DBSI-EIS may identify response to therapy within a very short time frame after termination of treatment. Similarly DBSI-EIS may potentially identify recurrence of a tumor in a shorter time frame than anatomical imaging alone.

In addition, the DBSI-EIS method disclosed herein enables multi-parametric imaging beyond the capabilities of existing visualization methods such as PET/CT. PET/CT imaging typically provides a single parameter of disease burden, abnormal tracer activity. The DBSI-EIS method disclosed herein enables the evaluation of multiple parameters in a single study, such as cellularity, perfusion and neuroinflammatory/edema markers.

With respect to perfusion imaging, the DBSI-EIS method disclosed herein enables visualization of perfusion at higher spatial resolution than existing methods, such as DCE or DSC-based perfusion imaging, allowing for more accurate identification of subtle abnormal areas of increased relative cerebral blood volume (rCBV) associated with brain tumors.

In various aspects, the modified DBSI method disclosed herein provides high-quality imaging of multiple parameters of tumors non-invasively and without need for extrinsic radiative markers. As a result, DBSI may be utilized repeatedly on a patient to detect a condition, diagnose a condition, monitor the effects of a treatment, and provide follow-up imaging without limitations associated with invasive procedures such as lumbar punctures or the accrual of markers such as gadolinium or radiative PET tracers in the tissues of a patient.

Figure 54:
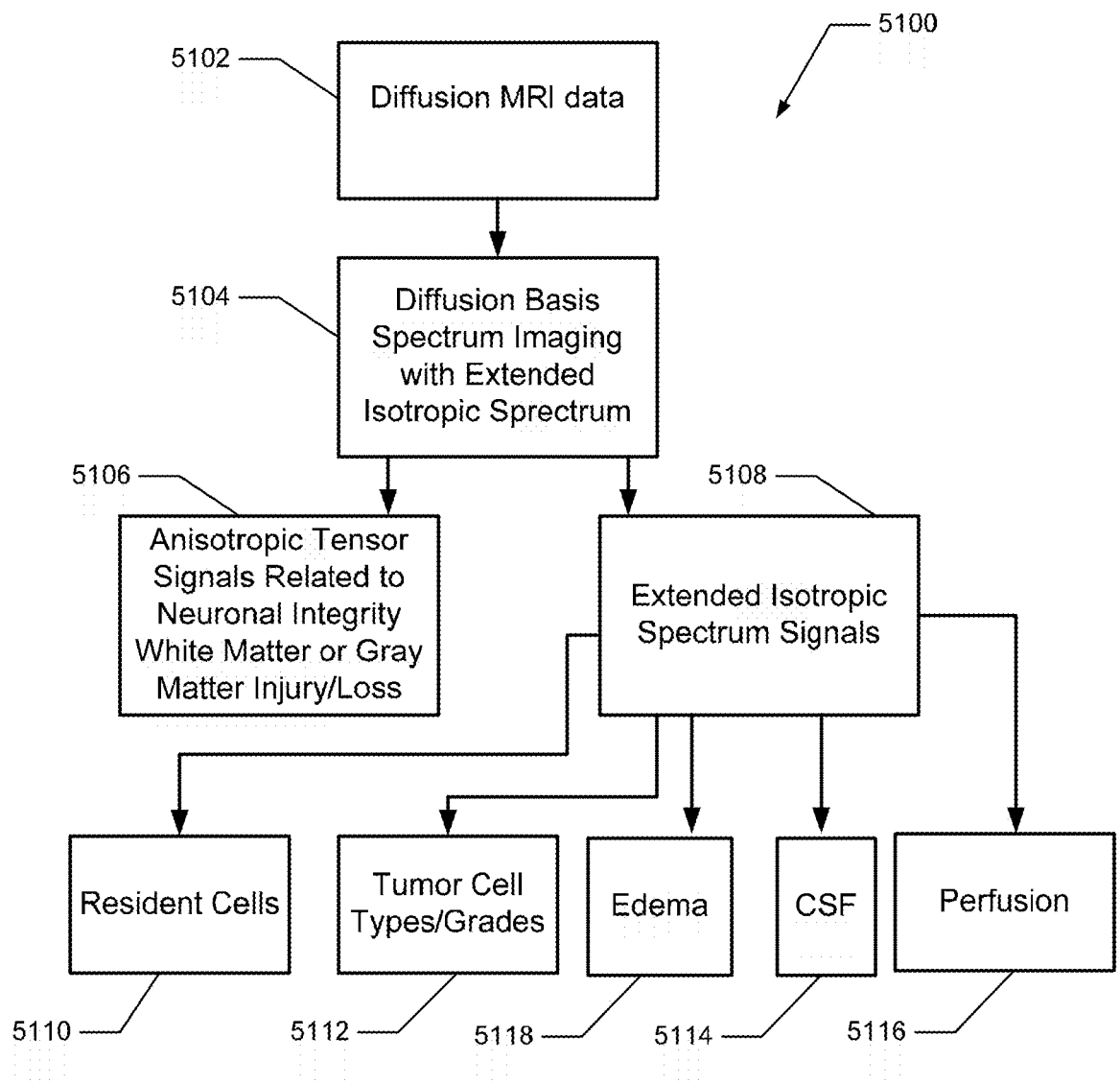
FIG. 54 is a flow chart illustrating a modified DBSI imaging method in one aspect.

FIG. 54 is a flow chart illustrating a modified DBSI method 5100 in one aspect. The method 5100 includes obtaining diffusion MRI data measured from a patient at 5102. In various aspects, the diffusion MRI data includes a plurality of diffusion MR signals associated with a plurality of voxels representing a region of interest within the patient including, but not limited to, the skull or brain of the patient. The plurality of diffusion MR signals obtained at step S102 may be subjected to analysis using a diffusion basis spectrum imaging with extended isotropic spectrum (DBSI-EIS) at step S104. DBSI-EIS may also be known as neuro-immune imaging (NII).

DBSI-EIS is a modification of the DBSI method described herein above. In various aspects, DBSI-EIS determined an anisotropic portion of the diffusion MR signals and an isotropic portion of the diffusion MR signals using the previous analysis described herein above in association with Equation 2, Equation 3, and Equation 4. In one aspect, the anisotropic portion of the diffusion MR signals is used to calculate a plurality of anisotropic tensor signals related to neuronal integrity at 5106. Non-limiting examples of anisotropic signals include: $\lambda_\perp$ and $\lambda_\parallel$ for each identified fiber within a voxel, fiber direction, and fiber volume fraction. In various aspects, changes in any one or more of the anisotropic signals may indicate distortion or displacement of neuron fibers due to tumor growth. In various other aspects, changes in any one or more of the anisotropic signals may indicate white matter or gray matter injury/loss.

Figure 55:
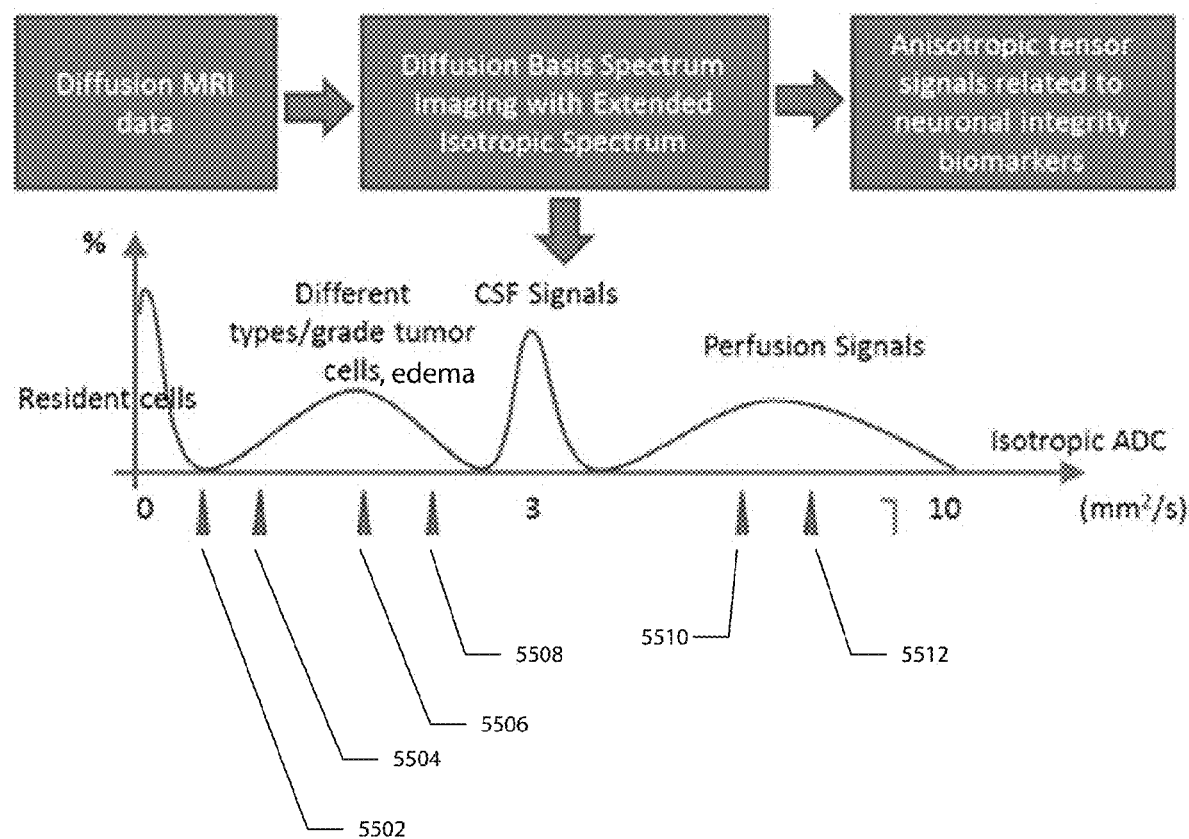
FIG. 55 is a graph summarizing the isotropic diffusion spectrum and structures associated with isotropic diffusion within various ranges of ADC on the isotropic diffusion spectrum.
Figure 78A:
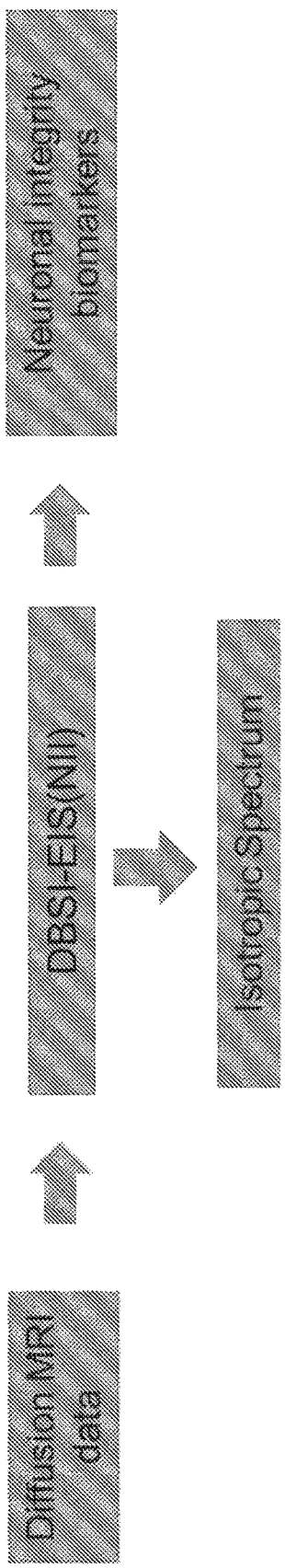
FIG. 78A is a block diagram of DBSI-EIS, or neuroimmune imaging (NII).
Figure 78B:
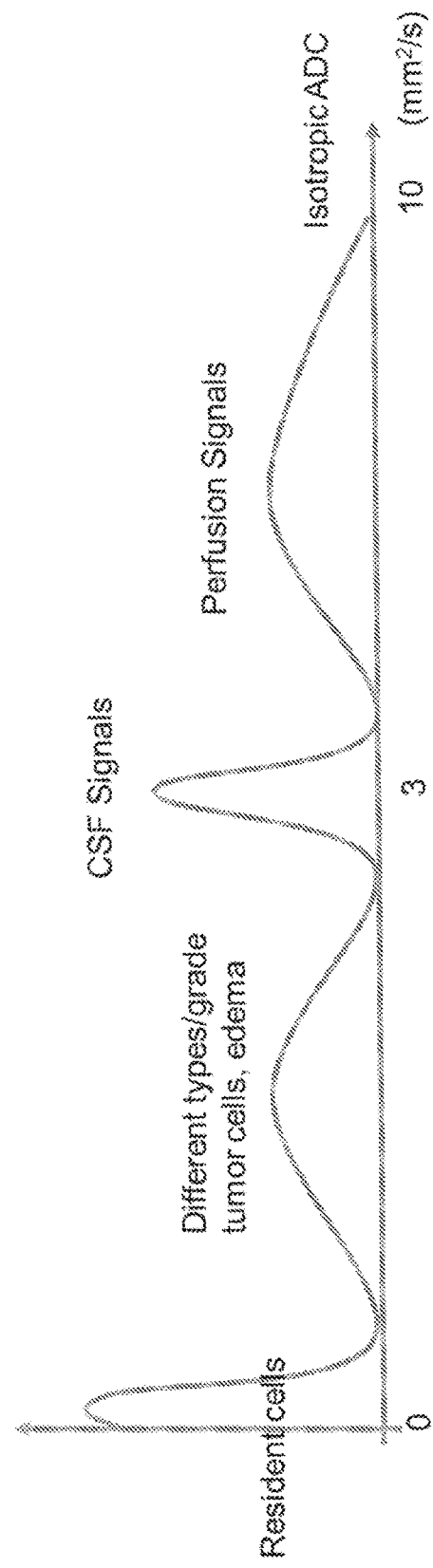
FIG. 78B is a sample graph the isotropic spectrum with isotropic ADC values for various signals.
Figure 79:
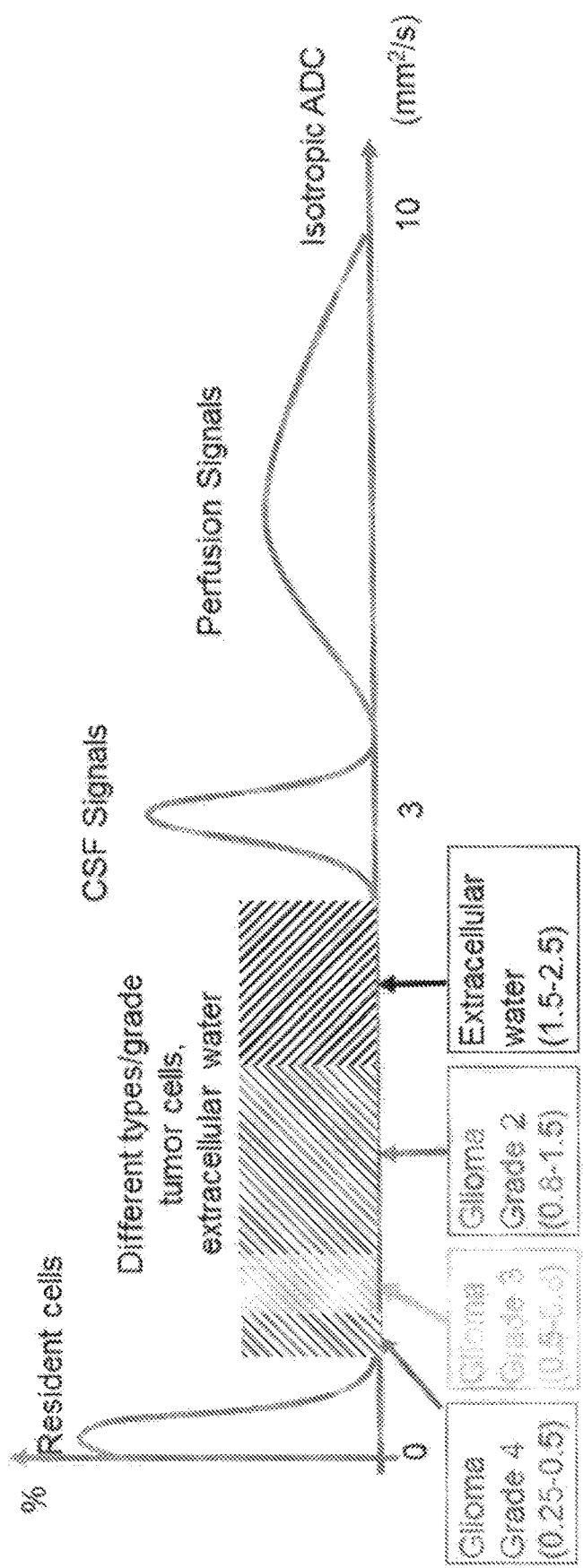
FIG. 79 is a graph showing the ADC values of tumor cells, such as Glioma grade 4, Glioma grade 3, Glioma grade 2, and extracellular water.
Figure 80A:
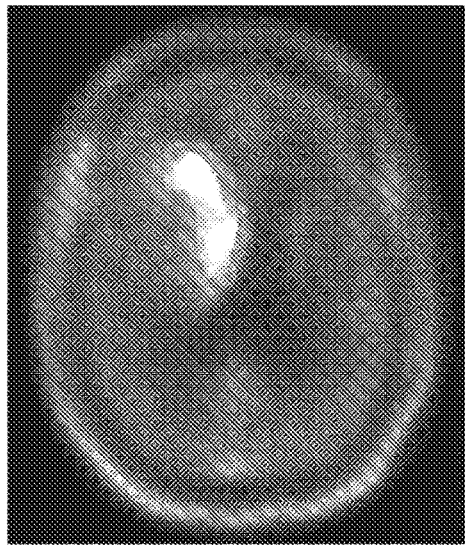
FIG. 80A is an FDOPA image showing heterogeneous 3D spatial distributions for Glioma tumor cells.
Figure 80B:
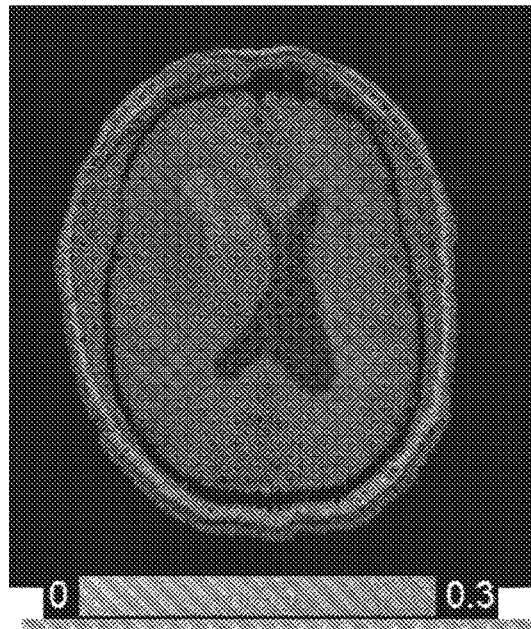
FIG. 80B is a DBSI-EIS image showing heterogeneous 3D spatial distributions for Glioma grade 2 tumor cells and DBSI-EIS tumor cell fraction.
Figure 80C:
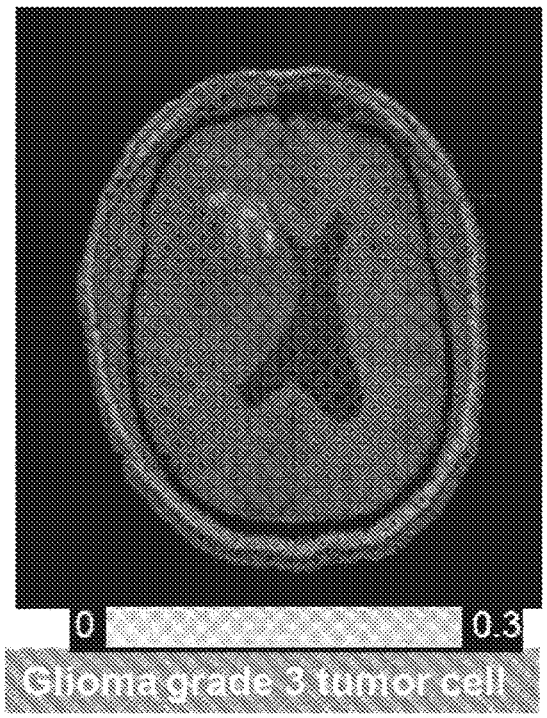
FIG. 80C is a DBSI-EIS image showing heterogeneous 3D spatial distributions for Glioma grade 3 tumor cells and DBSI-EIS tumor cell fraction.
Figure 80D:
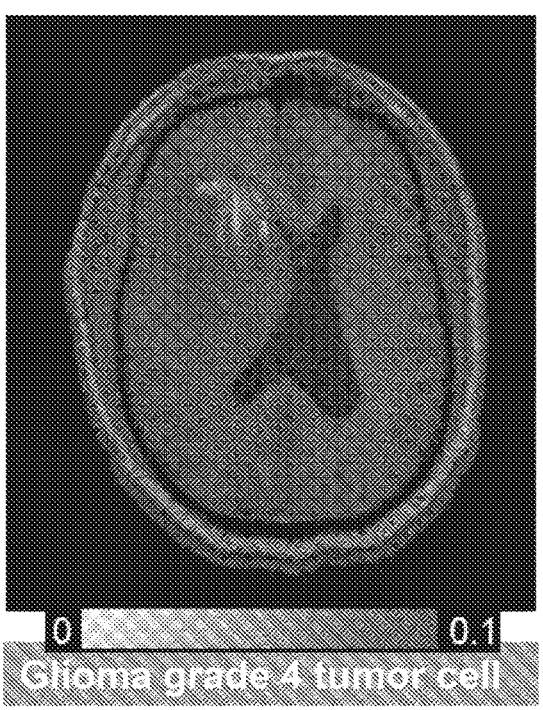
FIG. 80D is a DBSI-EIS image showing heterogeneous 3D spatial distributions for Glioma grade 4 tumor cells and DBSI-EIS tumor cell fraction.

Referring again to FIG. 54, the method 5100 may further include calculating a plurality of isotropic spectrum signals at 5108. In various aspects, the isotropic spectrum signals include subsets of the isotropic portion of the diffusion MR signals associated with a range of apparent diffusion coefficients (ADCs) as described herein previously. FIGS. 55, 78B, and 79 are graphs illustrating schematically an extended isotropic spectrum obtained in association with the DBSI-EIS method. It is to be noted that the isotropic spectrum analyzed according to various aspects of the DBSI-EIS method 5100 is characterized by ADC values ranging from 0 up to about 50 μm²/ms. In various aspects, the isotropic spectrum analyzed may be characterized by ADC values ranging from about 0 to about 10 mm²/s, from about 0 to about $20 \times 10^{-3}$ mm²/s, from about 0 to about $30 \times 10^{-3}$ mm²/s, from about 0 to about $40 \times 10^{-3}$ mm²/s, and from about 0 mm²/s and about $50 \times 10^{-3}$ mm²/s. By contrast, the ADC values characterizing the isotropic spectrum analyzed by the previous DBSI method described herein above typically ranged from 0 to about 3 μm²/ms, as illustrated in FIG. 31.

In various aspects, neuro-immune imaging can provide multiple parametrical quantification of different grades of tumor cells and capillary blood perfusion within the tumor in a single clinical imaging scan. There are numerous grading systems for the tumors of the central nervous system. The grading system used herein is the World Health Organization (WHO) grading system. The WHO grade has four categories of tumors. Grade I tumors are slow-growing, nonmalignant, and associated with long-term survival. Grade II tumors are relatively slow-growing but sometimes recur as higher grade tumors. They can be nonmalignant or malignant. Grade III tumors are malignant and often recur as higher grade tumors. Grade IV tumors reproduce rapidly and are very aggressive malignant tumors. Generally speaking, the lower grades can have less aggressive biology.

Figure 81A:
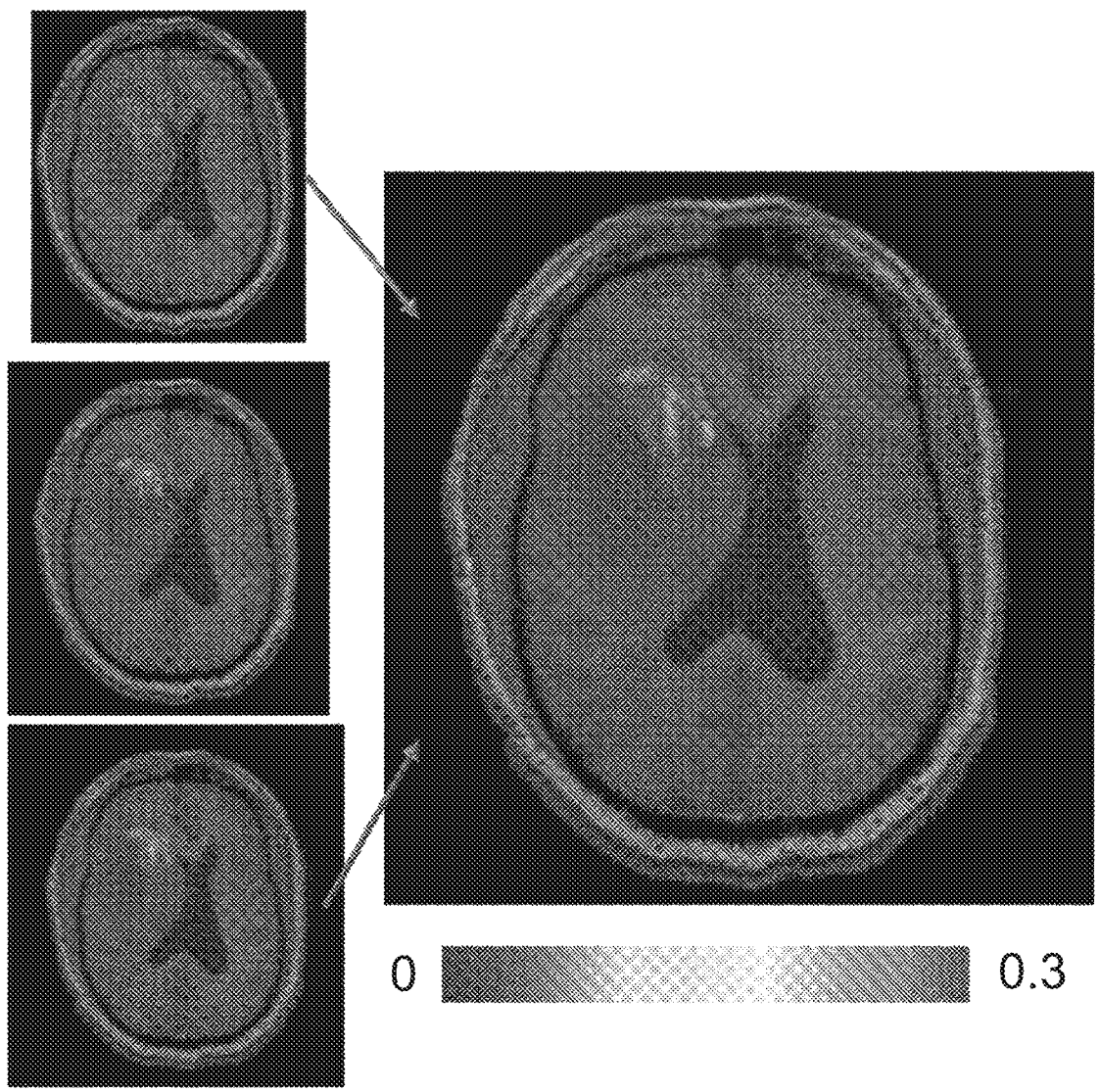
FIG. 81A is a 3D spatial distribution for all grades.
Figure 81B:
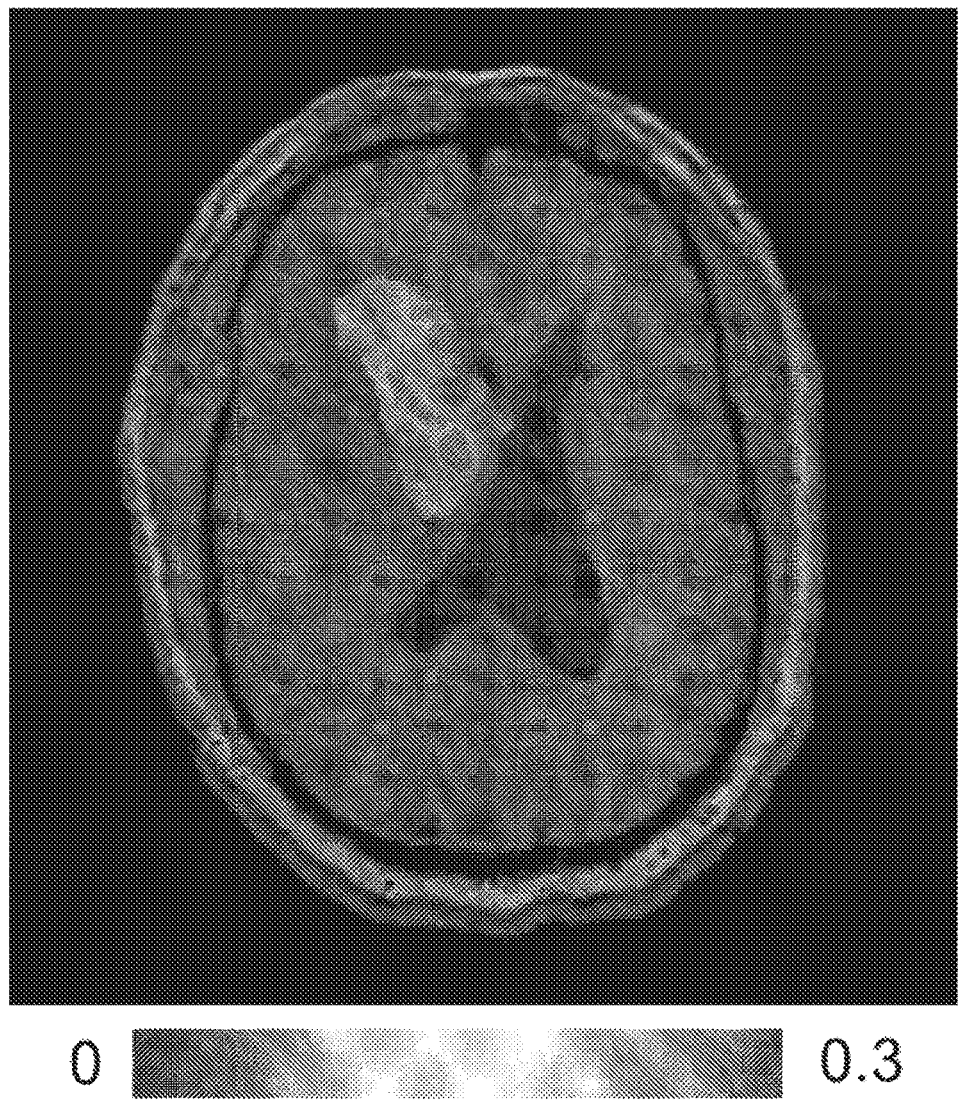
FIG. 81B is a DBSI-EIS perfusion 3D distribution.

Referring again to FIG. 55 and FIG. 79, the isotropic spectrum signals may be correlated with specific structures associated with a tumor in a patient including, but not limited to, resident healthy cells, tumor cells of various grades and/or types (a grade 1/2 brain tumor cell, a grade 3 brain tumor cell, a grade 4 tumor cell), edema, cerebrospinal fluid (CSF), and perfusion associated with the tumor. In various aspects, each isotropic spectrum signal may include a portion of the isotropic spectrum falling between ADC threshold values. As seen in FIGS. 55 and 78B, the ADC threshold values of tumor cells are between the ADC threshold values of resident cells on the lower end and CSF and perfusion ADC threshold values on the upper end. By way of non-limiting example, grade 4 tumor cells may be correlated with a portion of the isotropic diffusion spectrum between ADC threshold values 5502 and 5504, grade 3 tumor cells may be correlated with a portion of the isotropic diffusion spectrum between ADC threshold values 5504 and 5506, grade 1/2 tumor cells may be correlated with a portion of the isotropic diffusion spectrum between ADC threshold values 5506 and 5508, and perfusion associated with a tumor may be correlated with a portion of the isotropic diffusion spectrum between ADC threshold values 5510 and 5512. FIGS. 80A-80D are exemplary heterogeneous 3D spatial distributions for glioma tumor cells with different grades, where the scale below each image indicates the NII tumor cell fraction. FIG. 81A is an exemplary 3D spatial distribution for all grades and FIG. 81B is an exemplary DBSI-EIS perfusion 3D distribution.

In various aspects, the isotropic spectrum signals may be correlated with specific structures by an analysis of DBSI-EIS measurements along with corresponding clinical data obtained from the same structures using imaging modalities other than the DBSI-EIS method. In various aspects, any known clinical data may be used to associate isotropic spectrum signals with specific patient structures, including, but not limited to biopsy or autopsy data, CT data, PET data, any other suitable imaging modality. In some cases, the MRI visualization is followed by a biopsy to better characterize the cells and other structures associated with the tumor including grade(s) of tumor cells, vascularization of the tumor, and the heterogeneity of the tumor cells. The biopsy may provide information used to inform an appropriate course of treatment. In various other aspects, any known analysis method may be used to compare the DBSI-EIS isotropic spectra to clinical data without limitation.

Figure 56:
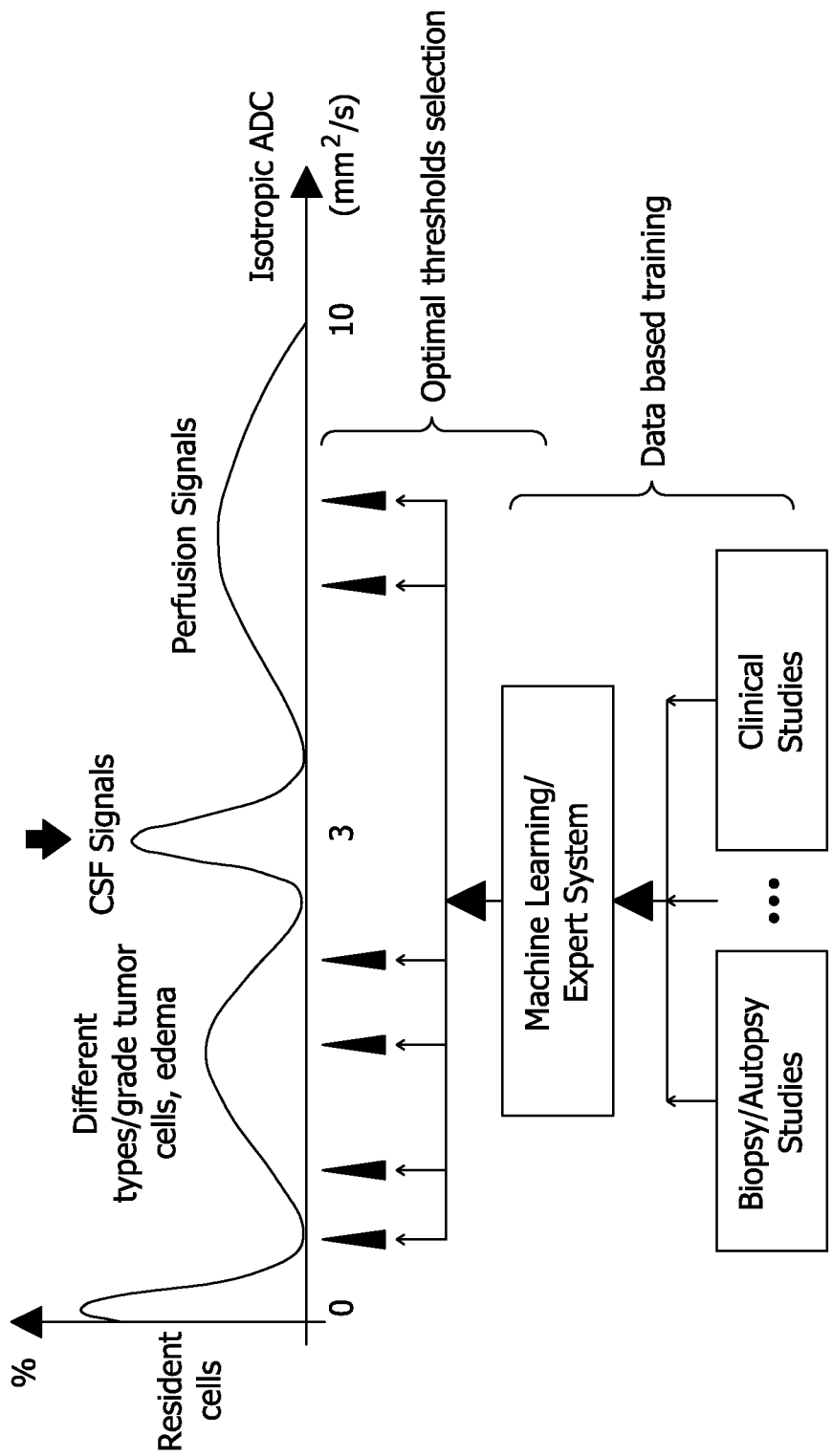
FIG. 56 is a flowchart summarizing a machine learning method of identifying isotropic spectrum signals in one aspect.

In one aspect, a machine learning or expert system may be used to identify specific isotropic spectrum signals and to associate the isotropic spectrum signals with specific structures associated with tumors in various patients. FIG. 56 is a schematic diagram summarizing a machine learning/expert system approach to identifying isotropic spectrum signals. Referring to FIG. 56, training data obtained from various clinical data including, but not limited to, biopsy PET images, biopsy, autopsy, CT, PET, and other clinical data, may be transferred into an expert system. During training, the expert system may identify a plurality of thresholds that define the upper and lower ADC values of specific isotropic spectrum signals associated with specific structures in the patient. In this aspect, any known suitable methods associated with machine learning may be used by the expert system to identify the plurality of thresholds. In one non-limiting example, the expert system, such as an IBM Watson Health expert system, may make use of a method involving optimization of one or more cost functions to identify the plurality of threshold values.

In various examples, the DBSI-EIS method may be used to characterize and quantify heterogeneity of diseased tissue of a patient. In one non-limiting example, the DBSI-EIS method may be used to characterize and quantify heterogeneity in a tumor in a patient, such as a brain tumor. The DBSI-EIS method may identify one or more anisotropic tensor signals related to neuronal integrity (i.e. injury or loss of white or gray matter due to tumor) as described herein above. Further, the DBSI-EIS method may further identify extended isotropic spectrum signals comprising subranges of the isotropic spectrum falling between upper and lower threshold values.

The isotropic spectrum signals can be between ADC values of about 0 mm$^2$/s and about 50×10$^{-3}$ mm$^2$/s. In an aspect, grade 4 tumor cells, grade 3 tumor cells, and grade ½ tumor cells may be correlated with a portion of the isotropic diffusion spectrum between ADC threshold values of about 0 mm$^2$/s and about 2×10$^{-3}$ mm$^2$/s. In another aspect, edema and CSF may be correlated with a portion of the isotropic diffusion spectrum between ADC threshold values of about 1.8×10$^{-3}$ mm$^2$/s and about 4×10$^{-3}$ mm$^2$/s. In another aspect, perfusion associated with a tumor may be correlated with a portion of the isotropic diffusion spectrum between ADC threshold values of about 4×10$^{-3}$ mm$^2$/s and about 10×10$^{-3}$ mm$^2$/s. Non-tumor tissue or resident cells may be correlated with a portion of the isotropic diffusion spectrum between ADC threshold values of 0 mm$^2$/s and about 0.3×10$^{-3}$ mm$^2$/s. Tumor cells may be correlated with a portion of the isotropic diffusion spectrum under an ADC threshold value less than the ADC value for CSF and more than the ADC value for non-tumor tissue. Tumor cells may be correlated with a portion of the isotropic diffusion spectrum under an ADC threshold value of 3×10$^{-3}$ mm$^2$/s or between ADC threshold values of about 0.25×10$^{-3}$ mm$^2$/s and about 3×10$^{-3}$ mm$^2$/s. Grade 4 tumor cells, grade 3 tumor cells, and grade 1/2 tumor cells may be correlated with a portion of the isotropic diffusion spectrum between ADC threshold values of about 0 mm$^2$/s and about 1.5×10$^{-3}$ mm$^2$/s or about 1.8×10$^{-3}$ mm$^2$/s. Grade 4 tumor tissue may be correlated with a portion of the isotropic diffusion spectrum between ADC threshold values of between about 0.25×10$^{-3}$ mm$^2$/s or 0.3×10$^{-3}$ mm$^2$/s and about 0.5×10$^{-3}$ mm$^2$/s. Grade 3 tumor tissue may be correlated with a portion of the isotropic diffusion spectrum between ADC threshold values of between about 0.5×10$^{-3}$ mm$^2$/s and about 0.8×10$^{-3}$ mm$^2$/s. Grade 2 tumor tissue may be correlated with a portion of the isotropic diffusion spectrum between ADC threshold values of between about 0.8 and about 1.5×10$^{-3}$ mm$^2$/s or about 1.8×10$^{-3}$ mm$^2$/s. Edema may be correlated with a portion of the isotropic diffusion spectrum between ADC threshold values of about 1.8×10$^{-3}$ mm$^2$/s and about 2.5×10$^{-3}$ mm$^2$/s. CSF may be correlated with a portion of the isotropic diffusion spectrum between ADC threshold values of about 2.5×10$^{-3}$ mm$^2$/s and about 4×10$^{-3}$ mm$^2$/s. Perfusion may be correlated with a portion of the isotropic diffusion spectrum between ADC threshold values of between about 4×10$^{-3}$ mm$^2$/s and about 10×10$^{-3}$ mm$^2$/s. Perfusion may be correlated with a portion of the isotropic diffusion spectrum greater than about 10×10$^{-3}$ mm$^2$/s. Perfusion associated with a tumor may be correlated with a portion of the isotropic diffusion spectrum ADC threshold values of greater than 3×10$^{-3}$ mm$^2$/s or between about 4×10$^{-3}$ mm$^2$/s and about 50×10$^{-3}$ mm$^2$/s.

The thresholds may be selected based on published studies, patient data, and histology studies and the threshold selection may be further refined and optimized. Multiple diffusion time based diffusion MRI method may improve the accuracy of grade separation. In one example, the DBSI-EIS method may use the ADC threshold values according to Table 1:

TABLE 1

Isotropic Spectrum Signals: Brain Tumors

| Tissue/Cell Type | Lower ADC Threshold ($\times 10^{-3}$ mm$^2$/s) | Upper ADC Threshold ($\times 10^{-3}$ mm$^2$/s) |
|---|---|---|
| Normal resident cells | 0 | 0.3 |
| Grade 4 Glioblastoma | 0.3 | 0.5 |
| Grade 3 glioblastoma | 0.5 | 0.8 |
| Grade 1/2 Glioblastoma | 0.8 | 1.8 |
| Edema | 1.8 | 2.5 |
| CSF | 2.5 | 4 |
| Perfusion | 4 | 10 or more |

In some embodiments, the range of ADC values can be between 0 mm$^2$/s and about $50 \times 10^{-3}$ mm$^2$/s. For example, an ADC values can be about $0.01 \times 10^{-3}$ mm$^2$/s; about $0.02 \times 10^{-3}$ mm$^2$/s; about $0.03 \times 10^{-3}$ mm$^2$/s; about $0.04 \times 10^{-3}$ mm$^2$/s; about $0.05 \times 10^{-3}$ mm$^2$/s; about $0.06 \times 10^{-3}$ mm$^2$/s; about $0.07 \times 10^{-3}$ mm$^2$/s; about $0.08 \times 10^{-3}$ mm$^2$/s; about $0.09 \times 10^{-3}$ mm$^2$/s; about $0.1 \times 10^{-3}$ mm$^2$/s; about $0.2 \times 10^{-3}$ mm$^2$/s; about $0.3 \times 10^{-3}$ mm$^2$/s; about $0.4 \times 10^{-3}$ mm$^2$/s; about $0.5 \times 10^{-3}$ mm$^2$/s; about $0.6 \times 10^{-3}$ mm$^2$/s; about $0.7 \times 10^{-3}$ mm$^2$/s; about $0.8 \times 10^{-3}$ mm$^2$/s; about $0.9 \times 10^{-3}$ mm$^2$/s; about $1 \times 10^{-3}$ mm$^2$/s; about $1.5 \times 10^{-3}$ mm$^2$/s; about $2 \times 10^{-3}$ mm$^2$/s; about $2.5 \times 10^{-3}$ mm$^2$/s; about $3 \times 10^{-3}$ mm$^2$/s; about $3.5 \times 10^{-3}$ mm$^2$/s; about $4 \times 10^{-3}$ mm$^2$/s; about $4.5 \times 10^{-3}$ mm$^2$/s; about $5 \times 10^{-3}$ mm$^2$/s; about $5.5 \times 10^{-3}$ mm$^2$/s; about $6 \times 10^{-3}$ mm$^2$/s; about $6.5 \times 10^{-3}$ mm$^2$/s; about $7 \times 10^{-3}$ mm$^2$/s; about $7.5 \times 10^{-3}$ mm$^2$/s; about $8 \times 10^{-3}$ mm$^2$/s; about $8.5 \times 10^{-3}$ mm$^2$/s; about $9 \times 10^{-3}$ mm$^2$/s; about $9.5 \times 10^{-3}$ mm$^2$/s; about $10 \times 10^{-3}$ mm$^2$/s; about $10.5 \times 10^{-3}$ mm$^2$/s; about $11 \times 10^{-3}$ mm$^2$/s; about $11.5 \times 10^{-3}$ mm$^2$/s; about $12 \times 10^{-3}$ mm$^2$/s; about $12.5 \times 10^{-3}$ mm$^2$/s; about $13 \times 10^{-3}$ mm$^2$/s; about $13.5 \times 10^{-3}$ mm$^2$/s; about $14 \times 10^{-3}$ mm$^2$/s; about $14.5 \times 10^{-3}$ mm$^2$/s; about $15 \times 10^{-3}$ mm$^2$/s; about $15.5 \times 10^{-3}$ mm$^2$/s; about $16 \times 10^{-3}$ mm$^2$/s; about $16.5 \times 10^{-3}$ mm$^2$/s; about $17 \times 10^{-3}$ mm$^2$/s; about $17.5 \times 10^{-3}$ mm$^2$/s; about $18 \times 10^{-3}$ mm$^2$/s; about $18.5 \times 10^{-3}$ mm$^2$/s; about $19 \times 10^{-3}$ mm$^2$/s; about $19.5 \times 10^{-3}$ mm$^2$/s; about $20 \times 10^{-3}$ mm$^2$/s; about $20.5 \times 10^{-3}$ mm$^2$/s; about $21 \times 10^{-3}$ mm$^2$/s; about $21.5 \times 10^{-3}$ mm$^2$/s; about $22 \times 10^{-3}$ mm$^2$/s; about $22.5 \times 10^{-3}$ mm$^2$/s; about $23 \times 10^{-3}$ mm$^2$/s; about $23.5 \times 10^{-3}$ mm$^2$/s; about $24 \times 10^{-3}$ mm$^2$/s; about $24.5 \times 10^{-3}$ mm$^2$/s; about $25 \times 10^{-3}$ mm$^2$/s; about $25.5 \times 10^{-3}$ mm$^2$/s; about $26 \times 10^{-3}$ mm$^2$/s; about $26.5 \times 10^{-3}$ mm$^2$/s; about $27 \times 10^{-3}$ mm$^2$/s; about $27.5 \times 10^{-3}$ mm$^2$/s; about $28 \times 10^{-3}$ mm$^2$/s; about $28.5 \times 10^{-3}$ mm$^2$/s; about $29 \times 10^{-3}$ mm$^2$/s; about $29.5 \times 10^{-3}$ mm$^2$/s; about $30 \times 10^{-3}$ mm$^2$/s; about $30.5 \times 10^{-3}$ mm$^2$/s; about $31 \times 10^{-3}$ mm$^2$/s; about $31.5 \times 10^{-3}$ mm$^2$/s; about $32 \times 10^{-3}$ mm$^2$/s; about $32.5 \times 10^{-3}$ mm$^2$/s; about $33 \times 10^{-3}$ mm$^2$/s; about $33.5 \times 10^{-3}$ mm$^2$/s; about $34 \times 10^{-3}$ mm$^2$/s; about $34.5 \times 10^{-3}$ mm$^2$/s; about $35 \times 10^{-3}$ mm$^2$/s; about $35.5 \times 10^{-3}$ mm$^2$/s; about $36 \times 10^{-3}$ mm$^2$/s; about $36.5 \times 10^{-3}$ mm$^2$/s; about $37 \times 10^{-3}$ mm$^2$/s; about $37.5 \times 10^{-3}$ mm$^2$/s; about $38 \times 10^{-3}$ mm$^2$/s; about $38.5 \times 10^{-3}$ mm$^2$/s; about $39 \times 10^{-3}$ mm$^2$/s; about $39.5 \times 10^{-3}$ mm$^2$/s; about $40 \times 10^{-3}$ mm$^2$/s; about $40.5 \times 10^{-3}$ mm$^2$/s; about $41 \times 10^{-3}$ mm$^2$/s; about $41.5 \times 10^{-3}$ mm$^2$/s; about $42 \times 10^{-3}$ mm$^2$/s; about $42.5 \times 10^{-3}$ mm$^2$/s; about $43 \times 10^{-3}$ mm$^2$/s; about $43.5 \times 10^{-3}$ mm$^2$/s; about $44 \times 10^{-3}$ mm$^2$/s; about $44.5 \times 10^{-3}$ mm$^2$/s; about $45 \times 10^{-3}$ mm$^2$/s; about $45.5 \times 10^{-3}$ mm$^2$/s; about $46 \times 10^{-3}$ mm$^2$/s; about $46.5 \times 10^{-3}$ mm$^2$/s; about $47 \times 10^{-3}$ mm$^2$/s; about $47.5 \times 10^{-3}$ mm$^2$/s; about $48 \times 10^{-3}$ mm$^2$/s; about $48.5 \times 10^{-3}$ mm$^2$/s; about $49 \times 10^{-3}$ mm$^2$/s; about $49.5 \times 10^{-3}$ mm$^2$/s; about $50 \times 10^{-3}$ mm$^2$/s; or about $50.5 \times 10^{-3}$ mm$^2$/s. Recitation of each of these discrete values is understood to include ranges between each value. Recitation of each of a range is understood to include discrete values within the range.

Figure 91:
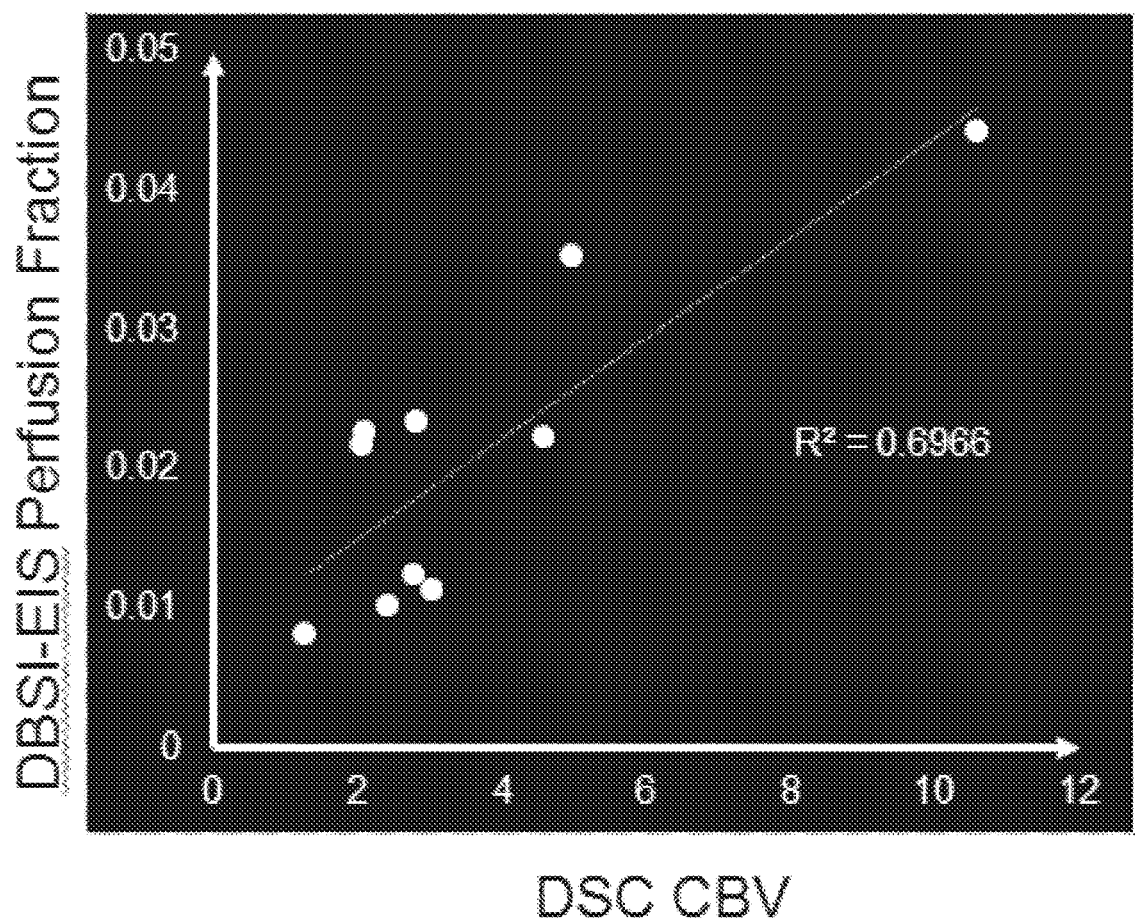
FIG. 91 is a graph showing how DBSI-EIS derived perfusion fraction correlates to DSC CBV.

In other aspects, the method may further include using the perfusion data from the extended isotropic spectrum to inform the threshold values or the grading of tumors. As seen in FIG. 91, the DBSI-EIS perfusion data generally correlates to CBV values, which generally correlates to tumor grade.

Figure 84:
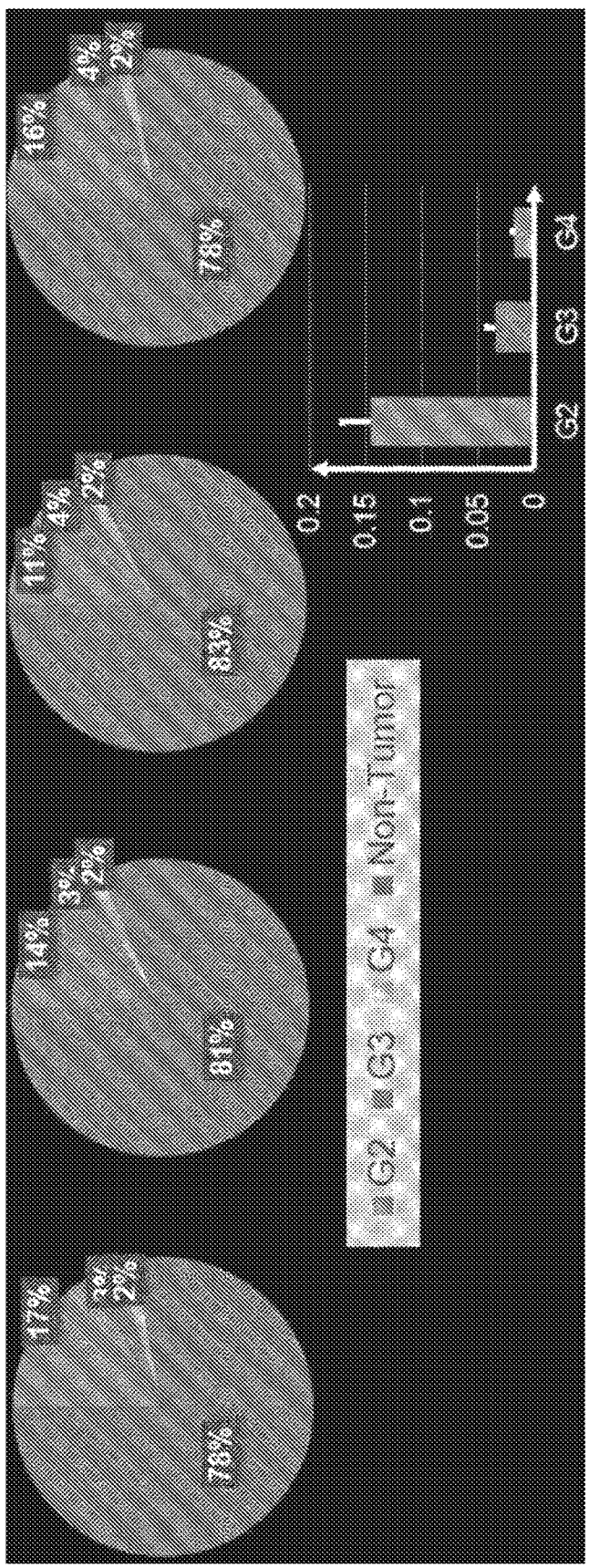
FIG. 84 shows DBSI-EIS-derived tumor grade ratios for low grade gliomas for several patients.
Figure 87A:
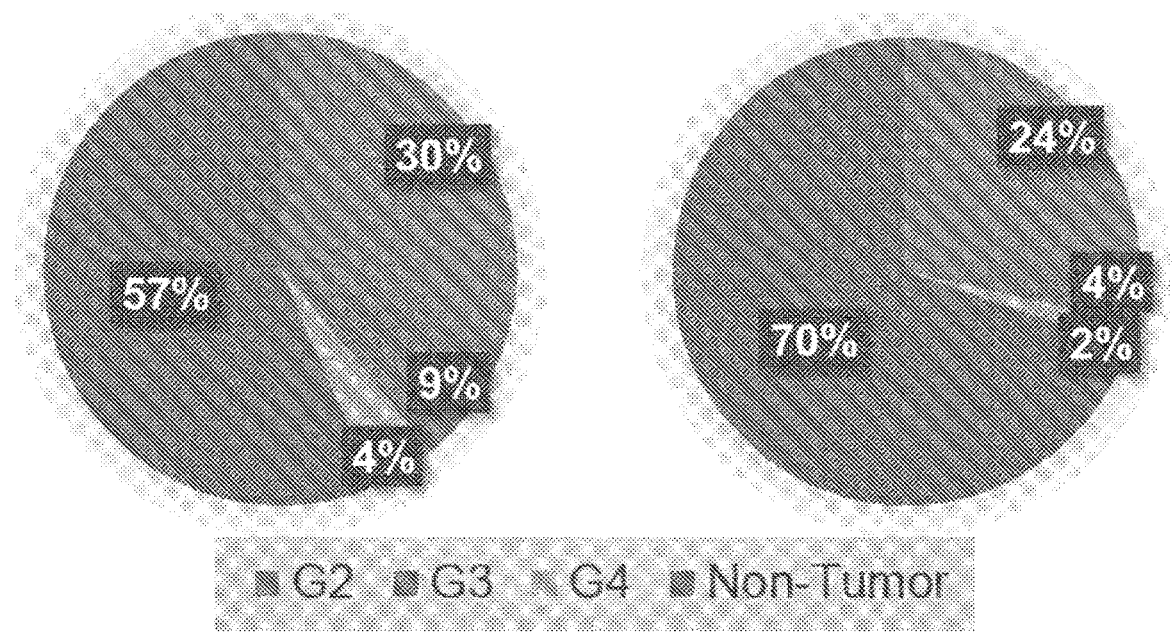
FIG. 87 shows DBSI-EIS-derived tumor grade ratios for high grade gliomas for several patients.
Figure 87B:
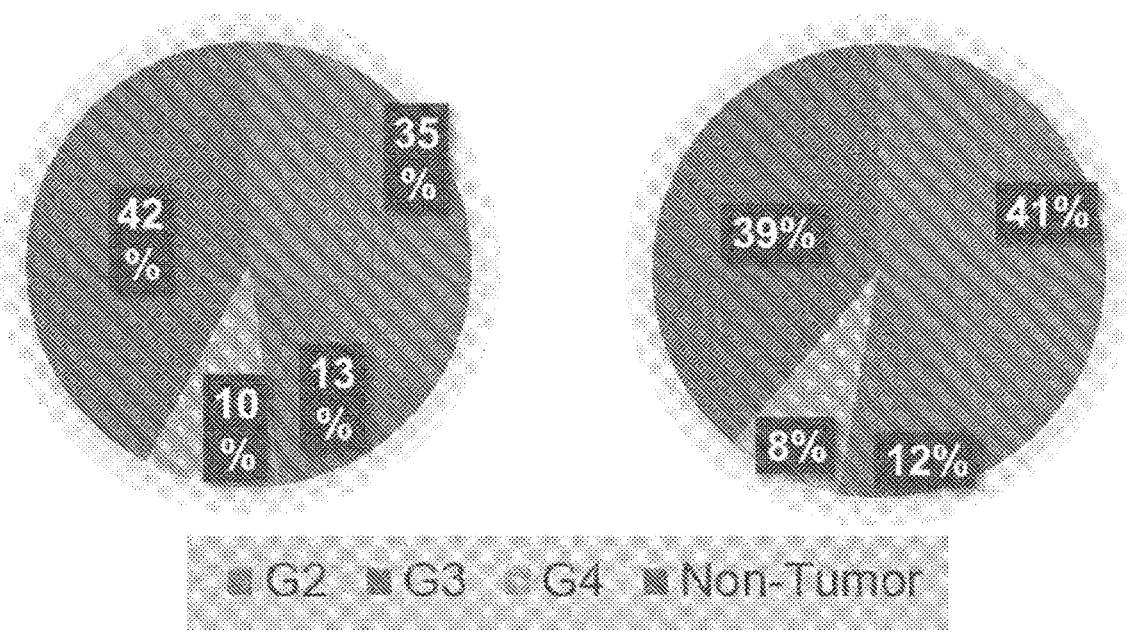

The method may further include determining a presence and an abundance of at least one structure within the patient based on a map of at least one extended isotropic spectrum signal. The map may include a projection of a percent contribution of one isotropic spectrum signal to the total isotropic spectrum onto an image reconstructed using the plurality of voxels. In another aspect, the map may be displayed as a percentage contribution of each isotropic spectrum signal to the total isotropic spectrum. For example, FIGS. 84 and 87A and 87B are pie charts of isotropic spectrum signals of various patients showing the percent contribution of grade 2 tumor cells, grade 3 tumor cells, grade 4 tumor cells, and non-tumor cells. In an aspect, the grade of the tumor is the highest grade of tumor cells identified in the patient beyond a threshold of about 5%. For example, the tumor is graded based on the highest grade tumor cell with a percent contribution greater than about 5%. If a cell fraction of grade 4 tumor cells is greater than 5% of the sum of non-tumor cells and tumor cell fraction, the tumor is classified as a grade 4 tumor. If the cell fraction of the grade 4 tumor cells is less than 5% and the cell fraction of grade 3 tumor cells is more than 5%, the tumor is classified as a grade 3 tumor. If the cell fraction of grade 4 tumor cells is less than 5% and the cell fraction of grade 3 tumor cells is less than 5%, then the tumor is classified as a low grade or grade 1/2 tumor. FIG. 84 shows pie charts for patients with grade 2 tumors, FIG. 87A shows a patient with a grade 3 tumor, and FIG. 87B shows a patient with a grade 4 tumor.

In various aspects, the DBSI-EIS method has been presented with respect to brain tumors. It is to be noted that the DBSI-EIS method may be applied similarly to a wide variety of tissues and disorders characterized by heterogeneous tissues or cells types associated with distinct isotropic spectrum signals. Non-limiting examples of disorders or tissues compatible with the DBSI-EIS method include: various kind of tumor/cancer (brain, spinal cord, prostate, ovarian, uterine, breast, and cervical cancer etc.); degeneration diseases (stroke, traumatic brain injury, Alzheimer's disease, Parkinson, ALS, multiple sclerosis, etc.), muscular injury and disorders (cardiac injury/inflammation due to disease and treatment, uterine/cervix injury/inflammation, skeleton muscle atrophy, etc.), acoustic neuroma; astrocytoma; anaplastic astrocytoma; anaplastic ependymoma; anaplastic oligodendroglioma; atypical teratoid rhaboid tumor (ATRT); brain stem glioma, chordoma; central neurocytoma; chondrosarcoma; choroid plexus; CNS lymphoma; craniopharyngioma; cysts; diffuse astrocytoma; dysembryoplastic neuroepithelial tumor; ependymoma; epidermoid; ganglioglioma; germ cell tumor; glioblastoma (GBM); glioma, hemangioma; hemangioblastoma; hemangiopericytoma; histiocytoma; hypothalamic hamartoma; juvenile pilocytic astrocytoma (JPA); lipoma; lymphoma; medulloblastoma; meningioma; metastatic brain tumor; neurilemmomas; neurofibroma; neuronal tumors; malignant lymphoma; malignant nerve sheath tumor; meningioma metastatic tumor; mixed neuronal-glial tumors; non-hodgkins lymphoma; olfactory neuroblastoma; oligoastrocytoma; oligodendroglioma; optic nerve glioma, pilocytic astrocytoma; pineal tumor; pineoblastoma; pituitary adenoma; pituitary tumor; pleomorphic xanthoastrocytoma; primitive neuroectodermal (PNET); rhabdoid tumor; subependymal giant cell astrocytoma; subependymoma; or schwannoma; an astrocytoma selected from grade I pilocytic astrocytoma, grade II—low-grade astrocytoma or diffuse astrocytoma, grade III anaplastic astrocytoma, or grade IV glioblastoma (GBM), or a juvenile pilocytic astrocytoma; or a glioma selected from brain stem glioma, ependymoma, mixed glioma, optic nerve glioma, or subependymoma, and any other suitable disorder.

In various aspects, the method may further include assessing prognosis, planning therapeutic intervention, or predicting therapeutic response. In other aspects, the method may further include diagnosing a subject with a tumor grade or a plurality of tumor grades. In yet another aspect, the method may further include administering a treatment and monitoring treatment response or tumor recurrence.

Figure 77:
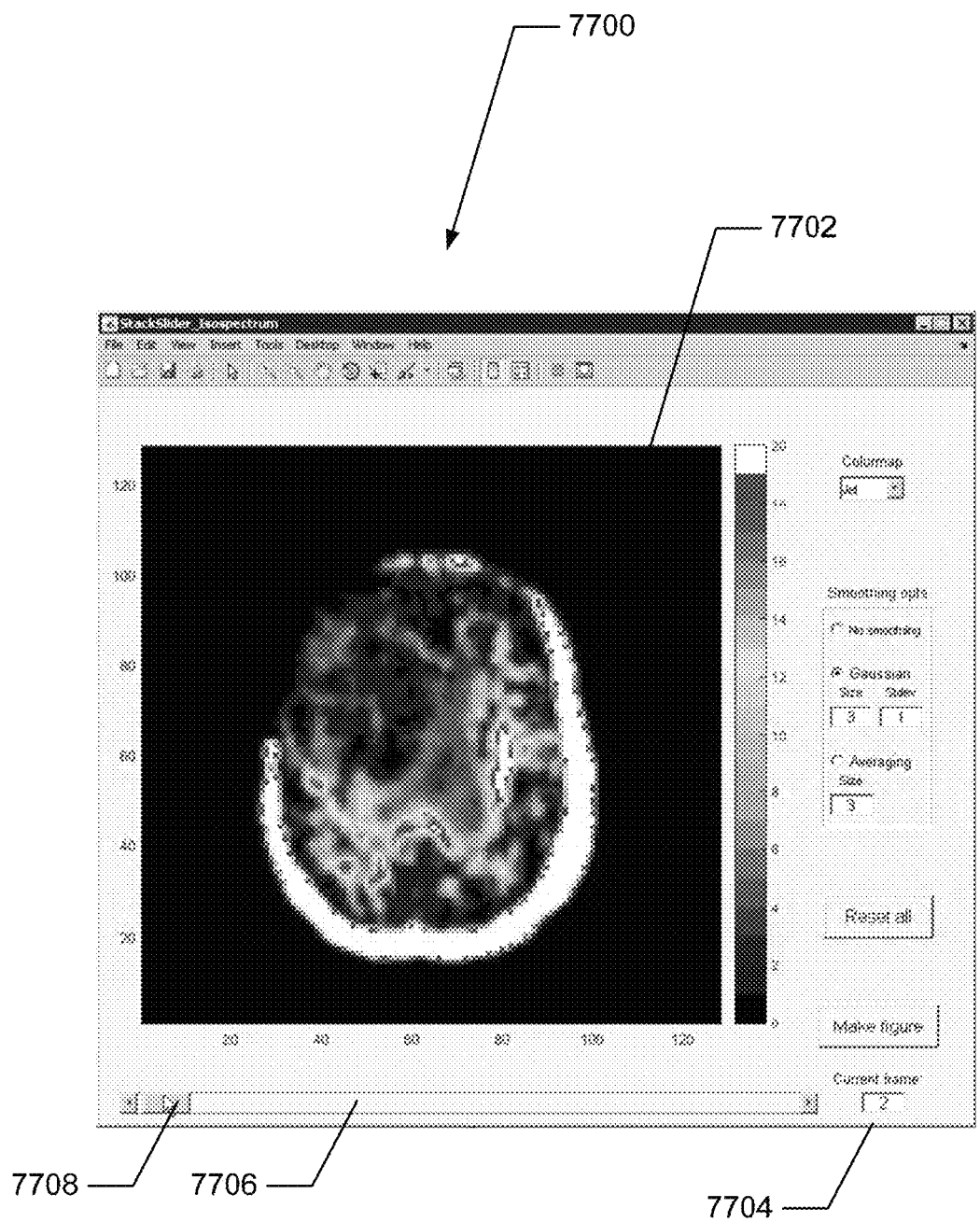
FIG. 77 is a display of a series of DBSI-EIS images of a patient in a movie-type GUI format.

In various other aspects, the DBSI-EIS images obtained using the methods described herein above may be displayed to a user in any suitable known format including, but not limited to: a graph of a plurality of anisotropic signal values or isotropic spectrum signal values, a grey-scale map of a plurality of anisotropic signal values or isotropic spectrum signal values, a two-dimensional (2D) movie format, a three-dimensional (3D) movie format, or any other suitable display format. In one aspect, the DBSI-EIS images may be displayed using a movie-style graphical user interface (GUI) to display individual maps corresponding to imaging slices in succession. By way of non-limiting example, FIG. 77 is a screen-shot of a GUI 7700 displaying a series of 2D maps 7702 in which the color scale 7703 corresponds to a single ADC value along an isotropic diffusion spectrum as a percentage of the contribution to the total isotropic diffusion spectrum. Each map is displayed as a frame in a movie displayed by the GUI 7700. In an aspect, the GUI may include a numerical display 7704 that may update as each frame is displayed. In one aspect, the numerical display 7704 may display the frame number in the series of maps. In another aspect, the numerical display 7704 may display the ADC value corresponding to the color map 7703 for a particular frame. In another aspect, the GUI display 7700 may further include a play button 7708 that may toggle between an ON position (to display the series of ADC maps) and an OFF position (to pause the display on a selected ADC map in the series). Further provided herein is an MRI system for detecting the presence of at least one structure in a patient tissue. The system may include an MRI scanner configured to obtain a plurality of diffusion MR signals for a plurality of voxels representing the patient tissue; and a computer system comprising a processor. The computer system may be configured to receive the plurality of diffusion data from the MRI scanner. The processor may be configured compute an anisotropic diffusion portion and an isotropic diffusion portion of the diffusion MR signals; calculate an isotropic diffusion spectrum, comprising a plurality of apparent diffusion coefficient (ADC) values; and calculate an associated percent contribution of each ADC value to a total isotropic spectrum magnitude. The isotropic diffusion spectrum may include an extended isotropic diffusion spectrum. The processor may be further configured to calculate at least one isotropic spectrum signal comprising a portion of the isotropic spectrum between a first ADC threshold value and a second ADC threshold value, each isotropic spectrum signal associated with a structure within the patient. The processor may be further configured to determine a presence and an abundance of at least one structure within the patient based on a map of at least one extended isotropic spectrum signal. The map may include a percent contribution of at least one isotropic spectrum signal to the total isotropic spectrum.

Figure 51:
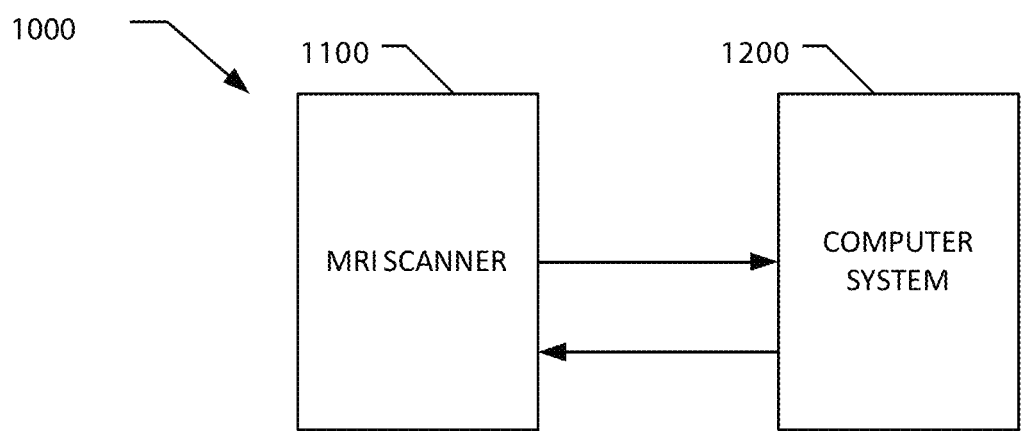
FIG. 51 is a schematic block diagram of an MRI system in one aspect.

In various aspects, the methods described herein may be implemented using an MRI system. FIG. 51 is an illustration of an MRI imaging system 1000 in one aspect. As illustrated in FIG. 51, the MRI system 1000 may include an MRI scanner 1100 operatively coupled and/or in communication with a computer system 1200. In this aspect, the computer system 1200 is configured to receive data including, but not limited to, diffusion data, from the MRI scanner 1100, and is further configured to execute a plurality of stored executable instructions encoding one or more aspects of the MRI method as described herein above. In another aspect, the computer system 1200 may be further configured to operate the MRI scanner 1100 to obtain, for example, diffusion data by executing an additional plurality of stored executable instructions.

Although the present invention is described in connection with an exemplary imaging system environment, embodiments of the invention are operational with numerous other general purpose or special purpose imaging system environments or configurations. The imaging system environment is not intended to suggest any limitation as to the scope of use or functionality of any aspect of the invention. Moreover, the imaging system environment should not be interpreted as having any dependency or requirement relating to any one or combination of components illustrated in the exemplary operating environment. Examples of well-known imaging systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Computer systems, as described herein, refer to any known computing device and computer system. As described herein, all such computer systems include a processor and a memory. However, any processor in a computer system referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

The term processor, as used herein, refers to central processing units, microprocessors, microcontrollers, reduced instruction set circuits (RISC), application specific integrated circuits (ASIC), logic circuits, and any other circuit or processor capable of executing the functions described herein. The above are examples only, and are thus not intended to limit in any way the definition and/or meaning of the term "processor."

As used herein, the term "database" may refer to either a body of data, a relational database management system (RDBMS), or to both. As used herein, a database may include any collection of data including hierarchical databases, relational databases, flat file databases, object-relational databases, object oriented databases, and any other structured collection of records or data that is stored in a computer system. The above examples are example only, and thus are not intended to limit in any way the definition and/or meaning of the term database. Examples of RDBMS's include, but are not limited to including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, California; IBM is a registered trademark of International Business Machines Corporation, Armonk, New York; Microsoft is a registered trademark of Microsoft Corporation, Redmond, Washington; and Sybase is a registered trademark of Sybase, Dublin, California)

In one embodiment, a computer program is provided to enable the data processing of the MRI method as described herein above, and this program is embodied on a computer readable medium. In an example embodiment, the computer system is executed on a single computer system, without requiring a connection to a server computer. In a further embodiment, the computer system is run in a Windows® environment (Windows is a registered trademark of Microsoft Corporation, Redmond, Washington). In yet another embodiment, the computer system is run on a mainframe environment and a UNIX® server environment (UNIX is a registered trademark of X/Open Company Limited located in Reading, Berkshire, United Kingdom). Alternatively, the computer system is run in any suitable operating system environment. The computer program is flexible and designed to run in various different environments without compromising any major functionality. In some embodiments, the computer system includes multiple components distributed among a plurality of computing devices. One or more components may be in the form of computer-executable instructions embodied in a computer-readable medium.

The computer systems and processes are not limited to the specific embodiments described herein. In addition, components of each computer system and each process can be practiced independent and separate from other components and processes described herein. Each component and process also can be used in combination with other assembly packages and processes.

Figure 52:
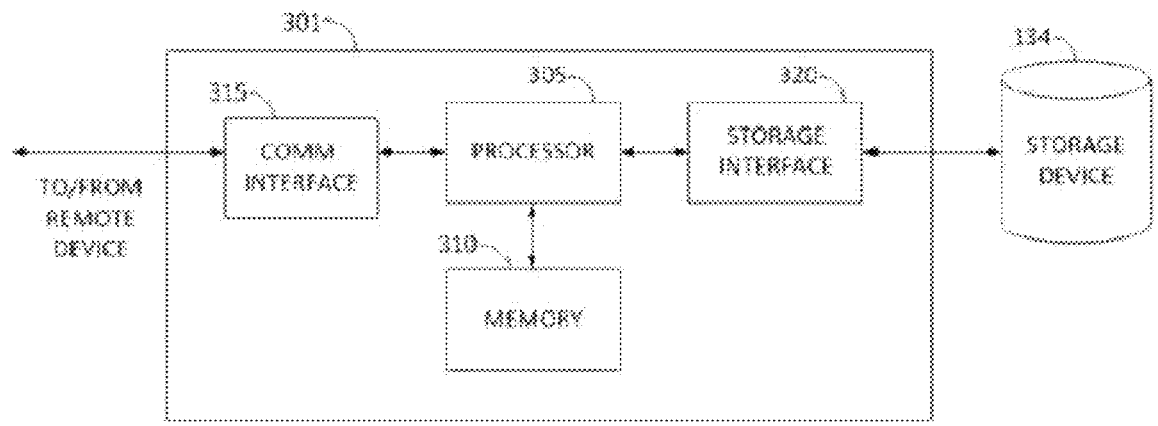
FIG. 52 is a schematic block diagram of an example server system.

In one embodiment, the computer system may be configured as a server system. FIG. 52 illustrates an example configuration of a server system 301 used to receive measurements from the MRI scanner 1100 (not illustrated). Referring again to FIG. 52, server system 301 may also include, but is not limited to, a database server. In this example embodiment, server system 301 performs all of the steps used to implement the MRI imaging method as described herein above. In various aspects, the computer system and/or database may be fully or partially implemented in a cloud computing environment such that data from the database is received from one or more computers (not shown) within the computer system or remote from the computer system.

In this aspect, the server system 301 includes a processor 305 for executing instructions. Instructions may be stored in a memory area 310, for example. The processor 305 may include one or more processing units (e.g., in a multi-core configuration) for executing instructions. The instructions may be executed within a variety of different operating systems on the server system 301, such as UNIX, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C#, C++, Java, or any other suitable programming languages).

The processor 305 is operatively coupled to a communication interface 315 such that server system 301 is capable of communicating with a remote device, such as the MRI scanner 1100, a user system, or another server system 301. For example, communication interface 315 may receive requests (e.g., requests to provide an interactive user interface to receive sensor inputs and to control one or more devices of system 1000 from a client system via the Internet.

Processor 305 may also be operatively coupled to a storage device 134. Storage device 134 is any computer-operated hardware suitable for storing and/or retrieving data. In some embodiments, storage device 134 is integrated in server system 301. For example, server system 301 may include one or more hard disk drives as storage device 134. In other embodiments, storage device 134 is external to server system 301 and may be accessed by a plurality of server systems 301. For example, storage device 134 may include multiple storage units such as hard disks or solid state disks in a redundant array of inexpensive disks (RAID) configuration. Storage device 134 may include a storage area network (SAN) and/or a network attached storage (NAS) system.

In some embodiments, processor 305 is operatively coupled to storage device 134 via a storage interface 320. Storage interface 320 is any component capable of providing processor 305 with access to storage device 134. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 134.

Memory area 310 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), registers, hard disk memory, a removable disk, a CD-ROM, or any other form of computer-readable storage medium known in the art. The above memory types are exemplary only, and are thus not limiting as to the types of memory usable for storage of a computer program.

Figure 53:
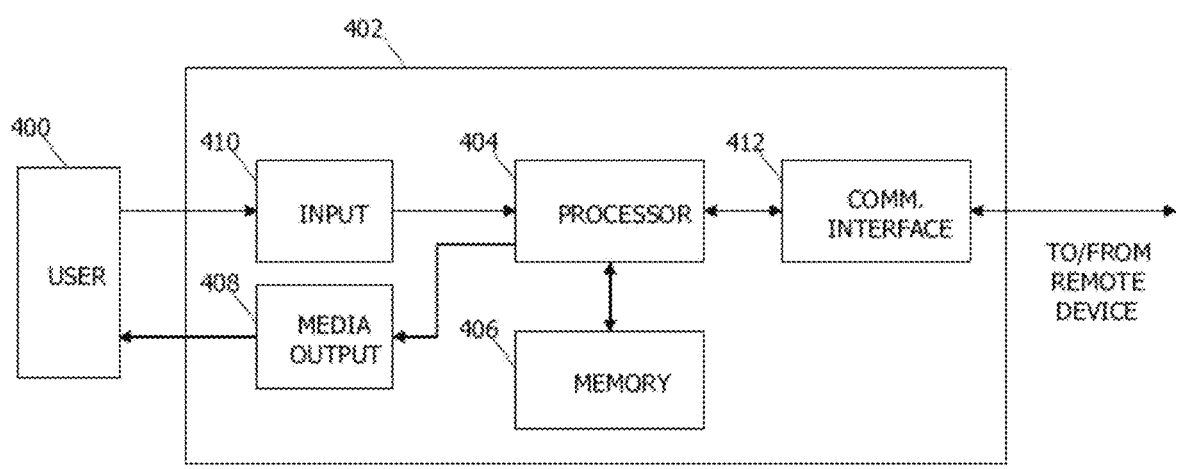
FIG. 53 is a block diagram of an example computing device.

In another embodiment, the computer system may be provided in the form of a computing device, such as a computing device 402 (shown in FIG. 53). Computing device 402 includes a processor 404 for executing instructions. In some embodiments, executable instructions are stored in a memory area 406. Processor 404 may include one or more processing units (e.g., in a multi-core configuration). Memory area 406 is any device allowing information such as executable instructions and/or other data to be stored and retrieved. Memory area 406 may include one or more computer-readable media. Therefore, the memory can be a non-transitory memory.

In another embodiment, the memory included in the computing device 402 may include a plurality of modules. Each module may include instructions configured to execute using at least one processor. The instructions contained in the plurality of modules may implement at least part of the method for simultaneously regulating a plurality of process parameters as described herein when executed by the one or more processors of the computing device. Non-limiting examples of modules stored in the memory of the computing device include: a first module to receive measurements from one or more sensors and a second module to control one or more devices of the MRI imaging system 1000.

Computing device 402 also includes one media output component 408 for presenting information to a user 400. Media output component 408 is any component capable of conveying information to user 400. In some embodiments, media output component 408 includes an output adapter such as a video adapter and/or an audio adapter. An output adapter is operatively coupled to processor 404 and is further configured to be operatively coupled to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, client computing device 402 includes an input device 410 for receiving input from user 400. Input device 410 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 408 and input device 410.

Computing device 402 may also include a communication interface 412, which is configured to communicatively couple to a remote device such as server system 302 or a web server. Communication interface 412 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WI MAX)).

Stored in memory 406 are, for example, computer-readable instructions for providing a user interface to user 400 via media output component 408 and, optionally, receiving and processing input from input device 410. A user interface may include, among other possibilities, a web browser and an application. Web browsers enable users 400 to display and interact with media and other information typically embedded on a web page or a website from a web server. An application allows users 400 to interact with a server application.

Exemplary embodiments of methods, systems, and apparatus for use in diffusion basis spectrum imaging are described above in detail. The methods, systems, and apparatus are not limited to the specific embodiments described herein but, rather, operations of the methods and/or components of the systems and/or apparatus may be utilized independently and separately from other operations and/or components described herein. Further, the described operations and/or components may also be defined in, or used in combination with, other systems, methods, and/or apparatus, and are not limited to practice with only the systems, methods, and apparatus described herein.

The order of execution or performance of the operations in the embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

It will be understood by those of skill in the art that information and signals may be represented using any of a variety of different technologies and techniques. For example, data, instructions, commands, information, signals, bits, symbols, and/or chips may be represented by voltages, currents, electromagnetic waves, magnetic fields or particles, optical fields or particles, or any combination thereof. Similarly, the various illustrative logical blocks, modules, circuits, and algorithm operations described herein may be implemented as electronic hardware, computer software, or a combination of both, depending on the application and the functionality. Moreover, the various logical blocks, modules, and circuits described herein may be implemented or performed with a general purpose computer, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Exemplary general purpose processors include, but are not limited to only including, microprocessors, conventional processors, controllers, microcontrollers, state machines, or a combination of computing devices.

When introducing elements of aspects of the invention or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

The following examples illustrate various aspects of the disclosure.

Example 1: DBSI-EIS Imaging of Recurrent Oligodendroglioma

Figure 57:
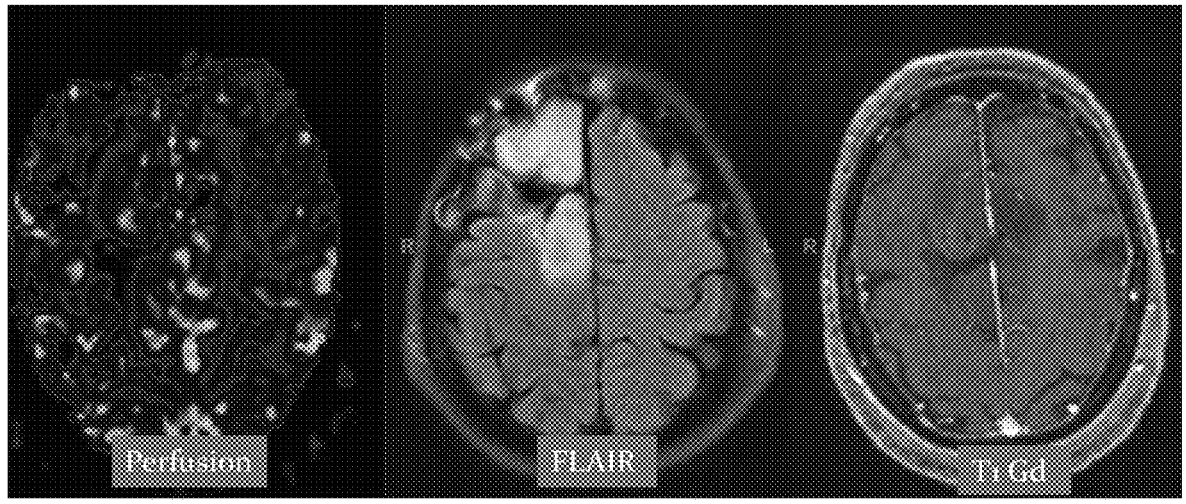
FIG. 57 contains images of a patient using perfusion imaging, FLAIR imaging, and T1 MRI imaging with Gd contrast.
Figure 58:
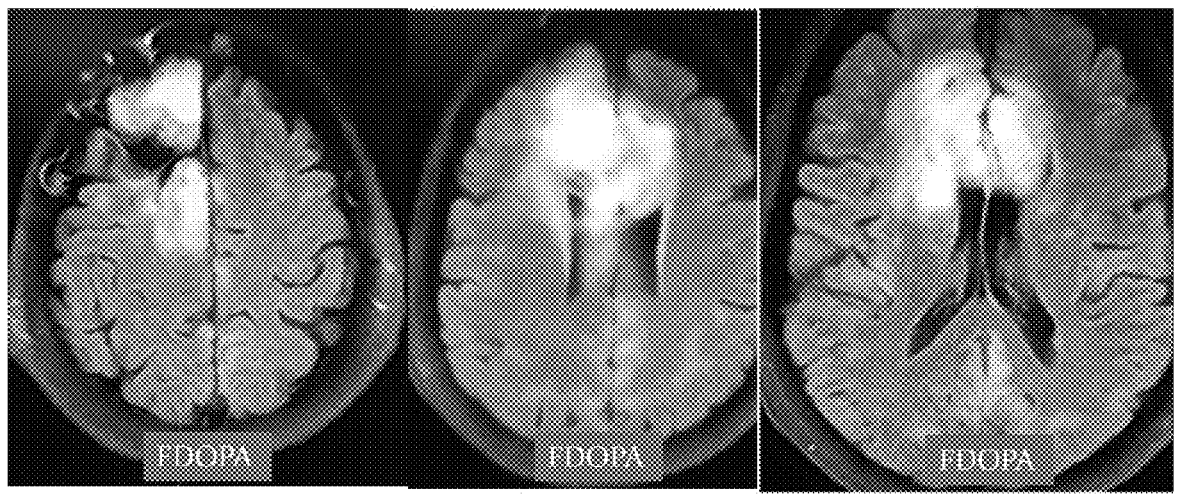
FIG. 58 contains images of a patient using FDOPA PET imaging.

To demonstrate the ability of the DBSI-EIS system to image the heterogeneity of brain lesions and tumors, the following experiment was conducted. A 66-year-old Caucasian female patient with recurrent oligodendroglioma, WHO grade II, IDH-1 negative, status post resection at the time of imaging was imaged using perfusion imaging, FLAIR imaging, and T1 MRI imaging with Gd contrast (see FIG. 57) at time. Additional images were obtained using FDOPA PET imaging (see FIG. 58). Compared to normal brain tissue, brain tumors have increased uptake of FDOPA, and FDOPA uptake can be measured with positron emission tomography (PET). FDOPA is transported across the blood-brain barrier. LAT1, an amino acid transporter, is one established marker of prognosis.

Figure 59A:
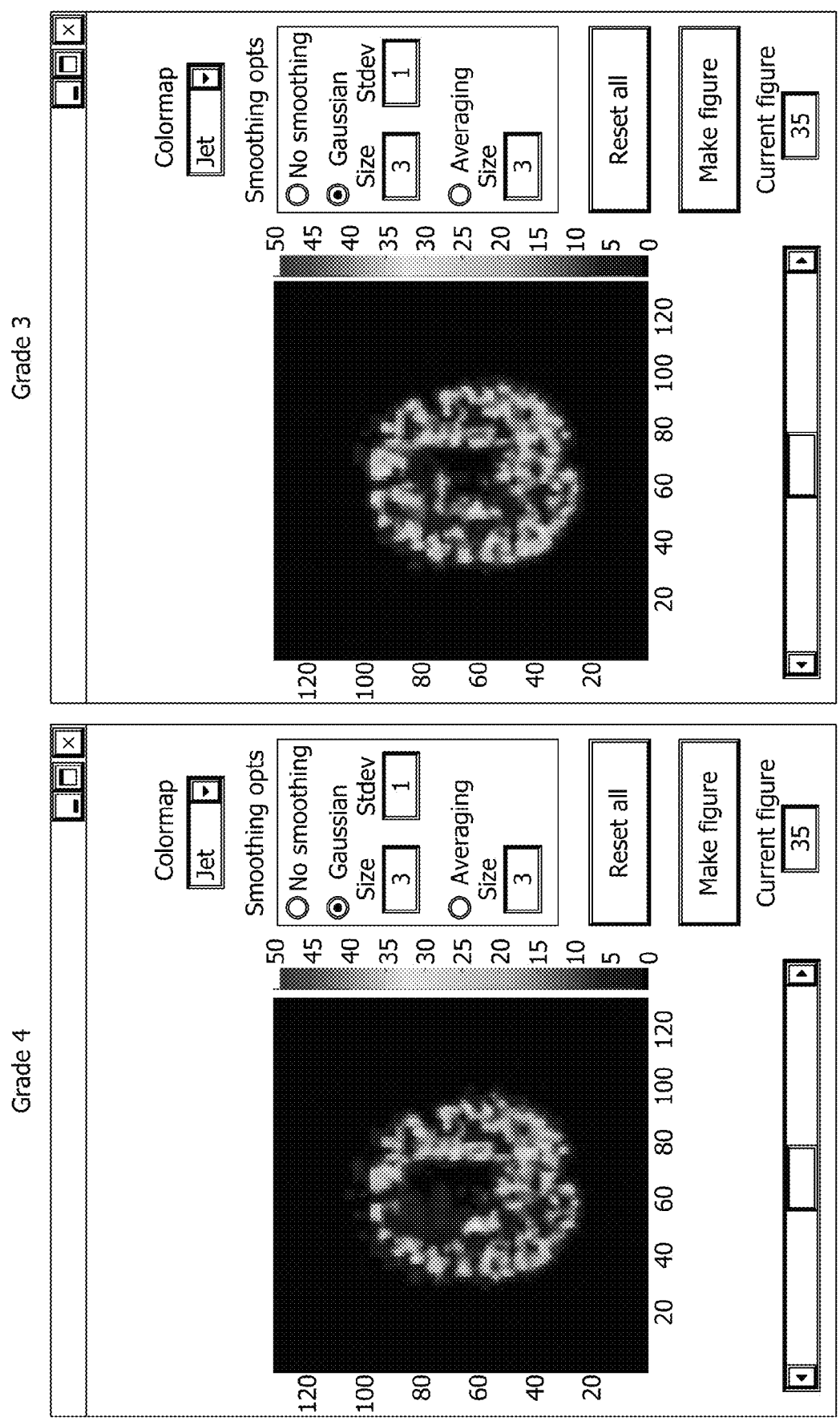
FIG. 59 contains a series of DBSI-EIS images with contrast corresponding to grade of brain tumor cell and a corresponding FDOPA PET image of a patient.
Figure 59C:
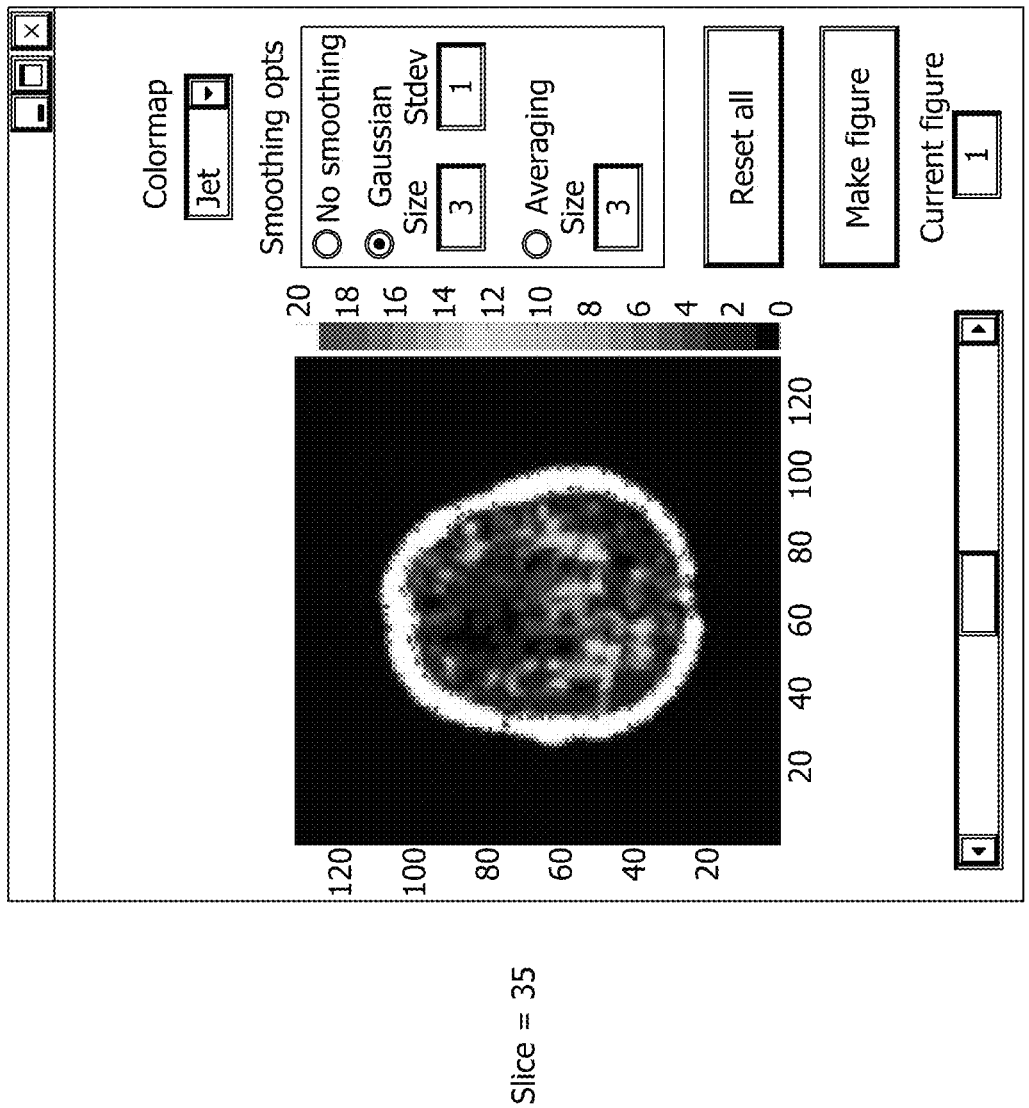
Figure 60:
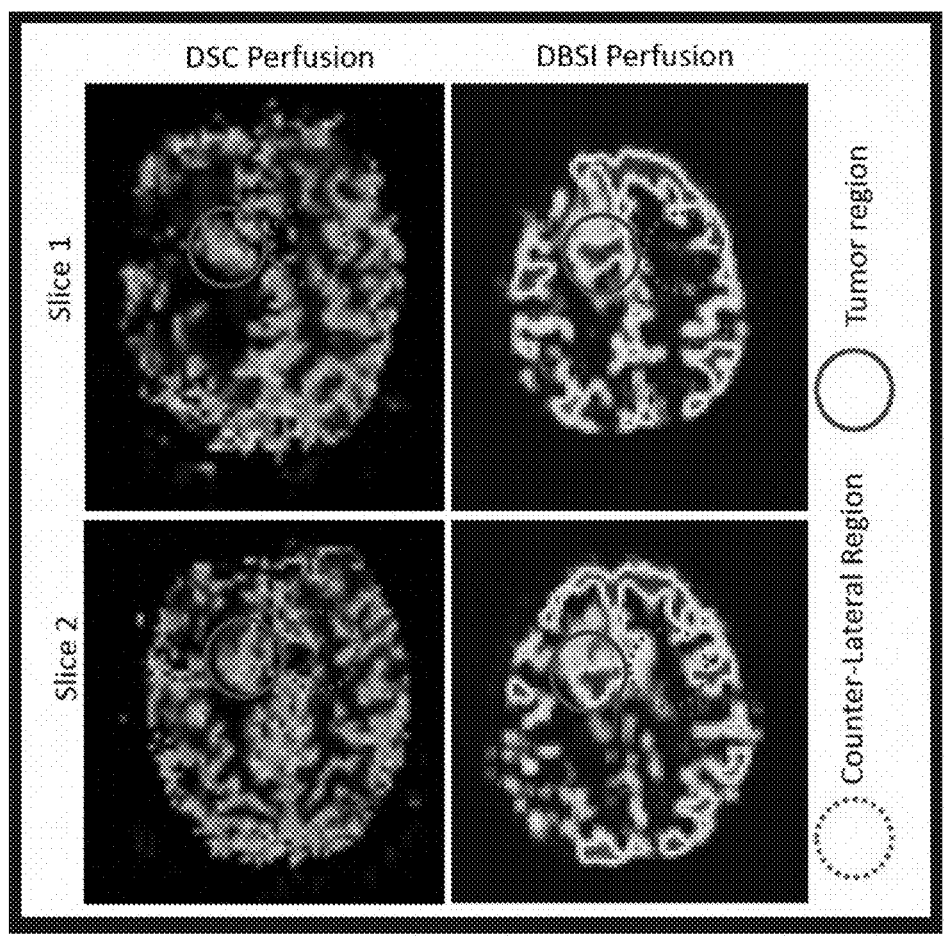
FIG. 60 contains a series of perfusion images comparing DBSI-EIS and DSC perfusion imaging.

DBSI-EIS images showing contrast based on the isotropic spectrum signal for Grade 4 glioblastoma cells, Grade 3 glioblastoma cells, Grade 1/2 glioblastoma cells, and a comparison FDOPA PET image are shown in FIG. 59. FIG. 60 is a series of images comparing DSC perfusion imaging and corresponding DBSI perfusion imaging. DBSI-EIS correctly indicated this patient has Grade 2 tumor without higher grade components. DBSI perfusion is consistent with DSC images.

The results of this experiment demonstrated the ability of DBSI-EIS to identify structural heterogeneity in a recurrent oligodendroglioma lesion, including various grades of glioblastoma and perfusion.

Example 2: DBSI-EIS Imaging of Secondary Oligodendroglioma

Figure 61:
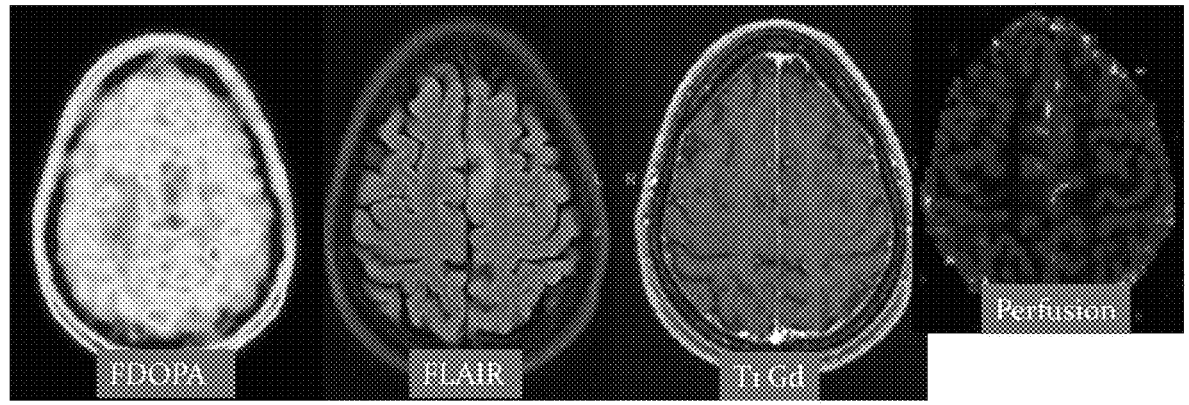
FIG. 61 contains images of a patient using perfusion imaging, FLAIR imaging, FDOPA PET imaging, and T1 MRI imaging with Gd contrast.
Figure 62:
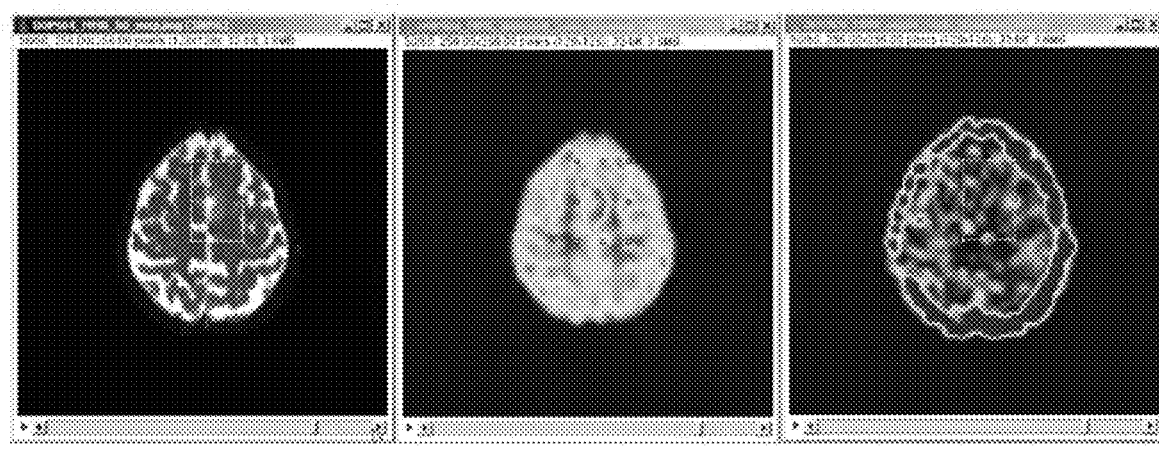
FIG. 62 contains a series of DBSI-EIS images with contrast based on B0, as well as the isotropic spectrum signals for cellularity and perfusion.

To demonstrate the ability of the DBSI-EIS system to image the heterogeneity of brain lesions and tumors, the following experiment was conducted. A 36-year-old Caucasian female with history of left breast cancer and BRCA1 mutation status post bilateral mastectomy and left breast radiation therapy, with a recent diagnosis of left frontal oligodendroglioma, and WHO grade II was imaged using perfusion imaging, FLAIR imaging, and T1 MRI imaging with Gd contrast and FDOPA PET imaging (see FIG. 61). DBSI-EIS images showing contrast based on BO, as well as the isotropic spectrum signal for cellularity and perfusion is shown in FIG. 62. DBSI-EIS images showing contrast based on the isotropic spectrum signal for Grade 4 glioblastoma cells, Grade 3 glioblastoma cells, Grade 1/2 glioblastoma cells, and a comparison FDOPA PET image are shown in FIG. 63. DBSI-EIS accurately found that the tumor is grade II without hyper perfusion, consistent with pathology study and PET images.

The results of this experiment demonstrated the ability of DBSI-EIS to identify structural heterogeneity in a recurrent oligodendroglioma lesion, including various grades of glioblastoma and perfusion.

Example 3: DBSI-EIS Imaging of Diffuse Astrocytoma

Figure 65:
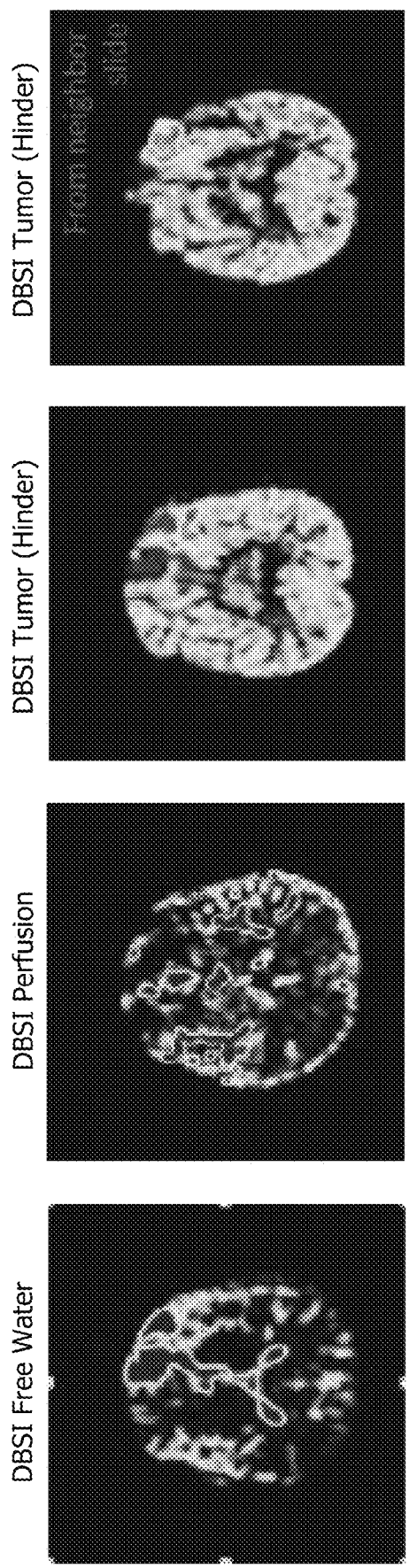
FIG. 65 is a series of DBSI images of a patient.
Figure 66A:
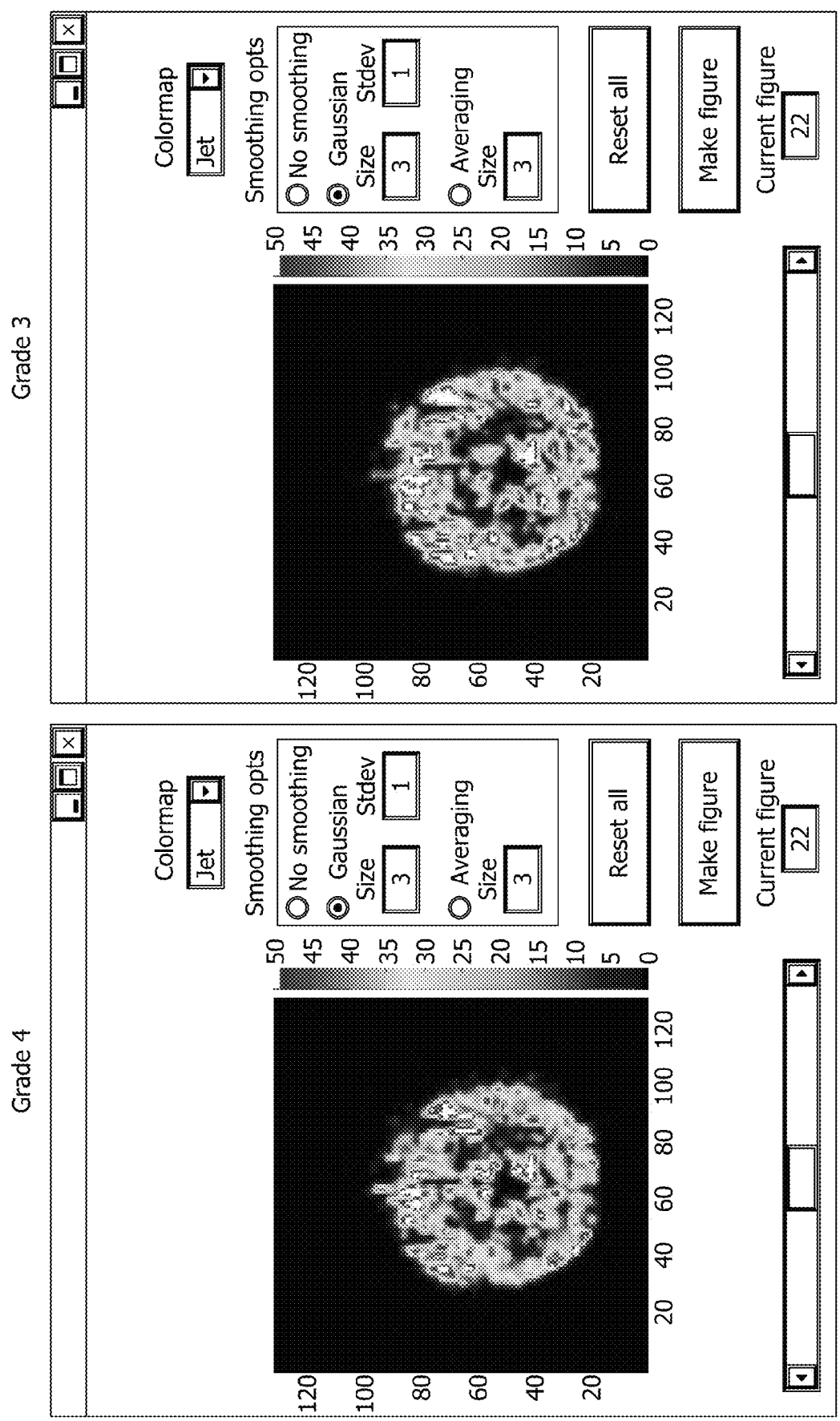
FIG. 66 contains a series of DBSI-EIS images of a patient with contrast corresponding to grade of brain tumor cell.
Figure 66C:
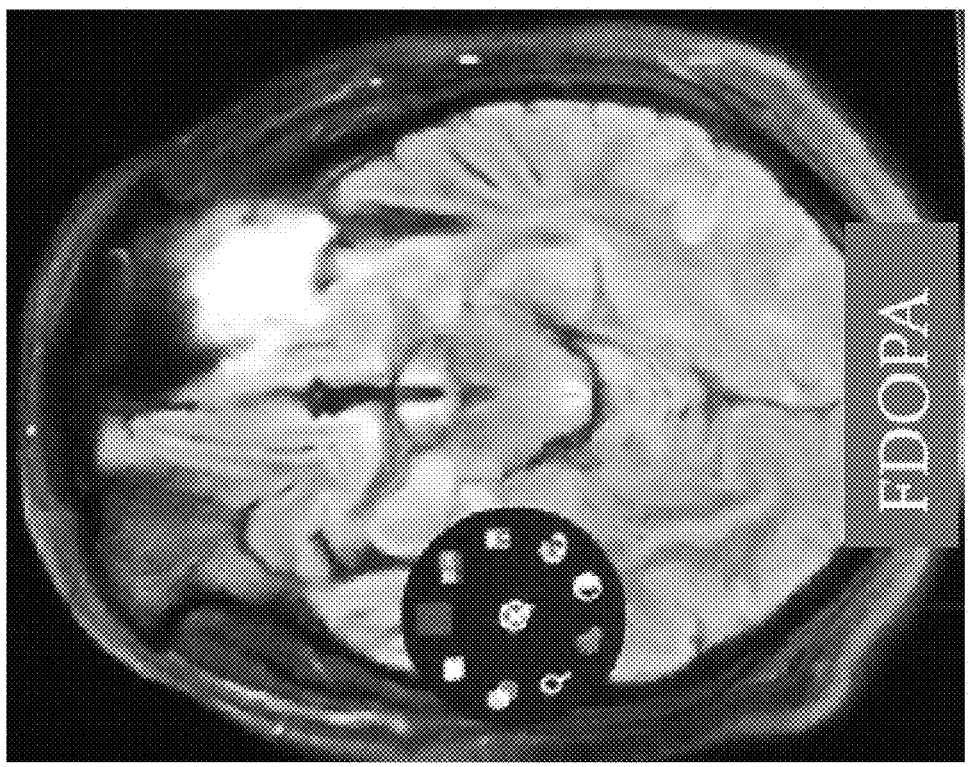

To demonstrate the ability of the DBSI-EIS system to image the heterogeneity of brain lesions and tumors, the following experiment was conducted. A 30 year old white male with diffuse astrocytoma, IDH mutant, WHO grade II, was imaged using perfusion imaging, FLAIR imaging, and T1 MRI imaging with Gd contrast and FDOPA PET imaging (see FIG. 64). DBSI images obtained using the previous DBSI method described herein above showing contrast based on free water, perfusion, and tumor are in FIG. 65. DBSI-EIS images showing contrast based on the isotropic spectrum signal for Grade 4 glioblastoma cells, Grade 3 glioblastoma cells, Grade 1/2 glioblastoma cells, and a comparison FDOPA PET image are shown in FIG. 66.

The results of this experiment demonstrated the ability of DBSI-EIS to identify structural heterogeneity in a secondary oligodendroglioma lesion, including various grades of glioblastoma and perfusion. DBSI-EIS accurately found that the tumor is grade II without hyper perfusion, consistent with pathology study and PET images.

Example 4: DBSI-EIS Imaging of Secondary Oligodendroglioma

Figure 67:
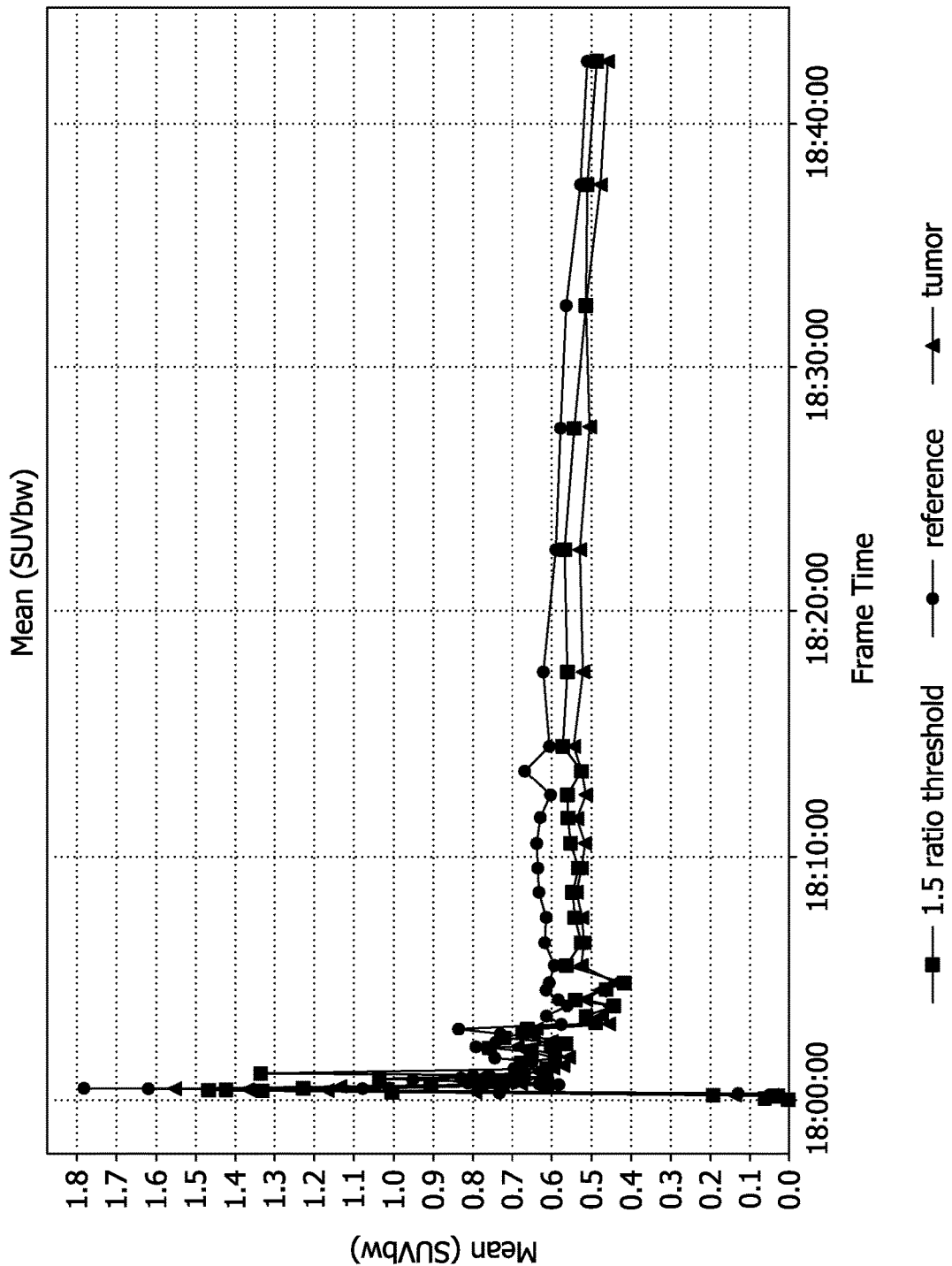
FIG. 67 is a graph summarizing mean SUVbw as a function of frame time.
Figure 70A:
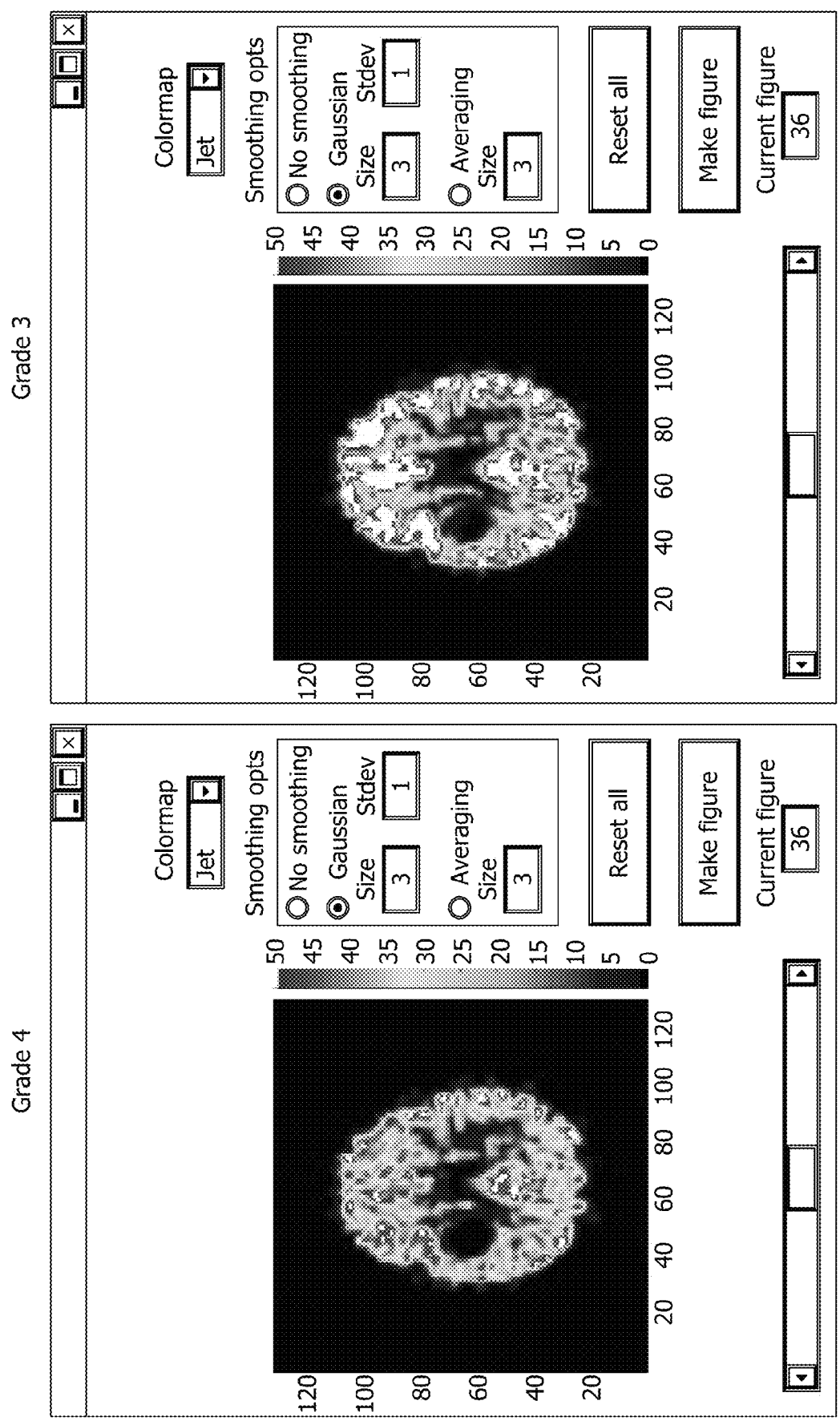
FIG. 70 contains a series of DBSI-EIS images of a patient with contrast corresponding to grade of brain tumor cell.

To demonstrate the ability of the DBSI-EIS system to image the heterogeneity of brain lesions and tumors, the following experiment was conducted. A 39-year-old African American male with a history of an anaplastic oligoastrocytoma, WHO grade III, status post subtotal resection, was imaged using perfusion imaging, FLAIR imaging, and FDOPA PET imaging (see FIG. 68 and FIG. 69). FIG. 67 is a graph summarizing mean SUVbw as a function of frame time, summarizing the PET FDOPA tracer binding dynamics. Referring to FIG. 67 there was no FDOPA evidence detecting tumor cells, which was inconsistent with pathology studies showing a Grade 2 tumor in this patient. DBSI-EIS images showing contrast based on the isotropic spectrum signal for Grade 4 glioblastoma cells, Grade 3 glioblastoma cells, and Grade 1/2 glioblastoma cells are shown in FIG. 70. PET FDOPA failed to identify the tumor cells, but DBSI-EIS accurately detected the correct tumor type and was consistent with pathology biopsy study.

The results of this experiment demonstrated the ability of DBSI-EIS to identify structural heterogeneity in a diffuse astrocytoma lesion, including various grades of glioblastoma and perfusion.

Example 5: DBSI-EIS Imaging of Oligodendroglioma Stage II

Figure 71:
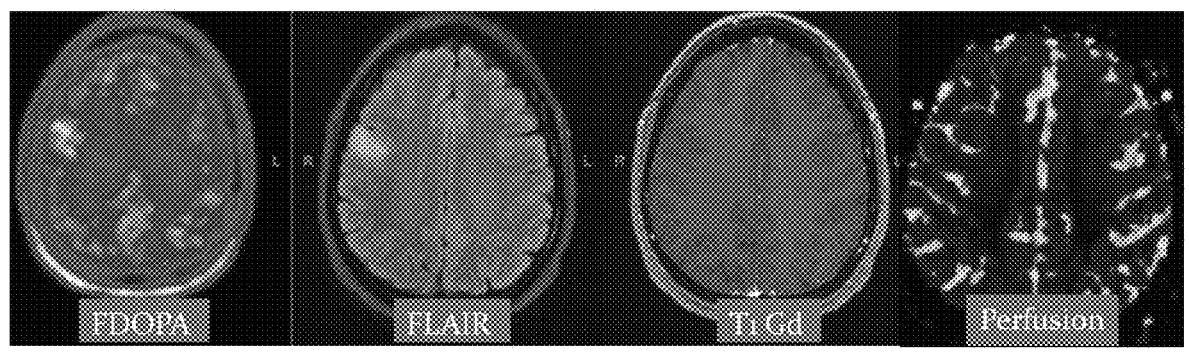
FIG. 71 contains images of a patient using perfusion imaging, FLAIR imaging, FDOPA PET imaging, and T1 MRI imaging with Gd contrast.
Figure 72:
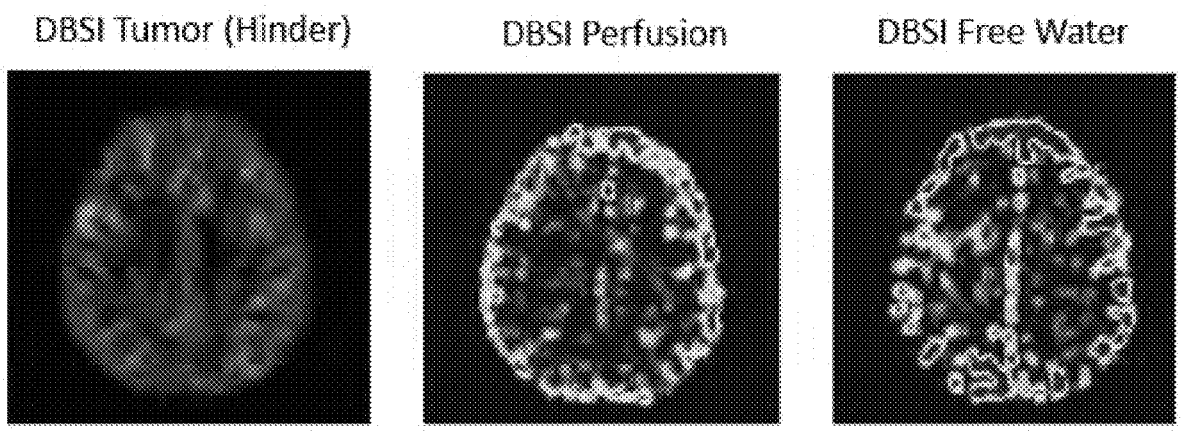
FIG. 72 is a series of DBSI images of a patient.
Figure 73A:
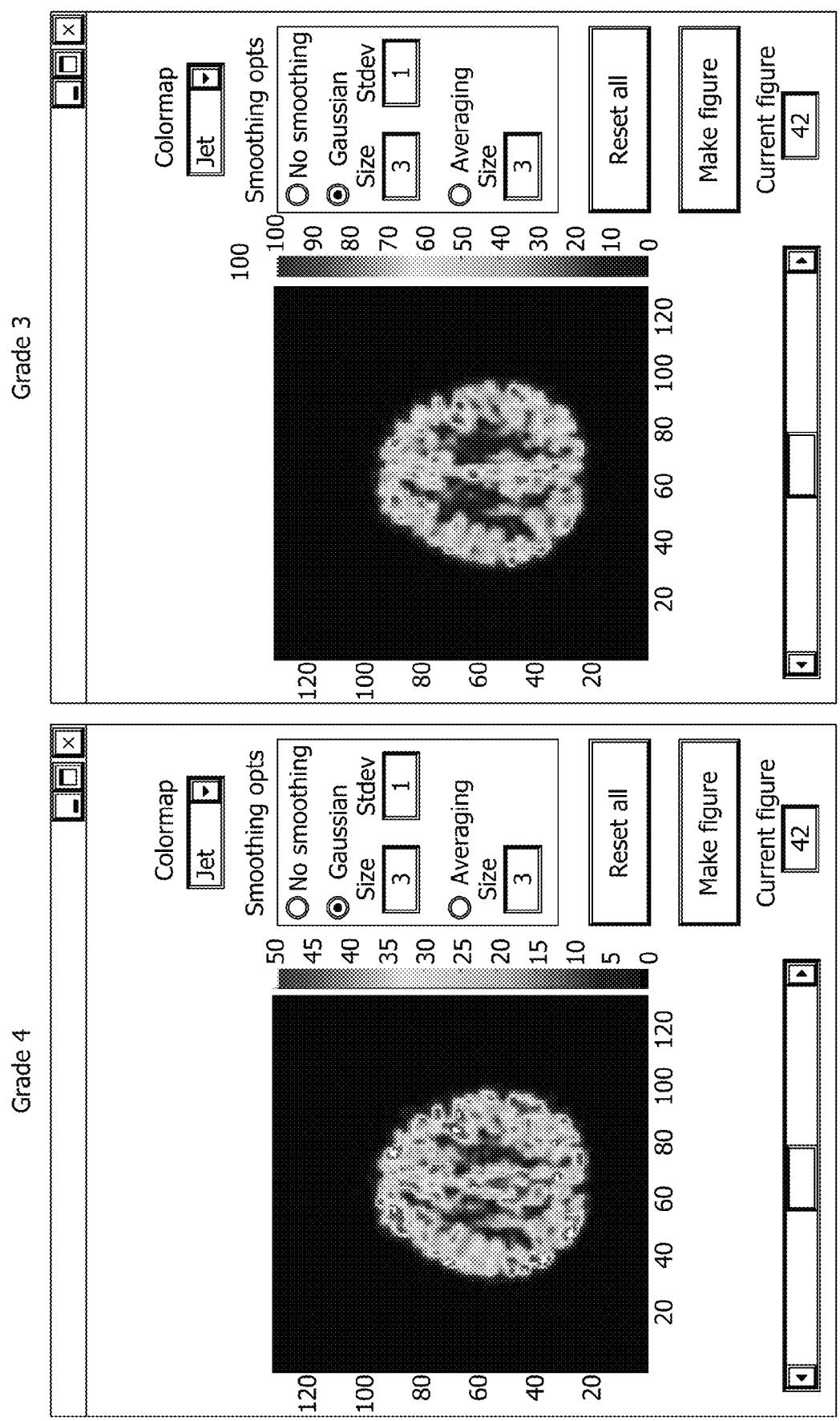
FIG. 73 contains a series of DBSI-EIS images of a patient with contrast corresponding to grade of brain tumor cell.

To demonstrate the ability of the DBSI-EIS system to image the heterogeneity of brain lesions and tumors, the following experiment was conducted. A 33 year-old white woman with speech difficulty and found to have a changing flair lesion in the right posterior frontal lobe (oligodendroglioma II), was imaged using perfusion imaging, FLAIR imaging, T1 MRI imaging with Gd contrast and FDOPA PET imaging (see FIG. 71). DBSI images obtained using the previous DBSI method described herein above showing contrast based on free water, perfusion, and tumor is in FIG. 72. DBSI-EIS images showing contrast based on the isotropic spectrum signal for Grade 4 glioblastoma cells, Grade 3 glioblastoma cells, and Grade 1/2 glioblastoma cells are shown in FIG. 73.

The results of this experiment demonstrated the ability of DBSI-EIS to identify structural heterogeneity in an oligodendroglioma lesion, including various grades of glioblastoma and perfusion.

Example 6: DBSI-EIS Imaging of Oligodendroglioma Stage II

Figure 74:
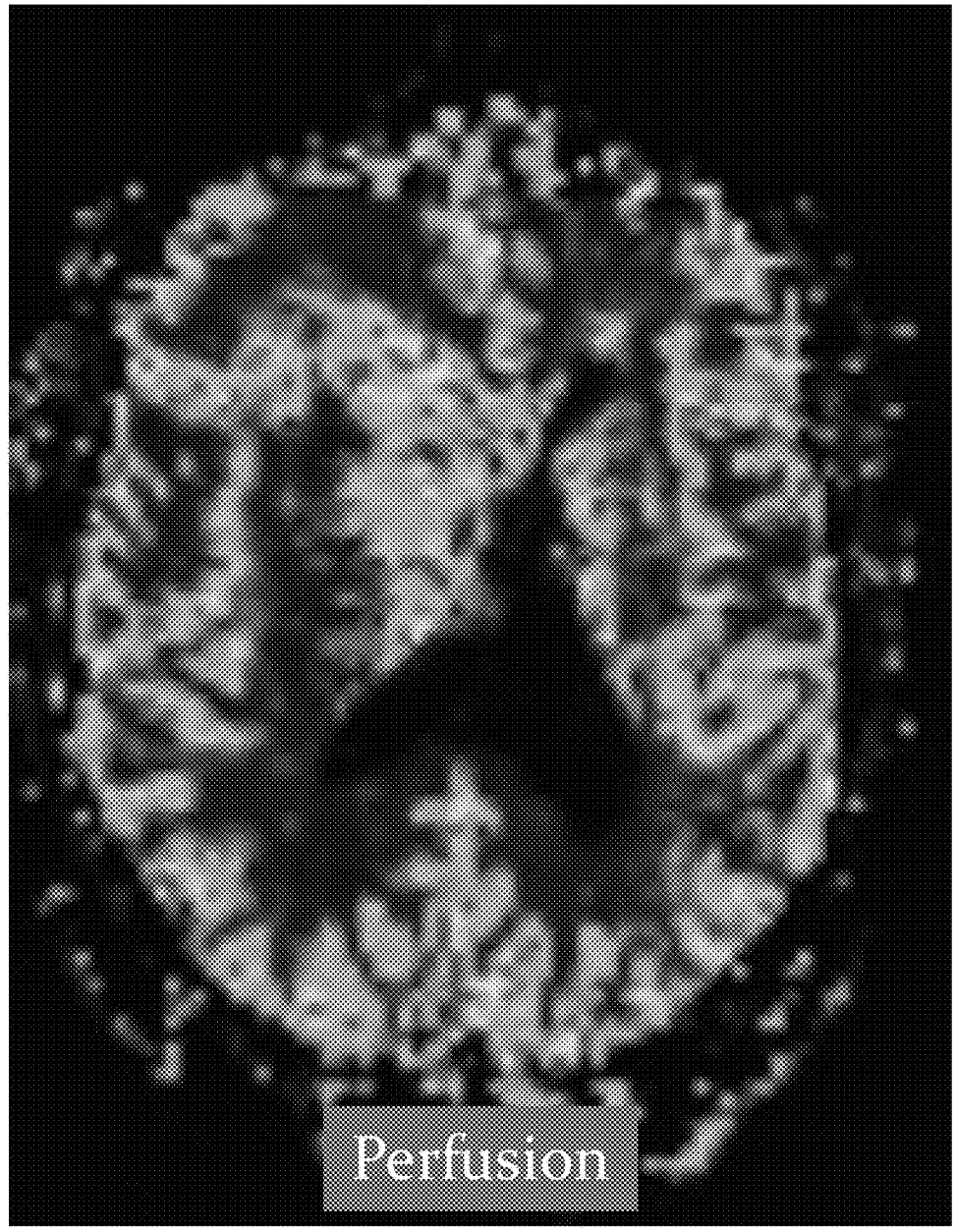
FIG. 74 contains a perfusion image of a patient.
Figure 75:
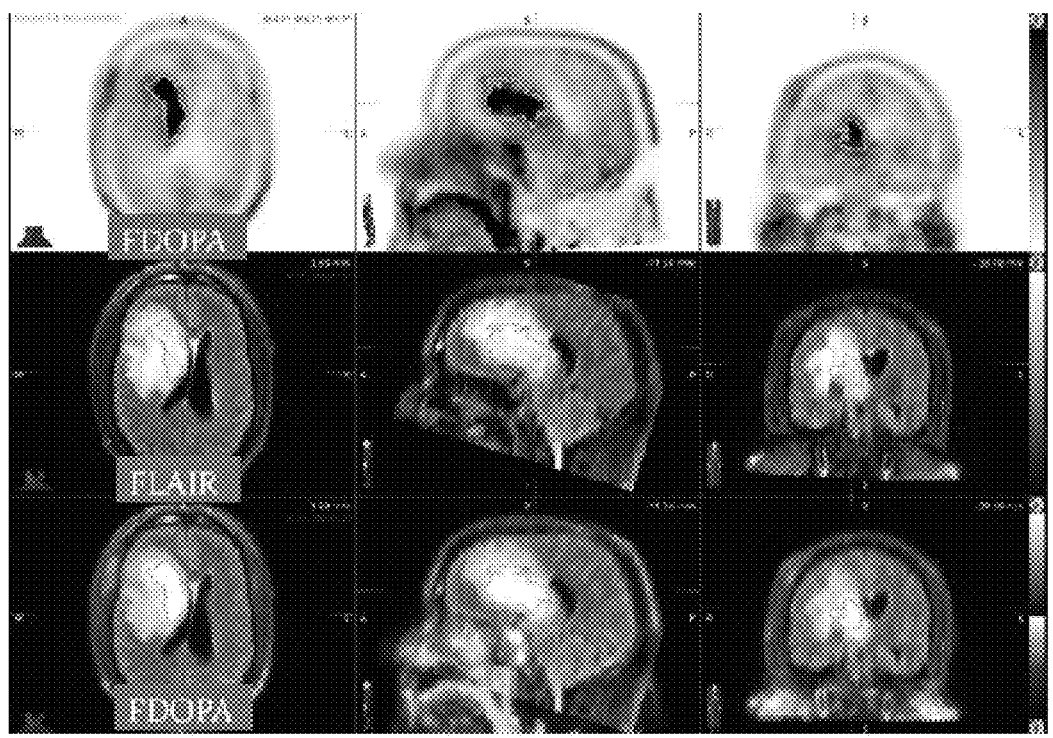
FIG. 75 contains images of a patient using FLAIR imaging and FDOPA PET imaging.
Figure 76A:
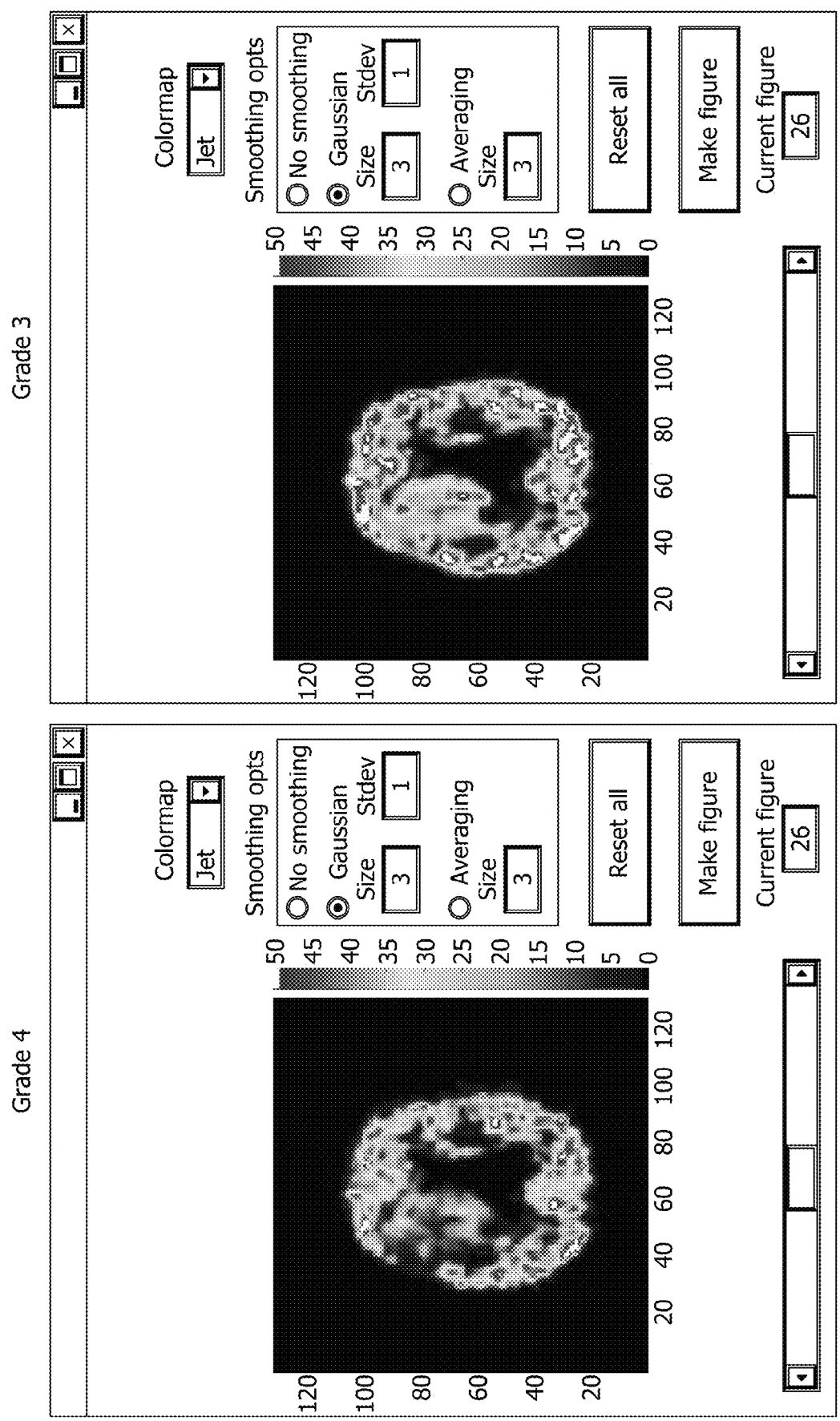
FIG. 76 contains a series of DBSI-EIS images of a patient with contrast corresponding to grade of brain tumor cell.

To demonstrate the ability of the DBSI-EIS system to image the heterogeneity of brain lesions and tumors, the following experiment was conducted. A 47 year-old white male with flair lesion in the right frontal lobe was imaged using perfusion imaging (FIG. 74), FLAIR imaging, and FDOPA PET imaging (see FIG. 75). DBSI-EIS images showing contrast based on the isotropic spectrum signal for Grade 4 glioblastoma cells, Grade 3 glioblastoma cells, and Grade 1/2 glioblastoma cells are shown in FIG. 76. DBSI-EIS identify the grade 3 tumor cell more in the peripheral zone of the tumor less in the center, consistent to pathology studies The results of this experiment demonstrated the ability of DBSI-EIS to identify structural heterogeneity in an oligodendroglioma lesion, including various grades of glioblastoma and perfusion.

Example 7: DBSI-EIS Imaging of Oligodendroglioma Stage II

To demonstrate the ability of the DBSI-EIS system to image the heterogeneity of brain lesions and tumors, the following experiment was conducted. The PET and MRI imaging were performed on a 3.0 Tesla PET/MRI system, Siemens Biograph mMR scanner (Siemens Health Care, Erlangen, Germany). The imaging protocol included 3D T1 (MPRAGE, 1 mm isotropic voxels), T2 FLAIR, Dynamic susceptibility contrast (DSC) perfusion weighted imaging, Diffusion MRI (78 directions with multiple b values, and b max=2000s/mm$^2$), and Dynamic PET imaging (acquisition for at least 45 minutes and up to 60 minutes after the intravenous injection of 5 mCi of [$^{18}$F] FDOPA). Compared to normal brain tissue, brain tumors have increased uptake of FDOPA, and FDOPA uptake can be measured with PET. FDOPA is transported across the blood-brain barrier, and LAT1, an amino acid transporter, is one established marker of prognosis.

Figure 82A:
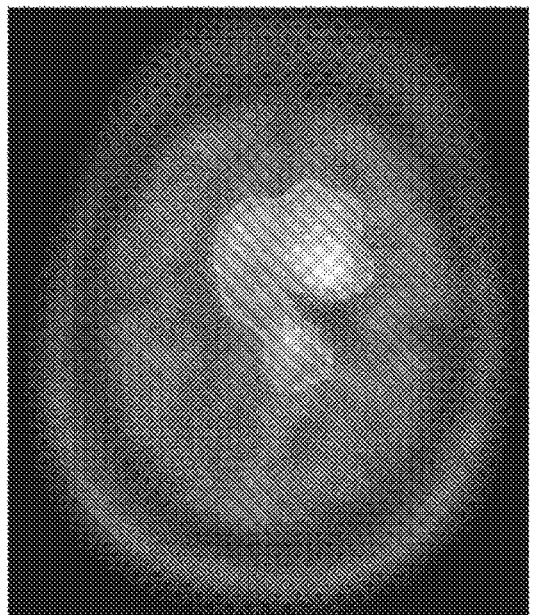
FIG. 82A is an FDOPA image of a patient with an oligodendroglioma WHO grade II.
Figure 82B:
FIG. 82B is a FLAIR image of the patient of FIG. 82A with an oligodendroglioma WHO grade II.
Figure 88A:
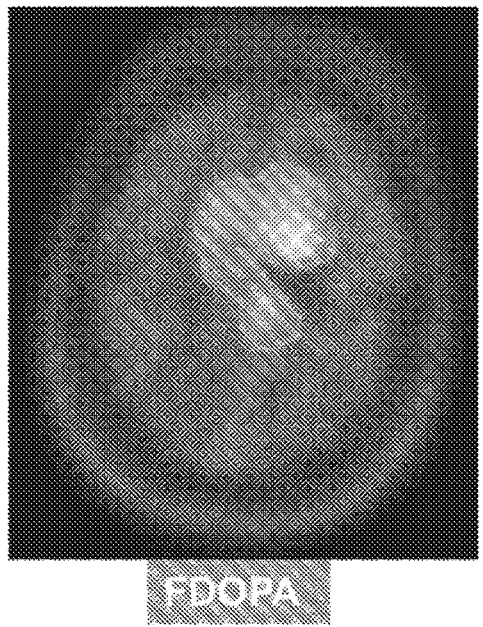
FIG. 88A is an FDOPA image of the patient of FIG. 82A with an oligodendroglioma WHO grade II.
Figure 88B:
FIG. 88B is a FLAIR image of the patient of FIG. 82A.
Figure 88C:
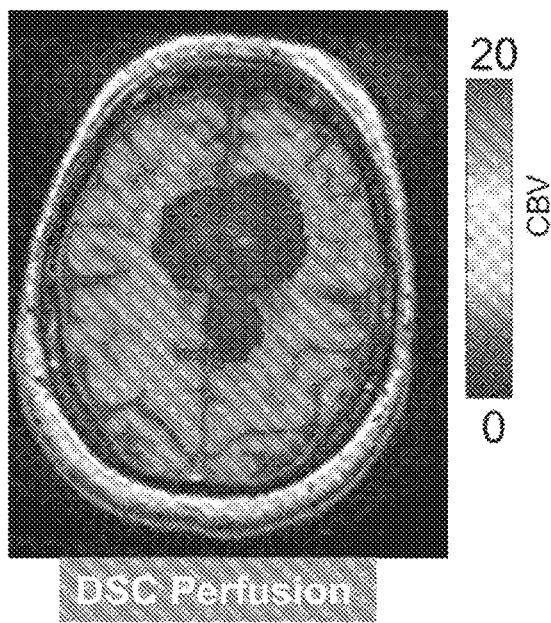
FIG. 88C is a DSC perfusion image of the patient of FIG. 82A.
Figure 88D:
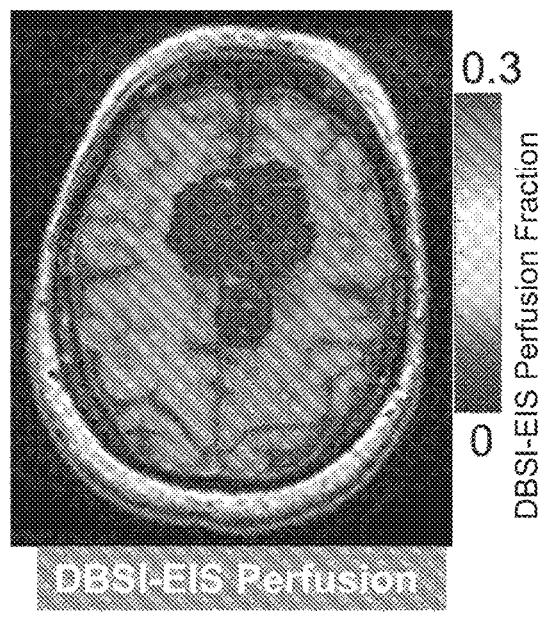
FIG. 88D is a DBSI-EIS perfusion image of the patient of FIG. 82A.

A 66 year-old female with a recurrent oligodendroglioma WHO grade II tumor was imaged using FDOPA PET imaging (see FIG. 82A and FIG. 88A), FLAIR imaging (see FIG. 82B and FIG. 88B), and perfusion imaging (see FIG. 88C and FIG. 88D). DBSI-EIS images showing contrast based on the isotropic spectrum signal for Grade 4 glioblastoma cells, Grade 3 glioblastoma cells, and Grade 1/2 glioblastoma cells are shown in FIGS. 83A-83C. DBSI-EIS (NII) detected grade 2 tumor cells dominated at the site of biopsy (arrow and white square region), which was consistent with pathological study. The tumor for this patient has substantial FDOPA uptake and matching FLAIR signal. The lesion demonstrated lacking of elevated perfusion based on the DSC T2* based perfusion cerebral blood volume (CBV) map and the DBSI-EIS (NII) detected perfusion fraction map. FIG. 91 is a graph showing how DBSI-EIS derived perfusion fraction correlates to DSC CBV.

The results of this experiment demonstrated the capability and accuracy of a multiple parametrical diffusion MRI methods, DBSI-EIS (NII), to noninvasively characterize the detailed 3D spatial distributions for different grades of tumor cells. In the same imaging session, NII quantified the spatial distribution for capillary blood perfusion within the tumors. FIG. 84 shows DBSI-EIS-derived tumor grade ratios for low grade gliomas for several patients.

Example 8: DBSI-EIS Imaging of Oligodendroglioma Stage III

To demonstrate the ability of the DBSI-EIS system to image the heterogeneity of brain lesions and tumors, the following experiment was conducted using the same imaging protocol as in Example 7.

Figure 85A:
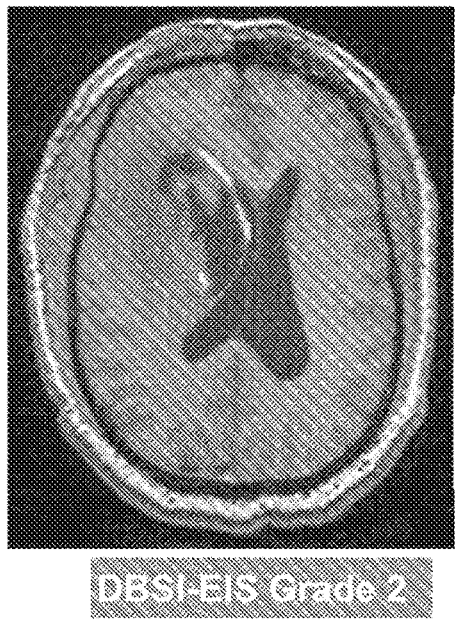
FIG. 85A is a DBSI-EIS grade 2 image of a patient with an oligodendroglioma WHO grade III.
Figure 85B:
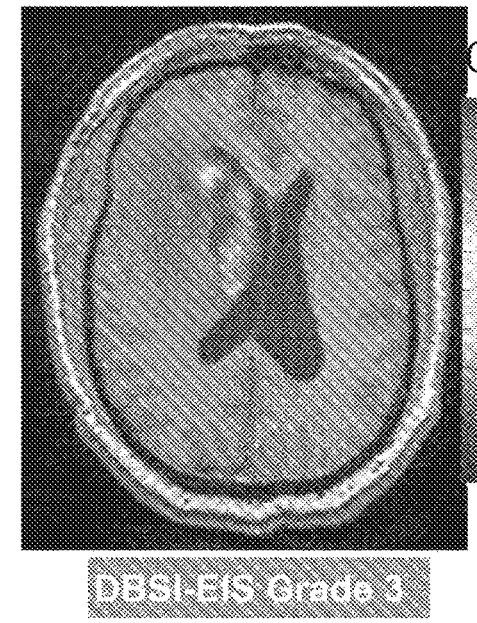
FIG. 85B is a DBSI-EIS grade 3 image of the patient of FIG. 85A.
Figure 85C:
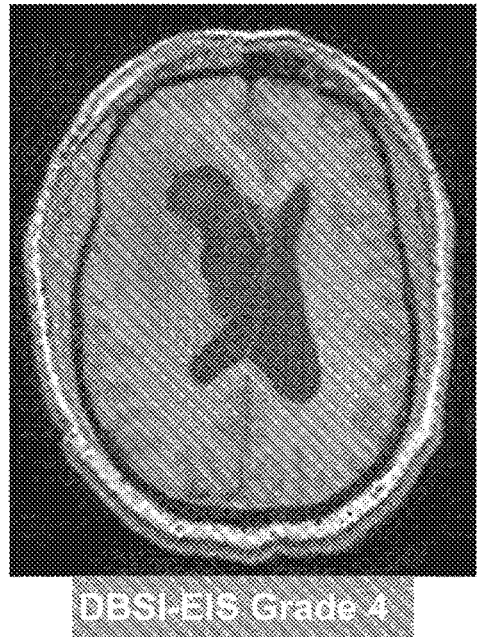
FIG. 85C is a DBSI-EIS grade 4 image of the patient of FIG. 85A.

A 48 year-old male with a newly diagnosed oligodendroglioma WHO grade III tumor was imaged using FDOPA PET imaging (see FIG. 89A), FLAIR imaging (see FIG. 89B), and perfusion imaging (see FIG. 89C and FIG. 89D). DBSI-EIS images showing contrast based on the isotropic spectrum signal for Grade 4 glioblastoma cells, Grade 3 glioblastoma cells, and Grade 1/2 glioblastoma cells are shown in FIGS. 85A-85C. DBSI-EIS (NII) detected grade 2 and 3 tumor cells at the site of biopsy (arrow and white square region), which was consistent with pathological study. The tumor for this patient has substantial FDOPA uptake and matching FLAIR signal. The lesion demonstrated the elevated perfusion based on the DSC T2* based perfusion CBV map and the DBSI-EIS (NII) detected perfusion fraction map. FIG. 91 is a graph showing how DBSI-EIS derived perfusion fraction correlates to DSC CBV.

The results of this experiment demonstrated the capability and accuracy of a multiple parametrical diffusion MRI methods, DBSI-EIS (NII), to noninvasively characterize the detailed 3D spatial distributions for different grades of tumor cells. In the same imaging session, NII quantified the spatial distribution for capillary blood perfusion within the tumors. FIG. 87A shows DBSI-EIS-derived tumor grade ratios for the grade 3 glioma for this patient.

Example 9: DBSI-EIS Imaging of Glioblastoma Stage IV

To demonstrate the ability of the DBSI-EIS system to image the heterogeneity of brain lesions and tumors, the following experiment was conducted using the same imaging protocol as in Example 7.

A 62 year-old male with a newly diagnosed glioblastoma WHO grade IV tumor was imaged using FDOPA PET imaging (see FIG. 90A), FLAIR imaging (see FIG. 90B), and perfusion imaging (see FIG. 90C and FIG. 90D). DBSI-EIS images showing contrast based on the isotropic spectrum signal for Grade 4 glioblastoma cells, Grade 3 glioblastoma cells, and Grade 1/2 glioblastoma cells are shown in FIGS. 86A-86C. DBSI-EIS (NII) detected grade 2, 3, and 4 tumor cells at the site of biopsy (arrow and white square region), which was consistent with pathological study. The tumor for this patient has substantial FDOPA uptake and matching FLAIR signal. The lesion demonstrated the elevated perfusion based on the DSC T2* based perfusion CBV map and the DBSI-EIS (NII) detected perfusion fraction map. FIG. 91 is a graph showing how DBSI-EIS derived perfusion fraction correlates to DSC CBV.

The results of this experiment demonstrated the capability and accuracy of a multiple parametrical diffusion MRI methods, DBSI-EIS (NII), to noninvasively characterize the detailed 3D spatial distributions for different grades of tumor cells. In the same imaging session, NII quantified the spatial distribution for capillary blood perfusion within the tumors. FIG. 87B shows DBSI-EIS-derived tumor grade ratios for the grade 4 glioma for this patient.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structures.

What is claimed is:

1. A method for analyzing a diffusion basis spectrum imaging (DBSI) magnetic resonance imaging (MRI), the method comprising:
   obtaining a plurality of diffusion magnetic resonance (MR) signals for a plurality of voxels representing at least a portion of a patient tissue;
   for each voxel of the plurality of voxels:
   computing, by a processor, an anisotropic diffusion portion and an isotropic diffusion portion of the plurality of diffusion MR signals; calculating, by the processor, an extended isotropic diffusion spectrum from the isotropic diffusion portion of the plurality of diffusion MR signals, the extended isotropic diffusion spectrum comprising a plurality of apparent diffusion coefficient (ADC) values;

calculating, by the processor, an associated percent contribution of each ADC value to a sum of the plurality of ADC values of the each voxel; and calculating at least one isotropic spectrum signal comprising a portion of the extended isotropic diffusion spectrum between a first ADC threshold value of 0 mm$^2$/s and a second ADC threshold value of 50×10 mm$^2$/s wherein the at least one isotropic spectrum signal is associated with at least one structure within the patient tissue;

generating at least one DBSI image including a map of the at least one isotropic spectrum signal, the map including a projection of a percent contribution of the at least one isotropic spectrum signal to the sum of the plurality of ADC values of the each voxel onto an anatomical image reconstructed using the plurality of voxels; and determining a presence and/or an abundance of the at least one structure within the patient tissue based on the map.

2. The method of claim 1, wherein determining the presence and/or the abundance of the at least one structure further comprises determining the presence and/or the abundance of one or more structures from the group consisting of a normal resident cell, a grade 1/2 tumor cell, a grade 3 tumor cell, a grade 4 tumor cell, cerebrospinal fluid (CSF), edema, and perfusion associated with vascular structures that perfuse a tumor tissue, the vascular structures comprising a region of perfusion, hyperperfusion, or hypoperfusion.

3. The method of claim 1, wherein calculating the extended isotropic diffusion spectrum further comprises using a higher sampling rate for data in the extended isotropic diffusion spectrum with ADC values between 0 mm$^2$/s and 3×10$^{-3}$ mm$^2$/s than a sampling rate used for data in the extended isotropic diffusion spectrum with ADC values greater than 3×10$^{-3}$ me/s.

4. The method of the claim 2, wherein:
non-tumor tissue is correlated with a portion of the extended isotropic diffusion spectrum between ADC threshold values of 0 mm$^2$/s and 0.3 mm$^2$/s;
tumor cells are correlated with a portion of the extended isotropic diffusion spectrum with an ADC threshold value less than the ADC value for CSF and more than the ADC value for non-tumor tissue;
tumor cells are correlated with a portion of the extended isotropic diffusion spectrum between ADC threshold values of 0.25 mm$^2$/s and 3 mm$^2$/s;
grade 4 tumor cells, grade 3 tumor cells, and grade 1/2 tumor cells are correlated with a portion of the extended isotropic diffusion spectrum between ADC threshold values of 0 mm$^2$/s and 1.8 mm$^2$/s;
grade 4 tumor tissue is correlated with a portion of the extended isotropic diffusion spectrum between ADC threshold values of between 0.25 mm$^2$/s and 0.5 mm$^2$/s;
grade 3 tumor tissue is correlated with a portion of the extended isotropic diffusion spectrum between ADC threshold values of between 0.5 mm$^2$/s and 0.8 mm$^2$/s;
grade 2 tumor tissue is correlated with a portion of the extended isotropic diffusion spectrum between ADC threshold values of between 0.8 mm$^2$/s and 1.8 mm$^2$/s;
edema is correlated with a portion of the extended isotropic diffusion spectrum between ADC threshold values of 1.8 mm$^2$/s and 2.5 mm$^2$/s; CSF is correlated with a portion of the extended isotropic diffusion spectrum between ADC threshold values of 2.5 mm$^2$/s and 4 mm$^2$/s;
perfusion is correlated with a portion of the extended isotropic diffusion spectrum between ADC threshold values of between 4 mm$^2$/s and 10 mm$^2$/s;
perfusion is correlated with a portion of the extended isotropic diffusion spectrum with ADC threshold values greater than 10 mm$^2$/s; or
perfusion associated with a tumor is correlated with a portion of the extended isotropic diffusion spectrum with ADC threshold values between 4 mm$^2$/s and 50 mm$^2$/s.

5. The method of claim 1, wherein the map comprises:
(i) a tumor grade or tumor grade ratio;
(ii) a tumor grade distribution;
(iii) grade 1 tumor cell fraction, grade 2 tumor cell fraction, grade 3 tumor cell fraction, or grade 4 tumor cell fraction; or
(iv) a perfusion value or perfusion fraction map.

6. The method of claim 1, further comprising quantifying a value for non-tumor cells; quantifying a value for grade 1/2 cells; quantifying a value for grade 3 cells; or quantifying a value for grade 4 cells.

7. The method of claim 6, wherein:
if a cell fraction of grade 4 tumor cells is greater than 5% of a sum of non-tumor cells and tumor cell fraction, the tumor is classified as a grade 4 tumor;
if the cell fraction of the grade 4 tumor cells is less than 5% and the cell fraction of the grade 3 tumor cells is more than 5%, the tumor is classified as a grade 3 tumor; or
if the cell fraction of grade 4 tumor cells is less than 5% and the cell fraction of the grade 3 tumor cells is less than 5%, then the tumor is classified as a low grade or grade 1/2 tumor.

8. The method of claim 1, further comprising:
assessing prognosis, planning therapeutic intervention, or predicting therapeutic response;
diagnosing a subject with a tumor grade or a plurality of tumor grades; or
administering a treatment and monitoring treatment response or tumor recurrence.

9. The method of claim 1, further comprising determining a perfusion fraction value, wherein the perfusion fraction correlates with cerebral blood volume (CBV) and tumor grade.

10. A method for generating an image utilizing diffusion basis spectrum imaging (DBSI) magnetic resonance imaging (MRI), the method comprising:
obtaining a plurality of diffusion magnetic resonance (MR) signals for a plurality of voxels representing at least a portion of a patient tissue;
for each voxel of the plurality of voxels:
computing, by a processor, an anisotropic diffusion portion and an isotropic diffusion portion of the plurality of diffusion MR signals;
calculating, by the processor, an extended isotropic diffusion spectrum from the isotropic diffusion portion of the plurality of diffusion MR signals, the extended isotropic diffusion spectrum comprising a plurality of apparent diffusion coefficient (ADC) values;
calculating, by the processor, an associated percent contribution of each ADC value to a sum of the plurality of ADC values of the each voxel; and calculating, by the processor, at least one isotropic spectrum signal comprising a portion of the extended isotropic diffusion spectrum between a first ADC threshold value of 0 mm²/s and a second ADC threshold value of 50×10 mm²/s, the at least one isotropic spectrum signal associated with a structure within the patient tissue; and generating at least one DBSI image comprising a map of the at least one isotropic spectrum signal, the map comprising a projection of a percent contribution of the at least one isotropic spectrum signal to the sum of the plurality of ADC values of the each voxel onto an image reconstructed using the plurality of voxels.

11. The method of claim 10, wherein the DBSI images are displayed to a user as a graph of a plurality of anisotropic signal values or isotropic spectrum signal values, a grey-scale map of a plurality of anisotropic signal values or isotropic spectrum signal values, a two-dimensional (2D) movie format, or a three-dimensional (3D) movie format.

12. The method of claim 10, wherein the structure within the patient tissue is selected from one or more of the group consisting of a normal resident cell, a grade 1/2 brain tumor cell, a grade 3 tumor cell, a grade 4 tumor cell, cerebrospinal fluid (CSF), edema, and perfusion associated with vascular structures that perfuse a tumor tissue.

13. The method of claim 12, wherein:
non-tumor tissue is correlated with a portion of the extended isotropic diffusion spectrum between ADC threshold values of 0 mm²/s and 0.3 mm²/s;
tumor cells are correlated with a portion of the extended isotropic diffusion spectrum with an ADC threshold value less than the ADC value for CSF and more than the ADC value for non-tumor tissue;
tumor cells are correlated with a portion of the extended isotropic diffusion spectrum between ADC threshold values of 0.25 mm²/s and 3 mm²/s;
grade 4 tumor cells, grade 3 tumor cells, and grade 1/2 tumor cells are correlated with a portion of the extended isotropic diffusion spectrum between ADC threshold values of 0 mm²/s and 1.8 mm²/s;
grade 4 tumor tissue is correlated with a portion of the extended isotropic diffusion spectrum between ADC threshold values of between 0.25 mm²/s and 0.5 mm²/s;
grade 3 tumor tissue is correlated with a portion of the extended isotropic diffusion spectrum between ADC threshold values of between 0.5 mm²/s and 0.8 mm²/s;
grade 2 tumor tissue is correlated with a portion of the extended isotropic diffusion spectrum between ADC threshold values of between 0.8 mm²/s and 1.8 mm²/s;
edema is correlated with a portion of the extended isotropic diffusion spectrum between ADC threshold values of 1.8 mm²/s and 2.5 mm²/s; CSF is correlated with a portion of the extended isotropic diffusion spectrum between ADC threshold values of 2.5 mm²/s and 4 mm²/s;
perfusion is correlated with a portion of the extended isotropic diffusion spectrum between ADC threshold values of between 4 mm²/s and 10 mm²/s; perfusion is correlated with a portion of the extended isotropic diffusion spectrum with ADC threshold values greater than 10 mm²/s;
or
perfusion associated with a tumor is correlated with a portion of the extended isotropic diffusion spectrum with ADC threshold values between 4 mm²/s and 50 mm²/s.

14. An magnetic resonance imaging (MRI) system for detecting a presence of at least one structure in a patient tissue, the system comprising:
an MRI scanner configured to obtain a plurality of diffusion magnetic resonance (MR) signals for a plurality of voxels representing the patient tissue; and
a computer system comprising a processor, wherein the computer system is configured to receive the plurality of diffusion MR signals from the MRI scanner, and wherein for each voxel of the plurality of voxels the processor is configured to:
compute an anisotropic diffusion portion and an isotropic diffusion portion of the plurality of diffusion MR signals; calculate at least one extended isotropic diffusion spectrum, comprising a plurality of apparent diffusion coefficient (ADC) values; and
calculate an associated percent contribution of each ADC value to a sum of the plurality of ADC values; and the processor is further configured to:
generate at least one diffusion basis spectrum imaging (DBSI) image including a map of the at least one extended isotropic diffusion spectrum, the map including a projection of the associated percent contribution onto an image reconstructed using the plurality of voxels.

15. The system of claim 14, wherein the processor is further configured to calculate at least one isotropic spectrum signal comprising a portion of the at least one extended isotropic diffusion spectrum between a first ADC threshold value of 0 mm²/s and a second ADC threshold value of 50×10 mm²/s, the at least one isotropic spectrum signal associated with the at least one structure within the patient tissue.

16. The system of claim 15, wherein the processor is further configured to determine the presence and/or an abundance of the at least one structure within the patient tissue based on the map of the at least one isotropic spectrum signal.

17. The system of claim 16, wherein the processor is further configured to project the map of the at least one isotropic spectrum signal onto the image reconstructed using the plurality of voxels.

18. The system of claim 17, wherein the processor is further configured to generate the map of the at least one isotropic spectrum signal by generating individual maps corresponding to individual imaging slices, and the system further comprising a graphical user interface (GUI) to display the individual maps.

19. The method of the claim 15, wherein:
non-tumor tissue is correlated with a portion of the at least one extended isotropic diffusion spectrum between ADC threshold values of 0 mm²/s and 0.3 mm²/s;
tumor cells are correlated with a portion of the at least one extended isotropic diffusion spectrum with an ADC threshold value less than the ADC value for CSF and more than the ADC value for non-tumor tissue;
tumor cells are correlated with a portion of the at least one extended isotropic diffusion spectrum between ADC threshold values of 0.25 mm²/s and 3 mm²/s;
grade 4 tumor cells, grade 3 tumor cells, and grade 1/2 tumor cells are correlated with a portion of the extended isotropic diffusion spectrum between ADC threshold values of 0 mm²/s and 1.8 mm²/s;
grade 4 tumor tissue is correlated with a portion of the at least one extended isotropic diffusion spectrum between ADC threshold values of between 0.25 mm²/s and 0.5 mm²/s;

grade 3 tumor tissue is correlated with a portion of the at least one extended isotropic diffusion spectrum between ADC threshold values of between 0.5 mm$^2$/s and 0.8 mm$^2$/s;

grade 2 tumor tissue is correlated with a portion of the at least one extended isotropic diffusion spectrum between ADC threshold values of between 0.8 mm$^2$/s and 1.8 mm$^2$/s;

edema is correlated with a portion of the at least one extended isotropic diffusion spectrum between ADC threshold values of 1.8 mm$^2$/s and 2.5 mm$^2$/s; CSF is correlated with a portion of the at least one extended isotropic diffusion spectrum between ADC threshold values of 2.5 mm$^2$/s and 4 mm$^2$/s;

perfusion is correlated with a portion of the at least one extended isotropic diffusion spectrum between ADC threshold values of between 4 mm$^2$/s and 10 mm$^2$/s;

perfusion is correlated with a portion of the at least one extended isotropic diffusion spectrum with ADC threshold values greater than 10 mm$^2$/s; or perfusion associated with a tumor is correlated with a portion of the at least one extended isotropic diffusion spectrum with ADC threshold values between 4 mm$^2$/s and 50 mm$^2$/s.

* * * * *